(12) United States Patent
Bahk

(10) Patent No.: US 11,576,690 B2
(45) Date of Patent: Feb. 14, 2023

(54) POSTERIOR SHOULDER ARTHROPLASTY IMPLANTS, SYSTEMS, AND METHODS

(71) Applicant: Michael Bahk, Thousand Oaks, CA (US)

(72) Inventor: Michael Bahk, Thousand Oaks, CA (US)

(*) Notice: Subject to any disclaimer, the term of this patent is extended or adjusted under 35 U.S.C. 154(b) by 0 days.

(21) Appl. No.: 17/425,567

(22) PCT Filed: Nov. 4, 2020

(86) PCT No.: PCT/US2020/058941
§ 371 (c)(1),
(2) Date: Jul. 23, 2021

(87) PCT Pub. No.: WO2021/092058
PCT Pub. Date: May 14, 2021

(65) Prior Publication Data
US 2022/0039811 A1 Feb. 10, 2022

Related U.S. Application Data

(60) Provisional application No. 63/051,502, filed on Jul. 14, 2020, provisional application No. 62/930,556, filed on Nov. 5, 2019.

(51) Int. Cl.
*A61F 2/40* (2006.01)
*A61B 17/17* (2006.01)
(Continued)

(52) U.S. Cl.
CPC ...... *A61B 17/1778* (2016.11); *A61B 17/1728* (2013.01); *A61B 17/921* (2013.01);
(Continued)

(58) Field of Classification Search
CPC .................................... A61F 2/4014
See application file for complete search history.

(56) References Cited

U.S. PATENT DOCUMENTS 10,368,999 B2    8/2019  Greiwe
2001/0047210 A1*  11/2001  Wolf .................... A61F 2/4014
                                                          606/87
(Continued)

FOREIGN PATENT DOCUMENTS

WO    2018039493 A1    3/2018
WO    2019060780 A2    3/2019

OTHER PUBLICATIONS

International Search Report and Written Opinion, PCT/US2020/058941, dated Mar. 16, 2021.

*Primary Examiner* — Zade Coley
(74) *Attorney, Agent, or Firm* — Polsinelli PC

(57) ABSTRACT

A stemless humeral head replacement system including a base plate and a humeral head implant. The base plate includes a bone facing side, an implant side opposite the bone facing side, a curvate perimeter, at least one fin protruding from the bone facing side a first distance and extending linearly a length along the bone facing side, and an implant engagement structure on the implant side. The humeral head implant includes a curvate implant surface and a base plate engagement structure opposite the curvate implant surface, the base plate engagement structure configured to couple to the implant engagement structure of the base plate.

17 Claims, 119 Drawing Sheets

(51) Int. Cl.
*A61B 17/92* (2006.01)
*A61F 2/30* (2006.01)
*A61F 2/46* (2006.01)

(52) U.S. Cl.
CPC ........ *A61F 2/30767* (2013.01); *A61F 2/4014* (2013.01); *A61F 2/4612* (2013.01); *A61F 2002/30011* (2013.01); *A61F 2002/3093* (2013.01); *A61F 2002/30332* (2013.01); *A61F 2002/30578* (2013.01); *A61F 2002/30604* (2013.01); *A61F 2002/30784* (2013.01); *A61F 2002/30881* (2013.01); *A61F 2002/30884* (2013.01); *A61F 2002/30892* (2013.01); *A61F 2002/30902* (2013.01); *A61F 2002/4022* (2013.01); *A61F 2002/4033* (2013.01); *A61F 2002/4037* (2013.01); *A61F 2002/4681* (2013.01); *A61F 2310/00796* (2013.01)

(56) References Cited

U.S. PATENT DOCUMENTS

| | | | |
|---|---|---|---|
| 2006/0009852 A1* | 1/2006 | Winslow | A61F 2/4003 623/19.14 |
| 2006/0149390 A1 | 7/2006 | Long et al. | |
| 2013/0261754 A1* | 10/2013 | Anthony | A61F 2/4003 623/19.14 |
| 2013/0261755 A1* | 10/2013 | Anthony | A61B 17/15 623/19.14 |
| 2014/0188231 A1 | 7/2014 | Poncet et al. | |
| 2016/0324648 A1 | 11/2016 | Hodorek et al. | |
| 2018/0064547 A1 | 3/2018 | Greiwe | |
| 2018/0271667 A1 | 9/2018 | Kemp et al. | |
| 2019/0015119 A1* | 1/2019 | Athwal | A61B 17/1684 |
| 2019/0159906 A1 | 5/2019 | Knox et al. | |
| 2019/0350719 A1 | 11/2019 | Greiwe | |

* cited by examiner

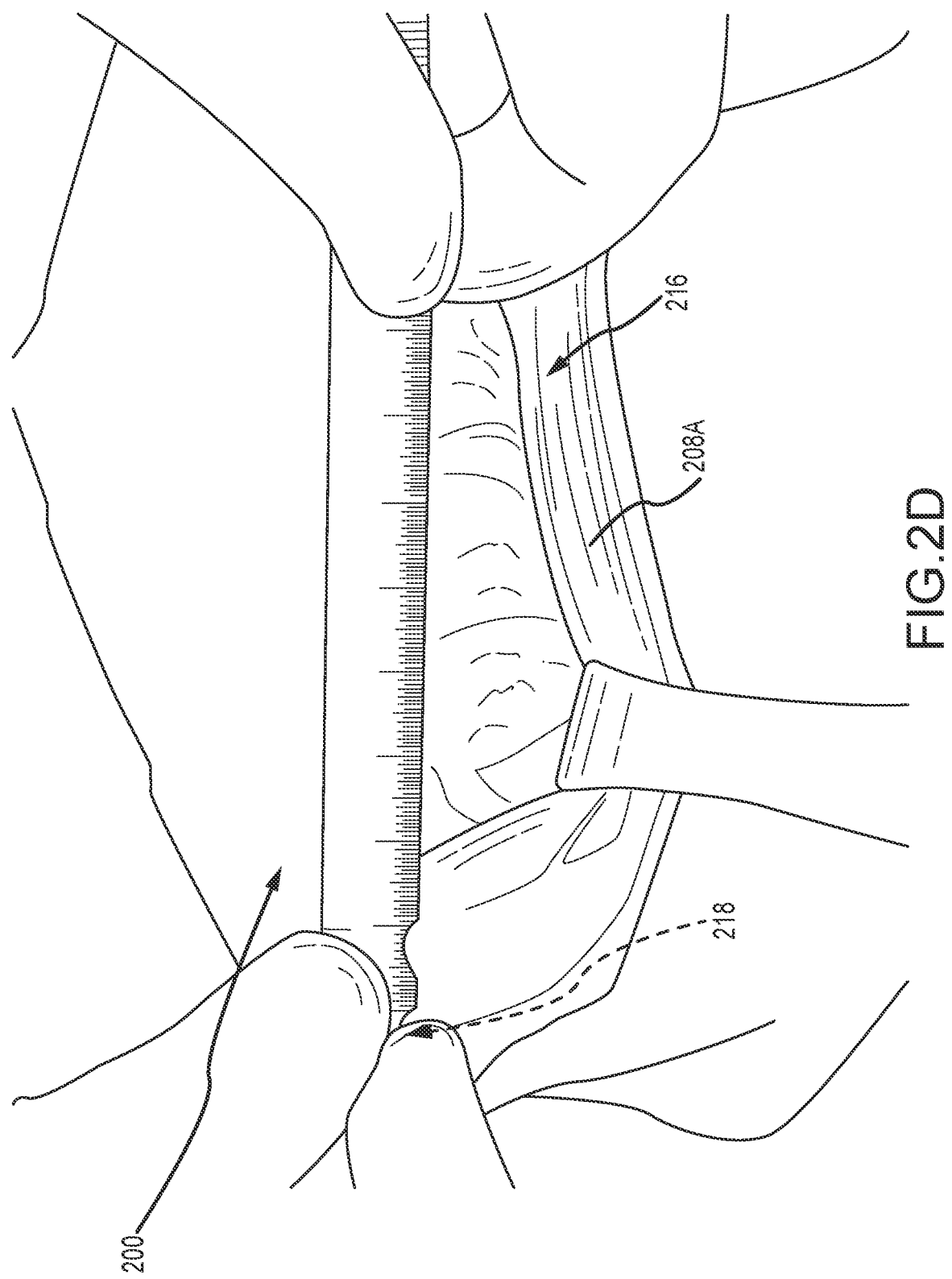

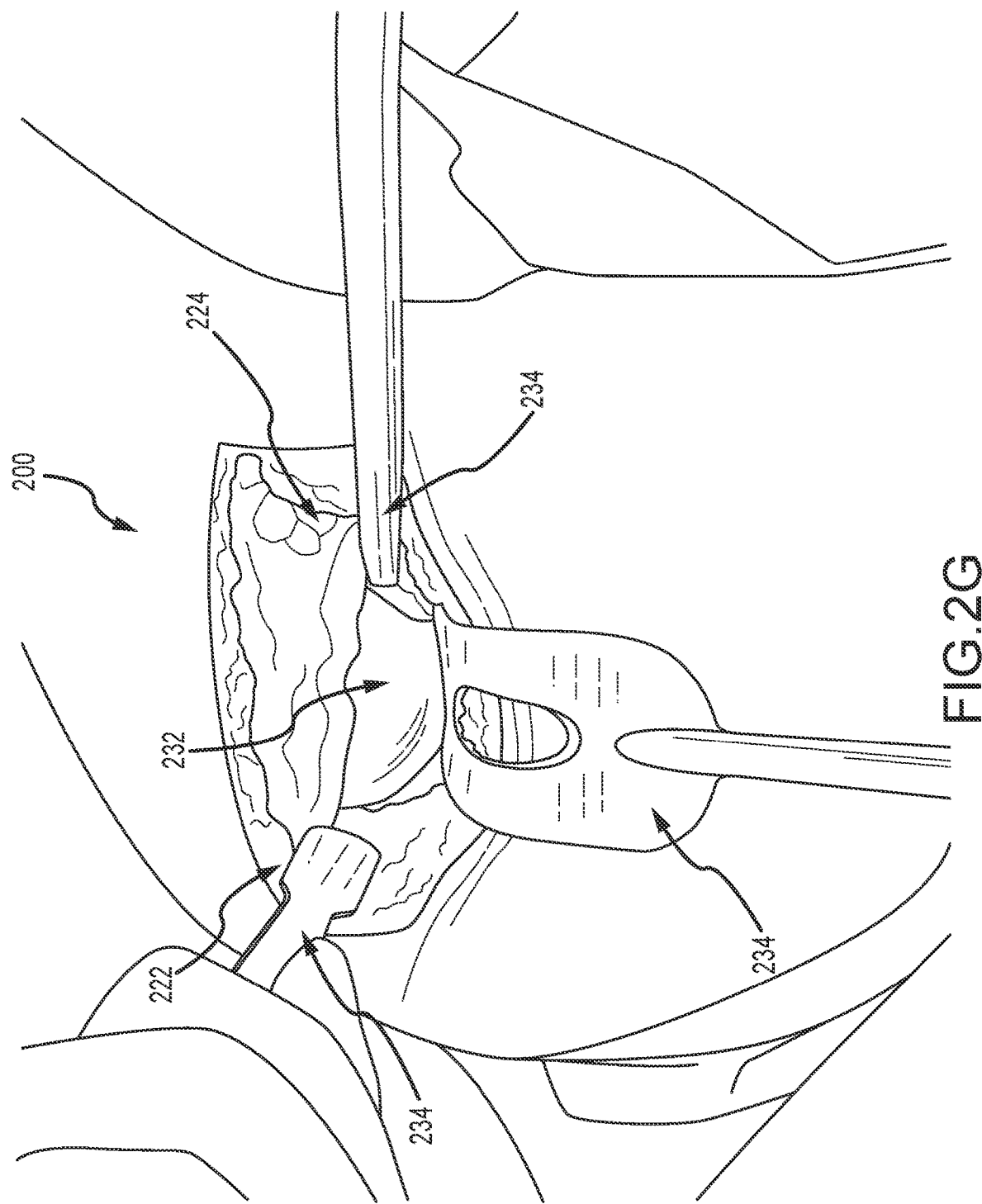

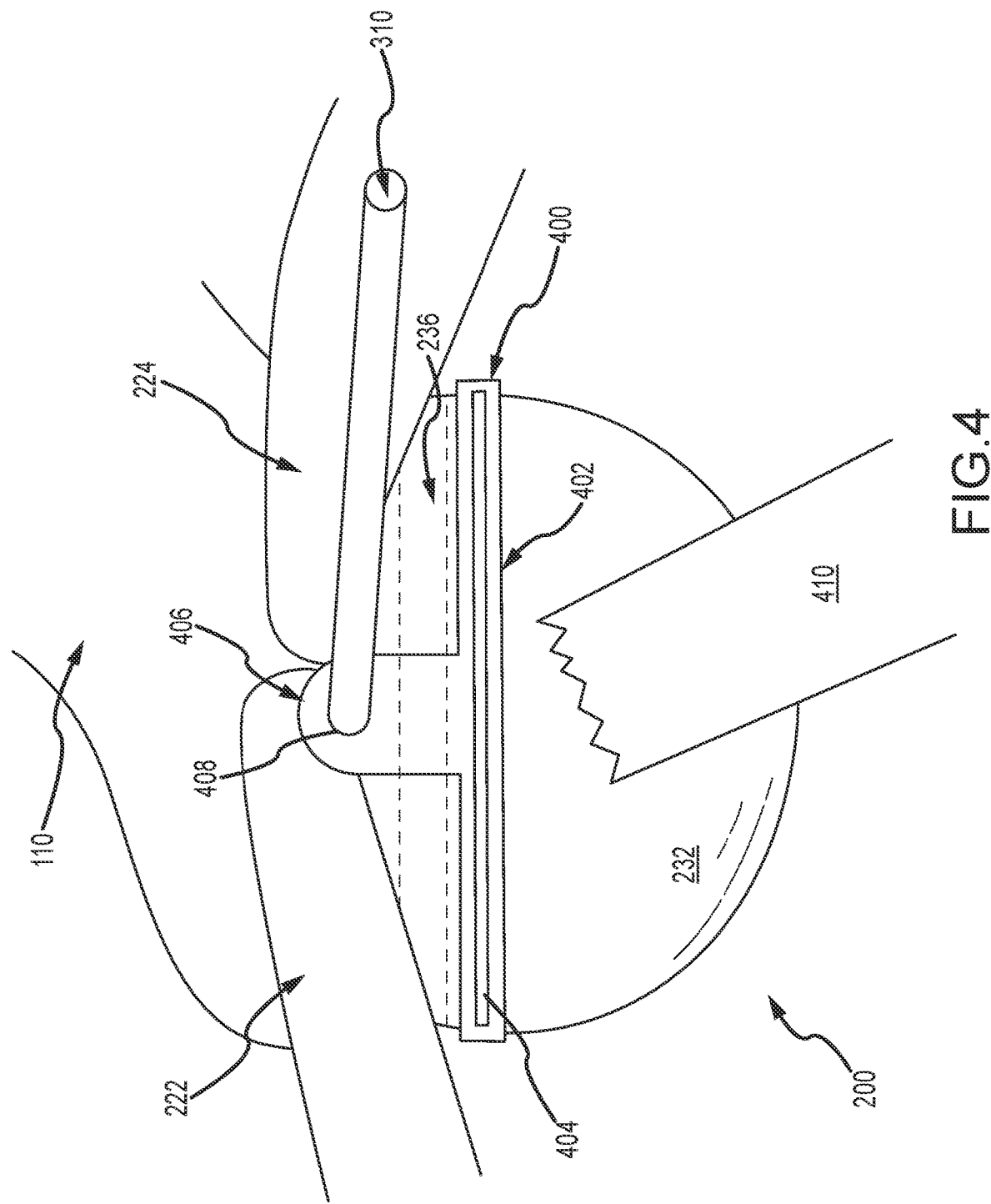

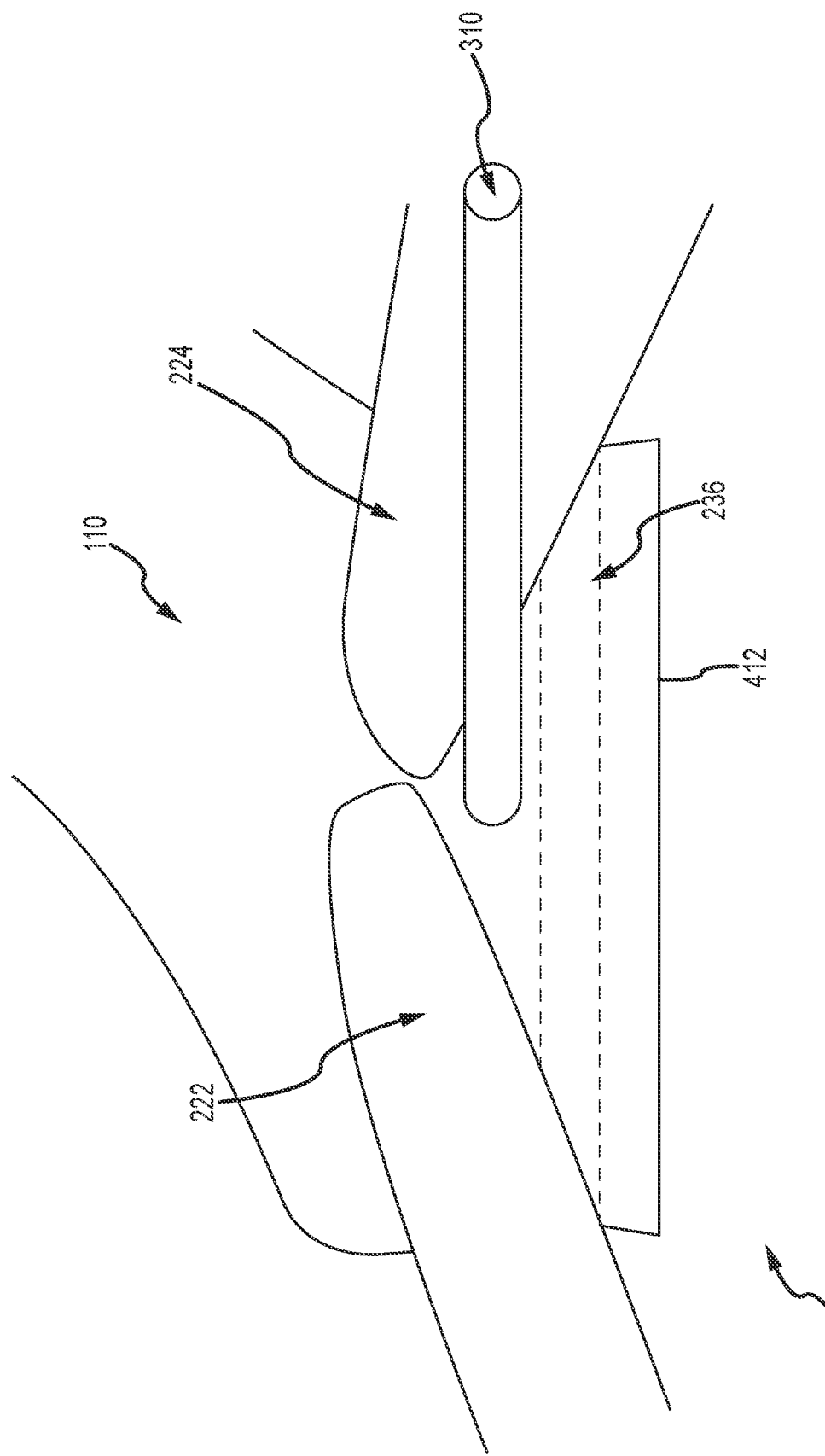

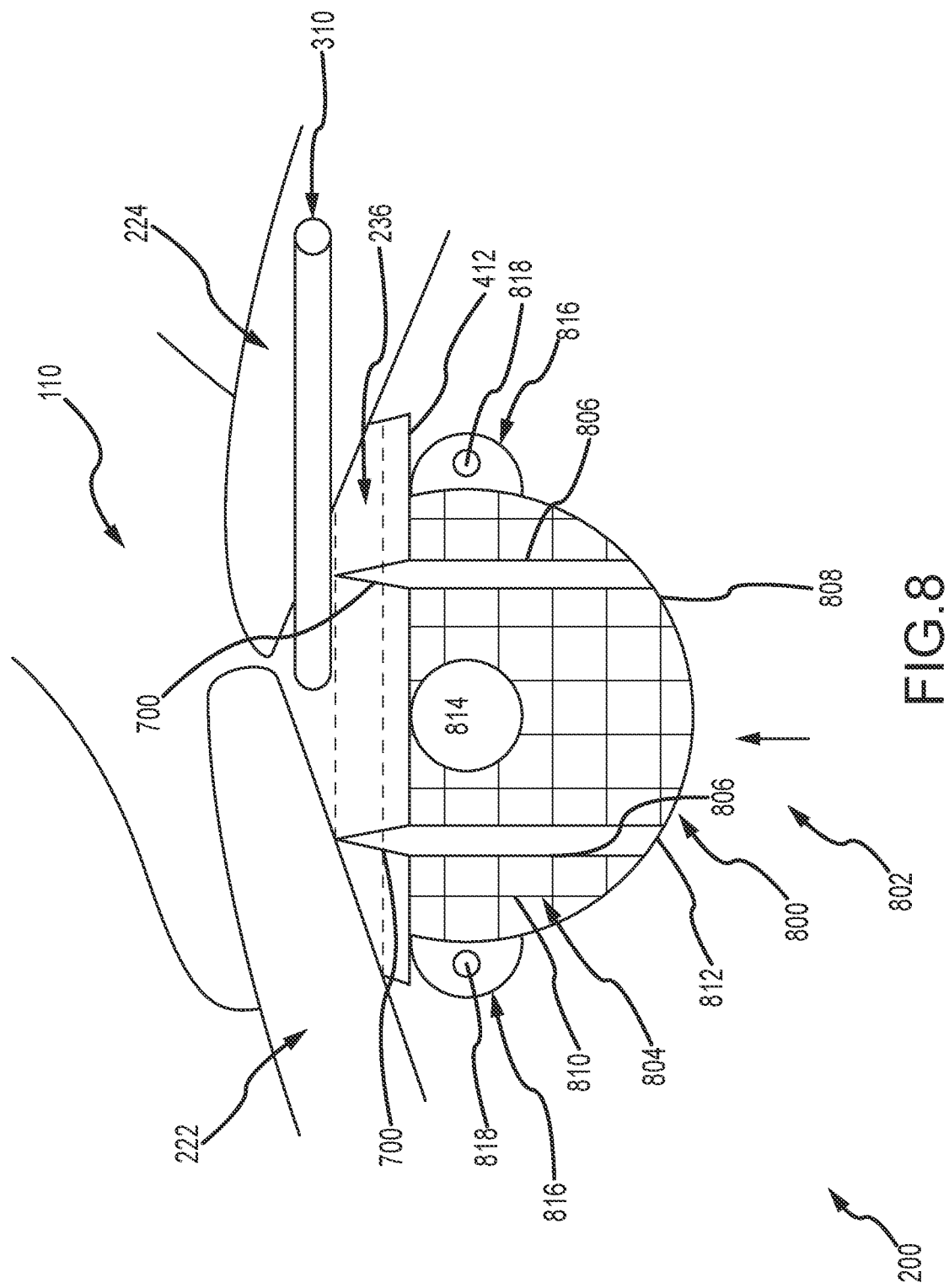

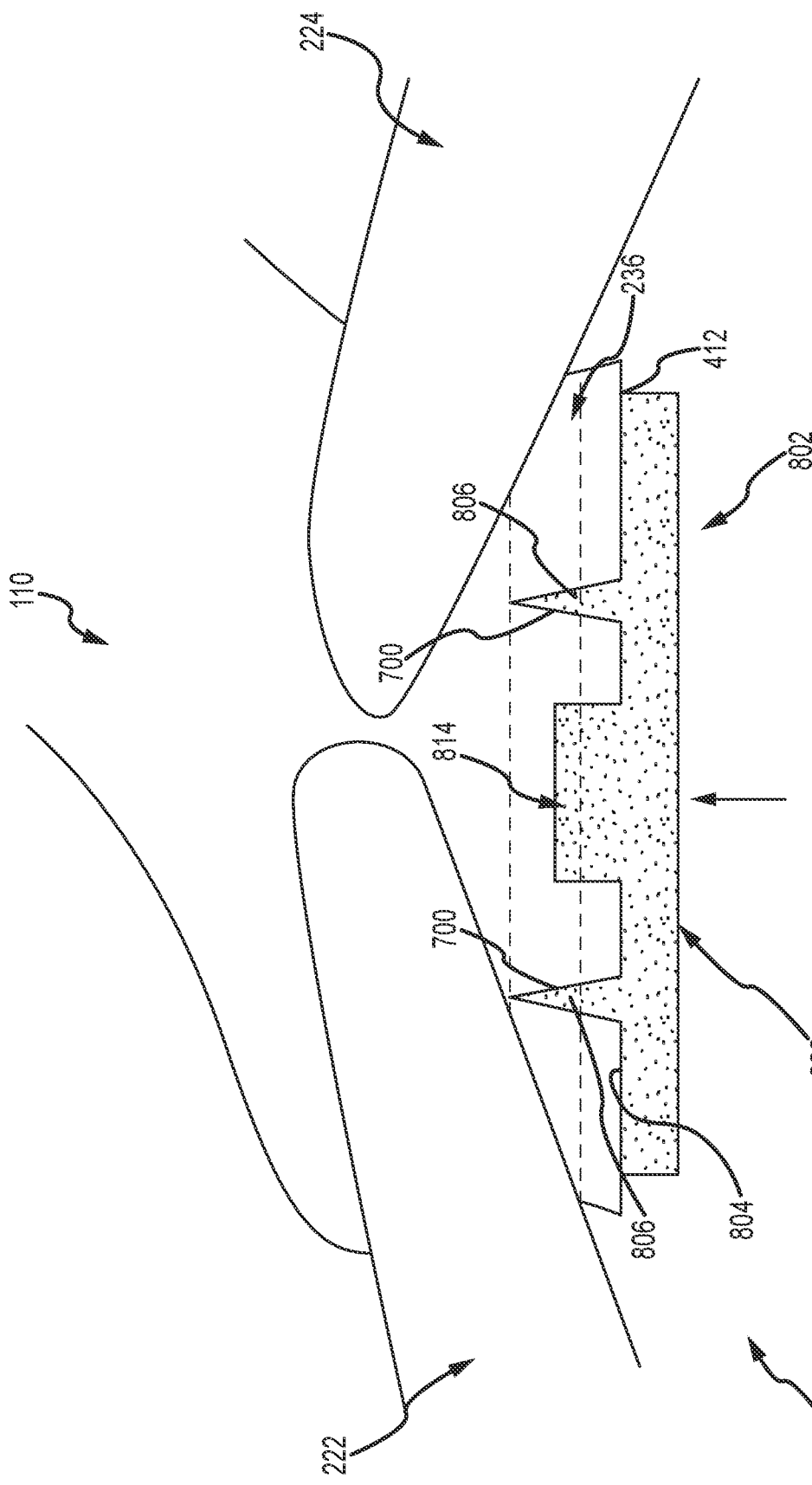

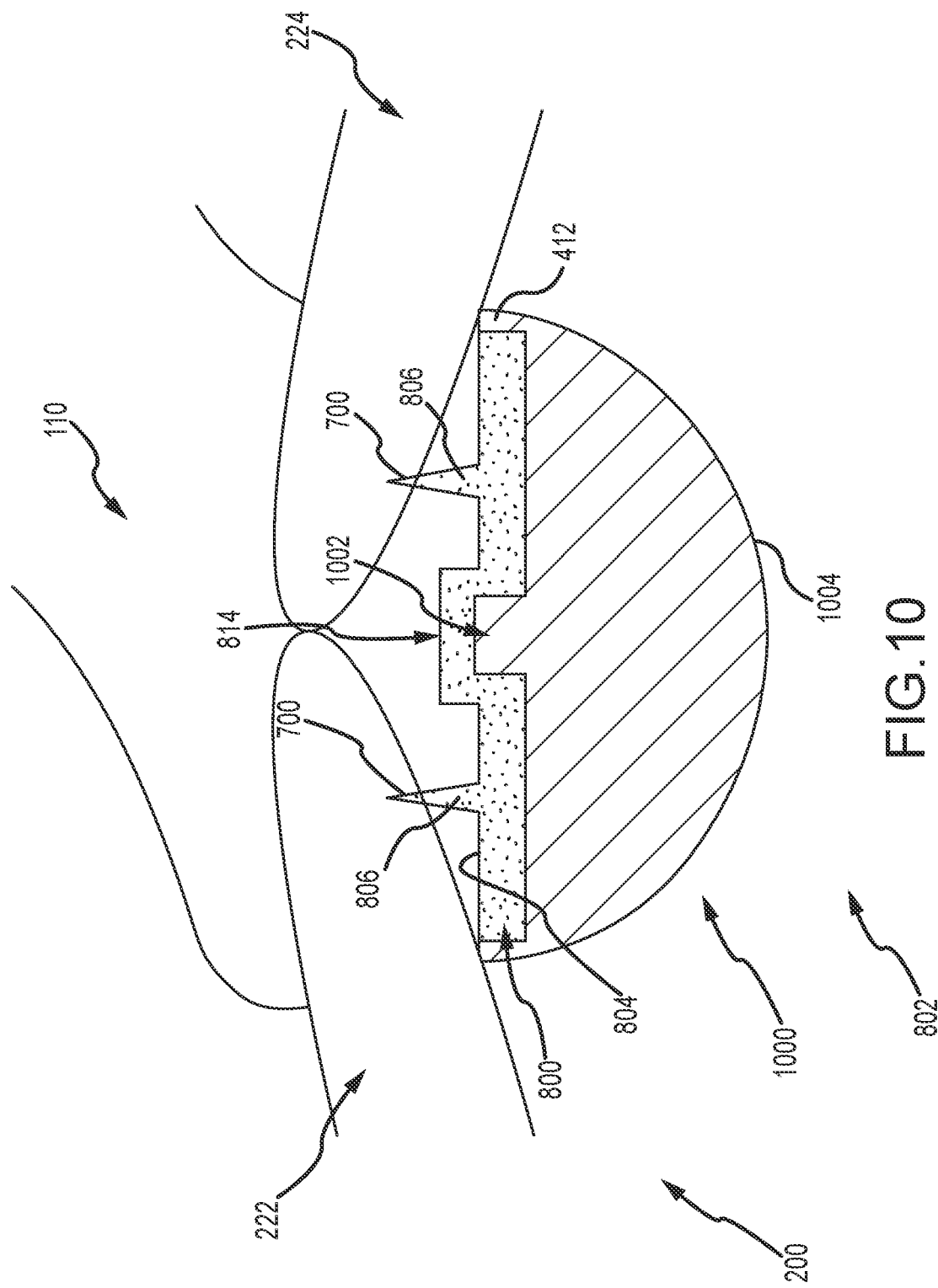

```
                    ┌──────────────────────────────────────────────────┐
1700 ─┐             │ POSITIONING THE TARGETING ARM 1802 AROUND THE HUMERAL │
      └─▶           │ HEAD 1850 AND ORIENTING THE BORE 1820 OF THE SLEEVE 1804 │
                    │ AT THE POSTERIOR ASPECT OF THE HUMERAL HEAD 1850 FOR │
                    │   DELIVERY OF A GUIDE PIN IN A POSTERIOR-TO-ANTERIOR │
                    │              DIRECTION [BLOCK 1702]              │
                    └──────────────────────────────────────────────────┘
```

- POSITIONING THE TARGETING ARM 1802 AROUND THE HUMERAL HEAD 1850 AND ORIENTING THE BORE 1820 OF THE SLEEVE 1804 AT THE POSTERIOR ASPECT OF THE HUMERAL HEAD 1850 FOR DELIVERY OF A GUIDE PIN IN A POSTERIOR-TO-ANTERIOR DIRECTION [BLOCK 1702]

- DELIVERING A GUIDE PIN 1824 THROUGH THE BORE 1820 OF THE SLEEVE 1804 AND INTO THE POSTERIOR ASPECT OF THE HUMERAL HEAD 1850 [BLOCK 1704]

- REMOVING THE TARGETING ARM 1802 FROM THE HUMERAL HEAD 1850 WHILE KEEPING THE GUIDE PIN 1824 IN POSITION IN THE BONE [BLOCK 1706]

- POSITIONING THE CUTTING GUIDE 1900 UP TO THE POSTERIOR ASPECT OF THE HUMERAL HEAD 1850 BY SLIDING THE BORE 1912 OF THE CUTTING GUIDE 1900 ALONG THE GUIDE PIN 1824 [BLOCK 1708]

- GUIDING A SECOND GUIDE PIN 1924 THROUGH A SECOND BORE 1912 OF THE CUTTING GUIDE 1900 TO LOCK THE ORIENATION OF THE CUTTING GUIDE 1900 RELATIVE TO THE HUMERAL HEAD 1850 [BLOCK 1710]

```
┌─────────────────────────────────────────────────────────┐
│ RESECTING THE HUMERAL HEAD 1850 WITH A CUTTING TOOL     │
│ (E.G., SAW BLADE) THAT IS GUIDED BY THE CUTTING SLOT 1908│
│        OF THE CUTTING GUIDE 1900 [BLOCK 1712]           │
└─────────────────────────────────────────────────────────┘
                            ↓
┌─────────────────────────────────────────────────────────┐
│  REMOVING THE CUTTING GUIDE 1900 FROM THE GUIDE PINS    │
│  1824, 1924, AND, IN SOME INSTANCES, REMOVING THE GUIDE │
│        PINS 1824, 1924 FROM THE BONE [BLOCK 1714]       │
└─────────────────────────────────────────────────────────┘
                            ↓
┌─────────────────────────────────────────────────────────┐
│ DETERMINING A SIZE OF GUIDE 2000 TO BE USED BY PLACING  │
│ THE PLATE 2002 FLAT ON THE RESECTED BONE SURFACE AND    │
│ PLACING THE GUIDE 2000 AS FAR SUPERIORLY AS POSSIBLE    │
│              WITHOUT OVERHANG [BLOCK 1716]              │
└─────────────────────────────────────────────────────────┘
                            ↓
┌─────────────────────────────────────────────────────────┐
│    DELIVERING FIRST AND SECOND GUIDE PINS 1824, 1924    │
│ THROUGH THE BORES 2022 OF THE GUIDE 2000 AND INTO THE   │
│   BONE 1852 ON A POSTERIOR SIDE THEREOF [BLOCK 1718]    │
└─────────────────────────────────────────────────────────┘
                            ↓
┌─────────────────────────────────────────────────────────┐
│CUTTING A CHANNEL 2024 INTO THE POSTERIOR CORTICAL BONE  │
│2026 AND THE RESECTED BONE SURFACE 1950 VIA GUIDANCE BY  │
│          THE CHANNEL SLOT 2014 [BLOCK 1720]             │
└─────────────────────────────────────────────────────────┘
```

```
REMOVING THE FIN AND SIZE GUIDE 2000 FROM THE PINS 1824,
1924, AND ALSO REMOVING THE PINS 1824, 1924 [BLOCK 1722]
          ↓
COUPLING THE BASE PLATE 2150 TO THE INSERTION DEVICE
2100, INSERTING THE MAJOR FIN 2158 INTO THE CHANNEL CUT
2024, AND SLIDING THE BASE PLATE 2150 IN A POSTERIOR-TO-
ANTERIOR DIRECTION [BLOCK 1724]
          ↓
SLIDING THE BASE PLATE 2150 WITH THE INSERTION DEVICE 2100
TILL THE BASE PLATE 2150 IS CENTRALLY POSITIONED RELATIVE
TO THE RESECTED BONE SURFACE 1950 [BLOCK 1726]
          ↓
DECOUPLING THE BASE PLATE INSERTION DEVICE 2100 FROM
THE BASE PLATE 2150 [BLOCK 1728]
          ↓
ENGAGING THE DISTAL ENGAGEMENT STRUCTURE 2102 OF THE
BASE PLATE IMPACTION DEVICE 2200 WITH THE BASE PLATE
2150, AND IMPACTING THE IMPACTION PLATE 2206 OF THE
DEVICE 2200 UNTIL THE BASE PLATE 2150 IS FULLY IMPACTED
INTO THE RESECTED BONE SURFACE 1950 OF THE HUMERUS
1852 [BLOCK 1730]
          ↓
ANCHORING THE BASE PLATE 2150 TO THE RESECTED BONE
SURFACE 1950 VIA ONE OR MORE FASTENERS 2300 [BLOCK 1732]
          ↓
ATTACHING THE HUMERAL HEAD IMPLANT TO THE BASE PLATE
2150 [BLOCK 1734]
```

FIG. 17C

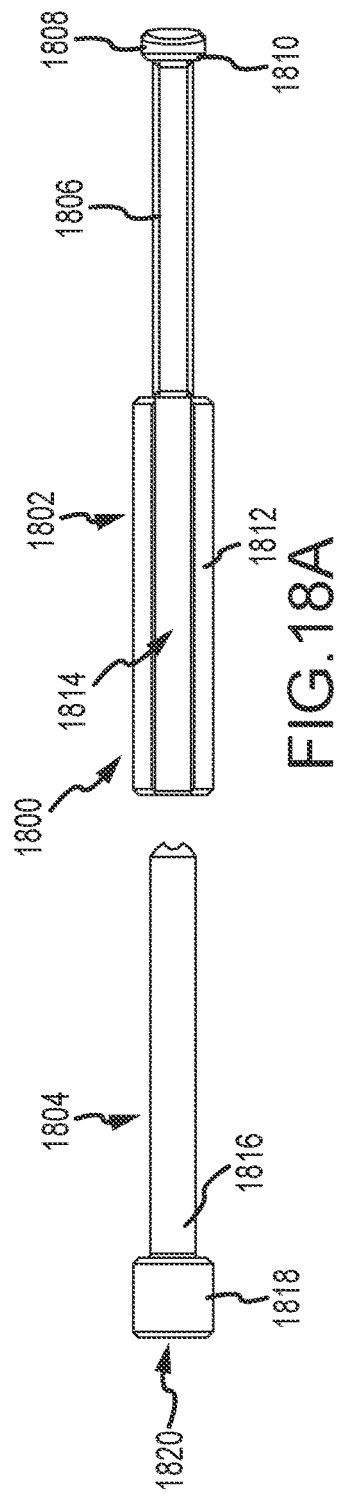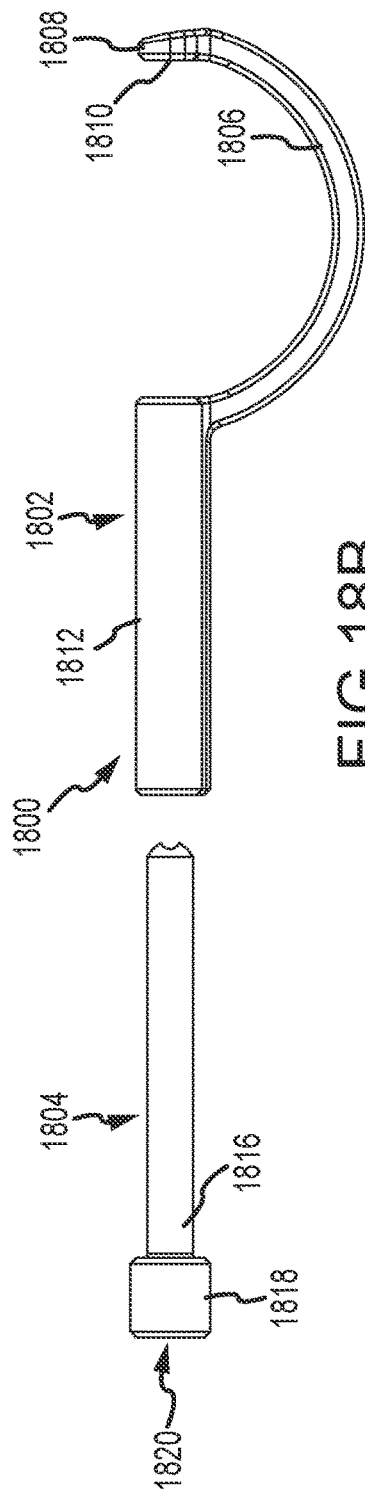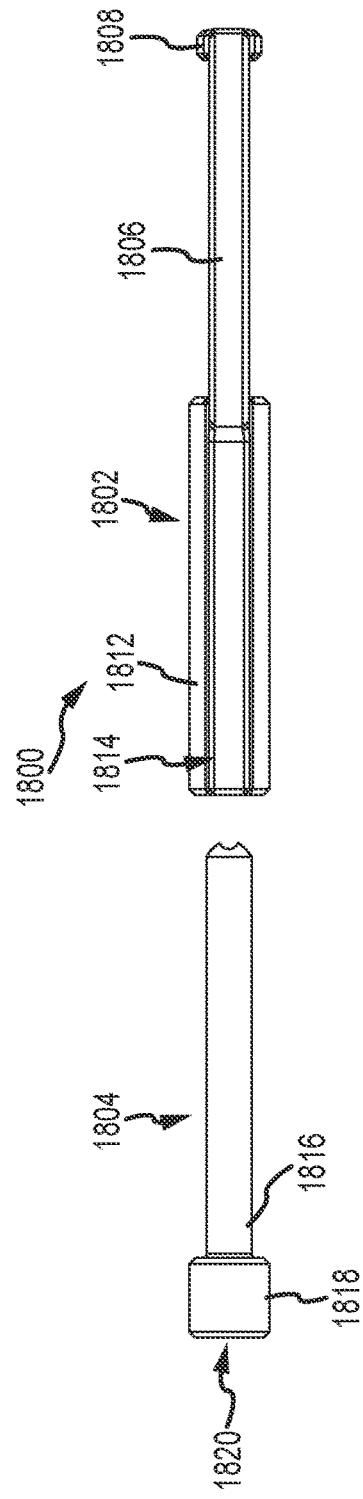

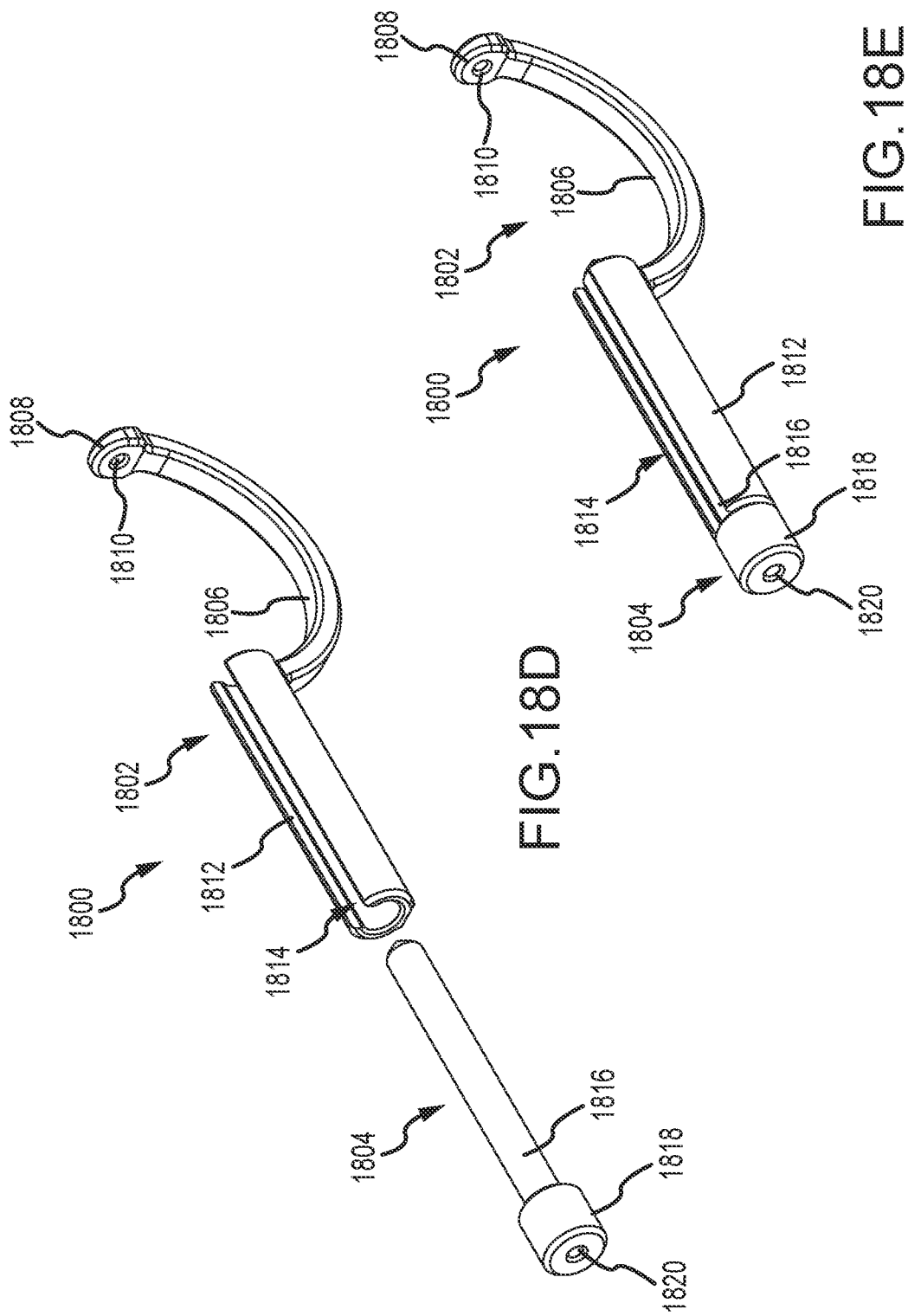

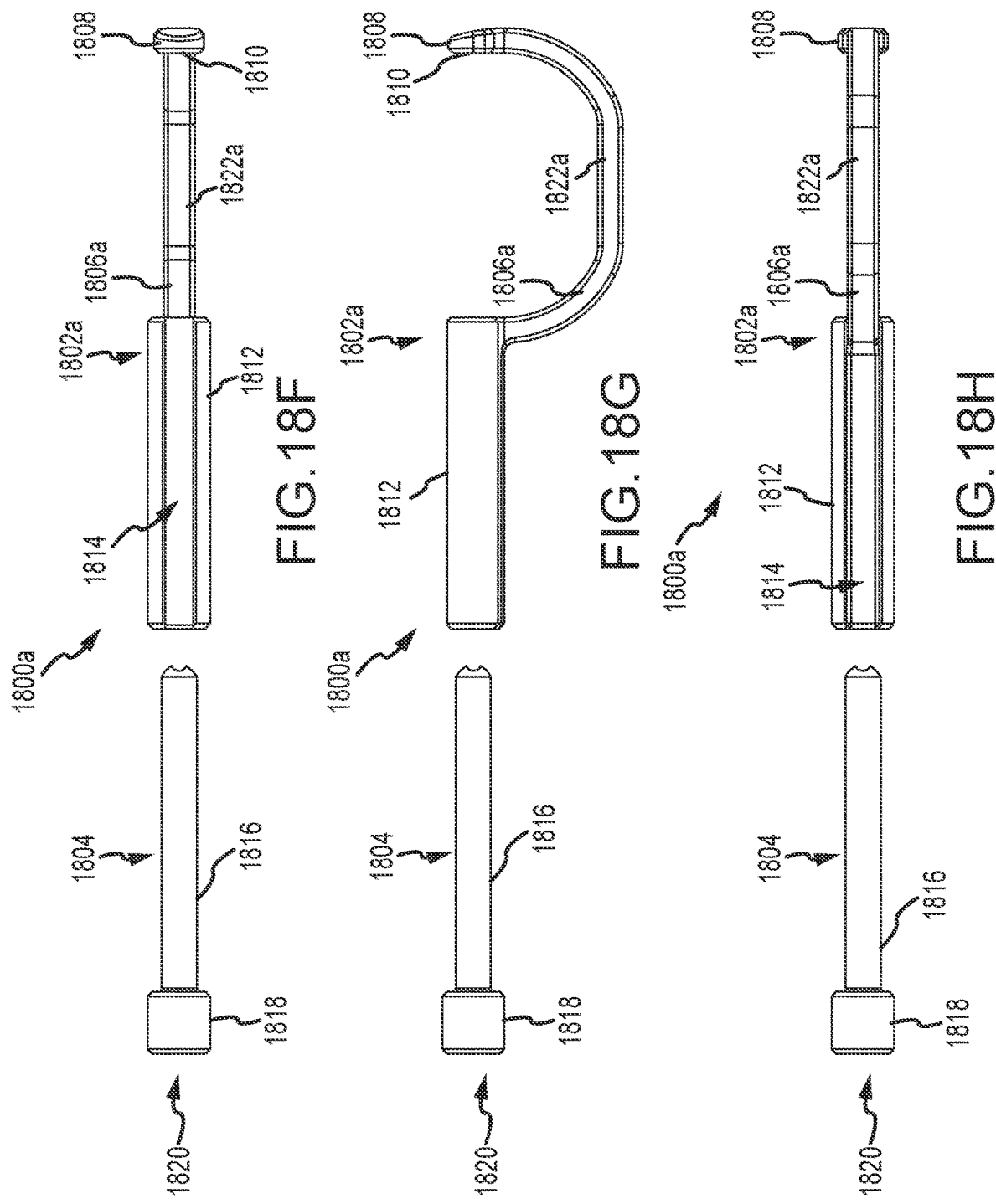

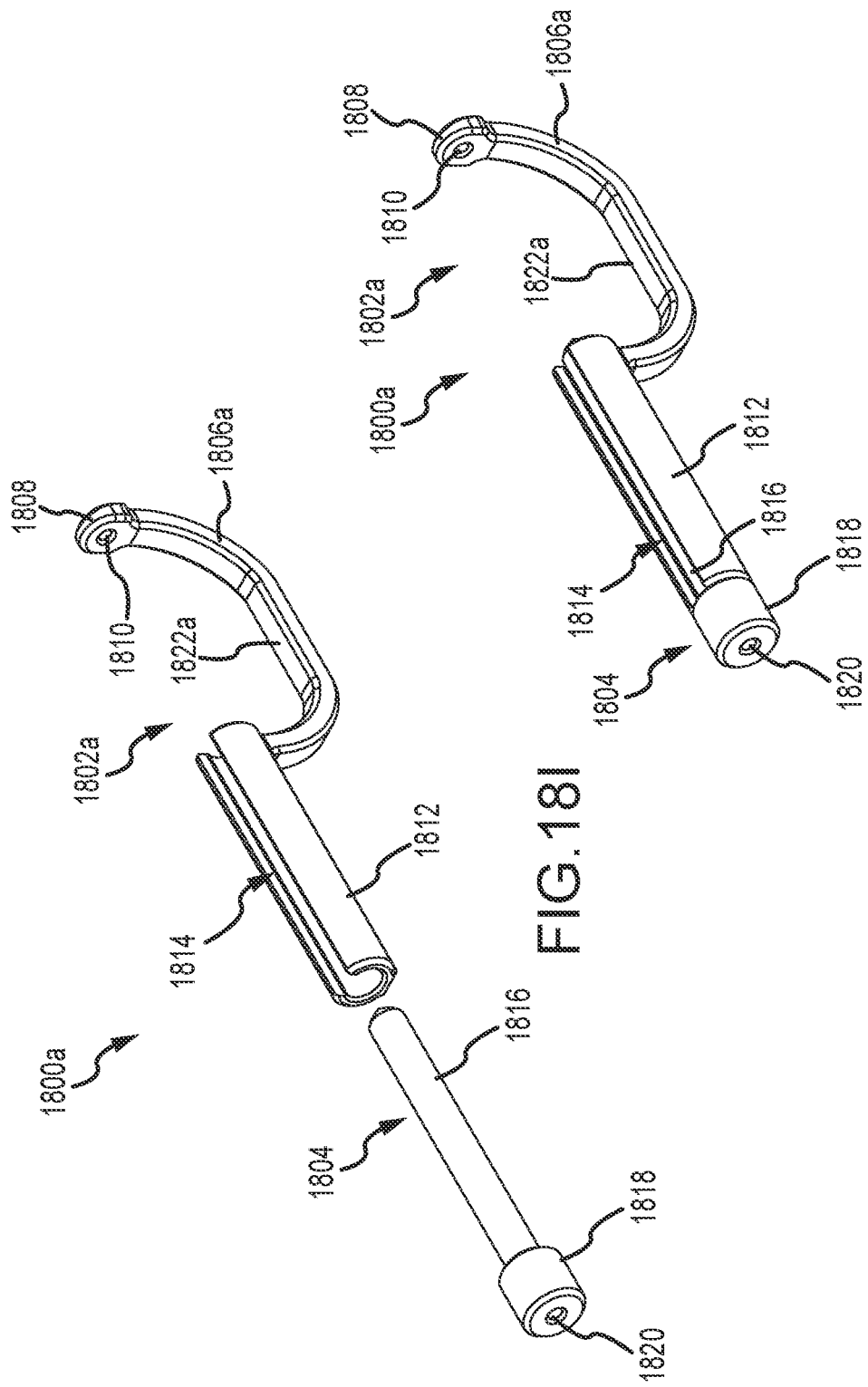

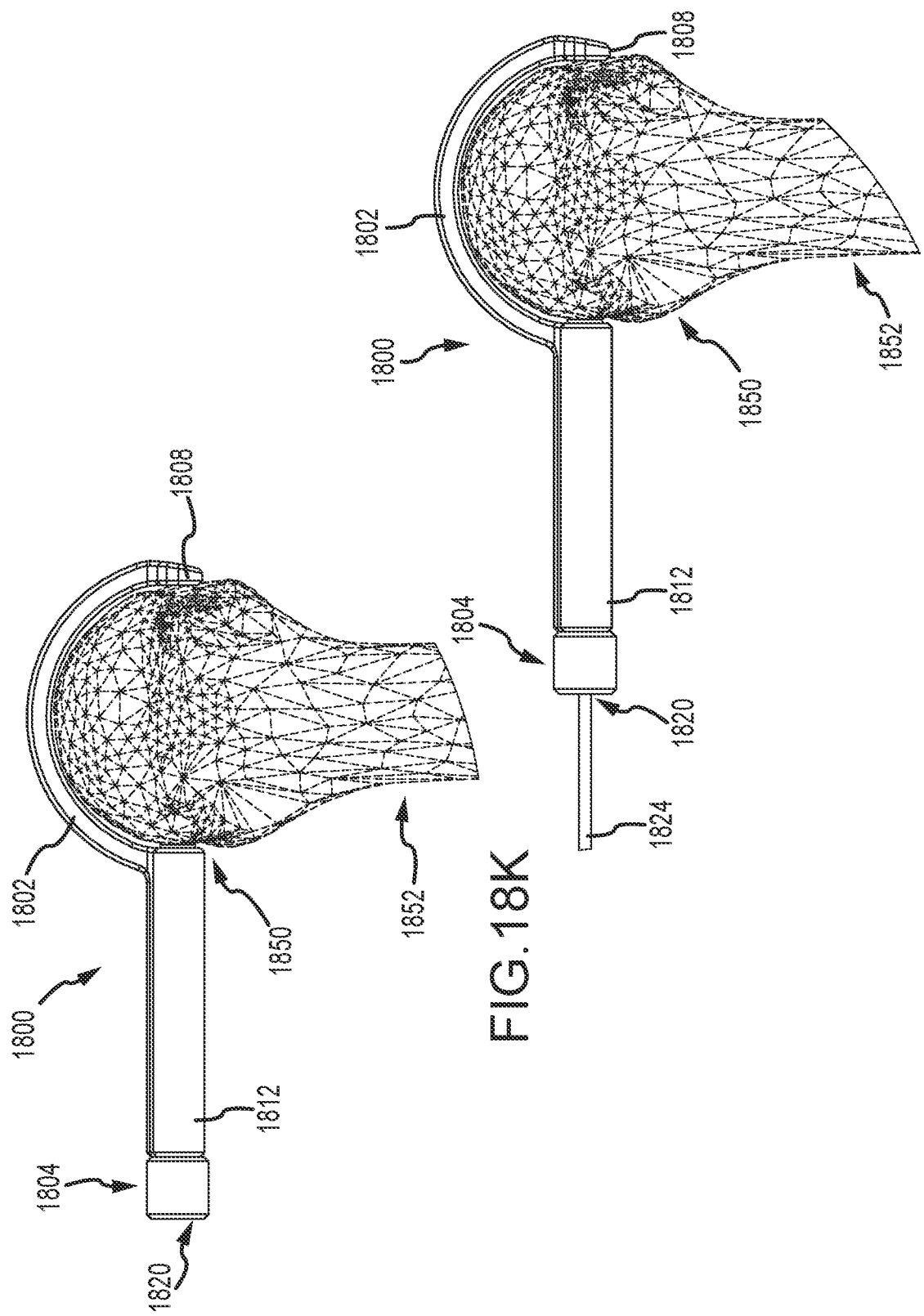

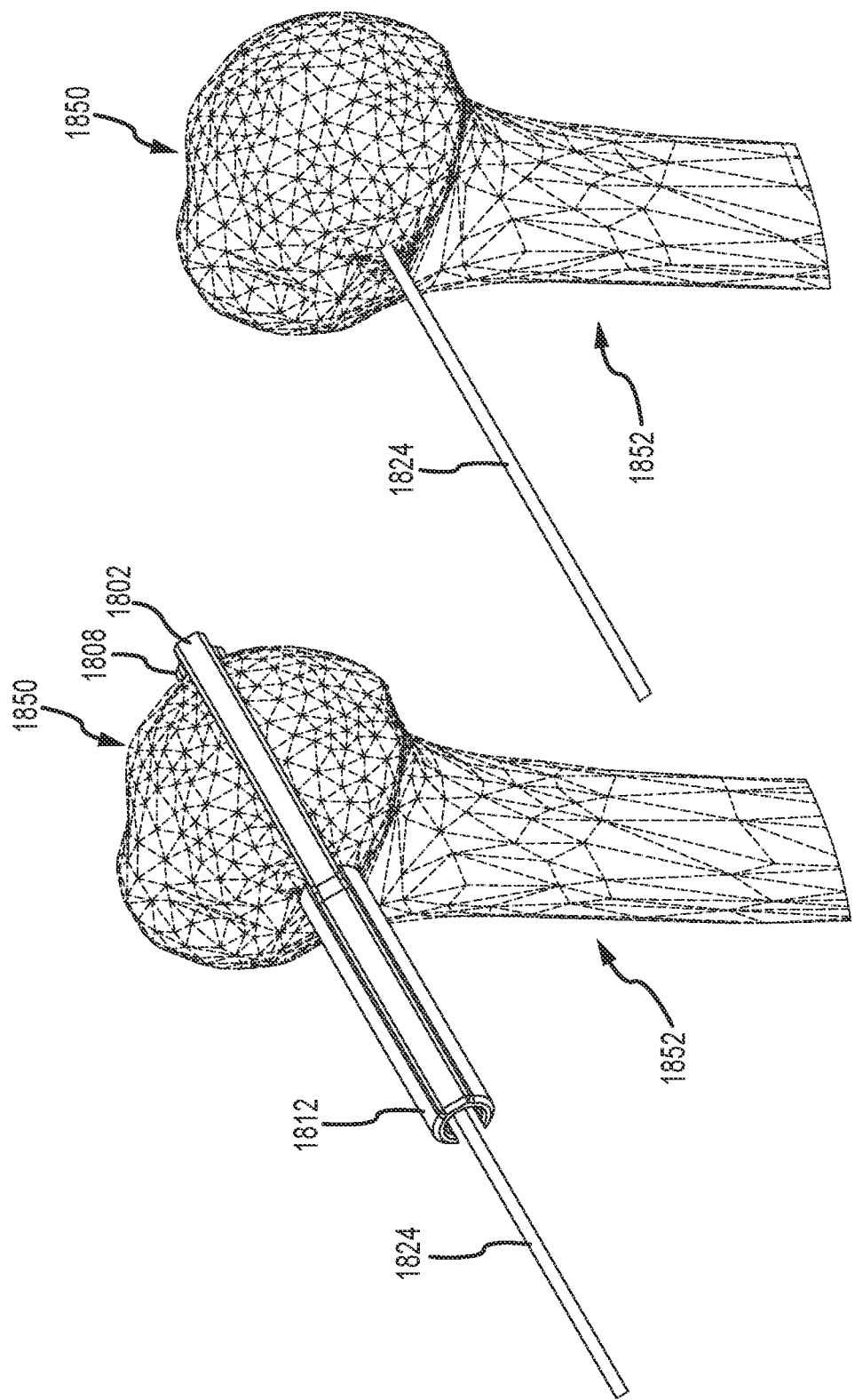

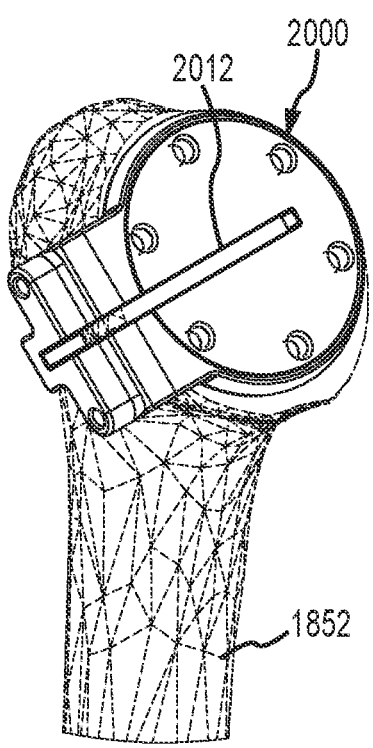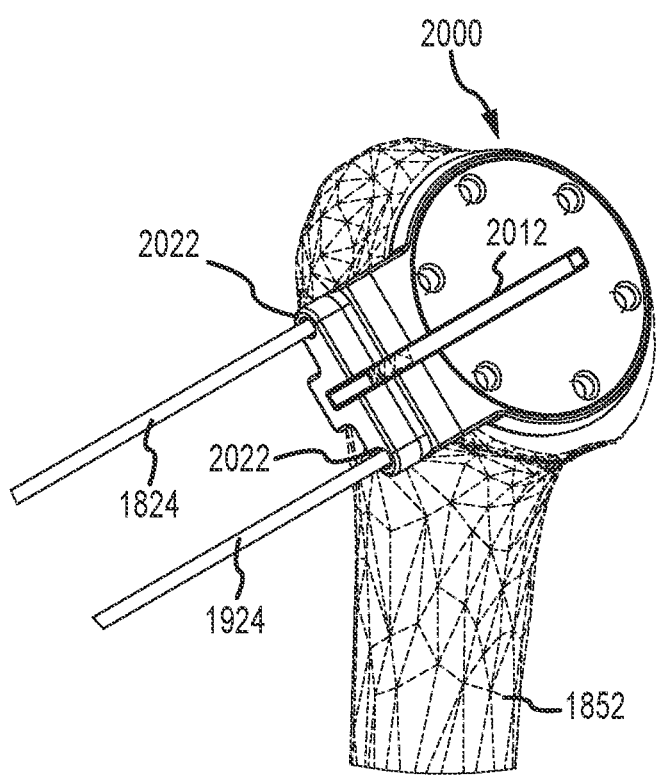
FIG.20F
FIG.20G
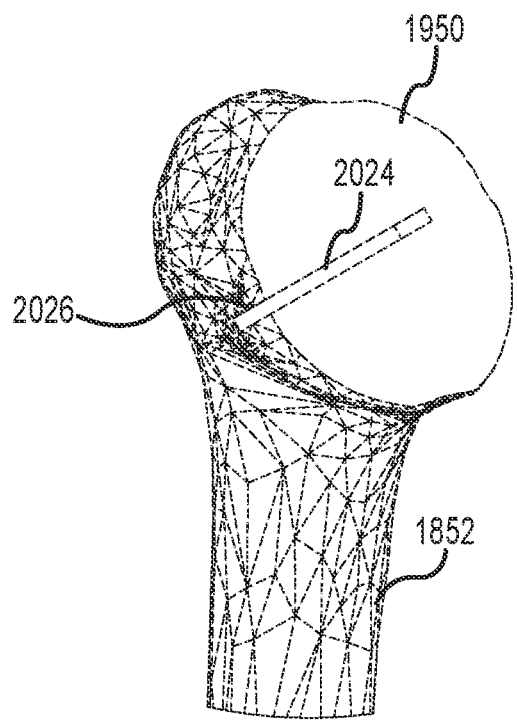
FIG.20H

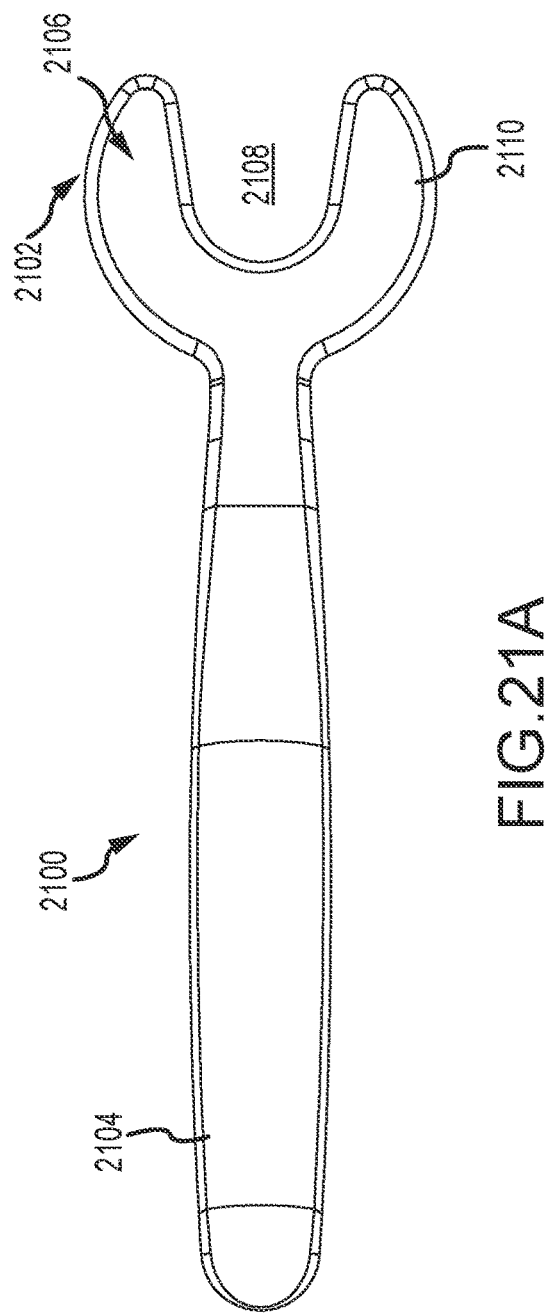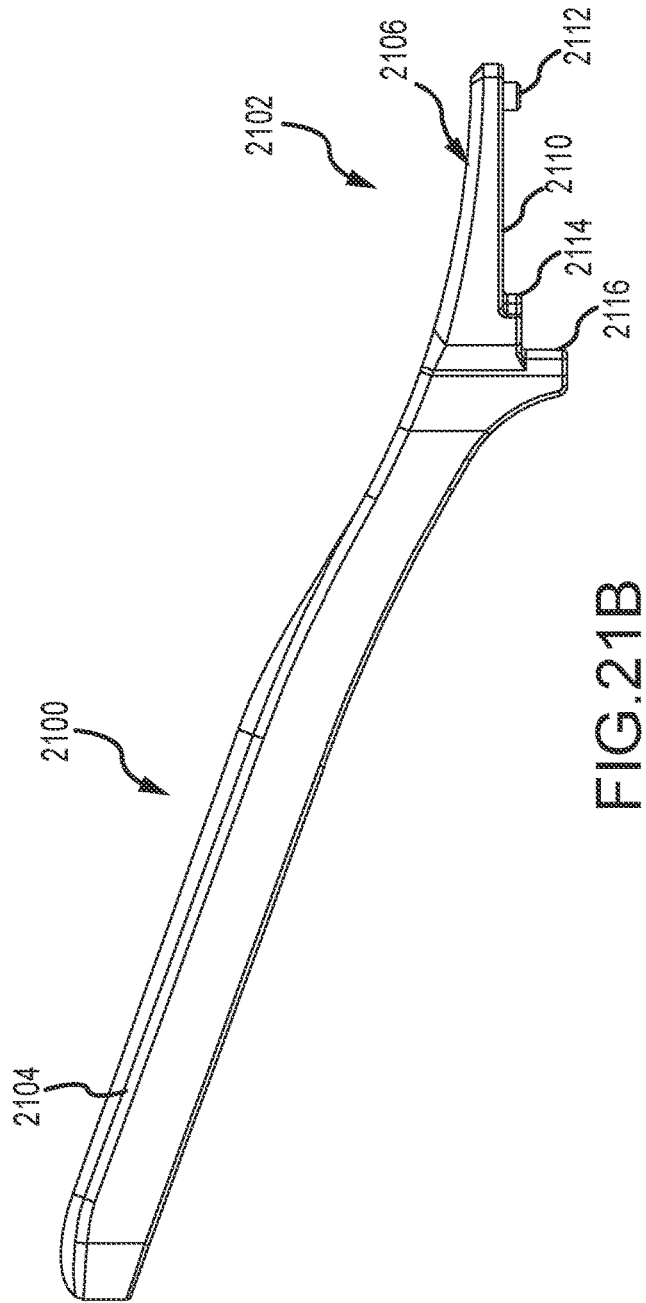

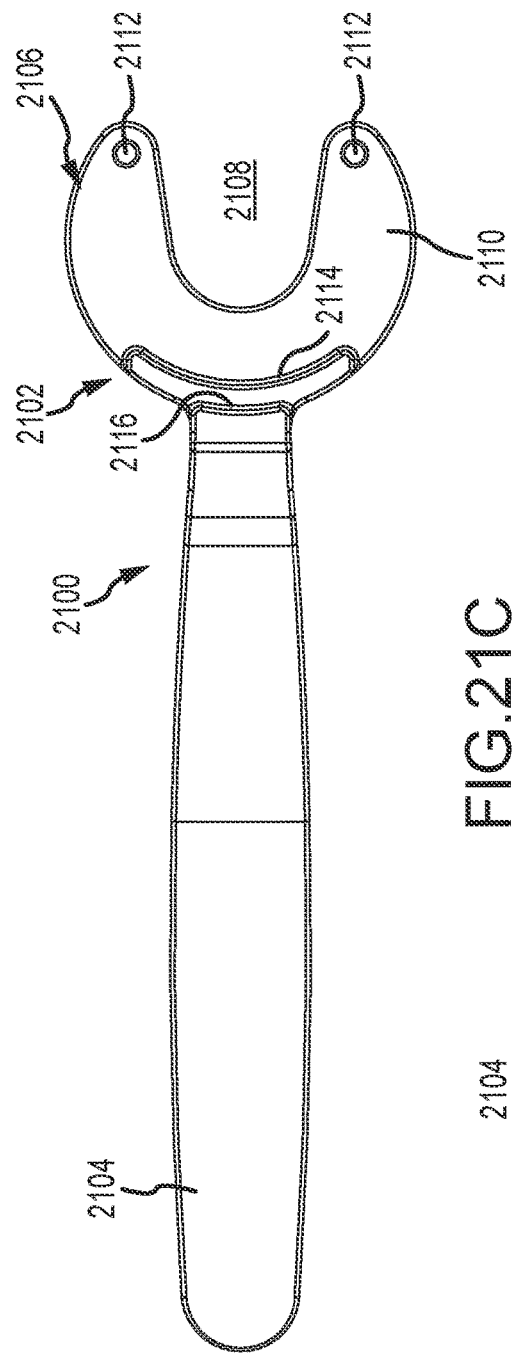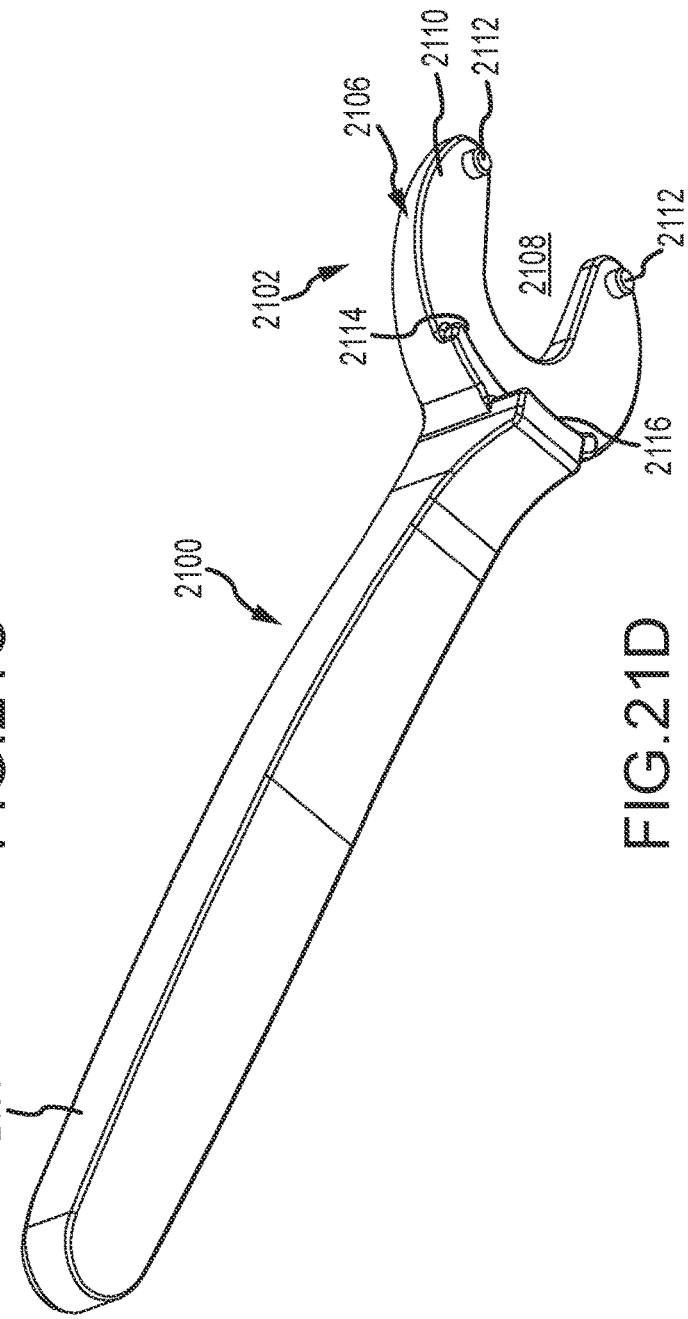
FIG.21C
FIG.21D

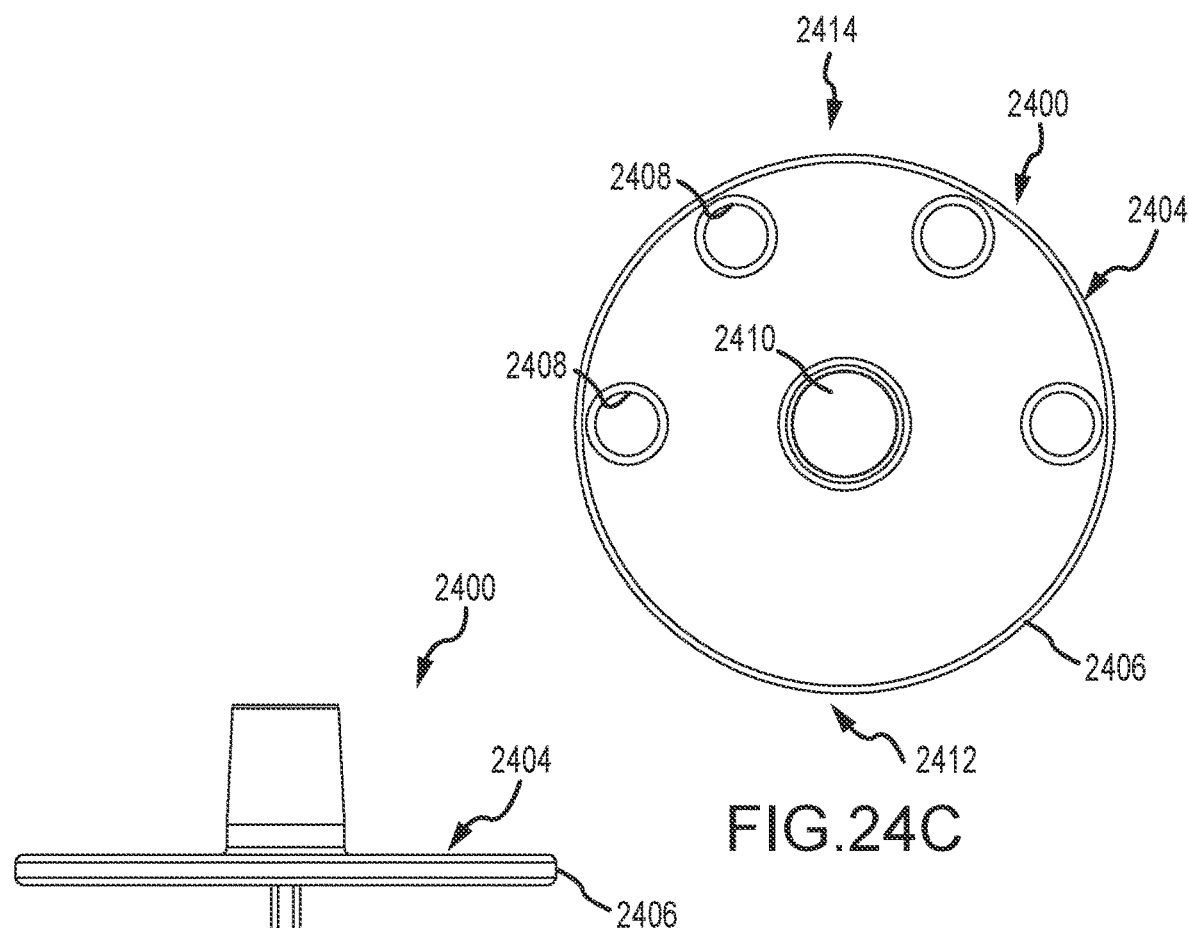
FIG.24C
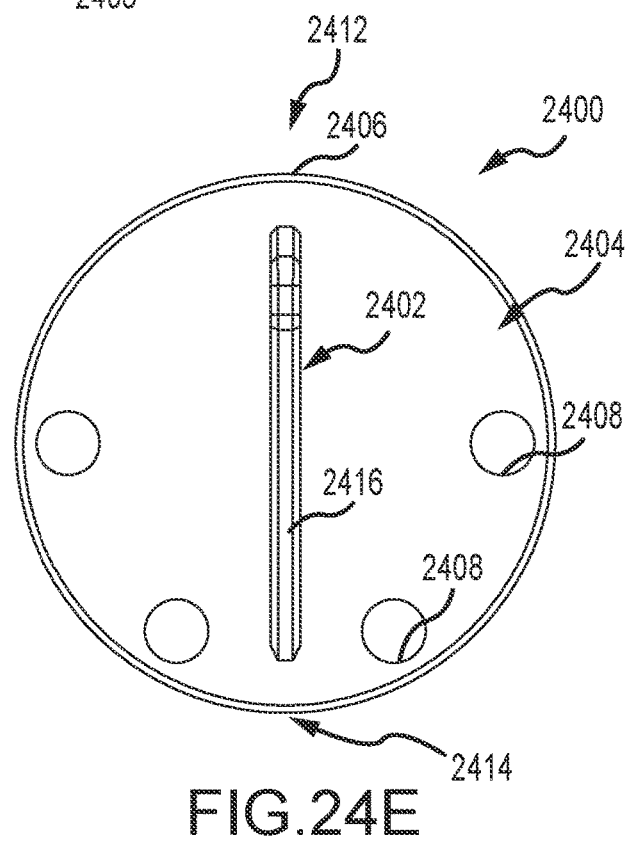
FIG.24D
FIG.24E

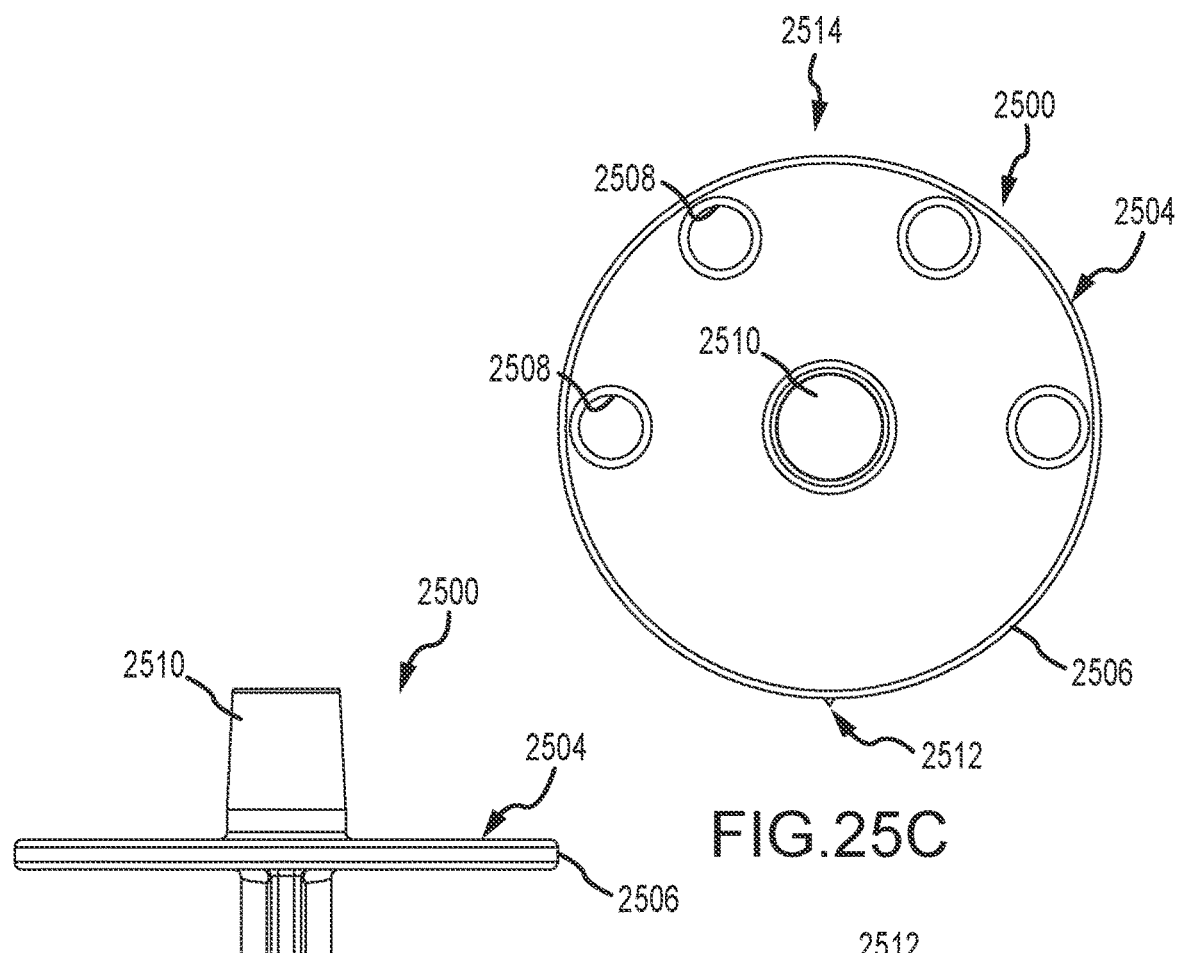
FIG.25C
FIG.25D
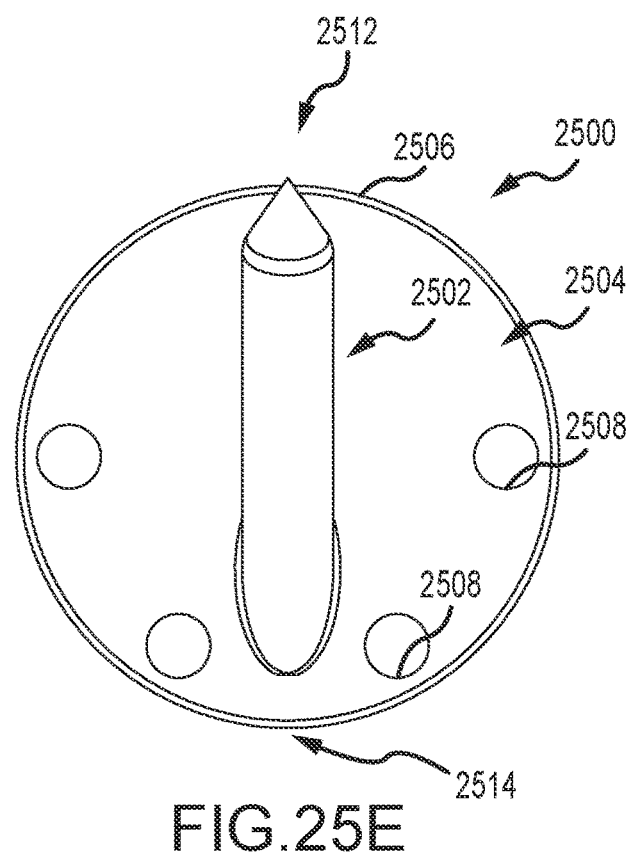
FIG.25E

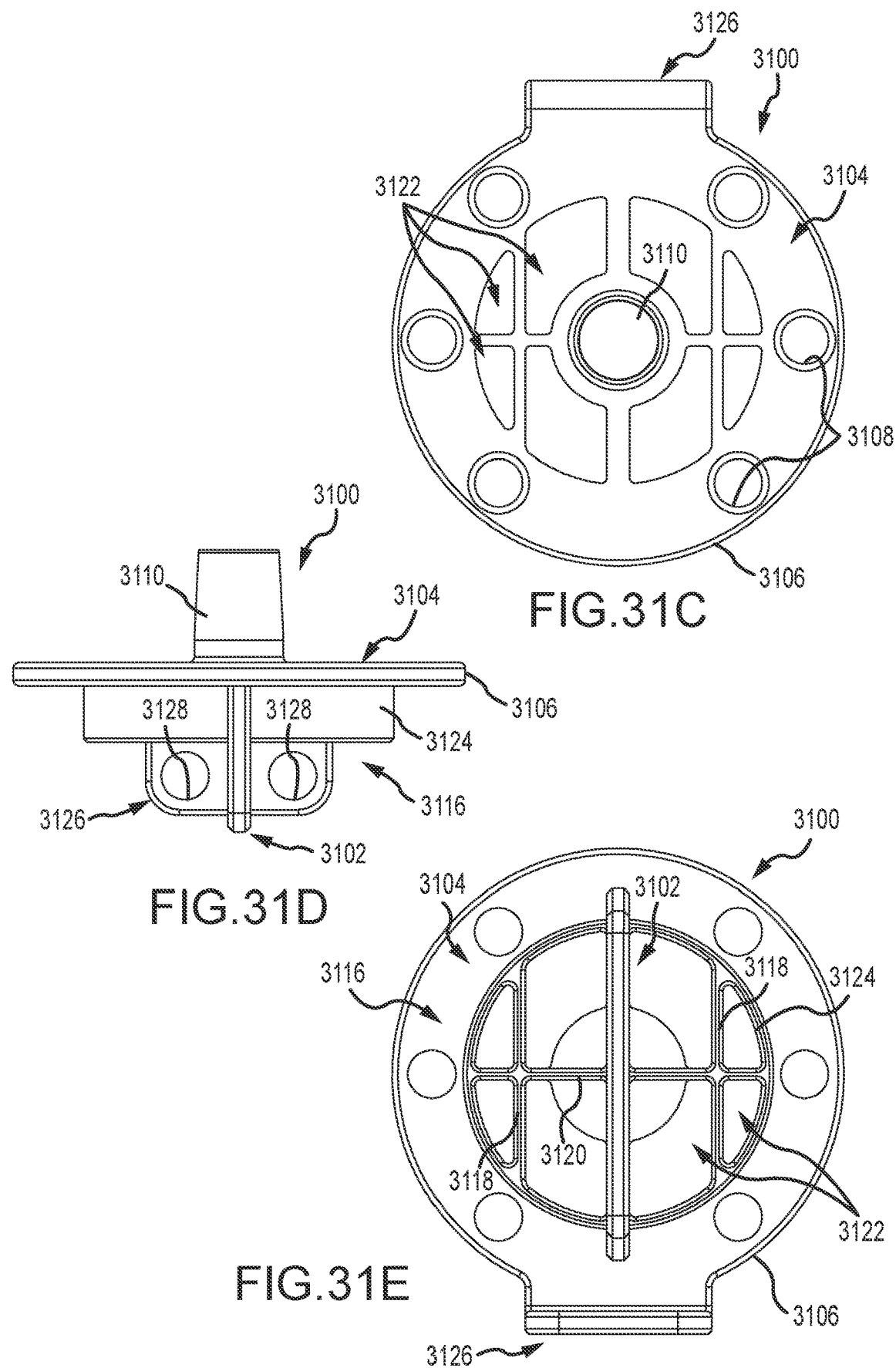

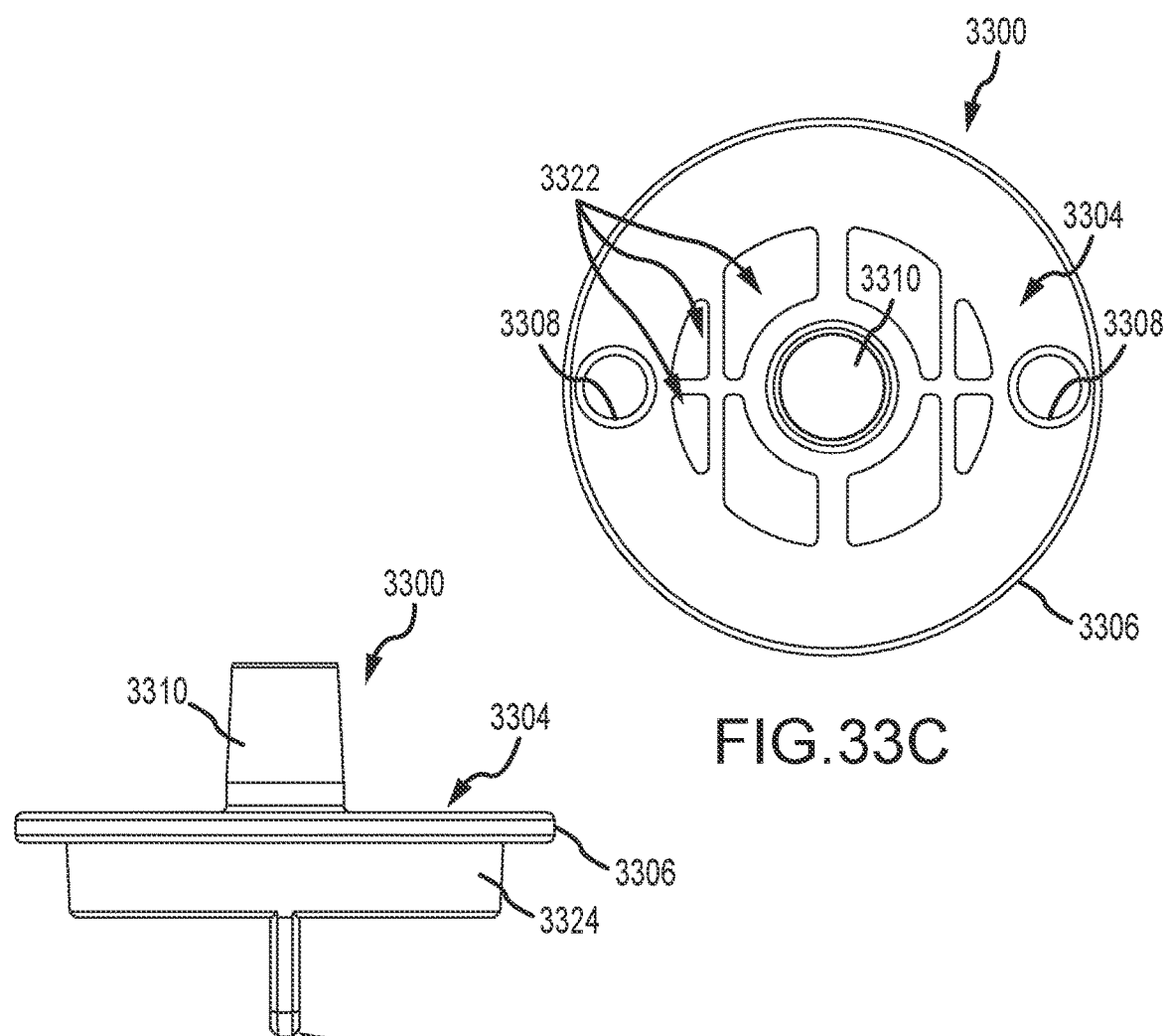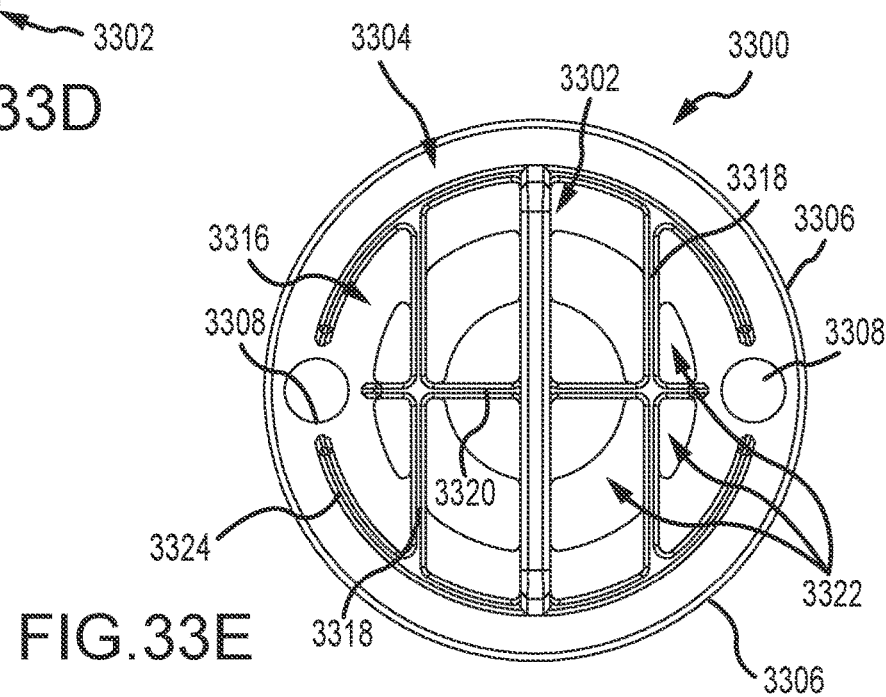

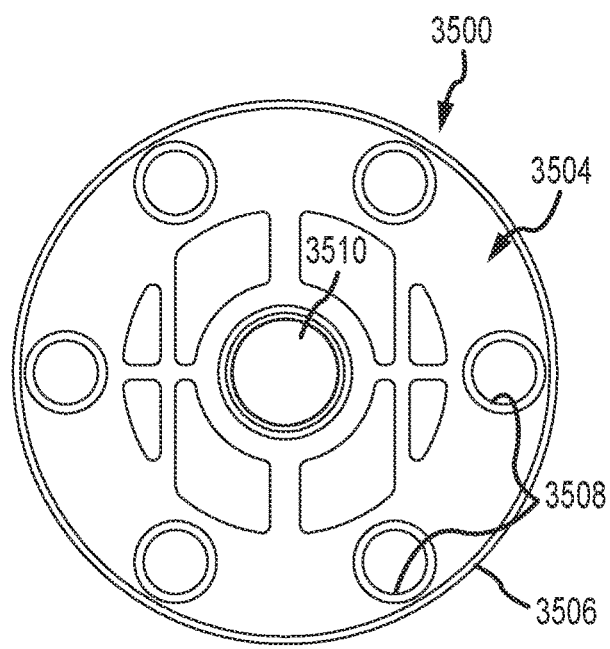
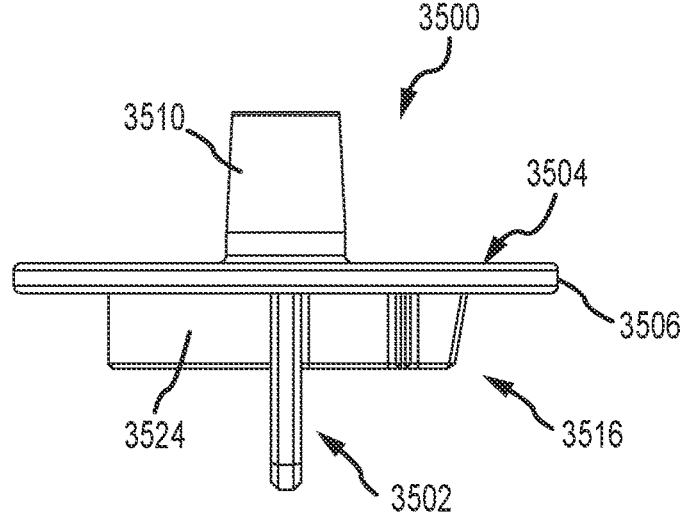
FIG.35D
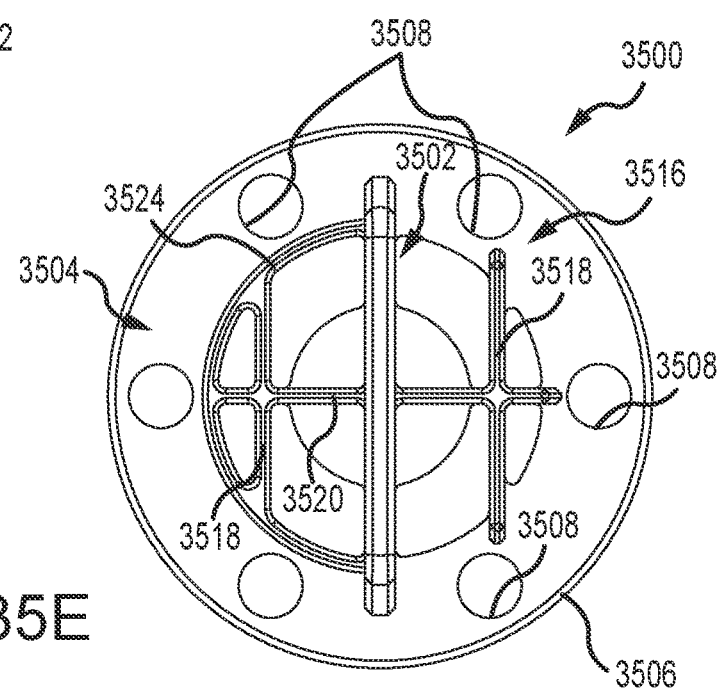
FIG.35C
FIG.35E

POSTERIOR SHOULDER ARTHROPLASTY IMPLANTS, SYSTEMS, AND METHODS

CROSS-REFERENCE TO RELATED APPLICATIONS

This application claims the benefit of U.S. Provisional Application No. 62/930,556, filed Nov. 5, 2019, and U.S. Provisional Application No. 63/051,502, filed Jul. 14, 2020, both of which are hereby incorporated by reference in their entireties.

FIELD OF THE INVENTION

The present disclosure is directed to shoulder arthroplasty methods, devices, and systems. More specifically, the present disclosure is directed to shoulder arthroplasty methods, devices, and systems for implanting stemless implants via a posterior approach.

BACKGROUND OF THE INVENTION

Conventional shoulder replacement surgery is performed via an anterior approach called the deltopectoral approach. FIGS. 1A and 1B illustrate the deltopectoral approach. More specifically, FIG. 1A is an anterior view of human shoulder 100, and FIG. 1B is an anterior view of the musculature of a human shoulder 100. As seen in FIG. 1A, an incision 102 is made on the anterior shoulder 100 in order to access the shoulder joint with the deltopectoral approach. As seen in FIG. 1B, the incision from FIG. 1A is positioned to provide an access region or plane 104 between the anterior musculature, specifically between the deltoid 106 and the pectoralis major 108. FIG. 1C illustrates an anterior view of a human shoulder 100, in particular a skeletal view of a proximal end of the humerus 110 and the attached, front rotator cuff tendon, known as the subscapularis 112. FIG. 1C does not show any musculature in order to clearly view the subscapularis 112. With the deltopectoral approach, the subscapularis is divided or cut, at line 114, to access the glenohumeral joint, generally known as the shoulder joint. Dividing the subscapularis allows the glenohumeral joint to be dislocated, which provides an extensile or full view of the humerus as it is protruded from the surrounding tissue.

Once the joint is fully accessed, the humerus may then be prepared for implantation of an implant by resecting the humeral head, and preparing the canal in the case of an implant with a stem, among other steps of the procedure. Because of the extensile position and view of the humerus, a humeral baseplate or stem portion of an implant may be placed into the cut humeral surface and canal in a direct facing manner (i.e., en face). That is, because the humerus can be protruded from the surrounding tissue for a full view of the cut humeral surface as a result of the severing of the subscapularis 112, the implant may be implanted via a direct facing application of the implant. The humeral head portion of the implant may then be impacted onto the baseplate or humeral stem portion of the implant in a direction normal to the plane of the cut humeral surface. After the humeral head is replaced, the glenoid is prepared and replaced. And then the shoulder joint is reduced and the subscapularis is repaired.

While the conventional anterior approach provides extensile exposure and comprehensive view of the humeral head, there are disadvantages. A major disadvantage of the anterior approach is that dividing the subscapularis requires the rotator cuff tendon to be repaired after the shoulder replacement surgery has been performed. Rotator cuff tendons often have difficulty healing and, if the tendon does not heal, patients may have persistent pain, impairment, dysfunction, and instability of the joint. It has been reported that 15-47% of subscapularis tendons do not heal after being divided, and 67% of patients have subscapularis dysfunction after total shoulder surgery. Other approaches, such as the rotator interval approach, are undesirable as they are difficult to perform and are fraught with challenges. Additionally, the rotator interval approach does not provide an extensile view of the shoulder joint. Instead, the view of the shoulder is limited in the rotator interval approach.

Accordingly, there is a need in the art for alternative approaches and devices, systems, and methods to replace the shoulder joint with adequate viewing of the joint and without damaging the subscapularis, among other needs. With these thoughts in mind, aspects of the present disclosure were developed.

SUMMARY

Aspects of the present disclosure may include a method of performing an arthroplasty procedure on a shoulder joining a humerus and a scapula via a plurality of muscles including a deltoid, a teres minor and an infraspinatus, the humerus having a humeral head and a humeral cortex. The method may include the following steps, among others. A step of accessing a posterior aspect of the humeral head between the infraspinatus and the teres minor. A step of positioning a reference guide up to the posterior aspect of the humeral head, the reference guide including at least one pin guide. A step of delivering at least one guide pin into the posterior aspect of the humeral head using the at least one pin guide of the reference guide. A step of positioning a first cutting guide up to the posterior aspect of the humeral head using the at least one guide pin as a guide, the first cutting guide including a first guiding surface. A step of cutting the humeral head in a posterior-to-anterior direction via guidance by the first guiding surface of the first cutting guide so as to form a resected bone surface. A step of cutting at least one channel into the resected bone surface and through a posterior aspect of the humeral cortex, the at least one channel extending in a posterior-anterior direction. A step of attaching a first component including a base plate of a joint replacement system to the resected bone surface, the base plate including at least one fin that is received within the at least one channel. A step of attaching a second component of the joint replacement system to the base plate.

In certain instances, attaching a base plate of a humeral head replacement system to the resected bone surface includes: coaxially aligning the at least one fin of the humeral head implant with the at least one channel in the resected bone surface; and tamping the humeral head implant in a posterior-to-anterior direction.

In certain instances, positioning the cutting guide up to the posterior aspect of the humeral head including operably coupling the cutting guide to the at least one guide pin.

In certain instances, cutting the humeral head including resecting the humeral head.

In certain instances, the at least one guide pin is delivered into the humeral head at a convergence of the infraspinatus and the teres minor. In certain instances, the at least one guide pin is delivered into the humeral head at a humeral head posterior margin of the humerus.

In certain instances, the method further includes: retracting the infraspinatus and the teres minor in order to access the posterior aspect of the humeral head. In certain instances, the method further includes: splitting the deltoid at a raphe. In certain instances, splitting the deltoid including identifying a heralding vein of the deltoid to determine an end point of the deltoid spit. In certain instances, splitting the deltoid including identifying an axillary nerve of the deltoid to determine an end point of the deltoid spit.

In certain instances, the humeral head is not dislocated from the scapula. In certain instances, the subscapularis remains intact during the arthroplasty procedure.

In certain instances, cutting the at least one channel into the resected bone surface is performed via guidance by a second cutting guide including at least one cutting slot.

In certain instances, the method further includes coupling the at least one guide pin to the second cutting guide.

In certain instances, the cutting of the at least one channel into the resected bone surface is done by a cutting tool in a posterior-to-anterior direction.

In certain instances, the method further includes: fastening the base plate to the resected bone surface via at least one fastener.

In certain instances, the base plate includes a pair of bores positioned on opposite sides of the at least one fin.

In certain instances, the reference guide further includes a curvate arm and a blunt tip.

In certain instances, positioning the reference guide up to the posterior aspect of the humeral head further including: wrapping the curvate arm around the humeral head and contacting the subscapularis with the blunt tip of the reference guide.

In certain instances, the reference guide further includes a linear marking, and the wherein positioning the reference guide up to the posterior aspect of the humeral head further including referencing the linear marking to the humeral head posterior margin in order to determine an alignment of the reference guide relative to the humerus.

In certain instances, the base plate further includes a lattice structure having a plurality of struts defining a plurality of openings, the at least one fin coupled to the lattice structure.

In certain instances, the base plate further includes an implant engagement structure opposite the at least one fin, and wherein the humeral head implant includes a base plate engagement structure configured to couple with the implant engagement structure of the base plate.

In certain instances, the implant engagement structure including a wedged slot, and the base plate engagement structure including a wedged structure configured to be received within the wedged slot.

In certain instances, attaching the humeral head implant of the humeral head replacement system to the base plate including sliding the humeral head implant in a posterior-to-anterior direction such that the wedged structure of the implant engagement structure is received within the wedged slot of the base plate engagement structure.

Aspects of the present disclosure may include a method of performing an arthroplasty procedure on a shoulder joining a humerus and a scapula via a plurality of muscles including a deltoid, a teres minor and an infraspinatus, the humerus having a humeral head and a humeral cortex. The method may include the following steps, among others. A step of accessing a posterior aspect of the humeral head. A step of cutting the humeral head in a posterior-to-anterior direction so as to form a resected bone surface. A step of cutting at least one channel into the resected bone surface and through a posterior aspect of the humeral cortex, the at least one channel extending in a posterior-anterior direction. A step of attaching a first component including a base plate of a joint replacement system to the resected bone surface, the base plate including at least one fin that is received within the at least one channel. A step of attaching a second component of the joint replacement system to the base plate.

In certain instances, the posterior aspect of the humeral head is accessed between the infraspinatus and the teres minor.

In certain instances, the method further includes: positioning a reference guide up to the posterior aspect of the humeral head, the reference guide including at least one pin guide; and delivering at least one guide pin into the posterior aspect of the humeral head using the at least one pin guide of the reference guide.

In certain instances, the reference guide including a curved arm configured to be positioned around the humeral head, a handle coupled to the curved arm, and a removable sleeve configured to be coupled to the handle, the removable sleeve including the at least one pin guide.

In certain instances, the method further includes decoupling the removable sleeve from the hollow handle with the at least one guide pin in the posterior aspect of the humeral head so as to permit removal of the curved arm from being positioned around the humeral head.

In certain instances, the method further includes: delivering a first guide pin into the posterior aspect of the humeral head; and positioning a first cutting guide up to the posterior aspect of the humeral head using the first guide pin as a guide, the first cutting guide including a first guiding surface, and wherein cutting the humeral head in the posterior-to-anterior direction is performed with the first cutting guide.

In certain instances, the method further includes delivering a second guide pin into the posterior aspect of the humeral head and through a guide hole of the cutting guide so as to lock a plane of resection associated with the first guiding surface.

In certain instances, the method further includes positioning a channel guide up to the posterior aspect of the humeral head via guidance by the first guide pin and second guide pin, wherein cutting the at least one channel into the resected bone surface and through a posterior aspect of the humeral cortex is performed via guidance by the channel guide.

In certain instances, the channel guide including a planar surface configured to abut the resected bone surface, a pair of pin guides for receiving the first and second guide pins, and at least one slot formed within the planar surface for guiding cuts into the resected bone surface.

In certain instances, the channel guide further including a backstop surface that extends generally perpendicular to the planar surface, the backstop surface configured to limit advancement of the channel guide by contacting the posterior aspect of the humeral head adjacent the resected bone surface.

In certain instances, attaching the base plate of the joint replacement system to the resected bone surface including tamping the base plate with an impaction tool. In certain instances, attaching the base plate of the joint replacement system to the resected bone surface including partially inserting the at least one fin into the at least one channel, and tamping the base plate with an impaction tool, wherein, when partially inserted, the planar surface of the base plate is angled relative to the resected bone surface. In certain instances, attaching the base plate of the joint replacement system to the resected bone surface including anchoring the base plate to the resected bone surface with one or more anchors.

In certain instances, at least one of the one or more anchors is delivered through the base plate and into the resected bone surface. In certain instances, at least one of the one or more anchors is delivered through the base plate and into an unresected portion of the humeral head.

In certain instances, the base plate further including a base structure having the at least one fin extending therefrom, a plurality of anchor holes formed in the base structure, and a protruding male taper extending from the base structure opposite the at least one fin. In certain instances, the base plate further including a base structure having the at least one fin extending therefrom, a plurality of anchor holes formed in the base structure, and a female socket taper extending from the base structure in the same direction as the at least one fin.

In certain instances, the joint replacement system is a total shoulder arthroplasty system, and the second component of the joint replacement system including a humeral head implant. In certain instances, the joint replacement system is a reverse total shoulder arthroplasty system, and the second component of the joint replacement system including a humeral cup.

In certain instances, a depth of the at least one channel that is cut into the resected bone surface is variable along a length extending in the posterior-anterior direction, and the at least one fin of the base plate having a variable depth along a length thereof.

A stemless humeral head replacement system including a base plate and a humeral head implant. The base plate includes a bone facing side, an implant side opposite the bone facing side, a curvate perimeter, at least one fin protruding from the bone facing side a first distance and extending linearly a length along the bone facing side, and an implant engagement structure on the implant side. The humeral head implant includes a curvate implant surface and a base plate engagement structure opposite the curvate implant surface, the base plate engagement structure configured to couple to the implant engagement structure of the base plate.

In certain instances, the base plate further including at least one fixation element protruding from the bone facing side a second distance.

In certain instances, the first distance is longer than the second distance.

In certain instances, the fixation element including a cylindrical wall intersecting the at least one fin. In certain instances, the cylindrical wall extends circumferentially to define a half-circle. In certain instances, the cylindrical wall extends circumferentially to define a full-circle. In certain instances, the at least one fixation element further including first and second linear walls positioned on opposite sides of the at least one fin, respectively, and generally parallel with the at least one fin. In certain instances, the at least one fixation element further including a third linear wall intersecting the at least one fin, the first linear wall, and the second linear wall.

In certain instances, the base plate further including a plurality of anchor holes extending there through. In certain instances, the base plate further including an anchor flange extending off of the curvate perimeter, the anchor flange including at least one anchor hole. In certain instances, the at least one anchor hole including a pair of anchor holes, the at least one fine including a central fin defining a plane that bisects the pair of anchor holes.

In certain instances, the implant engagement structure of the base plate including a protruding male taper. In certain instances, the protruding male taper is removably coupled to the base plate.

In certain instances, the base plate further including a pair of fixation elements protruding from the bone facing side, each of the pair of fixation elements including an anchor bore.

In certain instances, the at least one fin including at least one angled fin having a first end and a second end, the first distance being different at the first and second ends. In certain instances, the at least one angled fin including a central angled fin and a pair of peripheral angled fins. In certain instances, the at least one angled fin including a bulbous tip.

In certain instances, the base plate further including a scalloped edge fixation element protruding from the bone facing side adjacent the curvate perimeter.

In certain instances, the at least one fin extends through a central point of the base plate and to opposite edges of the curvate perimeter.

In certain instances, there is no stem protruding from the bone facing side of the base plate.

In certain instances, the base plate is configured to anchor to a resected bone surface via sliding in a direction parallel to the resected bone surface.

In certain instances, the system further includes a reference guide and a guide pin, the reference guide including a curvate arm configured to be positioned around a spherical bone and terminating at a blunt tip, and a sleeve having a guide hole that is configured to guide the guide pin through the spherical bone to the blunt tip.

In certain instances, the reference guide further including a handle, the sleeve configured to removably couple with the handle, wherein upon delivery of the guide pin via guidance by the guide hole of the sleeve, the sleeve may be decoupled from the handle so as to permit the reference curvate arm to be removed from being positioned around the spherical bone.

In certain instances, the system further includes a cutting guide including a first pin guide and a first planar surface configured to guide a planar resection of the spherical bone, the first pin guide configured to receive the guide pin there through so as to orient a bone facing side of the cutting guide towards the spherical bone.

In certain instances, the system further includes a channel guide including a planar referencing surface, a flange having a second pin guide extending from a perimeter of the referencing surface, and a slot formed within the planar referencing surface, the second pin guide configured to receive the guide pin there through so as to orient the planar referencing surface atop a resected bone surface, the slot extending atop the resected bone surface in a posterior-anterior direction.

In certain instances, the system further includes a base plate delivery tool including an first engagement structure including a first pair of tips at a distal end and a first handle at a proximal end, each of the first pair of tips including a first protrusion configured to engage a portion of the base plate, the first engagement structure including a curvate flange configured to abut the curvate perimeter of the base plate when coupled thereto, the first engagement structure further including a bone engagement flange protruding beyond the curvate flange and configured to engage a bone portion when sliding the base plate onto a resected bone surface.

In certain instances, the system further includes a base plate impaction tool including a second engagement structure including a second pair of tips at a distal end, a second handle at a proximal end, and a C-arm interconnecting the second engagement structure and the second handle, the C-arm including an impaction surface in line with the second engagement structure.

Aspects of the present disclosure may include a method of performing an arthroplasty procedure on a shoulder. The method may include the following steps. Accessing a posterior aspect of the humeral head. Cutting the humeral head in a posterior-to-anterior direction so as to form a resected bone surface. Cutting a channel into the resected bone surface and through a posterior aspect of the humeral cortex, the channel extending in a posterior-anterior direction. Positioning a base plate of a modular base plate assembly on the resected bone surface. The base plate may include a base plate structure having a first slot extending there through, and a fin on a bone facing side of the base plate that is at least partially received within the channel. Delivering a first modular fin through the first slot and into the resected bone surface. And, attaching a humeral head implant component to the modular base plate assembly.

In certain instances, the posterior aspect of the humeral head is accessed between the infraspinatus and the teres minor.

In certain instances, the method may further include: coupling a trunnion cap to an implant facing side of the base plate.

In certain instances, coupling the trunnion cap to the implant facing side of the base plate further may include coupling a trunnion plate over at least a portion of the trunnion cap and coupling the trunnion plate to the base plate structure.

In certain instances, the trunnion plate at least partially covers the first slot and first modular fin when coupled to the base plate structure.

In certain instances, the base plate structure further includes a second slot extending there through, and the method may further include: delivering a second modular fin through the second slot and into the resected bone surface.

In certain instances, the method may further include: securing the first modular screw to the base plate structure via a first fastener; and securing the second modular screw to the base plate structure via a second fastener.

In certain instances, the first and second modular fins are positioned within a first plane that is generally perpendicular to a second plane in which the fin on the bone facing side of the base plate is positioned within.

In certain instances, positioning the base plate of the modular base plate assembly on the resected bone surface may include sliding the fin in a posterior-anterior direction within the channel of the resected bone surface.

BRIEF DESCRIPTION OF THE DRAWINGS

FIG. 2D is a posterior view of the shoulder with the surgeon measuring various anatomical structures.

FIG. 2G is a posterior view of the shoulder exposing the humeral head.

FIG. 4 is an illustration of the humeral head from a posterior view with a cutting guide slidingly coupled to the guide pin.

FIG. 5 is an illustration of the humeral head from a posterior view with the humeral head resected and with the pin remaining in the bone.

FIG. 8 is an illustration of the remaining humeral head from a posterior view with a base plate positioned adjacent the resected bone surface.

FIG. 9 is an illustration of the remaining humeral head from a posterior view with the base plate positioned thereon and seated in a final seating position.

FIG. 10 is an illustration of the posterior shoulder with a humeral head implant coupled to the base plate.

FIGS. 17A-17C are flowcharts of an exemplary method of performing a shoulder arthroplasty procedure utilizing the systems and devices described herein.

FIGS. 18A-18E are, respectively, top, side, bottom, isometric exploded, and isometric views of a first embodiment of a reference guide.

FIGS. 18F-18J are, respectively, top, side, bottom, isometric exploded, and isometric views of a second embodiment of a reference guide.

FIG. 18K is a superior view of the humeral head with the first embodiment of the reference guide positioned around the humeral head.

FIG. 18L is a superior view of the humeral head with the first embodiment of the reference guide positioned around the humeral head, and a guide pin delivered into the humeral head via guidance by the reference guide.

FIG. 18M is a posterior-medial view of the humeral head with the first embodiment of the reference guide positioned around the humeral head and with the sleeve removed from the handle of the reference guide.

FIG. 18N is a posterior-medial view of the humeral head with the guide pin remaining in the bone after removal of the curved arm and sleeve of the reference guide.

FIG. 20F is an isometric view of the channel guide positioned on the resected surface of the humerus.

FIG. 20G is an isometric view of the channel guide positioned on the resected surface of the humerus with first and second guide pins extending through guide holes of the channel guide.

FIG. 20H is a posterior-medial view of the humerus showing a channel cut formed in the resected bone surface that was guided by the channel guide, the channel cut extending through the posterior cortex and through a central portion of the resected bone surface.

FIGS. 21A-21D are, respectively, top, side, bottom, and bottom isometric views of a base plate insertion device.

FIGS. 24A-24E are, respectively, top isometric, bottom isometric, top, side, and bottom views of a base plate having a single, angled fin.

FIGS. 25A-25E are, respectively, top isometric, bottom isometric, top, side, and bottom views of a base plate having a single, angled fin with a bulb tip.

FIGS. 31A-31E are, respectively, top isometric, bottom isometric, top, side, and bottom views of a base plate having a perimeter flange having a pair of anchor bores formed therein, a central fin, and a grid attachment structure encircled by a tubular wall.

FIGS. 33A-33E are, respectively, top isometric, bottom isometric, top, side, and bottom views of a base plate having a central fin, a grid attachment structure, and a tubular wall partially encircling the grid attachment structure.

FIGS. 35A-35E are, respectively, top isometric, bottom isometric, top, side, and bottom views of a base plate having a central fin, and a grid attachment structure that is partially encircled by a tubular wall at the superior end or inferior/calcar end of the base plate.

FIGS. 39A-39E are, respectively, top isometric, bottom isometric, top, side, and bottom views of a base plate having a single fin, which is part of a modular implant assembly.

FIG. 39F is an isometric top view of a modular base plate assembly including the base plate, a pair of modular fins, and a pair of set screws positioned above.

FIG. 39G is an isometric top view of the modular base plate assembly with the pair of modular fins inserted into key slots of the base plate and secured in place via the set screws.

FIG. 39H is an isometric top view of a modular male taper assembly of the modular base plate assembly positioned above the base plate with attached fins and set screws.

FIG. 39I is an isometric top view of the fully assembled modular base plate assembly.

FIGS. 39J-39K are, respectively, isometric top and side views of the fully assembled modular base plate assembly with a humeral head implant positioned above.

FIG. 39L is posterior-medial view of the humerus with the fully assembled modular base plate assembly positioned thereon.

DETAILED DESCRIPTION

The following disclosure describes and illustrates a surgical approach and associated tooling and implants for shoulder arthroplasty (e.g., shoulder replacement) that avoids cutting and repairing the subscapularis, as well as the associated harm and drawbacks of the deltopectoral approach. The surgical approach described herein is a posterior approach to the shoulder.

Figure 1A:
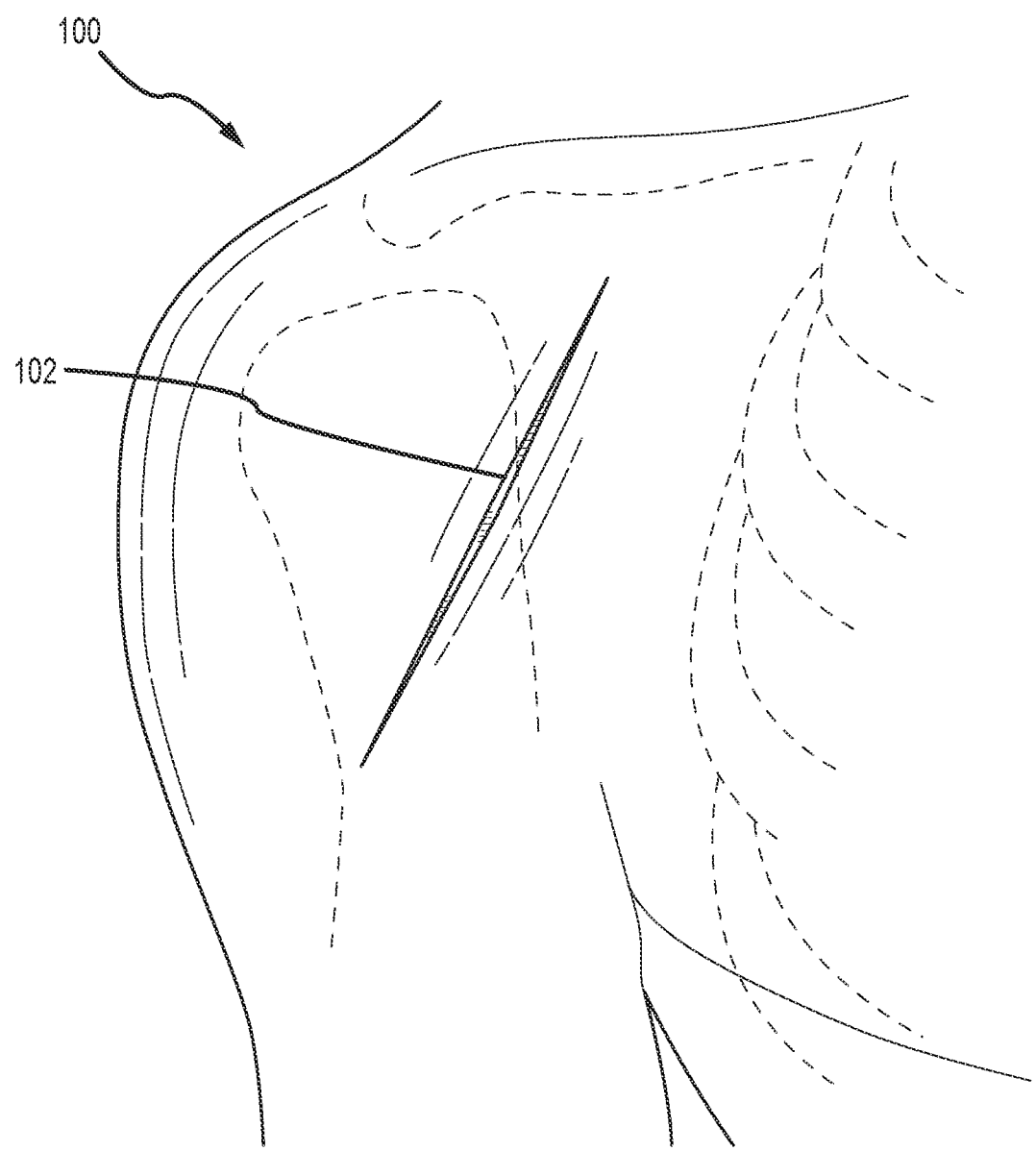
FIG. 1A is an anterior view of a shoulder.
Figure 1B:
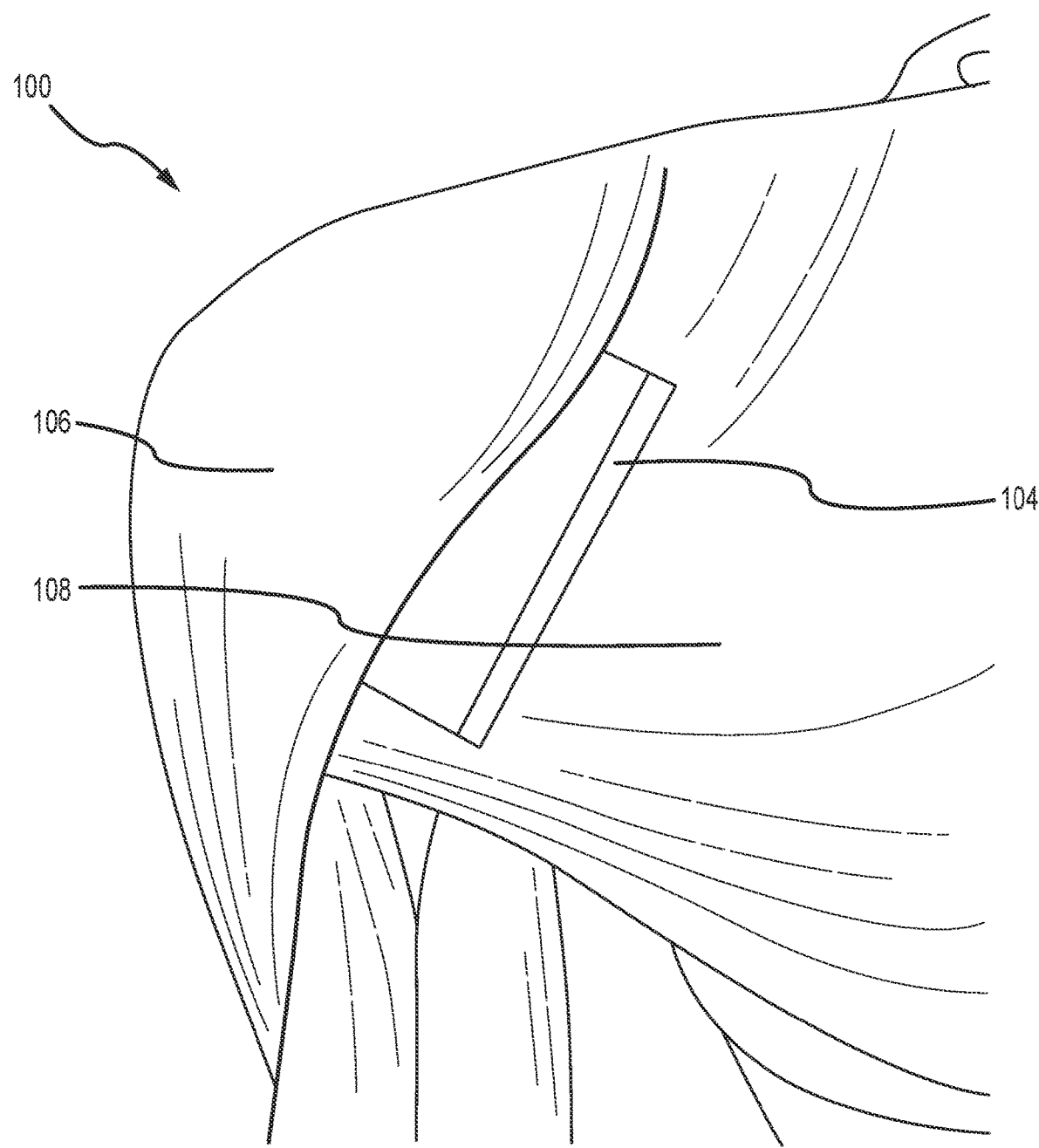
FIG. 1B is an anterior view of the musculature of the shoulder.
Figure 1C:
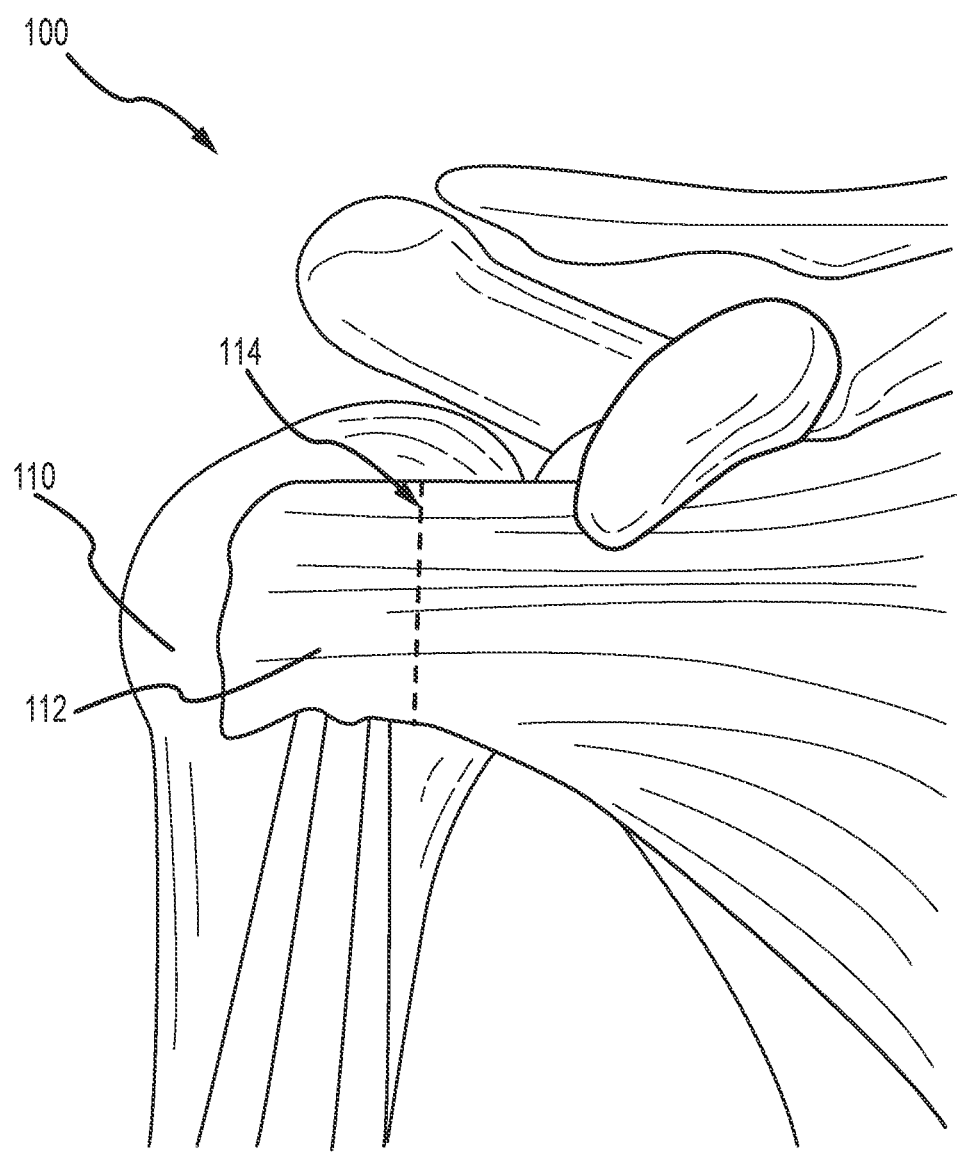
FIG. 1C is an anterior view of the skeletal structure of the shoulder, also showing the subscapularis.
Figure 2A:
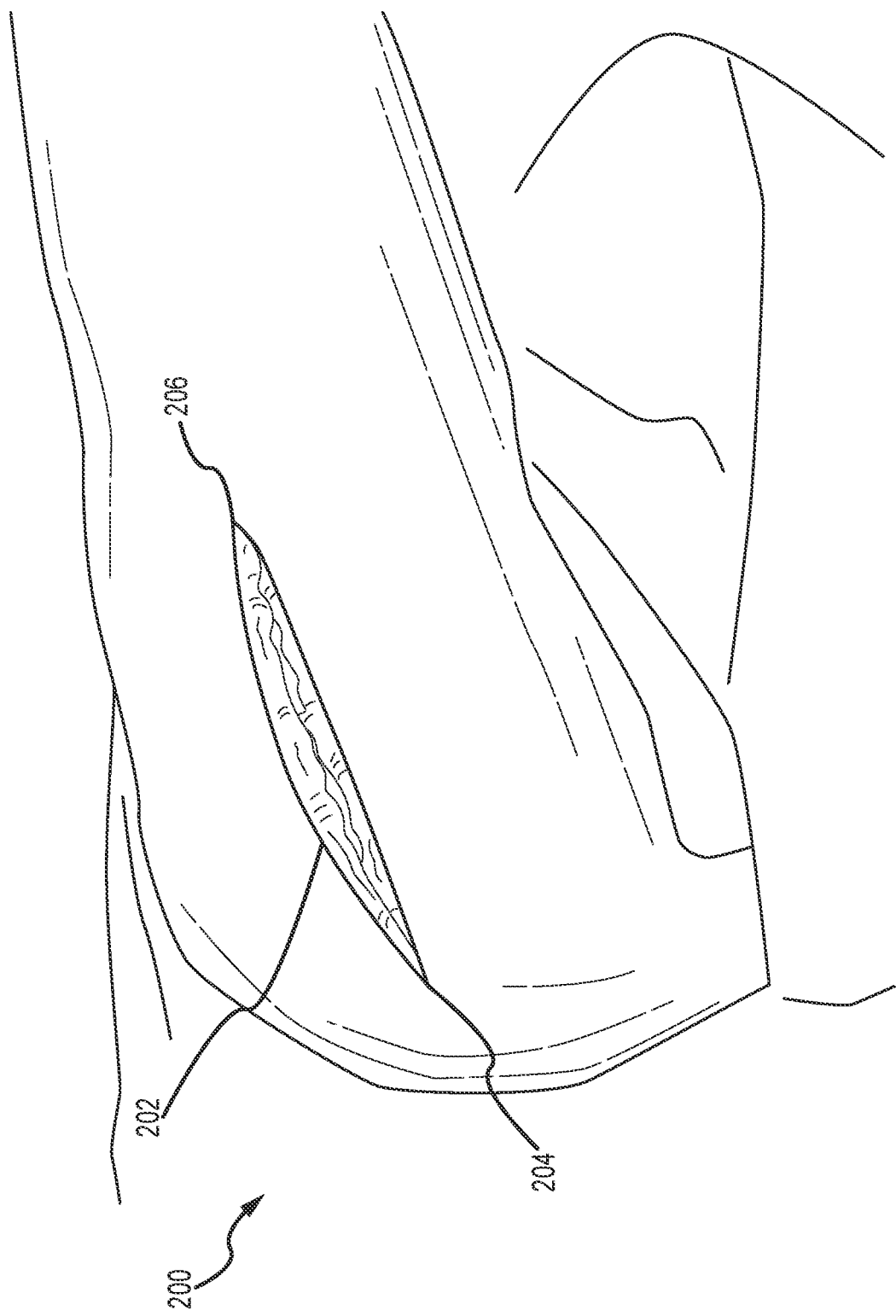
FIG. 2A is a posterior view of a shoulder of a patient with an incision on the posterior aspect of the shoulder.

To perform a shoulder arthroplasty via a posterior approach, the patient may be positioned in a lateral decubitus position. Referring to FIG. 2A, which is a posterior view shows a right shoulder 200 of a patient positioned in a lateral decubitus position, a skin incision 202 may be made on the posterior aspect of the shoulder 200 over the glenohumeral joint. The incision may start at the posterolateral corner of the acromion 204, extend distally down the axis of the arm to an end point 206. In certain instances, the length of the incision may be about 7 to 10 centimeters (cm) in length. In certain instances, the length of the incision may be shorter or longer than 7 to 10 cm.

Figure 2B:
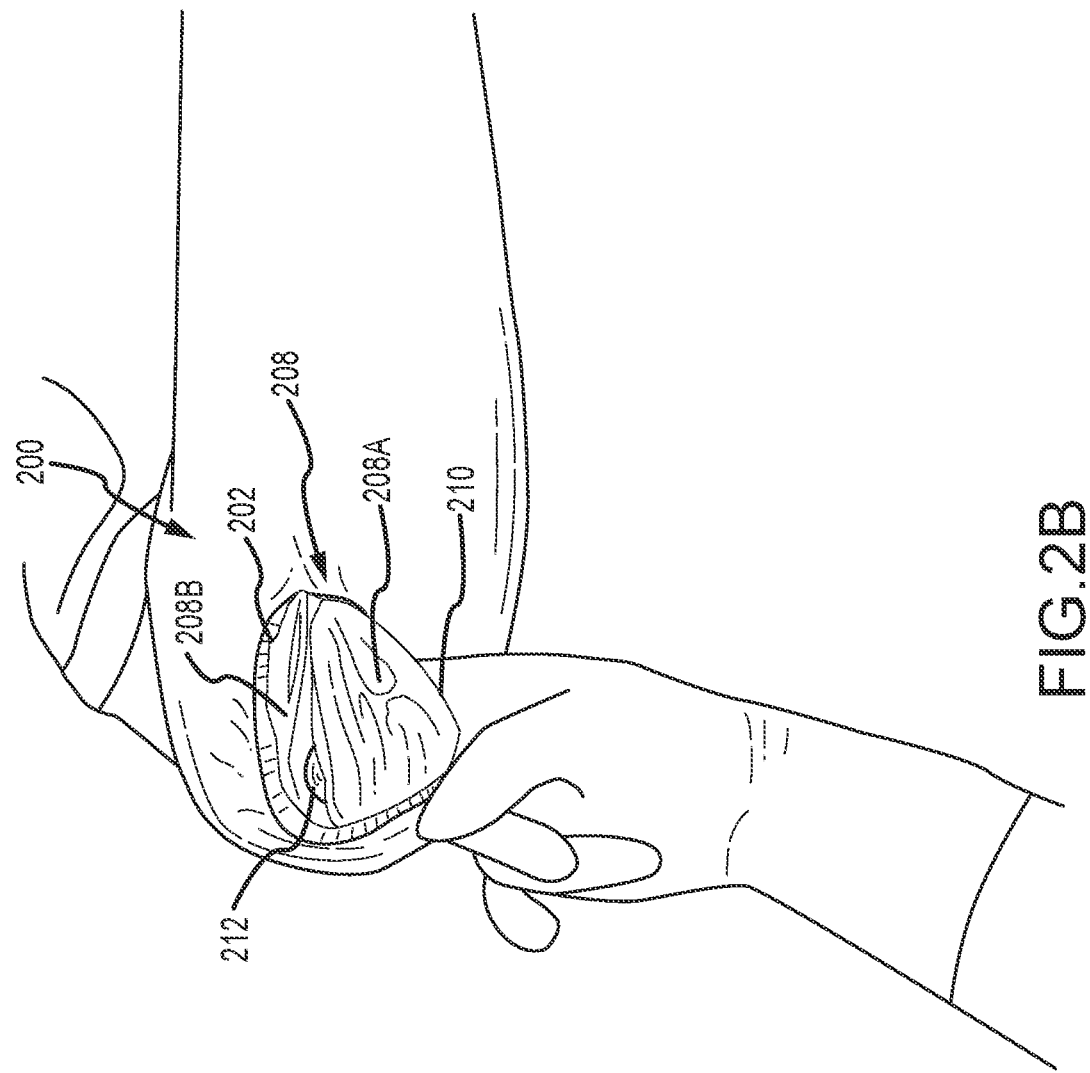
FIG. 2B is a posterior view of the shoulder with a surgeon identifying a raphe between heads of a deltoid.

Referring to FIG. 2B, which is a posterior view of the right shoulder 200 of the patient, the subcutaneous tissue may be divided in order to expose the deltoid muscle 208, which includes multiple heads of muscle 208A, 208B. Subcutaneous flaps of the deltoid muscle 208 may be raised medially to identify the posterior aspect of the deltoid muscle 208. A finger may be placed anterior to the deltoid edge 210 to define the deep plane between deltoid 208 and rotator cuff (not seen in FIG. 2B). The surgeon may search for and identify a raphe 212 between deltoid heads 208A, 208B, via finger palpations, for example. The raphe 212 is a fibrous connection or seam between the deltoid heads 208A, 208B. The raphe 212 provides a relatively bloodless plane through the deltoid muscle 208.

Figure 2C:
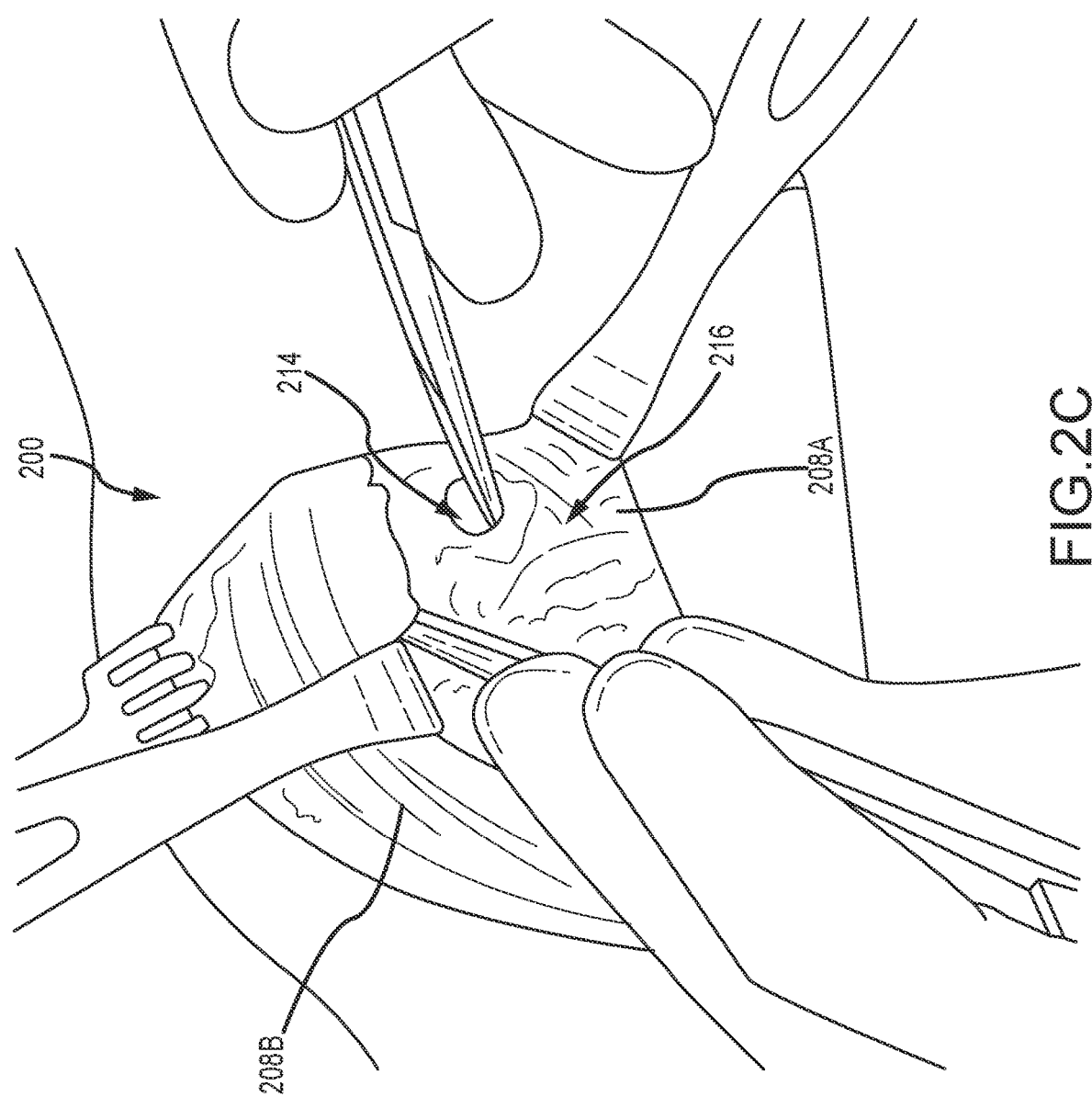
FIG. 2C is a posterior view of the shoulder with the surgeon identifying an axillary nerve and heralding vein in the deltoid.

Referring to FIG. 2C, the deltoid 208 is split along the raphe on the posterior side of the deltoid 208. In certain instances, the deltoid split is not extended past 7 cm in length in consideration of the traversing axillary nerve 214. A traversing vein 216 proximal and superficial to the axillary nerve 214 warns the surgeon to stop the deltoid split. It is noted that the deltoid 208 split in FIG. 2C is performed on a cadaver and extends past the nerve 214 and vein 216 in order to reference the anatomical features. On a living patient, the deltoid 208 split may stop at the vein 216. The vein 216 heralds the impending presence of the axillary nerve 214. As seen in FIG. 2C, identification of the heralding vein 216 marks the endpoint for the deltoid 208 split. In FIG. 2D, the heralding vein 216 is on average 71.8 mm from the acromion 218 while the axillary nerve 214 is on average 75.8 mm from the acromion 218.

Figure 2E:
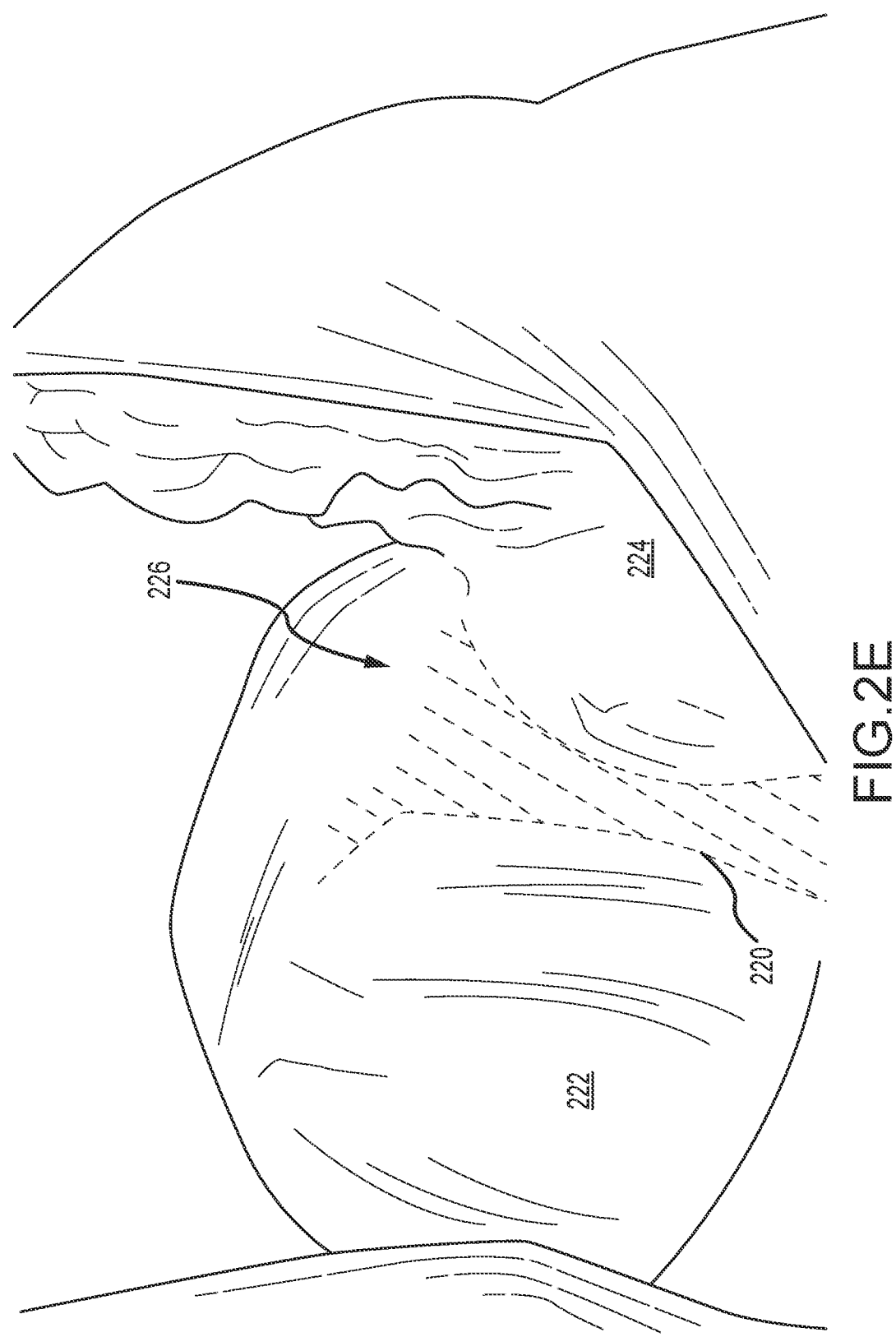
FIG. 2E is a posterior view of the shoulder showing the infraspinatus and teres minor muscles surrounding the glenohumeral joint.

Once the vein 216 and nerve 214 are identified, the posterior fascia may then be incised in order to expose the posterior rotator cuff muscles and tendons, as seen in FIG. 2E. The junction 220 between the infraspinatus 222 and teres minor 224 is identified, and will be termed the infraspinatus-teres minor junction (ITM) 220. The ITM 220 is internervous, meaning each muscle is supplied by different nerves. Because this plane is internervous, there is minimal risk to injuring the nerves that supply the infraspinatus 222 and teres minor 224. The infraspinatus 222 is supplied by the infraspinatus branch of the suprascapular nerve and the teres minor 224 is supplied by the axillary nerve.

Figure 2F:
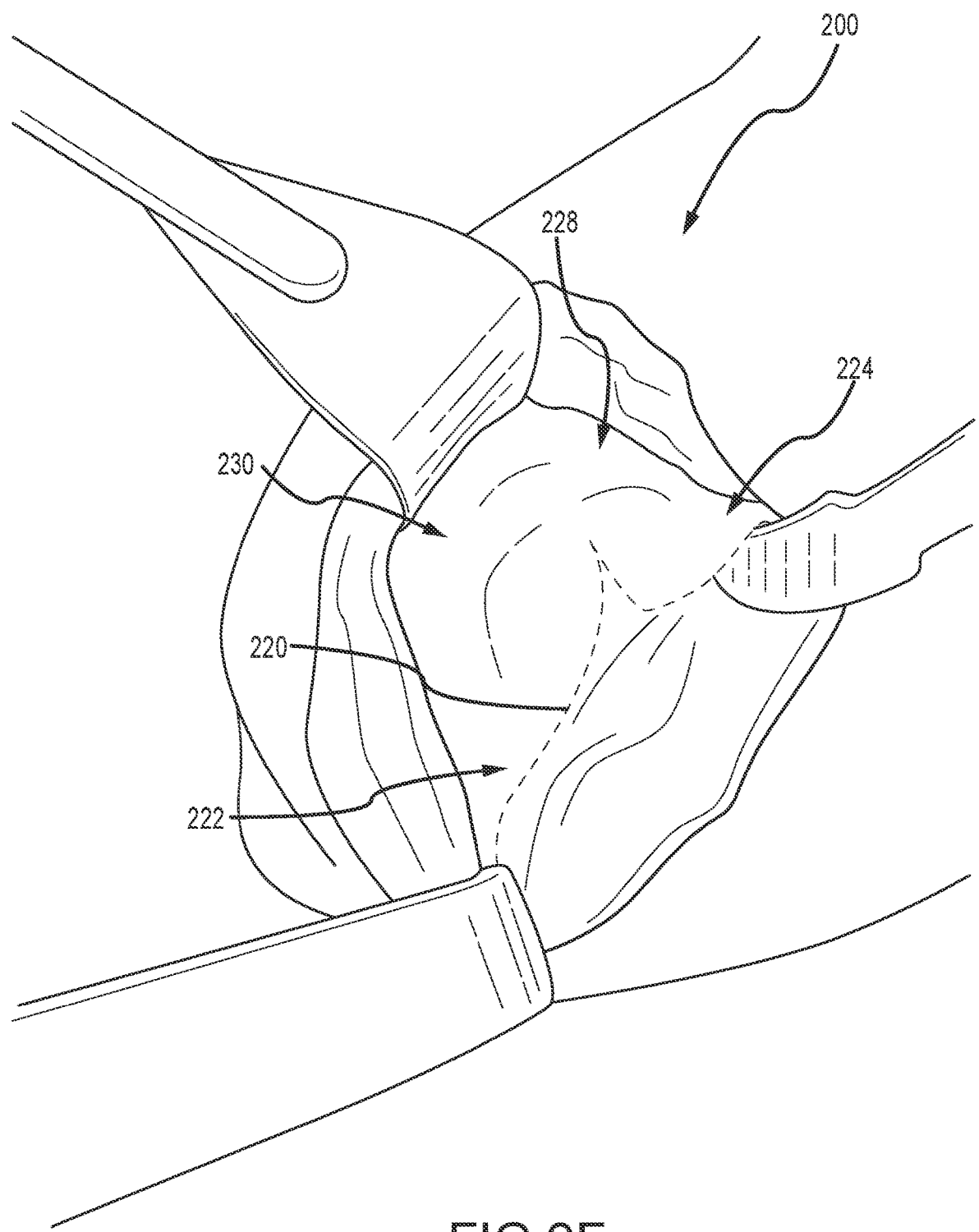
FIG. 2F is a posterior view of the shoulder showing the splitting of the muscles of the infraspinatus and teres minor along a border therebetween.

Identification of this internervous plane defined by the ITM 220, between the infraspinatus 222 and teres minor 224 may be aided by the following cues. First, at the level of interest, the teres minor (average 35.7 mm) is wider than the infraspinatus muscle and tendon (average 27.3 mm). Therefore, the infraspinatus 222 and teres minor 224 plane can feel more "superior" than expected. Second, the superior and lateral margin of the teres tendon 226 can take on a robust superior based triangular corner or central triangle, which may be a helpful landmark. Recognizing these two teres minor prototypical tendon variations can aid in correctly identifying the ITM 220 because variations exist which are a blend of these two morphologies. Third, palpation of the ITM 220 may be a helpful aid in that there is a natural low spot between the prominent teres minor 224 and infraspinatus muscle bodies 222 at or medial to the glenohumeral joint line. With internal rotation, the posterior rotator cuff musculature becomes more prominent and one can feel the ITM 220 dip into a valley. Fourth, as seen in FIG. 2F, the teres minor 224 appears to insert onto a teres tubercle or bony proximal humeral prominence 228 and the infraspinatus 222 appears to insert onto a prominence of the greater tuberosity 230. These two insertion tubercles can also be palpated in order to aid in identification of the ITM 220. The teres tubercle 228 is more distinct, localized and easier to palpate than the infraspinatus insertion 230. Morphologically, the teres tubercle 228 is similar to a mesa since it often appears to have a flat top and often a central dimple or hollowing. The infraspinatus tendon inserts onto a more gradual prominence of the greater tuberosity 230, an infraspinatus ridge. Fifth, the ITM 220 lies within the valley between the two peaks. Identifying the two peaks and then visually extending this valley from lateral to medial is another aid for ITM 220 interval identification. Finally, the teres minor 224 appears to be unipennate while the infraspinatus 222 is multi-pennate and the direction of the muscle fibers or muscle bellies can be a final clue to identification of the ITM 220.

Referring to FIG. 2G, the ITM 220 is split open, and the glenohumeral joint 232 is accessed via opening or dissecting of the posterior capsule (also known as the glenohumeral capsule). More particularly, the capsulotomy can take the form of a T capsulotomy, or an L capsulotomy, among other variations. As seen in the figure, retractors 234 may be used on a superior side to protect the rotator cuff and on an inferior side to protect the joint capsule. Of note, no rotator cuff tendons are severed. Instead, the glenohumeral joint 200 is accessed between the rotator cuff tendons. As seen in FIG. 2G, the glenohumeral joint 200 is exposed, but not dislocated. A limited in situ view of the joint 200 is obtained. The view is not extensile as in a deltopectoral view, meaning that the humerus is not extended from the surrounding tissue so as to provide a full view, partly because the humerus is still connected to the rotator cuff tendons. Access to the humeral head is provided by a side-facing approach to the humeral head 232 with this posterior approach. Stated differently, access to the humeral head 232 is de cote' or from the side with the posterior approach, as opposed to en face or direct-facing approach with the conventional deltopectoral approach.

Figure 2H:
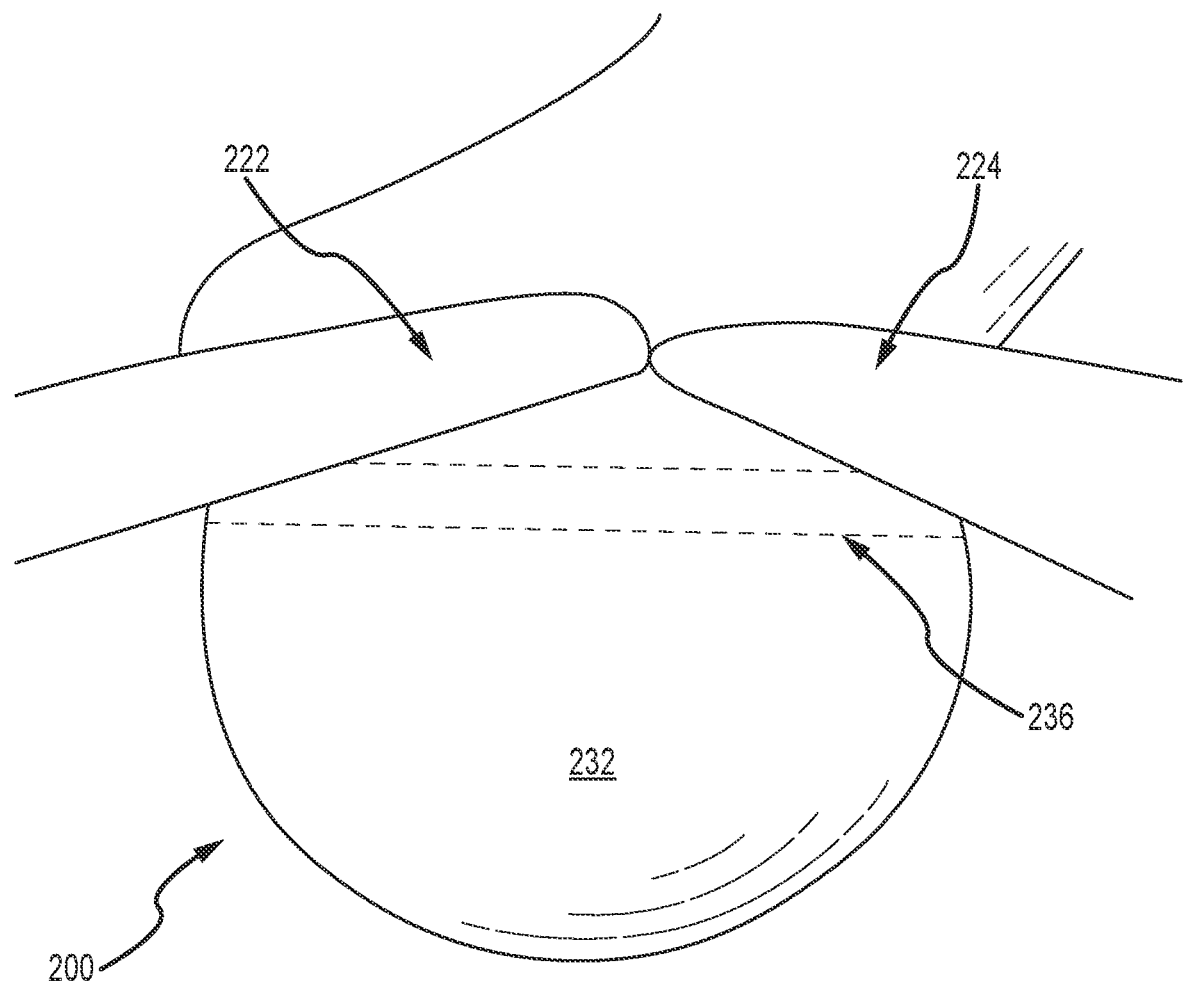
FIG. 2H is an illustration of the humeral head with retracted infraspinatus and teres minor.

Now that the joint 200 is exposed, the procedure may continue with the humeral head 232 in situ, without dislocation. Referring to FIG. 2H, the humeral head 232 may be assessed, and any osteophytes (i.e., bone spurs) may be removed in order to identify the boundary of the anatomical humeral head 232, shown bounded by a bare area or boundary 236 (also known as the humeral head posterior margin or anatomical neck) near the connection between the teres minor 224 to the humerus 110 and the infraspinatus 222 to the humerus 110. The boundary 236 encircles the humerus 110 just proximal of the connection between the humerus 110 and the teres minor 224 and the infraspinatus 222, respectively.

Figure 3A:
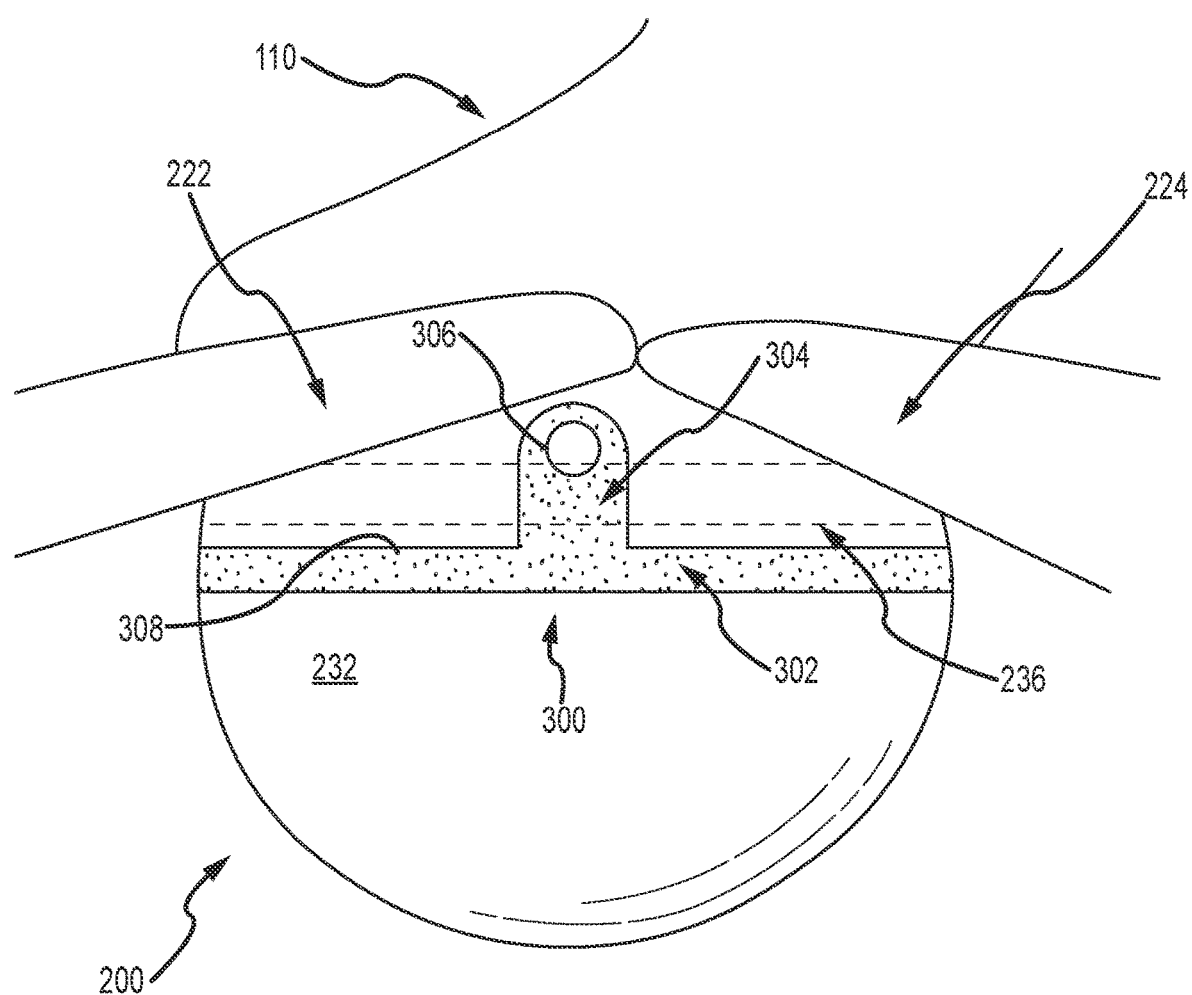
FIG. 3A is an illustration of the humeral head with a reference guide positioned thereon.

Once the humeral head 232 is exposed and the boundary 236 is identified, the surgeon may proceed to identify a cutting plane in order to provide an accurate in situ cut of the humeral head 232 from the posterior aspect of the joint 200. To that end, FIG. 3A, which is a close-up view of the posterior humeral head 100, depicts a posterior reference guide 300 positioned adjacent the posterior aspect of the humeral head 232. The posterior reference guide 300 includes a guide body 302 and a guide element 304 coupled to the guide body 302. The guide element 304 includes a guide hole 306 for guiding the insertion of a guide pin (not shown in FIG. 3A). In certain instances, the guide body 302 may be a planar structure that is aligned visually with the bare area boundary 236 so that a straight edge 308 of the guide body 302 and the boundary 236 are generally parallel to each other. The guide may be positioned on, proximal, or distal to the bare area. In certain instances, other posterior anatomic cues can be used for guide alignment such as the midpoint of the humeral head or most posterior point of the humeral head. In certain instances, other anatomic landmarks may include the superior margin of the humeral head and rotator cuff insertion or inferior margin of the humeral head. Intraoperative fluoroscopy can also be used to confirm appropriate varus and valgus neck angulation.

In certain instances, the guide body 302 may be curvate and wrap at least partially around the humeral head 232. In such an instance, the curvature of the guide body 302 may be adjustable to accommodate different sizes of humeral heads 232, or there may be different sizes of reference guides 300 with different sizes of guide bodies 302 to accommodate different humeral head 232 sizes. In the case of reference guides 300 of multiple sizes, the surgeon may, for example, choose the smallest size of guide 300 that can fit around the humeral head 232 to the bare area boundary 236.

Figure 3B:
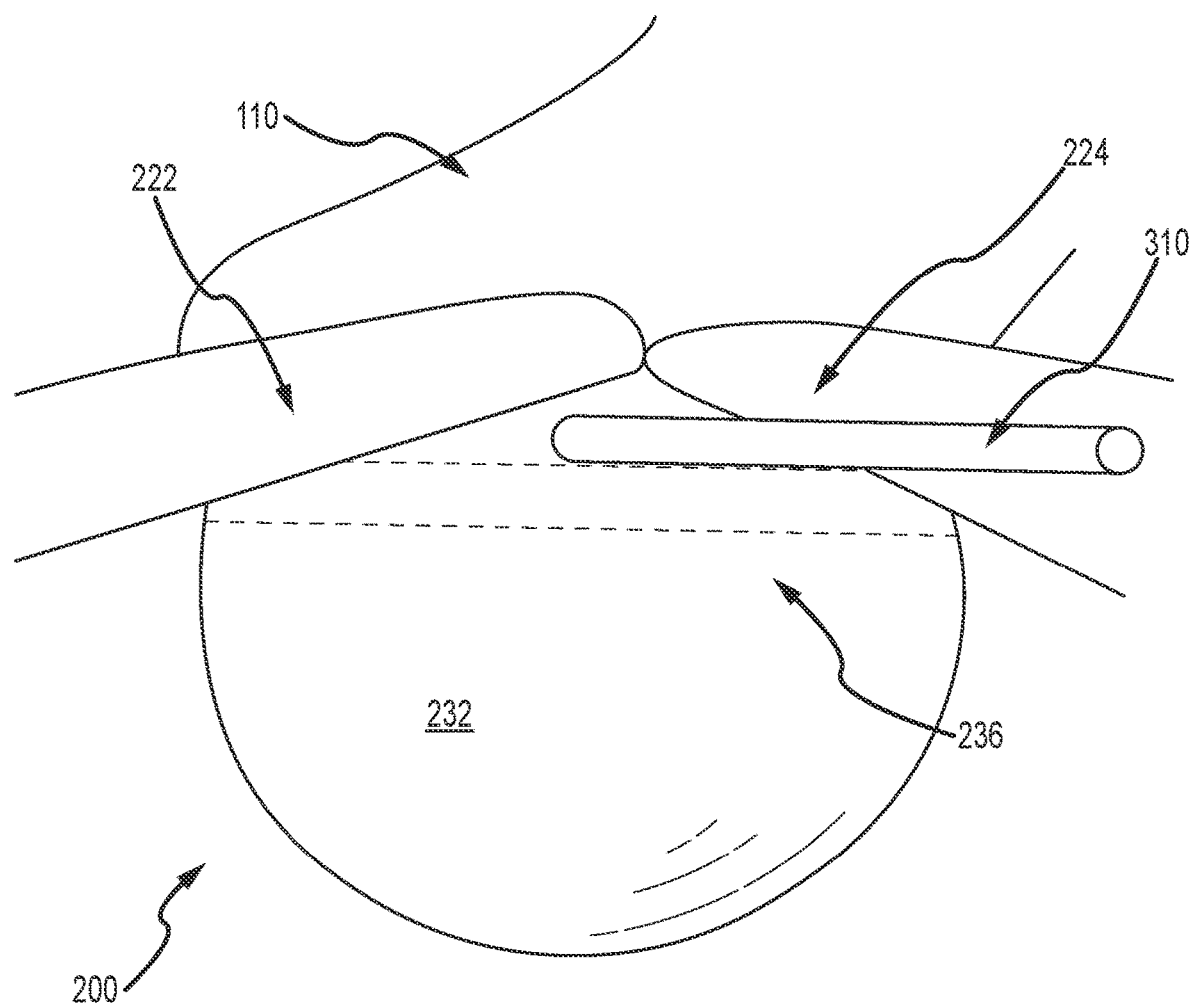
FIG. 3B is an illustration of the humeral head with a guide pin attached to the bone.

Once the reference guide 300 is positioned adjacent the humeral head 232 such that the edge 308 is generally parallel with the boundary 236, a pin (not shown in FIG. 3A) may be inserted into the bone via guidance by the guide hole 306 of the guide element 304. Then, as shown in FIG. 3B, the reference guide 300 may be removed, leaving the guide pin 310 positioned in the posterior side of the humerus 110. In certain instances, the guide pin 310 may be positioned slightly distal to the humeral head posterior margin 236 so as to not obscure the humeral head 232. The guide pin 310 may be used to align tools and guides for preparing the humerus 110 for the implantation of an implant.

Figure 3C:
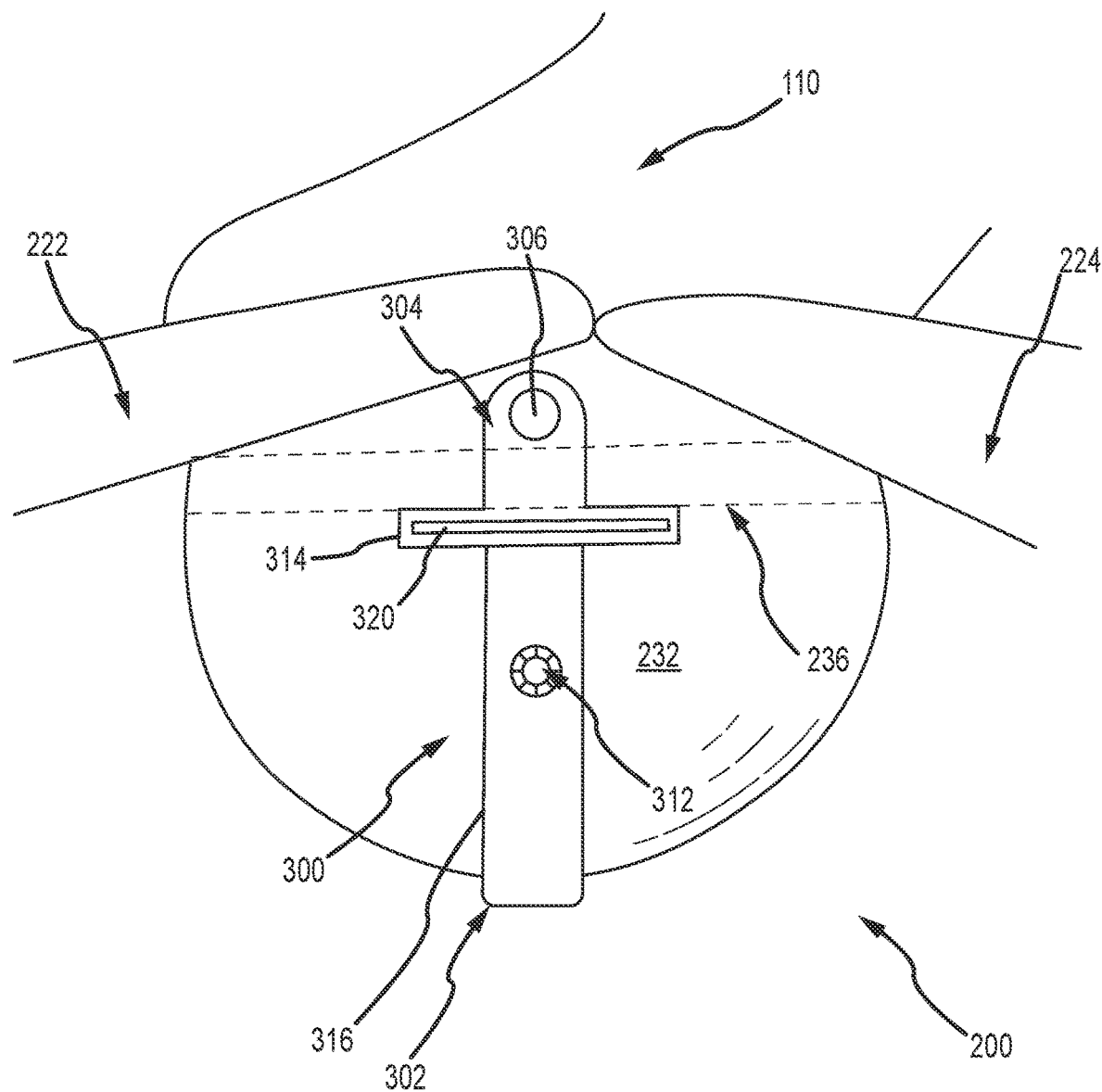
FIG. 3C is an illustration of the humeral head from the posterior side with an alternative embodiment of a reference guide.

With the posterior approach, the anterior humeral head 232 is not visible. A full, en face, superior 360 degree view of the humeral head is not possible given the attachment of the subscapularis, among other reasons. Therefore, it may be difficult to assess and gauge the inclination and version of the humeral head cut. Accordingly, a reference guide 300 that aids in the identification of the anterior humeral head and in positioning guide pins is presented in FIGS. 3C and 3D. While the reference guide 300 in FIGS. 3A and 3B aligns generally parallel with the humeral head posterior margin 236, the, the reference guide 300 of FIGS. 3C and 3D may wrap around the spherical portion of the humeral head. FIG. 3C is a posterior view of the humeral head 232 of the humerus 110 with the guide 300 positioned near the confluence of the infraspinatus 222 and the teres minor 224. The reference guide 300 includes a guide body 302, a guide element 304 having a guide hole 306 for guiding a pin 310, shown in FIG. 3D, an adjustment structure 312 for adjusting a length of the guide body 302, and a reference element 314 for aiding in aligning the guide 300 for varus-valgus orientation or for adjusting the length of the guide body 302.

Figure 3D:
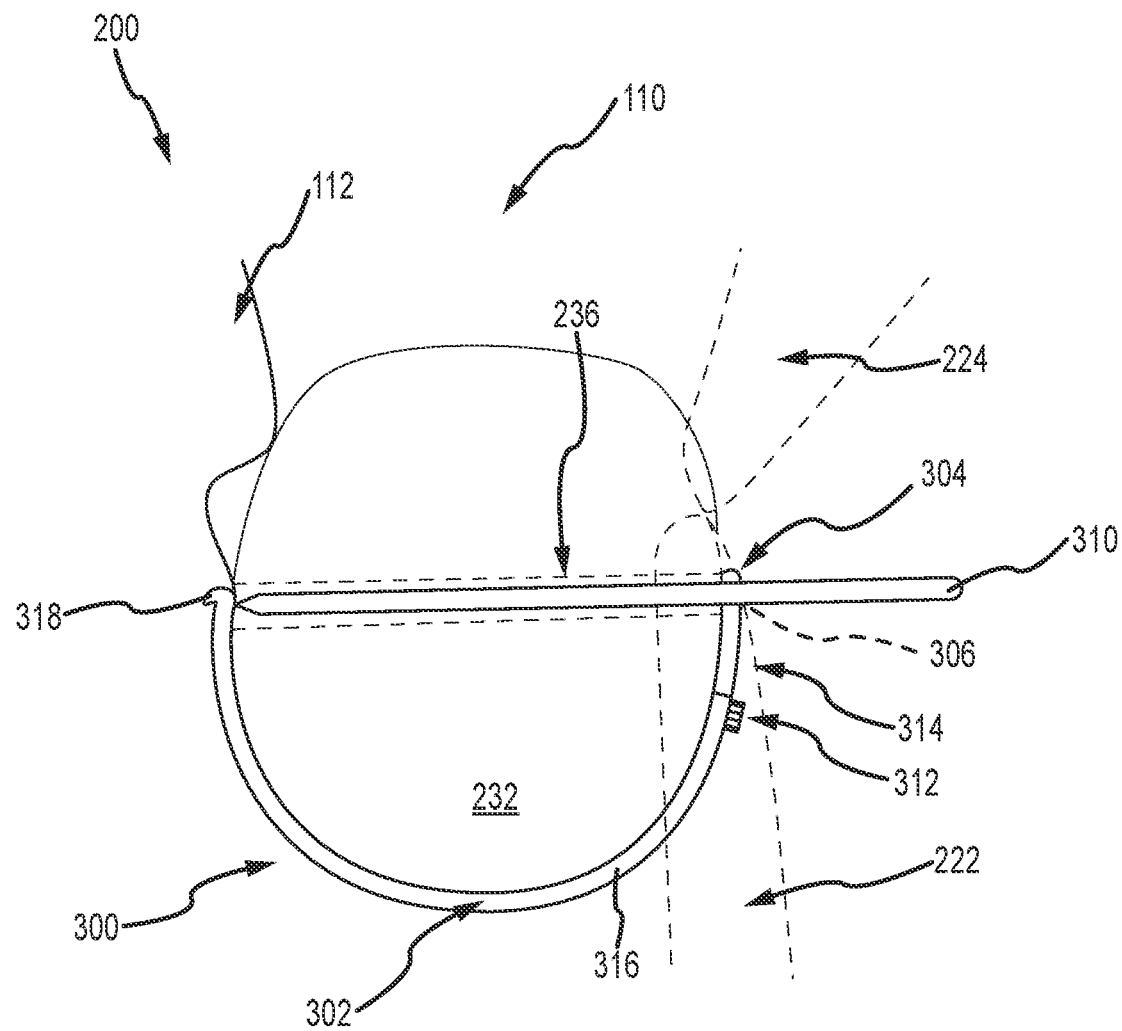
FIG. 3D is an illustration of the humeral head from a superior side with the reference guide of FIG. 3C positioned around the humeral head.

As seen in FIG. 3D, which is a superior view of the humeral head 232 with the posterior aspect of the shoulder 200 on the right, the reference guide 300 is positioned on the humeral head 232 with the teres minor 224 and the infraspinatus 222 split open and retracted for positioning of the guide 300. As seen in the figure, the guide body 302 of the reference guide 300 is curvate and wraps around the spherical head 232 of the humerus 110. The guide body 302 includes a curved arm 316 that terminates at a blunt tip 318. As seen in FIG. 3D, the blunt tip 318 may contact the subscapularis 112 and/or capsule at the point of which it connects with the humeral head 232. This contact point may provide a terminus or stopping point for the reference guide 300 because the resection of the humeral head 232 will be proximal to the subscapularis 112 to avoid damage to it. The blunt tip 318 may be positioned about one hundred eighty degrees on an arc of the curved arm 316 from the guide hole 306 of the guide element 304 in order to help guide and create a hemisphere cut. The size and shape of the tip 318 can be designed to accept the pin at or proximal to the blunt tip 318.

Since the anterior side of the shoulder joint 200 is not visible during the posterior surgical approach, the blunt tip 318 contacting the subscapularis 112 provides proprioceptive guidance to the surgeon who is operating at the posterior side of the patient. Once the blunt tip 318 contacts the subscapularis 112, the length of the curved arm 316 can be adjusted via the adjustment structure 312 (e.g., adjustable knob, thumbscrew) so it generally matches the contour of the spherical head 232 of the humerus 110. The tip 318 of the guide may aid in the location of an anterior point that is about one hundred eighty degrees opposite the desired posterior cut point. In other words, if the desired posterior cut point is identified, the corresponding anterior point one hundred eighty degrees around the arc of the guide can safely be measured and identified in order to provide guidance for the hemispherical humeral head cut. Additionally or alternatively, the guide tip 318 may first identify the anterior cut point via proprioception identification and then secondarily the diametrical 180 degree posterior cut point can then be chosen with posterior anatomical cues.

The reference element 314 may include a linear marking 320, shown in FIG. 3C, that may be aligned generally parallel with the humeral head posterior margin 236 or varus-valgus head and neck angulation. At this point, the guide pin 310 may be inserted into the posterior aspect of the humeral head 232 in a posterior-anterior trajectory via guidance by the guide hole 306 of the guide element 304. At full insertion, the distal tip of the guide pin 310 may contact the blunt tip 318 and prevent further insertion of the pin 310, which could damage the subscapularis 312, among other anatomical features. It is noted that the guide element 304 may include a cylinder body having the guide hole 306 therein. The cylinder body may guide the delivery of the guide pin 310 in a single orientation such that the pin 310 will be guided to contact the opposite end of the curved arm 316 or the blunt tip 318. In this way, the guide pin 310 may be delivered "blind" while having certainty that the distal end of the pin 310 will contact the blunt tip 318 and be prevented from further penetration.

A humeral head size can be measured from radiographs. An exemplary humeral head may have a diameter of about 40 millimeters (mm). In this instance, a reference guide 300 accommodating a 40 mm head can be used. There may be, for example, multiples sizes of reference guides 300 fitting all sizes of humeral heads. For instance, the reference guides 300 may be sized to accommodate humeral heads of between 40 and 44 mm. In operation, the reference guide 300 may be slid into the glenohumeral joint from a posterior to anterior direction following the contour of the humeral head 232. This can be done at the midpoint of the humeral head 232. The blunted tip 318 will be stopped by the anterior soft tissue attachments (capsule, subscapularis 112) or the tissues which should not be cut or violated in the posterior approach. The posterior aspect of the reference guide 300 can then be adjusted with the adjustment structure 312 (e.g., knob) to properly center the guide pin placement. The reference element 314 may aid the surgeon in varus-valgus orientation. Then, the guide pin 310 can then be inserted into the bone via guidance by the guide hole 306 in a posterior-to-anterior trajectory capturing the patient's inclination and version. This can be bicortical pin placement. In certain instances, a second pin (not shown) can be placed to fully capture or lock the position and orientation of the guide 300 on the bone.

Figure 3E:
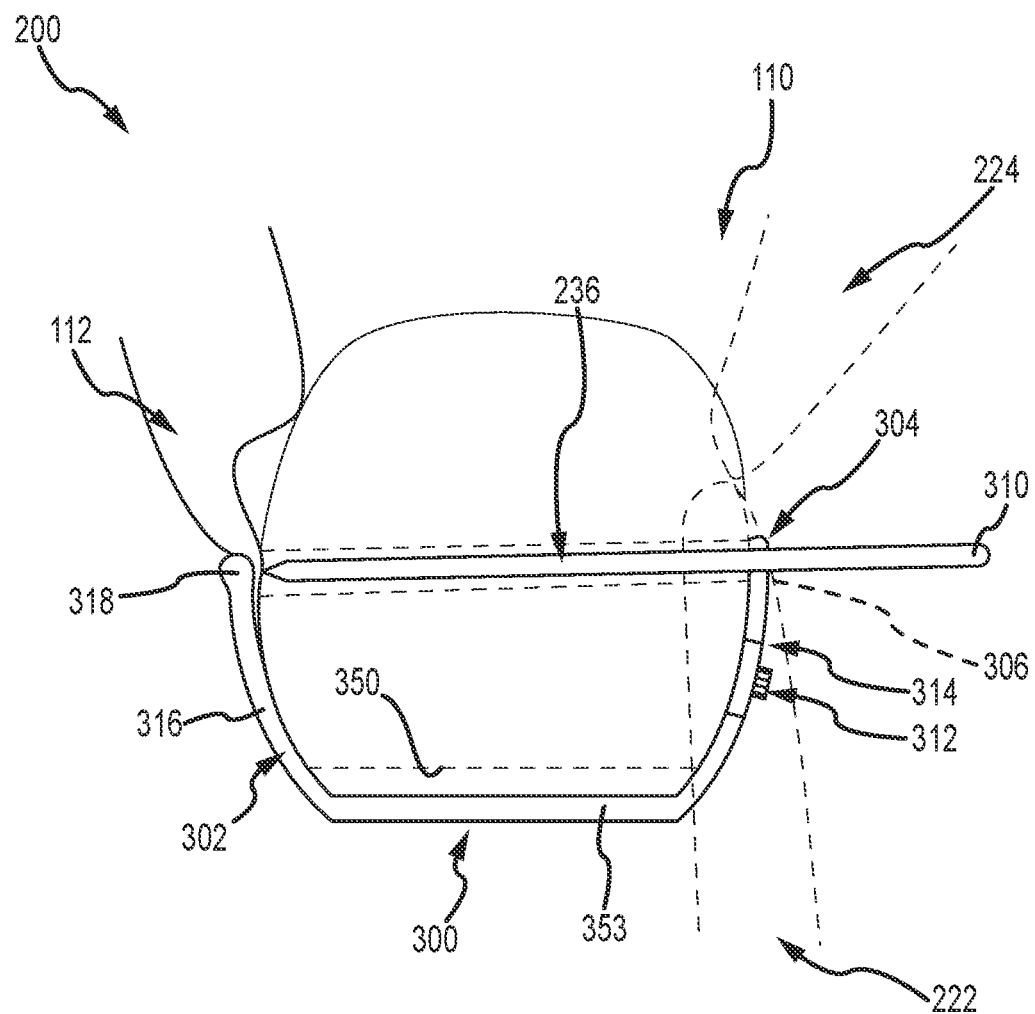
FIG. 3E is an illustration of the humeral head from a superior side with a reference guide positioned on the humeral head after a preliminary humeral head resection was performed.

If the glenohumeral joint 200 is contracted such that the guide arm 302 cannot be delivered between the humeral head 232 and glenoid to the anterior aspect of the glenohumeral joint 200, the reference guide 300 of FIG. 3E may be used. Prior to using the guide 300 of FIG. 3E, a preliminary, minor or smaller cut can be performed to the humeral head 232 in order to decompress the glenohumeral joint 200 and create space for the guide 300. This arbitrary humeral head cut, as referenced by the resected bone surface 350, removes the most proximal pole (not shown in FIG. 3E as it is resected off) of the humeral head 232 to create space for the guide 300. The guide 300 for tight glenohumeral joints may include the same features as the guide of FIG. 3D, except, in certain instances, the guide body 302 includes a linear section 353 that at about a midpoint between the blunt tip 318 and the guide hole 306. The linear section 353 of the guide body 302 may generally correspond with the location of the resection of the bone surface 350 when the guide 300 is positioned against the patient's bone. In this way, the guide 300 can fit into joints 200 with less clearance between the bones as opposed to a guide with a fully arcuate guide body 302. As seen in FIG. 3E, the guide 300 includes the tip 318 that is about one hundred eighty degrees from the posterior pin guide hole 306 to capture the diametrical point from a desired posterior point. The tip 318 of the guide 300 may have a blunt aspect to protect the anterior soft tissues and to abut and stop against the anterior front tissues to help gauge the anterior point where the subscapularis 112 and soft tissues begin.

After the reference guide 300 is removed from the bone, the guide pin 310 is left is position on the bone, as seen in FIG. 3B. Next, a cutting guide 400, shown in FIG. 4A, may be coupled with the guide pin 310 in order to guide the humeral head cut. The cutting guide 400 may include a guide body 402 having a planar cutting slot 404 formed in the guide body 402. The cutting guide 400 may also include a guide element 406 coupled to the guide body 402 and having a guide hole 408 formed in the guide element 406. The guide element 406 may extend generally perpendicular from the guide body 402 so that when the guide pin 310 is received within the guide hole 408, the cutting slot 404 is positioned proximally of the humeral head posterior margin 236. The guide body 402 of the cutting guide 400 may be curvate or planar. A curvate guide body 402 would at least partially wrap around the humeral head 232, whereas a planar guide body 402 would be positioned tangentially on the spherical humeral head 232.

Once the cutting guide 400 is positioned adjacent the bone, the rotational orientation of the cutting guide 400 may be determined by pivoting the guide 400 about the pin 310. In certain instances, the cutting guide 400 may include a second guide hole (not shown in FIG. 4) defined on the guide element 406, or otherwise, for the surgeon to insert a second pin into the bone in order to secure the position and orientation of the guide 400 relative to the bone. Once the orientation of the cutting guide 400 is set, a cutting tool such as a saw blade 410 may be inserted into the planar slot 404 and the bone may be cut or otherwise resected. It is noted, that the cutting tool 410 cuts the bone in a posterior-to-anterior trajectory. That is, the cutting tool 410 makes first contact with the posterior aspect of the humeral head 232, and proceeds to be advanced in a posterior-to-anterior trajectory.

Figure 6:
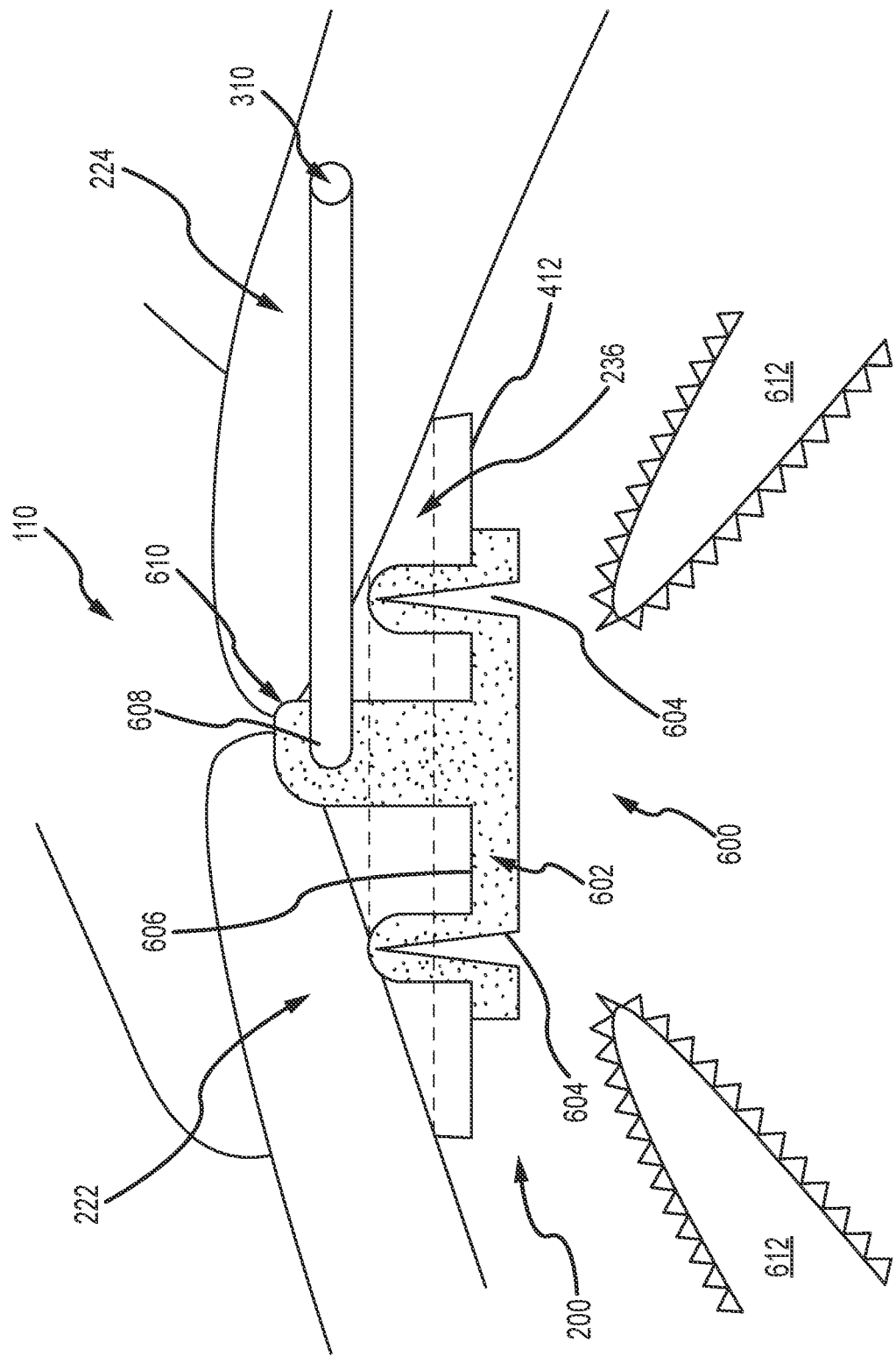
FIG. 6 is an illustration of the remaining humeral head from a posterior view with a track guide coupled to the guide pin, and saw blades positioned to make track cuts into the resected bone surface.

Once the humeral head is resected, the cutting guide 400 may be removed from the guide pin 310, as shown in FIG. 5. As seen in FIG. 5, the cutting tool formed a planar bone surface 412 just proximal of the humeral head posterior margin 236. Next, a track cutting guide 600 may be coupled to the guide pin 310 in order to orient the track cutting guide 600 for making keel-cuts into the resected bone surface 412 of the humerus 110, the keel-cuts extending generally in a posterior-anterior direction and proximal-to-distal direction. As seen in FIG. 6, the track cutting guide 600 includes a track body 602 having a pair of cutting slots 604, also known as channel slots or keel-cutting slots, formed in the body 602. The track body 602 may include a referencing surface 606 that is planar and designed to abut the resected bone surface 412 when track guide 600 is coupled to the guide pin 310. And when coupled to the pin 310, the cutting slots 604 are designed to cut into the resected bone surface 412 in a direction generally perpendicular to a plane defined by the resected bone surface 412. The pin 310 is received by the track guide 600 through a guide hole 608 of a guide element 610 coupled to the track body 602. The guide element 610 extends from the track body 602 in a generally perpendicular fashion. As seen in FIG. 6, a cutting tool 612, such as a reciprocal saw, may be used to cut track channels or keels into the resected bone surface 412 via guidance by the pair of cutting slots 604. As stated with respect to making the resection of the humeral head, cutting the track channels into the resected bone surface 412 is done in a posterior-to-anterior trajectory or proximal-to-distal direction. It is noted that the distal end of the track guide 600 may also include a similar track body 602 as shown in FIG. 6. That is, the pair of cutting slots 604 may be defined on the proximal side of the track cutting guide 600 (as shown in FIG. 6) and on the distal side of the cutting guide 600, which is not seen in FIG. 6 because the distal side of the guide 600 is obscured by the bone remainder of the humerus 100.

Figure 7:
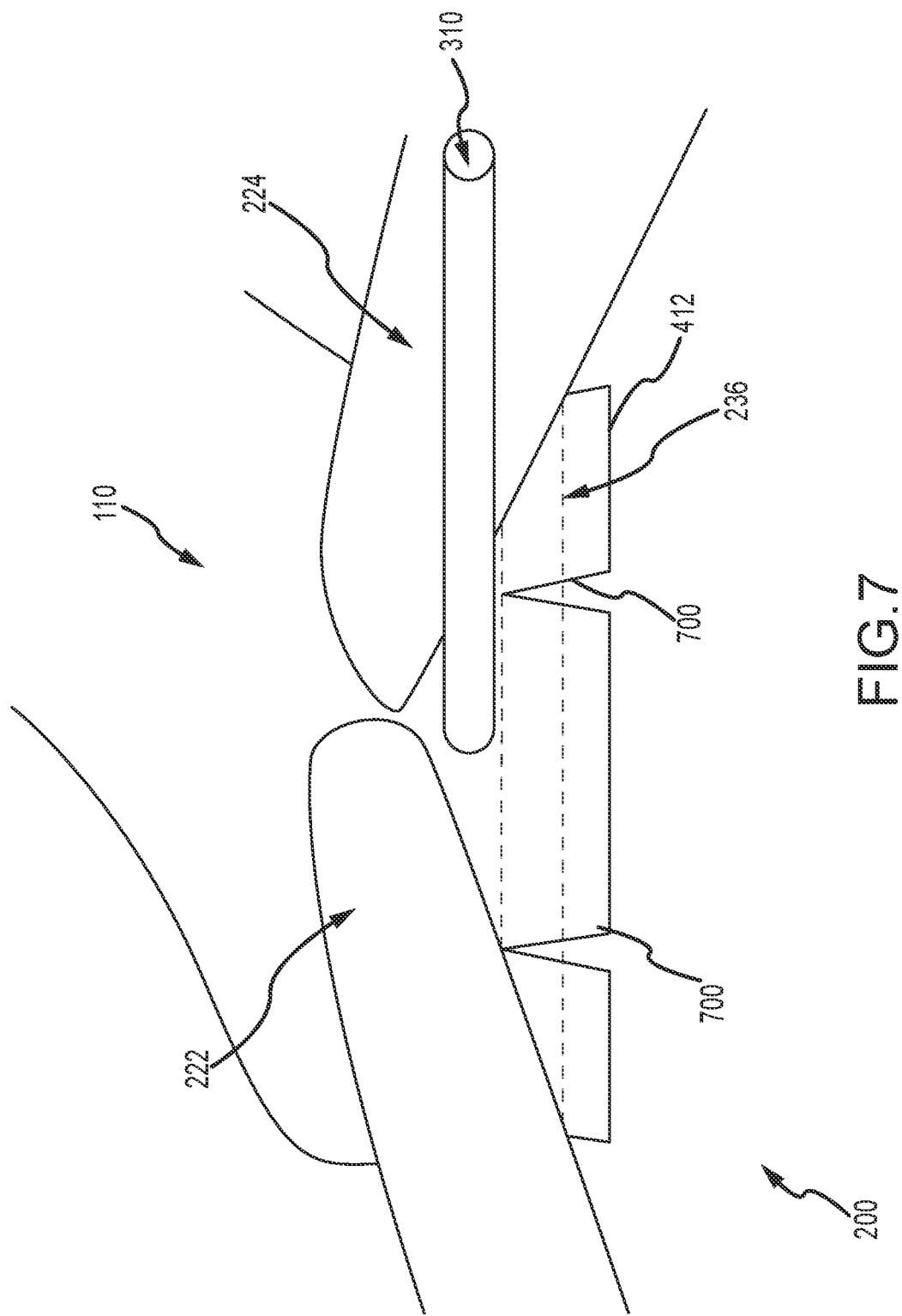
FIG. 7 is an illustration of the remaining humeral head from a posterior view with the track guide removed in order to show the resected bone surface and track cuts in the bone.

Once the track cuts are made, the track guide 600 may be removed from the guide pin 310, leaving the guide pin 310 positioned in the bone, as seen in FIG. 7. As seen in the figure, the resected bone includes the planar resection surface 412 and the two track cuts (also known as channel cuts or keel cuts) 700. In the illustrated example in FIG. 7, the track cuts 700 are angled with a wider base at the resected surface 412, and a point opposite the wider base. In other instances, the track cuts 700 may be rectangular channels with generally parallel sides. This type of shape generally matches the saw blades used to resect bone. In certain instances, a posterior portion of the track cuts 700 may be enlarged relative to an anterior portion of the track cuts 700 in order to ease insertion of the implant into the track cuts 700 from the posterior side of the bone. A thicker saw blade, chisel, or a wedge dilator and tamp could be utilized to create the enlarged posterior portion of the track cuts 700. The exact shape of the cuts 700 may be differently shaped based on the shape and configuration of the implant to be used in the procedure.

As seen in FIG. 8, which is a posterior view of the humerus 110, a base plate 800 of a stemless humeral head replacement system 802 may be attached to the resected bone. As seen in FIG. 8, a bone facing side 804 of the base plate 800 is shown. On the bone facing side 804 are a pair of track fins 806, also known as fins or keels. The pair of track fins 806 extend across the bone facing side 804 from a posterior edge 808 to an anterior edge (not visible in FIG. 8). The base plate 800 may include a lattice structure 810 with a generally circular or oval perimeter 812. The lattice structure may be a grid-like structure with openings in between interlinked portions of material that collectively form the base plate 800. The permits bone growth into and through the base plate 800 thereby facilitating osseointegration.

The base plate 800 may additionally include a fixation element 814 positioned centrally on the base plate 800, and a pair of flanges 816, each including a bore 818 for receiving a fastener (e.g., screw) for fastening the base plate 800 to the bone. The fixation element 814 may be one or more protrusions, such as blades, spikes, or the like, that extend from the bone facing side 804 of the plate 800. In certain instances, as seen in FIGS. 8 and 9, the pair of track fins 806 may extend farther from the bone facing side 804 of the plate 800 than the fixation element 814. In certain instances, the pair of track fins 806 may extend about the same distance from the bone facing side 804 of the plate 800 as the fixation element 814. And in certain instances, the pair of track fins 806 may extend from the bone facing side 804 of the plate 800 a shorter distance than the fixation element 814.

In operation, the guide pin 310 may be removed if it is not already removed, and the base plate 800 may be positioned adjacent the resected bone surface 412 with the anterior edge of the track fins 806 on the bone facing side 804 positioned on the posterior edge of the track cuts 700 formed in the resected bone surface 412. The surgeon may then apply force (e.g., tamp) to the base plate in a posterior-to-anterior direction relative to the humerus 110. This force will cause the base plate 800 to slide across the posterior humeral cortex of the resected bone surface 412 with the track fins 806 extending across and into the track cuts 700 of the bone. This type of delivery may be considered a de cote delivery, as opposed to an en face delivery. The surgeon may continue to tamp the base plate 800 until the anterior edge of the base plate 800 is just posterior to the anterior edge of the resected bone surface 412 so the base plate 800 is fully in the bone without overhanging the anterior edge of the resected bone surface 412. To prevent the base plate 800 from premature orthogonal engagement, a skid between the baseplate and 412 can be temporarily used.

It is noted that in a base plate 800 embodiment as shown in FIGS. 8 and 9, the track fins 806 may be positioned partially in the track cuts 700, but not fully within the track cuts 700 in order to permit the fixation element 814 to pass over the resected bone surface 412 until the fixation element 814 is generally positioned centrally within the resected bone surface 412. At this point, as shown in FIG. 9, which is the posterior view of the humerus 110, the surgeon may apply a force normal (i.e., orthogonal), seen by the arrow in FIG. 9, to the base plate 800 to seat the base plate 800 into the resected bone surface. This force (e.g., tamp) generally seats the fixation element 814 within the relatively softer bone in the central part of the humerus 110. And the force also fully seats the track fins 806 within the track cuts 700. The track cuts 700 facilitate or guides the base plate traveling in the posterior-to-anterior trajectory to be positioned correctly for final seating of the base plate 800 on the bone. The track cuts 700 also provide a partial insertion of the base plate 800 within the resected bone surface 412; thus, only a final seating is needed to seat the base plate 800 via the orthogonal force. Once the base plate 800 is fully seated on the resected bone surface 412, fasteners may be used to secure the base plate 800 to the bone via insertion through the bores 818 of the flanges 816 of the base plate 800 shown in FIG. 8. The flanges 816 are located on the outer rim of the base plate 800, which enables the fasteners to anchor to the stronger peripheral bone, as opposed to the softer bone near the canal. These fasteners may be unicortial or bicortical and can include screws and pegs. Additionally or alternative, modular fins may be utilized, small or big, instead of screws or pegs. Adding screws, fins, or pegs aid in resisting shear failure forces in the planes different from a plane defined by the major fin. If a surgeon desires deeper fins to help resist sheer in these additional other planes, secondary fins may be added in a modular fashion.

In certain instances, the base plate 800 may not include flanges 816 with bores 818. That is, the base plate 800 may be sufficiently secured to the bone without the use of fasteners.

The base plate 800 and track fins 806 may be constructed of a porous material, be grit blasted, or textured to increase fixation to the bone. Additionally or alternatively, the track fins 806 and baseplate 800 may have a hydroxyapatite coating or be constructed of a porous metal to allow for boney ingrowth.

Conventional base plates, on the other hand, are used in an en face environment with extensile view of the resected bone surface. Thus, the base plates may be tamped onto the bone surface with an application of force generally normal to the resected bone surface. With the posterior approach described herein, the resected bone surface does not provide sufficient space for a stemmed implant or conventional base plates that require application of force in the normal direction as the primary means for positioning and securing the base plate to the bone.

In FIG. 10, which shows a posterior view of the humerus 110, a humeral head implant 1000 of the stemless humeral head replacement system 802 is coupled to the base plate 800 by applying a force (e.g., tamping) of the humeral head implant 1000 normal (orthogonal) to the base plate 800. In FIG. 10, the humeral head implant 1000 is shown in cross-section, in order to see that an attachment structure 1002 of the implant 1000 that is positioned centrally on the base plate facing side of the implant 1000. The attachment structure 1002 may couple with a corresponding portion of the base plate 800. The attachment structure 1002 is opposite the spherical head surface 1004 of the implant 1000 that will interface with the glenoid component of the replacement system 802.

Figure 11A:
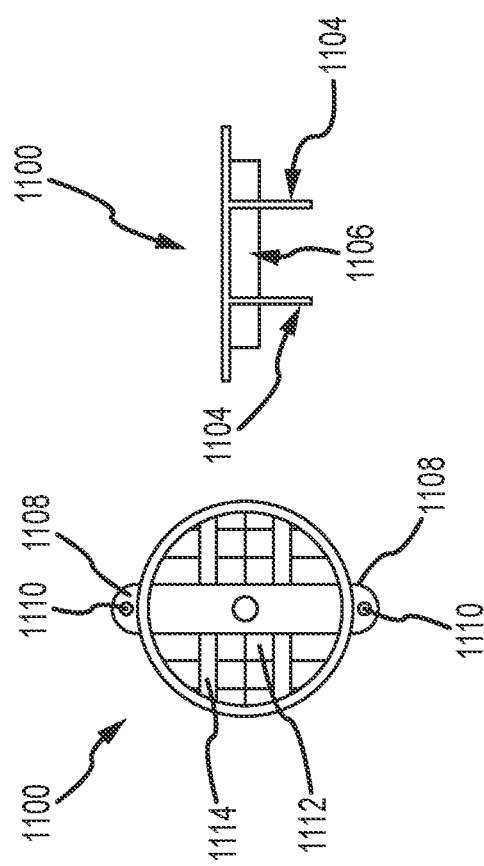
FIG. 11A is a top and side view of a base plate in certain instances of the present disclosure.
Figure 11B:
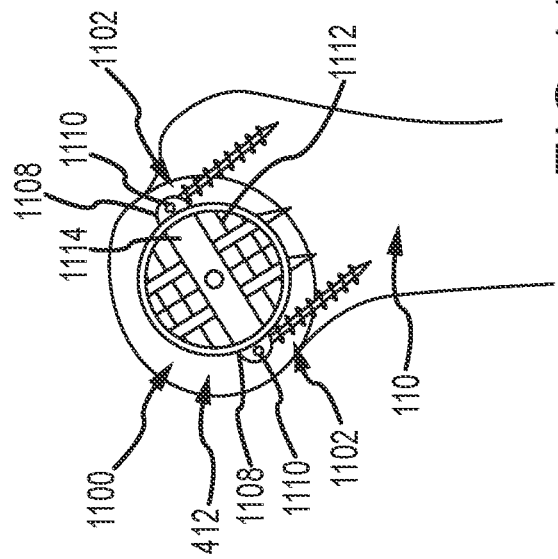
FIG. 11B is an isometric view of the base plate of FIG. 11A attached to a resected bone surface of the humerus.

FIGS. 11A and 11B illustrate another embodiment of a base plate 1100. FIG. 11A shows the base plate 1100 from a top side (humeral head-facing side), and a side view. FIG. 11B shows an isometric posterior view of a humerus 110 with the base plate 1100 installed thereon and secured to the humerus 110 via fasteners 1102. As seen in FIG. 11A, the base plate 1100 includes a circular body having a pair of track fins 1104 on the bone facing side of the plate 1100 that extend linearly from one edge to the other. Perpendicular to the track fins 1104 is a fixation element 1106 also extending away from the bone facing side of the plate 1100. The fixation element 1106 is oriented generally perpendicular to the fins, and it is designed to be press fit into the resected humeral surface. The fixation element 1106 may be one or more blades, spikes, or protrusions that extend downward from the bone facing side of the plate for fixation to the bone when the plate is press-fit into its final seating position.

The base plate 1100 additionally includes a pair of flanges 1108, each with a bore 1110 for receiving a fastener therein, as shown in FIG. 11B for securing the base plate 1100 to the resected bone surface 412. As seen in FIG. 11A, the flanges 1108 are oriented on opposite sides of the base plate 1100 such that, when the base plate 1100 is tamped into position via application of a posterior-to-anterior force, the flanges are positioned medially and laterally on the resected humeral surface 412. That is, neither of the flanges 1108 are positioned on the anterior side of the humerus 110, which will be obscured, and otherwise difficult to access for using fasteners to anchor the base plate 1100 to the bone.

And as seen in FIG. 11A, the track fins 1104 are extend farther from the base plate than the fixation element 1106. This permits the guided sliding of the base plate 1100 over the resected bone surface 412 until the base plate 1100 is centrally positioned over the bone surface 412. Then, an orthogonal application of force (e.g., tamp) may be used to seat the base plate 1100 to the bone, along with securing fasteners through the bore 1110 of the flanges 1108.

As seen in the top view of the base plate 1100 of FIG. 11A, the base plate 1100 includes a lattice or netting structure that includes various openings 1112 through the adjacent structures 1114 forming the base plate 1100. This type of structure permits bone ingrowth through the base plate 1100. When the base plate 1100 is press fit into the proximal bone of the humerus 110 the boney surface of the resected bone surface 412 may be caused to extend through the fixation elements 1106 up to and even slightly past the lattice structure. One of the purposes of having the base plate 1100 extend across a large portion of the resected surface 412 and having distributed fixation elements 1106 is to distribute the load to the entire resected humeral head surface 412. This, along with the fasteners 1102, which are oriented along the outer rim of bone, fasten the base plate 1100 to the stronger bone, as opposed to conventional base plates which anchor to the central, weaker bone. That is, most conventional stemless base plates have large central fins and fixation is primarily centrally located. The base plates described herein utilize a distributed fixation structure that relies on more peripheral fixation, and less central fixation.

While the base plates described herein show a pair of track fins, there may base plates with only one track fin. And in certain instances, there may be base plates with more than two track fins. In certain instances, the track fins may be arrange with one central fin. In certain instances, the track fins may be arranged with peripheral fins, with or without a central fin. And the various embodiments of base plates can also have variable attachment structures between the base plate and the humeral head implant, such as male tapers, female tapers, wedge tapers, screw fixation, and dove tail constructs, among other structures.

Figure 12B:
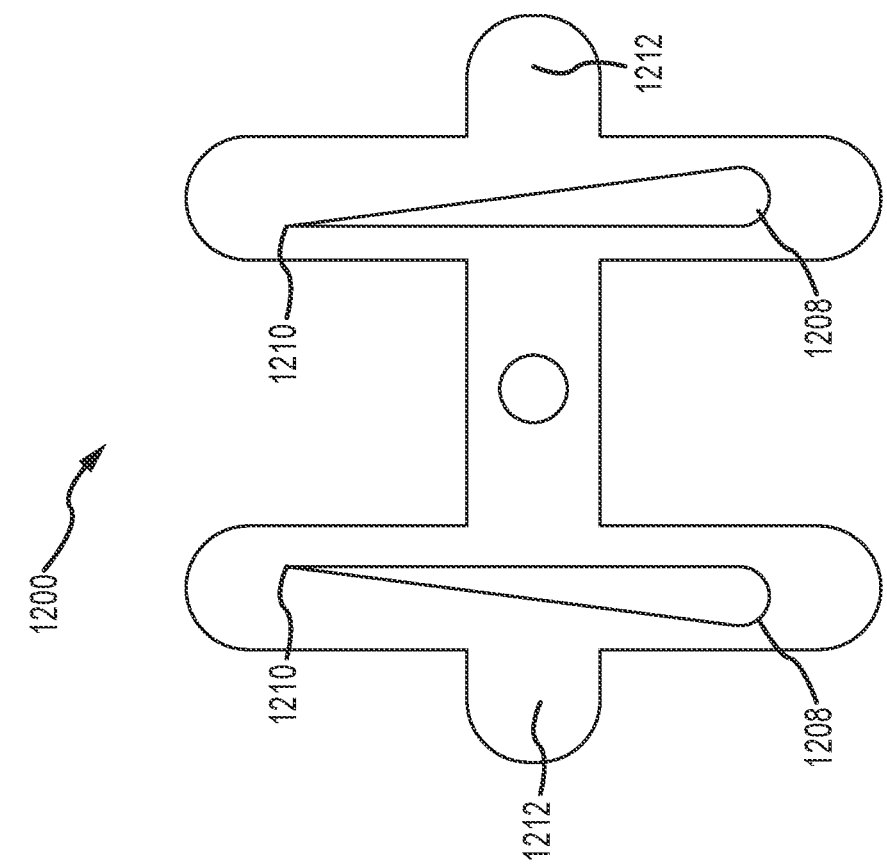
FIGS. 12A and 12B are, respectively, a top isometric view and a bottom view of a base plate in certain instances of the present disclosure.
Figure 12A:
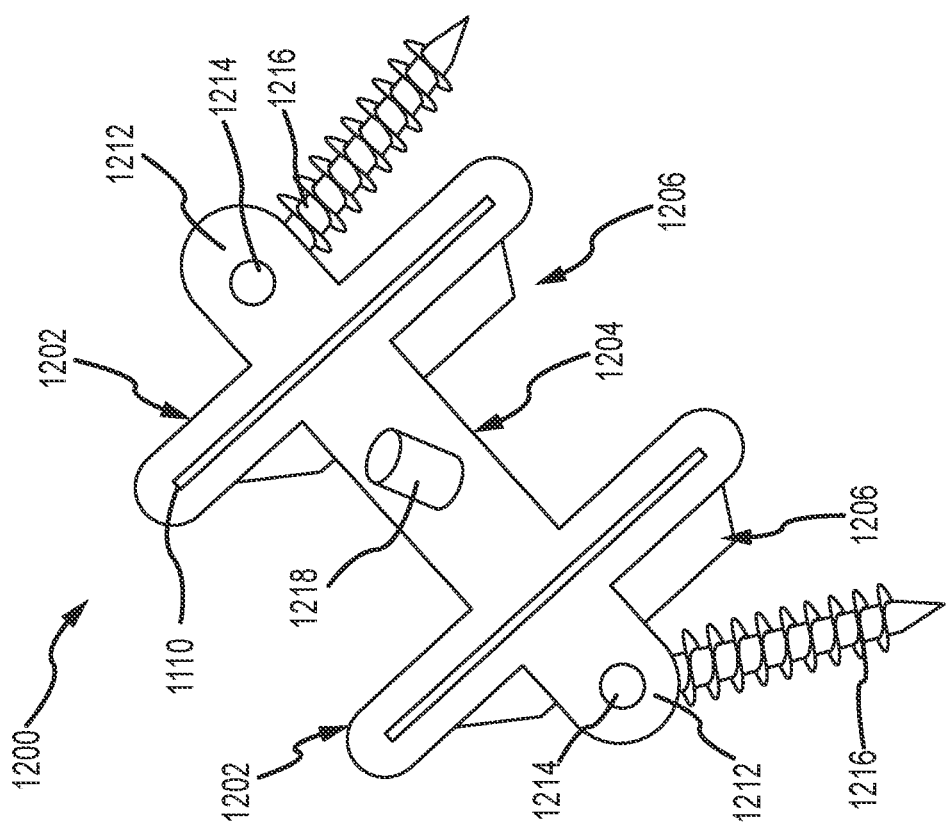
Figure 14:
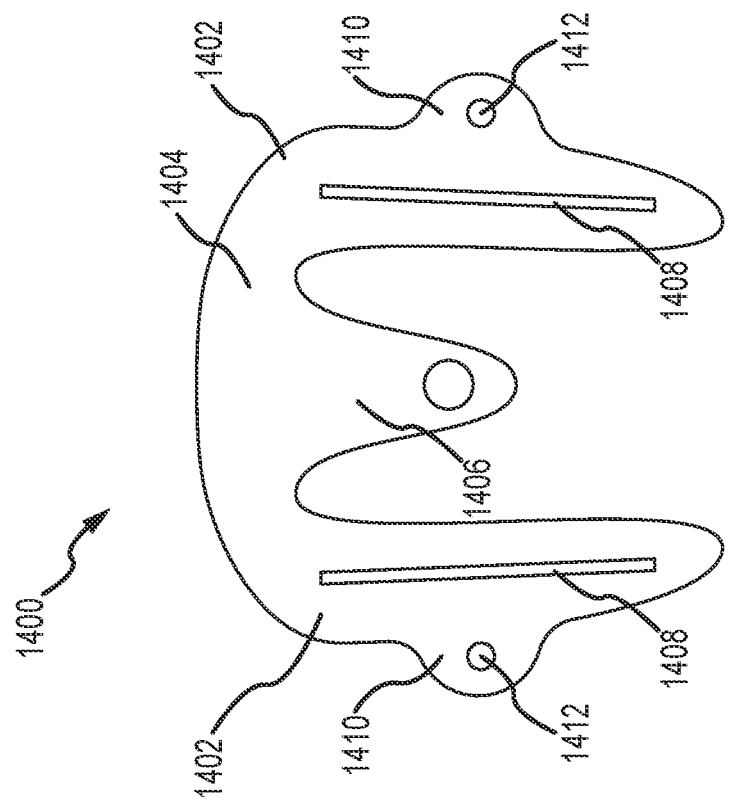
FIG. 14 is a bottom view of a base plate in certain instances of the present disclosure.
Figure 13:
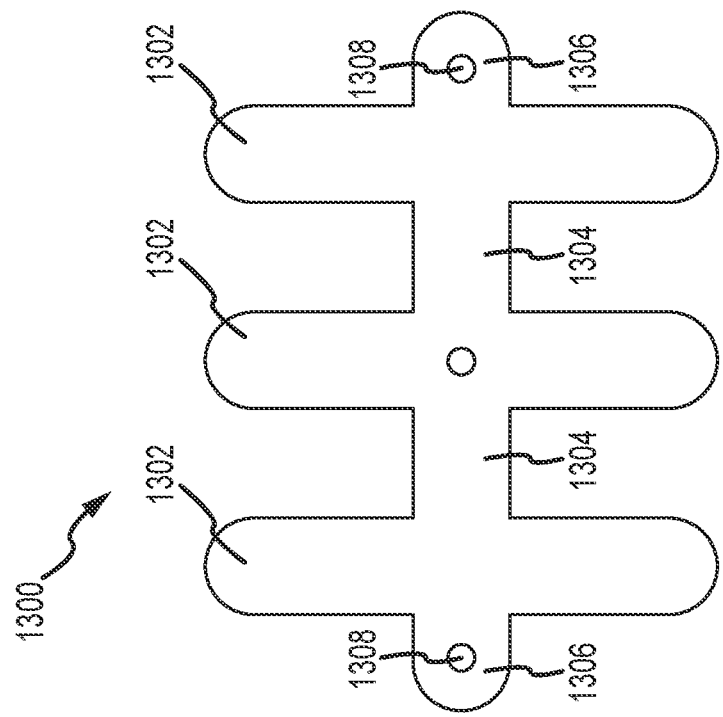
FIG. 13 is a top view of a base plate in certain instances of the present disclosure.

FIGS. 12-14 illustrate additional or alternative embodiments of the base plate. FIG. 12A illustrates an isometric top view of a base plate 1200 having an H-shaped body. More particularly, the base plate 1200 includes a pair of track bodies 1202 coupled together via a cross-member 1204. On each of the track bodies 1202, on a bone facing side as seen in FIG. 12B, is a track fin 1206. As seen in FIG. 12B, the track fins 1206 are tapered from a wider base 1208 to a pointed tip 1210. The pointed tip 1210 would be inserted first into the track channels formed in the resected bone surface, and, as the base plate 1200 is driven anteriorly, the track fins 1206 would wedge within the track channels. Track fins such as shown in FIG. 12B may be incorporated into any embodiment described herein without limitation. It is noted that the body of the base plate 1200 also includes flanges 1212 with bores 1214 for receiving fasteners 1216. The base plate 1200 also includes an implant engagement element 1218 on the top side of the plate 1200 for coupling with a humeral head implant (not seen).

FIGS. 13 and 14 illustrate additional embodiments of base plates 1300, and 1400, respectively. FIG. 13 shows a top view of a base plate 1300 having three body sections 1302, connected to each other via a cross-member 1304. There are a pair of flanges 1306 at outer ends, each with a bore 1308 for receiving a fastener. A bottom or bone-facing side of the base plate 1300 may include three track fins with one on each of the body sections 1302.

FIG. 14 shows a bone-facing view of a base plate 1400 having two body sections 1402 connected via a cross-member 1404. Coupled to the cross-member 1404 is an extension member 1406 jutting inward to a central location between the two body sections 1402. Each of the body sections 1402 includes a track fin 1408. There are a pair of flanges 1410, each including a bore 1412 for receiving a fastener. The arrangement of track fins 1408 in this embodiment are peripheral with no track fin centrally located.

Figure 16B:
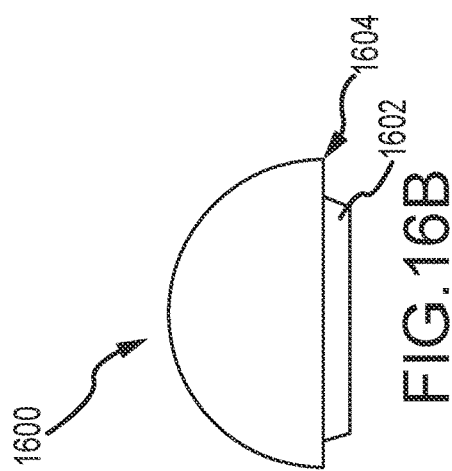
FIGS. 16A-16C are, respectively, first side, second side, and bottom side views of a humeral head implant having wedge shaped fins for connecting with the connecting structure of the base plate of FIG. 15.
Figure 16A:
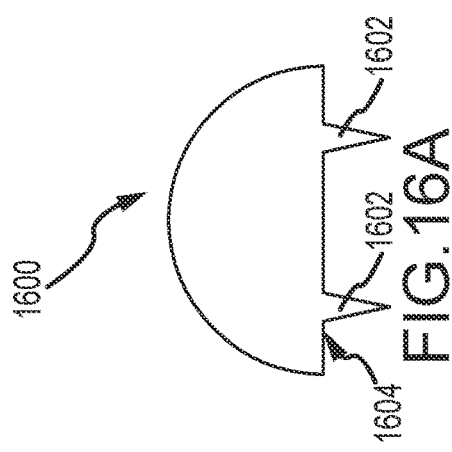
Figure 16C:
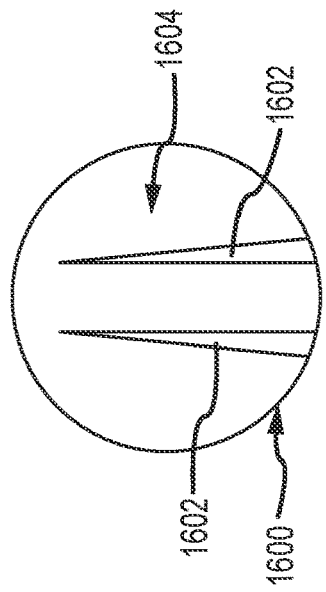
Figure 15:
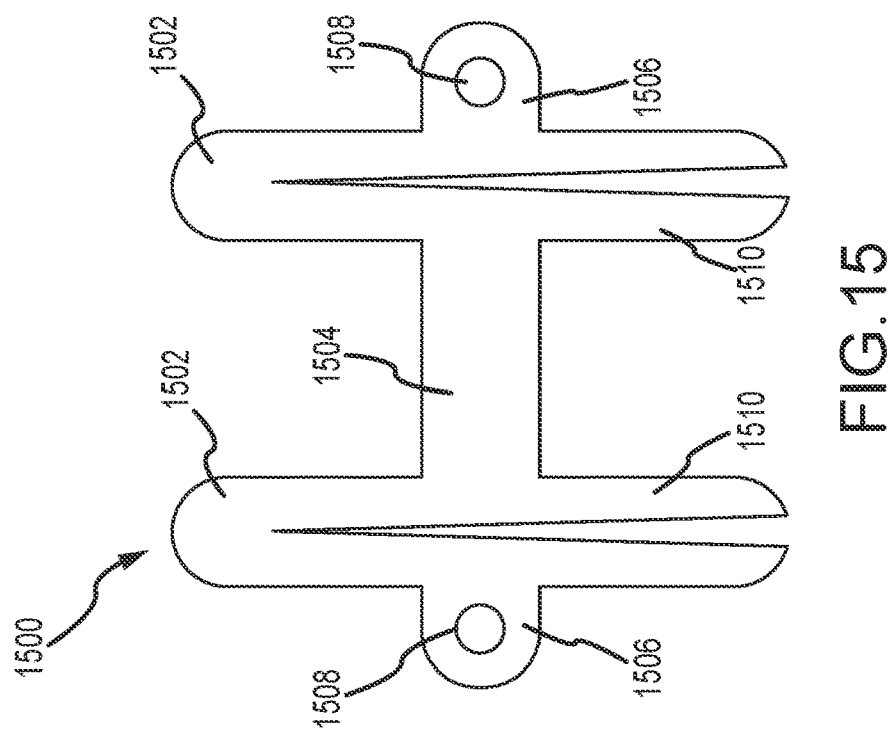
FIG. 15 is a top view of a base plate having a wedge shaped slot connection structure on a top surface thereof.

FIGS. 15 and 16A-16C show an additional or alternative arrangement of connection between a base plate 1500 and a humeral head implant 1600. FIG. 15 shows a top side of a base plate 1500 having a pair of body sections 1502 connected by a cross-member 1504, and a pair of flanges 1506 with bores 1508 extending through the flanges 1506. On each of the body section 1502 is a wedged-slot 1510 for receiving a corresponding wedged-fin 1602 on the bottom surface 1604 of the humeral head implant 1600 of FIGS. 16A-16C. FIG. 16A is a first side view of the implant 1600. FIG. 16B is a second side view of the implant 1600, rotated ninety degrees from the first side view. And FIG. 16C is a bottom or bone-facing view of the implant 1600. In operation, the implant 1600 of FIGS. 16A-16C can be fully seated or coupled with the base plate 1500 of FIG. 15 via transverse sliding of the implant 1600 relative to the base plate 1500 without application of orthogonal force. Thus, the implant 1600 can be coupled to the base plate 1500 via posterior-to-anterior sliding of the implant 1600 during surgery, thereby avoiding a need for orthogonal force application. Alternatively, the humeral head 1600 can be press fit into the humeral tracks directly as a uni-body construct forgoing the need of a base plate. This embodiment may have one or more tracks/fins.

The following includes a discussion of additional or alternative systems, devices, and methods for use in shoulder arthroplasty procedures. It is noted that features, elements, and/or steps of a method from the previous embodiments may be incorporated into the embodiments in the forthcoming disclosure without limitation. And features, elements, and/or steps of a method from the forthcoming disclosure may be incorporated into the embodiments disclosed previously without limitation.

FIGS. 17A-17C are flowcharts of an exemplary method 1700 of performing a shoulder arthroplasty procedure utilizing the systems and devices described herein. Reference will be made to these figures throughout the disclosure as the tools and systems are introduced and described.

FIGS. 18A-18E are, respectively, top, side, bottom, isometric exploded, and isometric views of a first embodiment of a reference guide 1800 (also known as an inclination guide). The reference guide 1800 includes a targeting arm 1802 and a sleeve or barrel 1804. The targeting arm 1802 has a curved section 1806 that terminates at a blunt tip 1808 having an indentation 1810 therein. Opposite the tip 1808, the curved section 1806 couples to a tubular handle 1812 that has a longitudinal opening or slot 1814. The sleeve 1804 includes a tubular body 1816, a stop structure 1818 at a proximal end thereof, and a bore 1820 extending longitudinally through the sleeve 1804. The bore 1820 is large enough to permit the passage and guidance of a guide pin. And when the sleeve 1804 is positioned within the tubular handle 1812 of the targeting arm 1802, as seen in FIG. 18E, a guide pin passing through the bore 1820 is targeted at the indentation at the blunt tip 1808 of the targeting arm 1802. This ensures the guide pin does not extend past the targeting arm 1802 and damage the soft tissue on the anterior side of the humeral head.

The curved section 1806 of the targeting arm 1806 is generally circular with a constant radius to accommodate fitting around most humeral heads, which are generally spherical in shape. In certain instances, there may be multiple sizes of targeting arms 1802 to accommodate different size humeral heads.

In certain instances, the shoulder joint may be too tight to accommodate placement of the targeting arm 1802 shown in FIGS. 18A-18E. In such a case, the targeting arm 1802a of FIGS. 18F-18J may be utilized. FIGS. 18F-18J are, respectively, top, side, bottom, isometric exploded, and isometric views of a second embodiment of a reference guide 1800a. The reference guide 1800a of FIGS. 18F-18J is the same as the reference guide 1800 in FIGS. 18A-18E, except for the targeting arm 1802a in FIGS. 18F-18J includes a curved section 1806a including a linear section 1822a. In this way, a distance between a pin axis extending through the bore 1820 of the sleeve 1804 to the indentation 1810, and the linear section 1822a is less than the radius associated with the curved section 1806 of the targeting arm 1802 of FIGS. 18A-18E. In certain instances, a preliminary cut to the pole of the humeral head may be performed to make way for positioning of the targeting arm 1802a around the humeral head.

FIG. 18K is a superior view of the humeral head 1850 with the first embodiment of the reference guide 1800 positioned around the humeral head 1850. It is noted that accessing the posterior humeral head is described previously and is not repeated in this section. It is assumed that the posterior aspect of the humeral head 1850 is accessed as previously described. Accordingly, block 1702 of the method 1700 of performing a shoulder arthroplasty of FIG. 17A may include positioning the targeting arm 1802 of the reference guide 1800 around the humeral head 1850, and orienting the bore 1820 of the sleeve 1804 at the posterior aspect of the humeral head 1850.

Block 1704 may include delivering a guide pin 1824 through the bore 1820 of the sleeve 1804 and into the posterior aspect of the humeral head 1850. This is shown in FIG. 18L, which is a superior view of the humeral head 1850 with the first embodiment of the targeting arm 1802 of the reference guide 1800 positioned around the humeral head 1850, and with a guide pin 1824 delivered into the posterior aspect of the humeral head 1850 via guidance by the reference guide 1800. It is noted that the blunt tip 1808 provides a stop in case the guide pin 1824 extends all the way through the humerus 1852, but the guide pin 1824 is not required to extend this far anteriorly.

Block 1706 may include retracting the sleeve 1804 from within the tubular handle 1812 thereby causing the guide pin 1824 to be removed from within the bore 1820 of the sleeve 1804. This can be seen in FIG. 18M, which is a posterior-medial view of the humeral head 1850 with the first embodiment of the targeting arm 1802 of the reference guide 1800 positioned around the humeral head 1850 and with the sleeve 1804 removed from the handle 1812. It can be seen that the guide pin 1824 is still positioned within the space previously occupied by the sleeve 1804.

Removal of the sleeve 1804 from the handle 1812 permits the removal of the targeting arm 1802 from being positioned around the humeral head 1850 while leaving the guide pin 1824 in place. Accordingly, block 1706 of the method 1700 of FIG. 17A may include removing the targeting arm 1802 from the humeral head 1850 while keeping the guide pin 1824 in position in the bone, as seen in FIG. 18N, which is a posterior-medial view of the humeral head 1850 with the guide pin 1824 remaining in the bone after removal of the targeting arm 1802 and sleeve 1804 of the reference guide 1800.

FIGS. 19A-19E are, respectively, isometric front, top, front, bottom, and isometric back views of a humeral head cutting guide 1900. The humeral head cutting guide 1900 includes an elongate body 1902 with a curvate front face 1904, and a curvate back face 1906. The curvate back face 1906 is contoured to generally match a curvature of a humeral head. The elongate body 1902 further includes a cutting slot 1908 extending from side edge 1910 to side edge 1910. The cutting slot 1908 is sized and shaped to accept a cutting element (e.g., saw blade) there through. The cutting slot 1908 includes parallel, planar cutting surfaces that oppose each other and defines a cutting plane so that a saw blade positioned therein will guide a resection of the bone along the cutting plane. The elongate body 1902 also includes pin guides in the form of bores 1912 extending from the front face 1904 to the back face 1906. One of the bores 1912 is centrally positioned along the length of the cutting slot 1908. Two bores 1912 are positioned near each of the ends of the cutting slot 1908. The bores 1912 may be positioned differently on the cutting guide 1900. The illustration in the figures is merely representative of one exemplary cutting guide 1900 with an arrangement of bores 1912.

The bores 1912 are sized and shaped to receive a guide pin there through. When a single guide pin is received within a bore 1912, the cutting guide 1900 may be rotated around the pin to adjust the varus-valgus cutting plane or humeral head-neck-shaft angle. When a second guide pin is delivered or received within another bore 1912, then the rotation of the cutting guide 1900 is restricted so as to permit guided cutting of the bone via the cutting slot. Stated another way, the first guide pin captures the inclination. Then, the cutting guide 1900 is placed over the first guide pin and is rotated clockwise or counterclockwise until the desired varus/valgus angle is achieved. This desired humeral head-neck-shaft angle is then locked into place with a second guide pin. Then the humeral head may be cut.

Referring to FIG. 17A, the method 1700 may include, at block 1708, positioning the cutting guide 1900 up to the posterior aspect of the humeral head 1850 by sliding the bore 1912 of the cutting guide 1900 along the guide pin 1824. This step can be seen in FIG. 19F, which is an isometric view of the cutting guide 1900 positioned on the posterior aspect of the humeral head 1850 with a first guide pin 1824 positioned through the bore 1912 of the cutting guide 1900. In this orientation, the angle of the cutting plane can be adjusted by pivoting or rotating the cutting guide 1900 about the pin 1824.

Figure 19A:
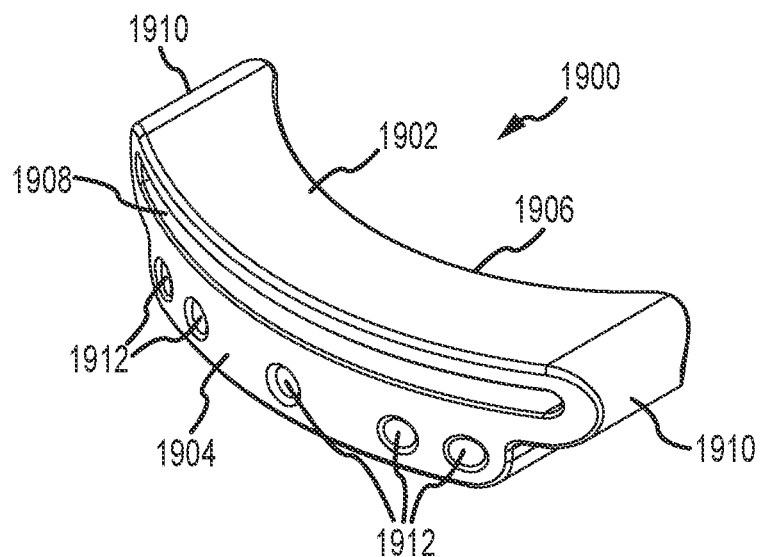
FIGS. 19A-19E are, respectively, isometric front, top, front, bottom, and isometric back views of a humeral head cutting guide.
Figure 19B:
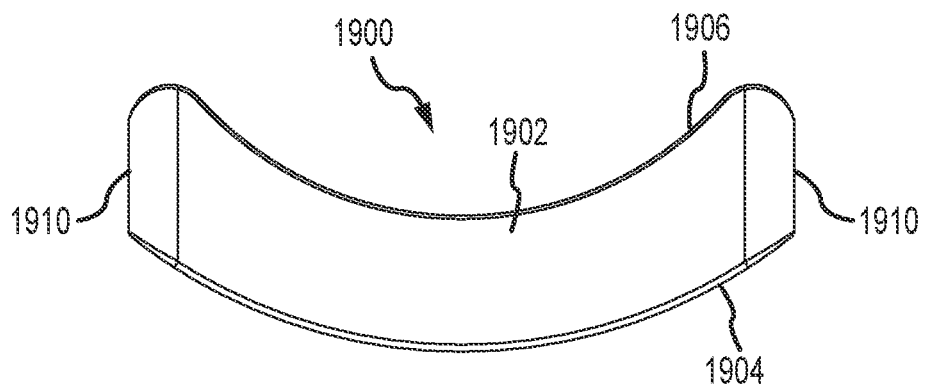
Figure 19C:
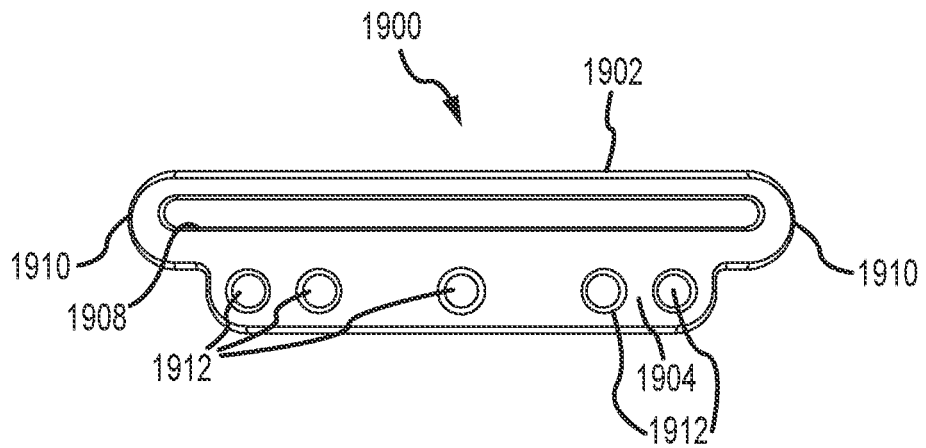
Figure 19D:
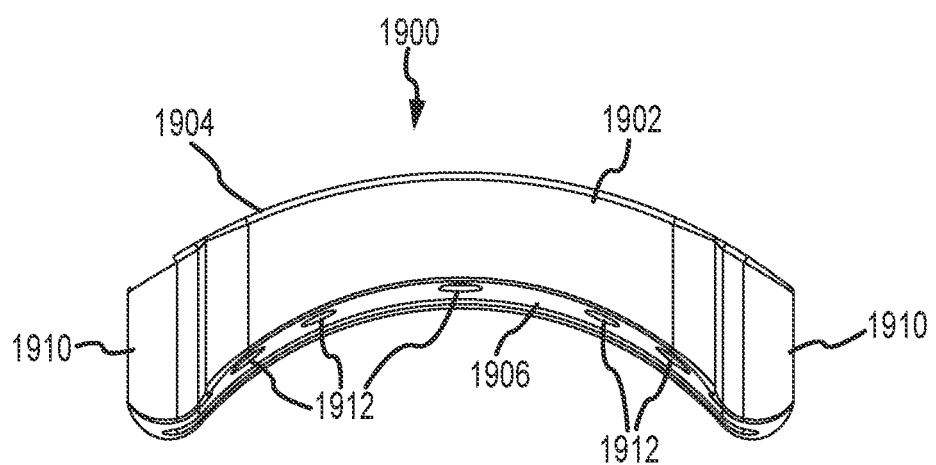
Figure 19E:
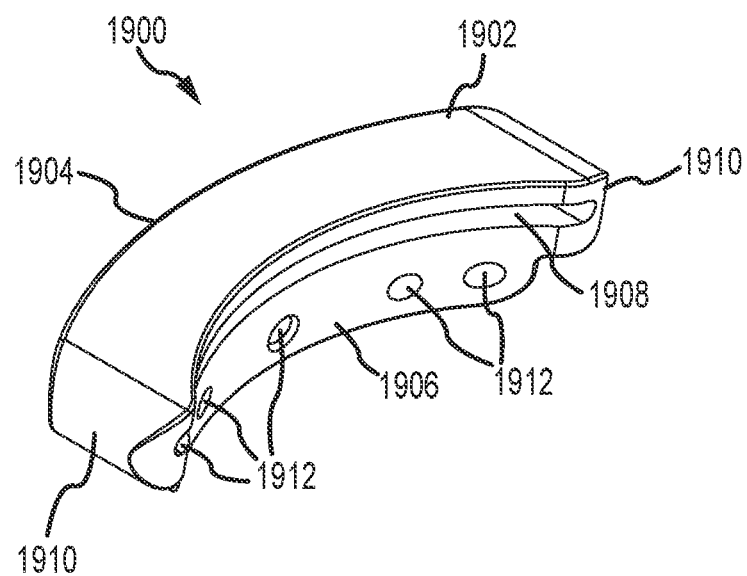
Figure 19G:
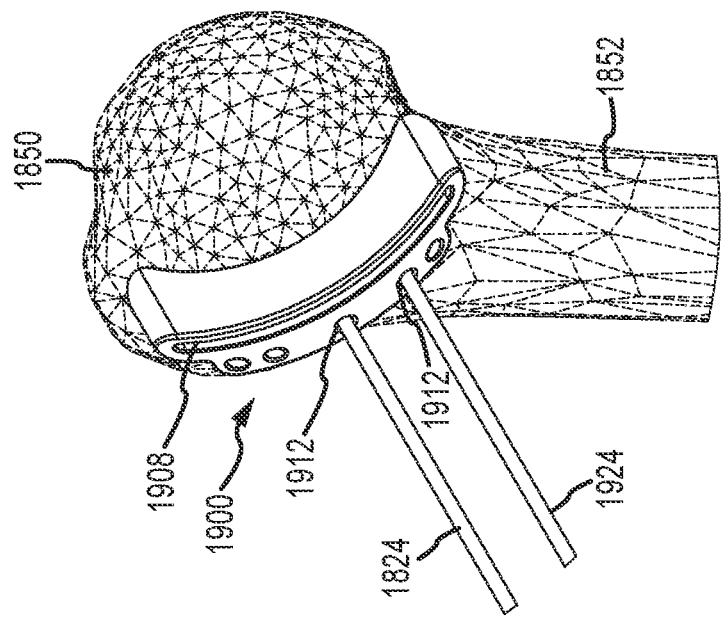
FIG. 19G is an isometric view of the cutting guide positioned on the posterior aspect of the humeral head with a second guide pin delivered through the guide and into the bone.
Figure 19F:
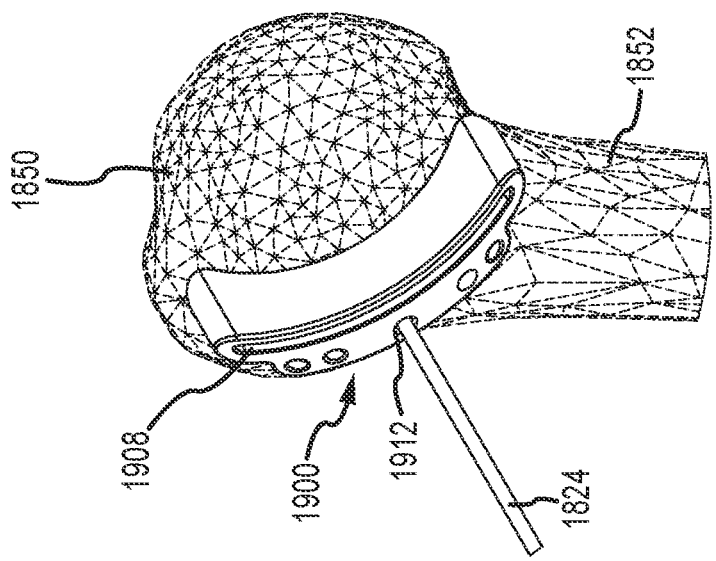
FIG. 19F is an isometric view of the cutting guide positioned on the posterior aspect of the humeral head with a first guide pin positioned through the cutting guide.

Once, the cutting plane is determined, a second guide pin 1924 may be delivered through a second bore 1912 of the cutting guide 1900 to lock the orientation of the cutting guide 1900 relative to the humeral head 1850, seen in block 1710 of FIG. 17A. This step is illustrated in FIG. 19G, which is an isometric view of the cutting guide 1900 positioned on the posterior aspect of the humeral head 1850 with a second guide pin 1924 delivered through a second bore 1912 of the guide 1900.

Figure 19I:
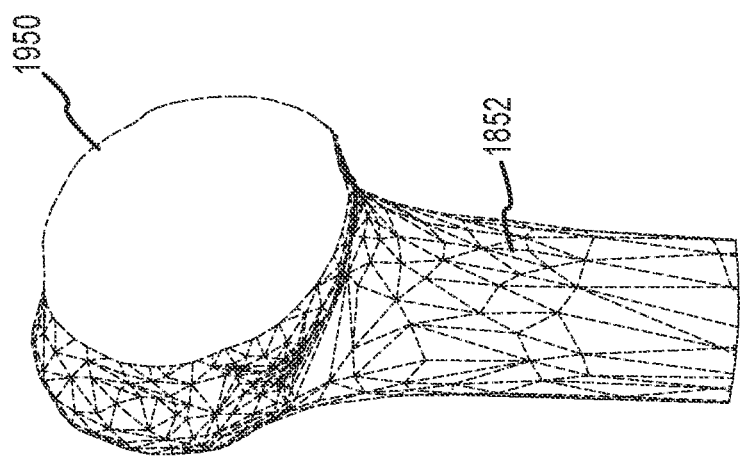
FIG. 19I is a posterior-medial view of the humeral head following the resection and with the cutting guide and first and second guide pins removed from the bone.
Figure 19H:
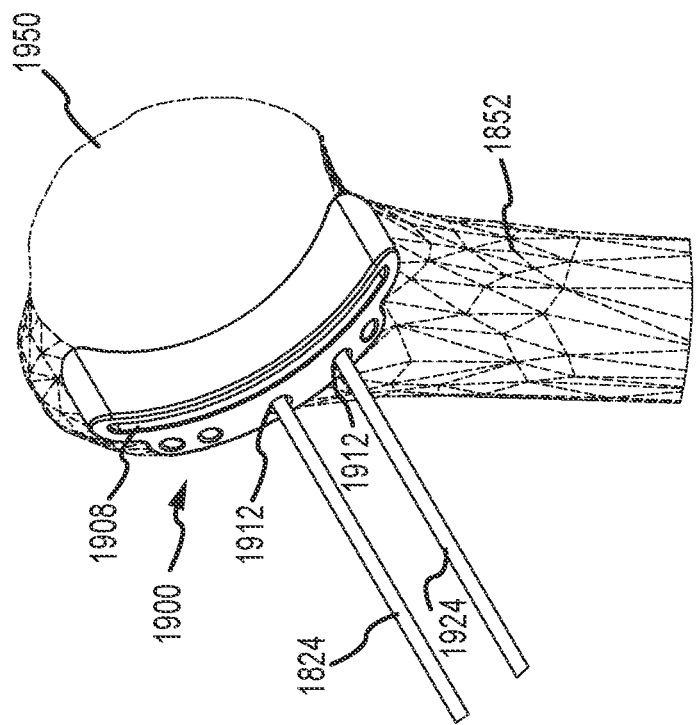
FIG. 19H is an isometric view of the cutting guide positioned on the posterior aspect of the humeral head, and showing the humeral head following a resection so as to form a resected bone surface.
Figure 20B:
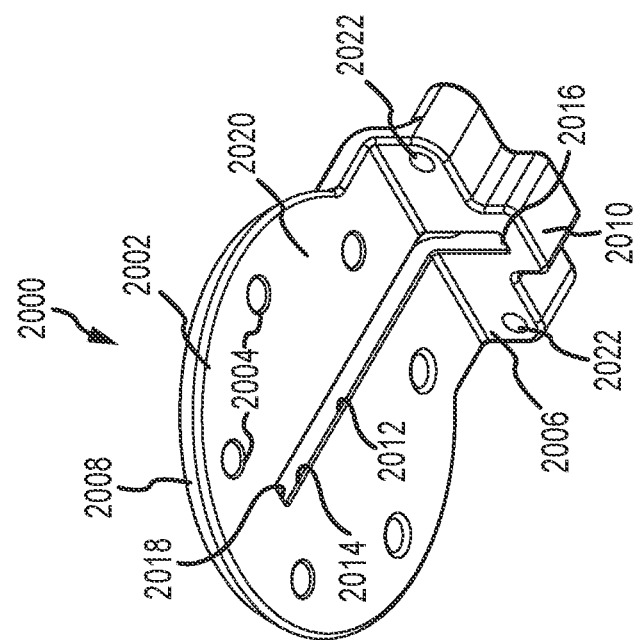
FIGS. 20A-E are, respectively, top isometric, bottom isometric, top, front and bottom views of a channel guide.
Figure 20A:
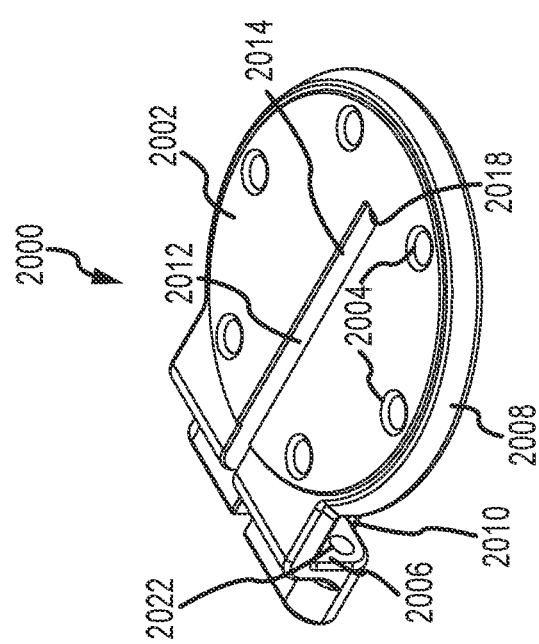
Figure 20C:
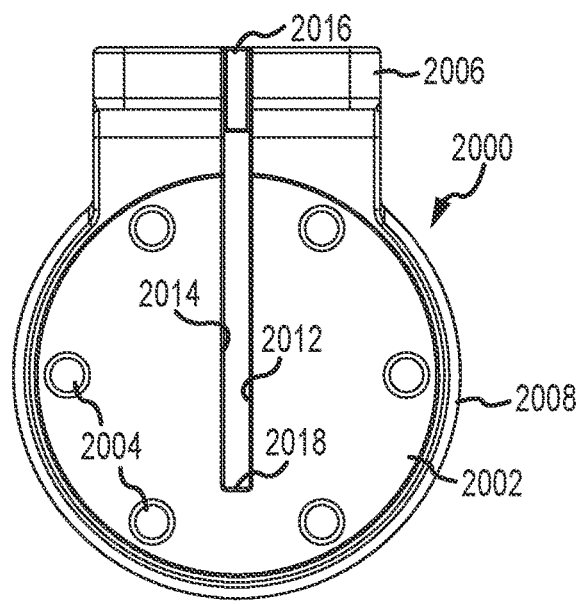
Figure 20D:
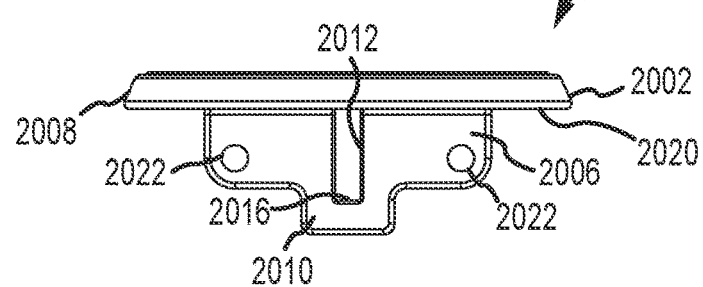
Figure 20E:
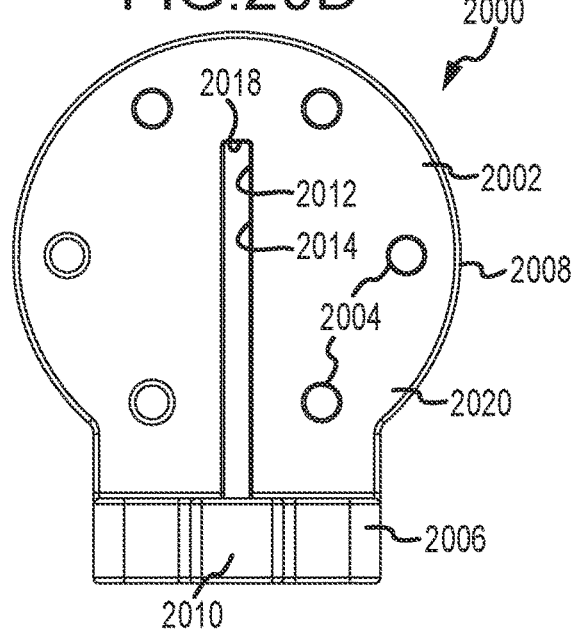

Block 1712 of the method 1700 of FIG. 17B includes resecting the humeral head 1850 with a cutting tool (e.g., saw blade) that is guided by the cutting slot 1908 of the cutting guide 1900. This step is illustrated in FIG. 19H, which is an isometric view of the cutting guide 1900 positioned on the posterior aspect of the humeral head 1850, and showing a resected bone surface 1950 formed by the resection.

Block 1714 of the method 1700 of FIG. 17B includes removing the cutting guide 1900 from the guide pins 1824, 1924, and, in some instances, removing the guide pins 1824, 1924 from the bone. This step is illustrated by FIG. 19I, which is a posterior-medial view of the humeral head following the resection and with the cutting guide 1900 and first and second guide pins 1824, 1924 removed from the bone.

FIGS. 20A-E are, respectively, top isometric, bottom isometric, top, front and bottom views of a size and fin guide, also known as a channel guide, 2000. The size and fin guide 2000 may help guide the location of the central fin of a base plate and help measure the size of the humeral head for the purposes of implant sizing. As seen in the figures, the size and fin guide 2000 includes a circular plate 2002 having anchor bore indicators 2004 positioned around a perimeter thereof for the surgeon to see where corresponding anchors will be placed once the base plate is used. The plate 2002 is coupled to an angle element 2006 that extends off of the perimeter 2008 in a parallel orientation and then angles generally perpendicular to the plate 2002. The angle element 2006 includes an extended portion 2010 that is centrally positioned and that extends downwardly. A channel slot 2012 is formed within the angle element 2006 and the plate 2002. The channel slot 2012 is bounded by a pair of parallel, planar longitudinal edges 2014, a depth stop 2016 within the angle element 2006, and an anterior stop 2018 within the plate 2002.

The size and fin guide 2000 also includes a pair of pin guides in the form of bores 2022. A bore 2022 is positioned on the angle element 2006 on either side of the channel slot 2012. The bores 2022 are sized and shaped to receive a guide pin there through to orient the plate 2002 on the resected bone surface and to orient the channel slot 2012 for cutting a channel through the posterior cortical bone and through the resected bone surface. The channel can be cut into generally a central portion of the resected bone surface at a point posterior to the anterior margin of the resected bone surface.

The size and fin guide 2000 is sized and shaped so that a bottom surface 2020 of the plate 2002 can be positioned on the resected bone surface with the angle element 2006 lipped over the edge of the resected bone surface and acting as a stop to prevent further anterior placement. The guide 2000 may have a thickness and sphericity (matching radius of curvature) to match the natural residual humeral head arc. In a certain instance, the guide 2000 may be a 40 mm guide having a 3 mm thickness and a 40 mm diameter or curvature of the perimeter 2008 in order to match the size of the patient's resected bone perimeter and help guide proper humeral head replacement sizing and sphericity and thickness. The size of channel slot 2012 for a 40 mm guide 2000 will be a certain size, whereas the size of the channel slot 2012 for a smaller guide 2000 may be smaller. Similarly, the size of channel slot 2014 for a guide 2000 larger than 40 mm may be larger.

Block 1716 of the method 1700 of FIG. 17B includes determining a size of guide 2000 to be used by placing the plate 2002 flat on the resected bone surface and placing the guide 2000 as far superiorly as possible without overhang. In certain instances, the largest size of guide 2000 will be chosen that does not have any overhang. This step is illustrated in FIG. 20F, which depicts an isometric view of the size and fit guide 2000 positioned on the resected surface 1950 of the humerus 1852. As seen in the figure, there is no overhang of the perimeter 2008 over the edge of the resected bone surface 1950. The guide 2000 is oriented such that the channel slot 2014 is aligned parallel with a posterior-anterior direction.

Block 1718 of the method 1700 of FIG. 17B includes delivering first and second guide pins 1824, 1924 through the bores 2022 of the guide 2000 and into the bone 1852 on a posterior side thereof. It is noted that in certain instances, the pins 1824, 1924 may have remained in the bone following the use of the cutting guide 1900. In such an instance, the fit and size guide 2000 may be slid over and onto the pins 1824, 1924. FIG. 20G depicts an isometric view of the fit and size guide 2000 positioned on the resected surface 1950 of the humerus 1852 with the first and second guide pins 1824, 1924 extending through bores 2022 of the guide 2000.

Block 1720 of the method 1700 of FIG. 17B includes cutting a channel 2024 into the posterior cortical bone 2026 and the resected bone surface 1950 via guidance by the channel slot 2014. It is noted that the depth of the cut is limited via the depth stop 2016 within the angle element 2006, and the length of the cut in the anterior direction is limited via the anterior stop 2018 within the plate 2002.

Block 1722 of the method 1700 of FIG. 17C includes removing the fin and size guide 2000 from the pins 1824, 1924, and also removing the pins 1824, 1924. FIG. 20H depicts a posterior-medial view of the humerus 1852 showing the channel cut 2024 formed in the resected bone surface 1950 and through the posterior cortical bone 2026 that was guided by the guide 2000.

FIGS. 21A-21D are, respectively, top, side, bottom, and bottom isometric views of a base plate insertion device 2100. The device 2100 includes a base plate engagement structure 2102 at a distal end, and a handle 2104 at a proximal end. The engagement structure 2102 includes a C-shaped plate 2106 defining a void 2108 at a central portion thereof. On a bottom surface 2110 of the plate 2106 and near each of the distal tips of the C-shaped plate 2106 is a nub or protrusion 2112 extending away from the bottom surface 2110. The nubs 2112 are sized and shaped to be received in a corresponding recess of a top surface of a base plate (not shown) to facilitate coupling of the insertion device 2100 to the base plate. Opposite the nubs 2112 on the bottom surface 2110 of the plate 2106 is a cylindrical wall 2114 that extends downward form the bottom surface 2110 and has a radius of curvature matching the C-shaped plate 2106. The cylindrical wall 2114 is sized and shaped to match the perimeter of the base plate. And positioned proximal of the cylindrical wall 2114 and extending farther away from the bottom surface 2110 is a stop element 2116. The stop element 2116 is sized and shaped to contact the posterior surface of the humerus and prevent further anterior movement of the base plate and the insertion device 2100.

Figure 21E:
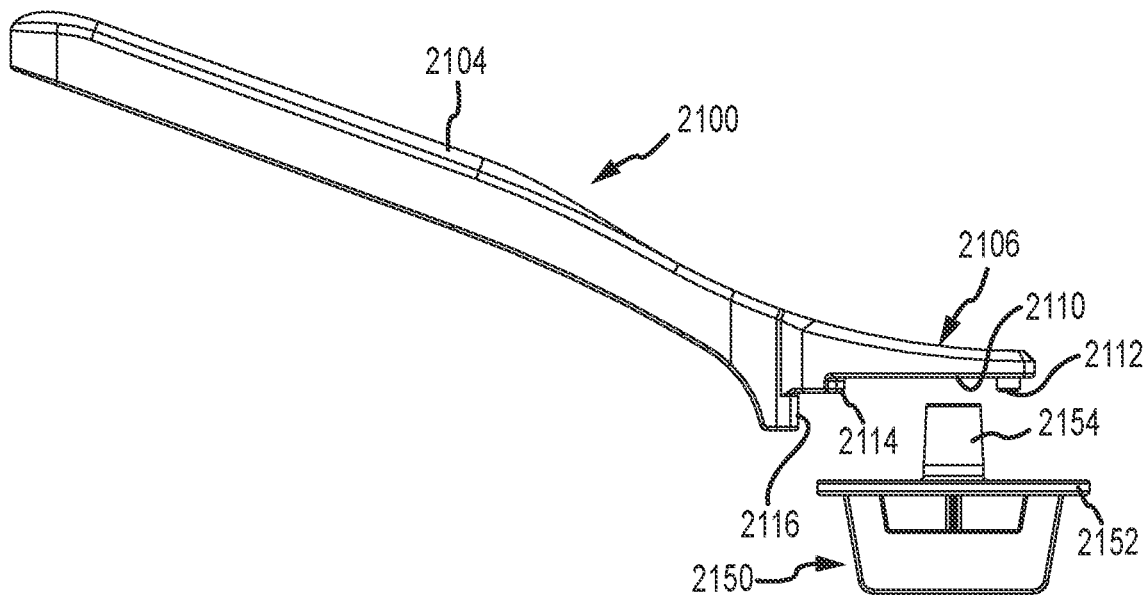
FIGS. 21E-21G are, respectively, side, top isometric, and bottom isometric views of the base plate insertion device positioned relative to the base plate.
Figure 21F:
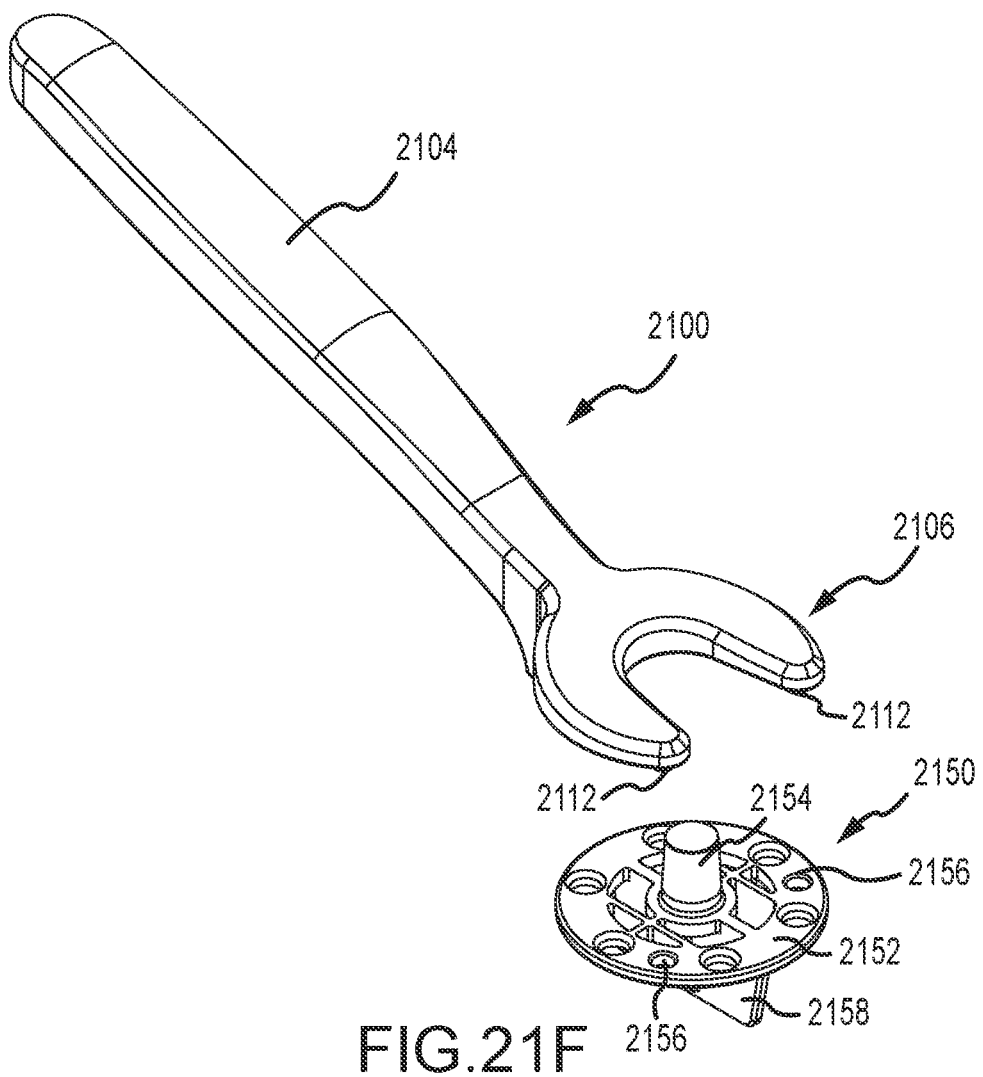
Figure 21G:
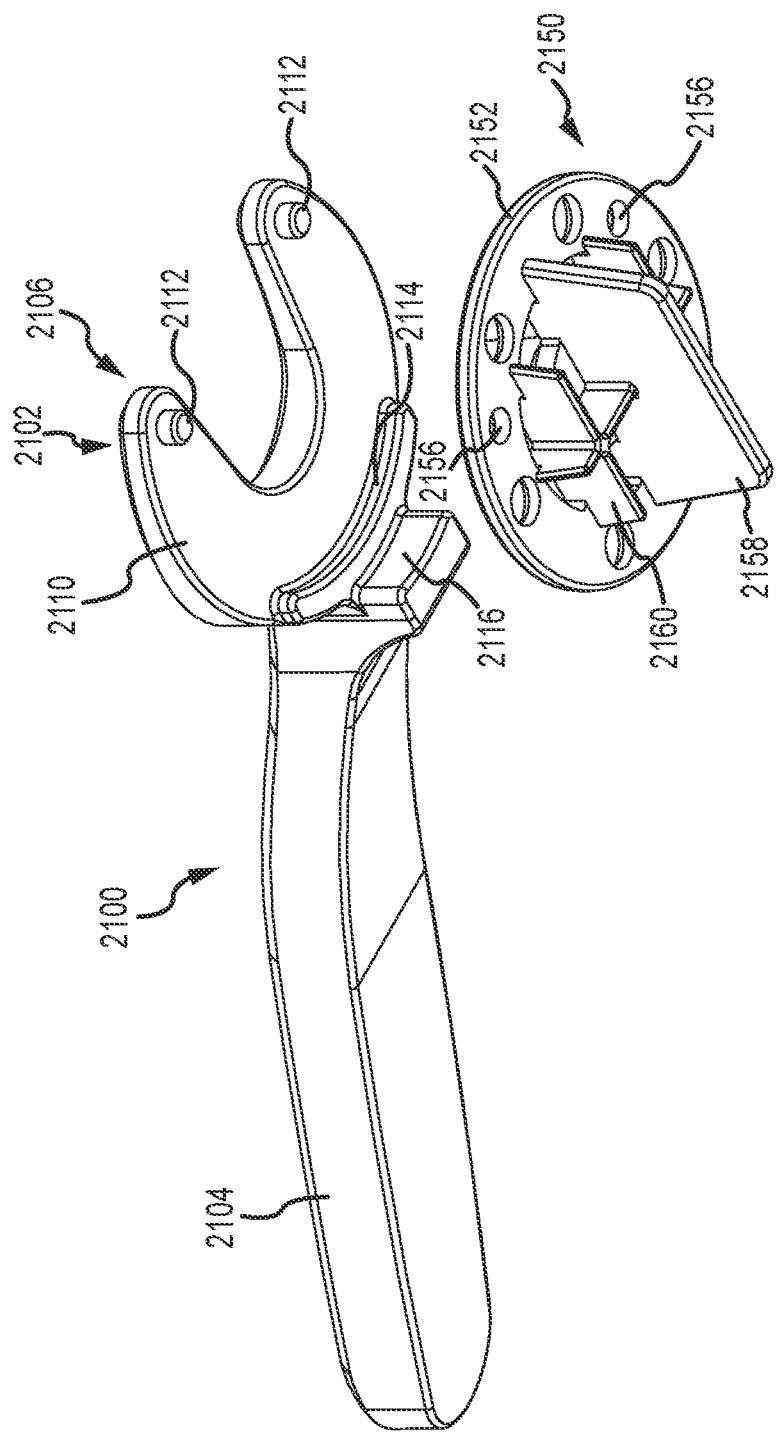

FIGS. 21E-21G depict, respectively, side, top isometric, and bottom isometric views of the base plate insertion device 2100 positioned relative to an exemplary base plate 2150. As seen in FIGS. 21E and 21F, the base plate 2150 includes a base structure 2152 having a circular perimeter, and a male taper or trunnion 2154 extending upwards from the base structure 2152. The male taper or trunnion 2154 is the part of the base plate 2150 that is inserted into a humeral head implant and provides humeral head fixation to the baseplate. The term "male taper" refers to its protruding nature and its rise from the base structure 2152 outward. The male taper 2154 fits within the void 2108 of the C-shaped plate 2106 when the device 2100 is coupled to the base plate. The base plate 2150 may also include a pair of recesses 2156 sized and shaped to receive the nubs 2112 of the device 2100, as seen in FIGS. 21F and 21G. In certain instances, the base plate 2150 may not include the recesses 2156.

Figure 21H:
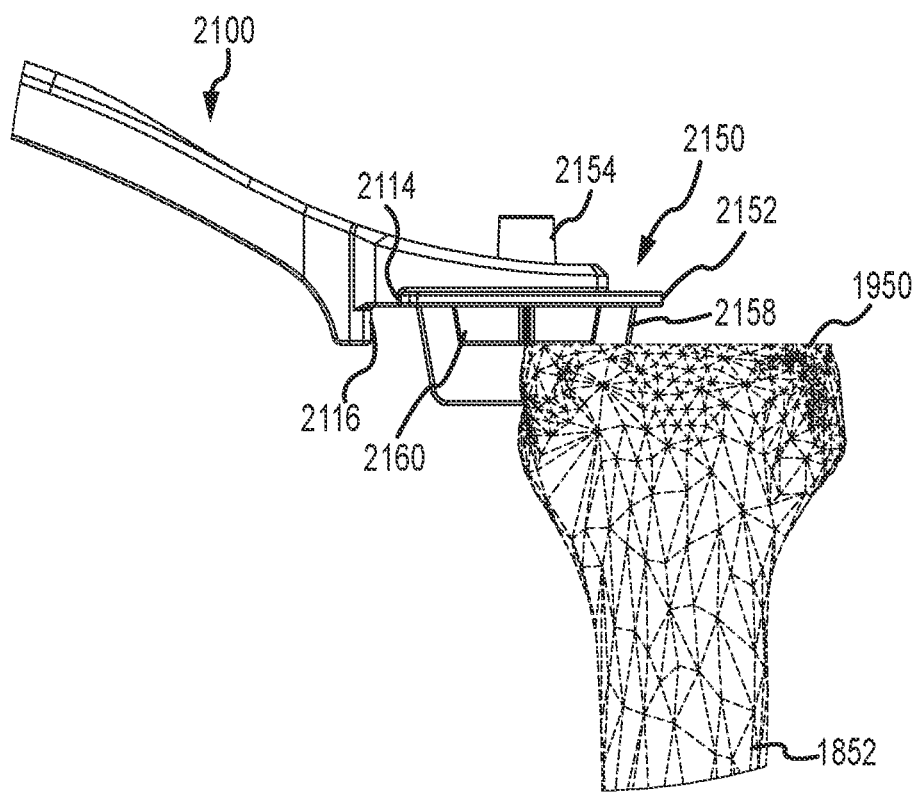
FIG. 21H is a side view of the base plate insertion device coupled with the base plate, and engaging the fin of the base plate with the channel cut formed in the resected bone surface of the humerus.

As seen in FIGS. 21F-21H, the base plate 2150 includes a central fin 2158 extending downward from the base structure 2152, and an attachment structure 2160 in the form of a pair of smaller fins, one positioned on each side of the central fin 2158, and one fin extending generally perpendicular to the central fin 2158 and the smaller fins. The central fin 2158 may be considered a major fin, and the smaller fins of the attachment structure 2160 may be considered minor fins. The major fin, being longer than the minor fins, may be used to guide the base plate within the channel cut in the resected bone surface. And when the base plate 2150 is correctly positioned atop the resected bone surface, the base plate 2150 may be driven into the bone so as to cause the attachment structure to affix to the bone.

Block 1724 of the method 1700 of FIG. 17C includes the steps of coupling the base plate 2150 to the insertion device 2100, inserting the major fin 2158 into the channel cut 2024, and sliding the base plate 2150 in a posterior-to-anterior direction. This step is illustrated in FIG. 21H, which depicts a side view of the base plate insertion device 2100 coupled with the base plate 2150, and engaging the major fin 2158 of the base plate 2158 with the channel cut 2024 formed in the resected bone surface 1950 of the humerus 1852. As seen in the figure, the attachment structure 2160 (minor fins) are positioned above the resected bone surface 1950 so as to permit sliding of the base plate 2150 with the major fin 2158 positioned in the channel cut 2024. In this position, the perimeter of the base structure 2152 is in contact with the matching radiused cylindrical wall 2114, the trunnion 2154 is positioned within the void 2108 of the C-shaped plate 2106, and the nubs (not seen) are positioned within the recesses (not seen) in the base plate 2150.

Figure 21I:
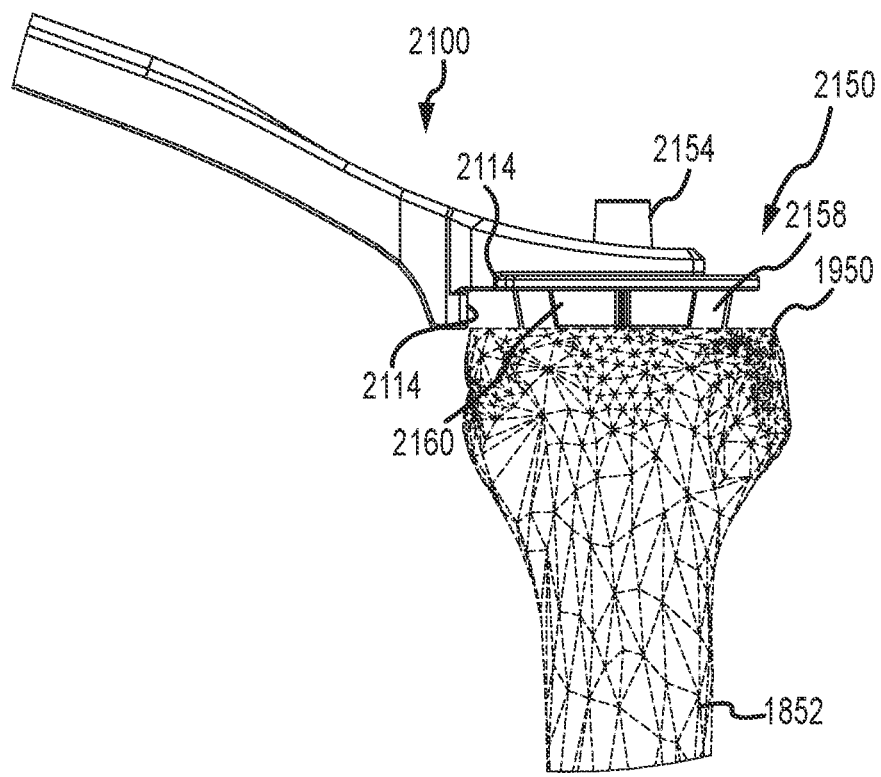
FIG. 21I is a side view of the base plate insertion device coupled with the base plate, with the base plate further slid into the channel cut in a posterior-to-anterior direction.

Block 1726 of the method 1700 of FIG. 17C includes sliding the base plate 2150 with the insertion device 2100 till the base plate 2150 is centrally positioned relative to the resected bone surface 1950. In this position, the distal end of the major fin 2158 should be adjacent the end of the channel cut 2024. Also, in this position, as seen in FIG. 21I, the stop element 2116 is aligned with the edge of the posterior surface of the humerus and provide visual and/or tactile feedback to the surgeon to stop anterior movement of the base plate with the insertion device 2100. FIG. 21I illustrates block 1726 and shows a side view of the base plate insertion device 2100 coupled with the base plate 2150, with the base plate 2150 further slid into the channel cut 2024 in a posterior-to-anterior direction.

Figure 21J:
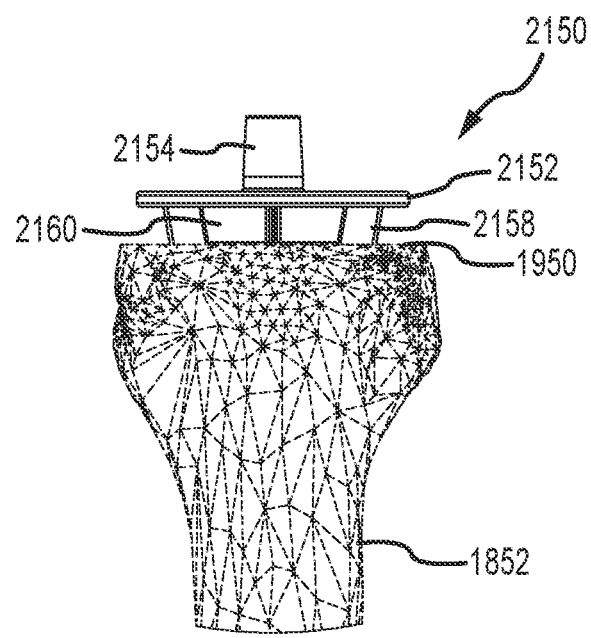
FIG. 21J is a side view of the base plate positioned centrally within the resected bone surface of the humerus with the base plate insertion device decoupled therefrom.
Figure 21K:
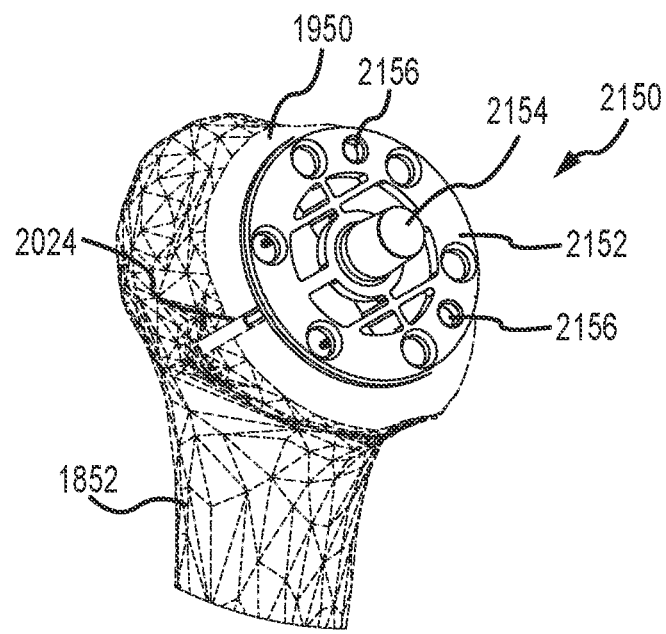
FIG. 21K is an isometric view of the base plate positioned on the resected bone surface of the humerus with the base structure of the base plate positioned proud of the resected bone surface.

Block 1728 of the method 1700 of FIG. 17C includes decoupling the base plate insertion device 2100 from the base plate 2150. This step is illustrated in FIGS. 21J and 21K. FIG. 21J is a side view of the base plate 2150 positioned centrally within the resected bone surface 1950 of the humerus 1852 with the base plate insertion device (not shown) decoupled therefrom. FIG. 21K is an isometric view of the base plate 2150 positioned on the resected bone surface 1950 of the humerus 1852 with the base structure 2152 of the base plate 2150 positioned proud (above) of the resected bone surface 1950.

Figure 22A:
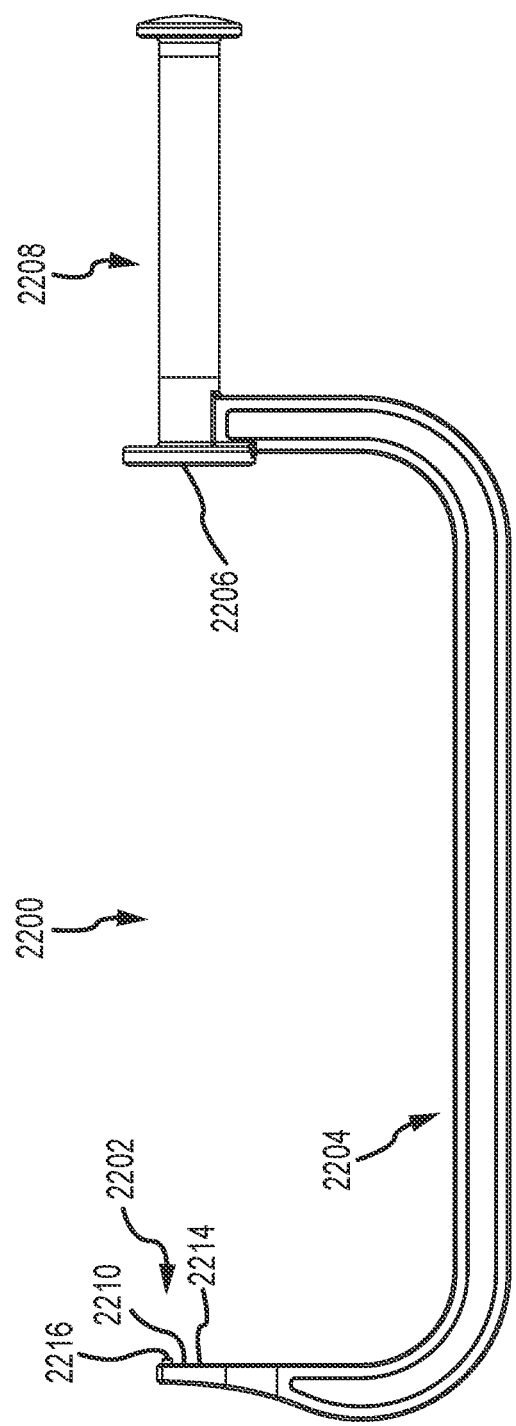
FIGS. 22A-22C are, respectively, side, isometric, and distal end close-up views of a base plate impaction device.
Figure 22B:
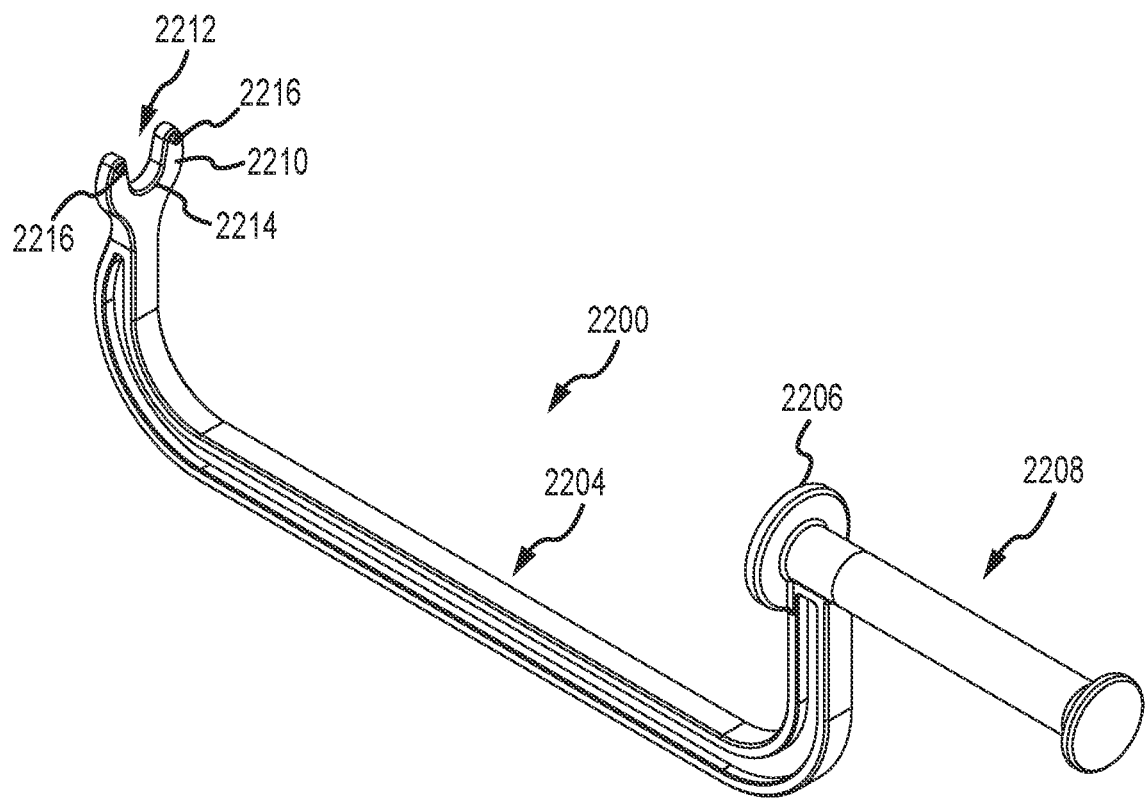
Figure 22C:
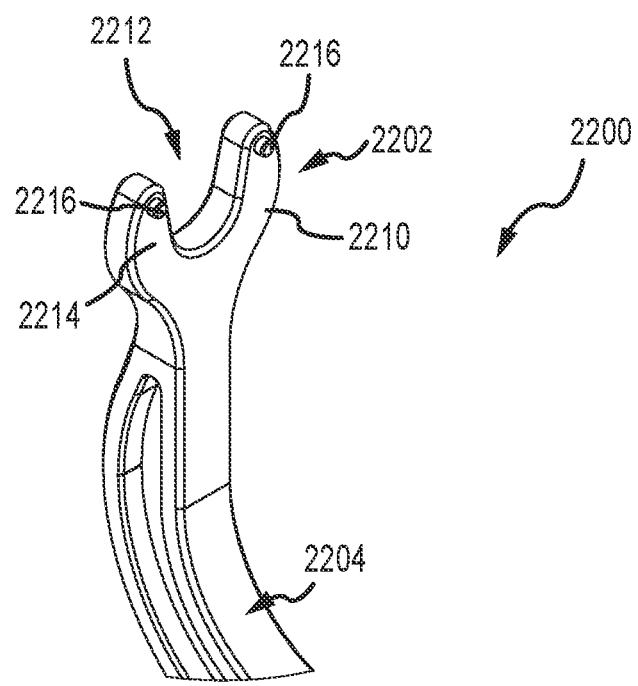

FIGS. 22A-22C are, respectively, side, isometric, and distal end close-up views of a base plate impaction device 2200. As seen in FIGS. 22A and 22B, the device 2200 includes a base plate engagement structure 2202 at a distal end, a C-shaped arm 2204 proximally of the engagement structure 2202, an impaction plate 2206, and a handle 2208 at a proximal end. The engagement structure 2102 includes a C-shaped plate 2210 defining a void 2212 at a central portion thereof. On a bottom surface 2214 of the plate 2206 and near each of the distal tips of the C-shaped plate 2206 is a nub or protrusion 2216 extending away from the bottom surface 2214. The nubs 2216 are sized and shaped to be received in a corresponding recess of a top surface of a base plate (not shown) to facilitate coupling of the impaction device 2200 to the base plate.

The engagement structure 2202 is generally coaxial with the impaction plate 2206, and the handle 2208, which is positioned directly beneath the impaction plate 2206. In this way, as a surgeon impacts the impaction plate 2206, the force is transmitted through the C-shaped arm 2204 and to the engagement structure 2202, which puts a compressive force on the base plate. FIG. 22C is a close-up view of the engagement structure 2202. And it can be appreciated that the general size and shape is similar to the engagement structure 2102 of the insertion device 2100 described previously since both devices are designed to couple to the base plate 2150.

Figures 22D, 22E:
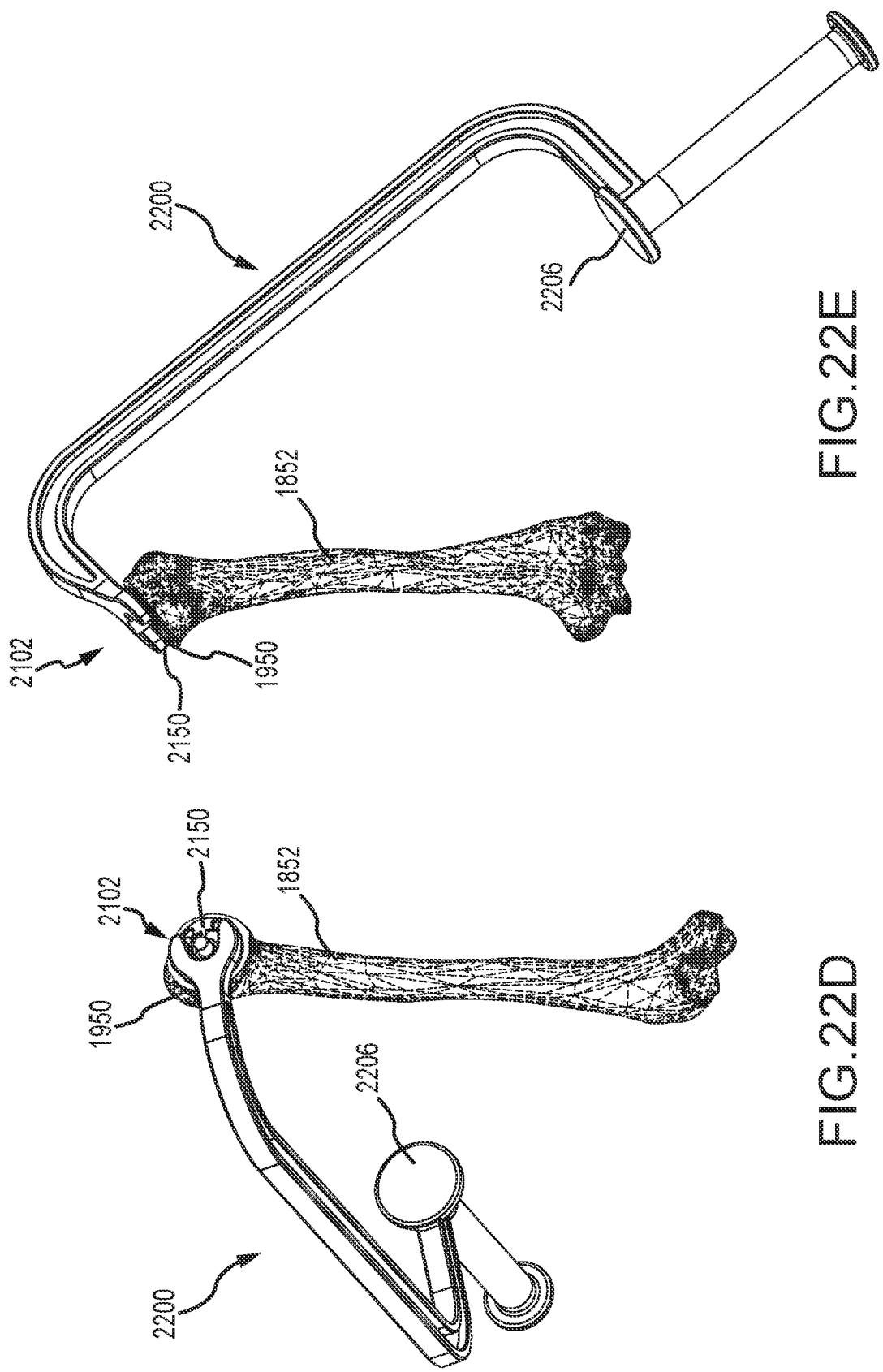
FIG. 22D is an isometric view of the base plate impaction device with the distal engagement structure in contact with the base plate.
FIG. 22E is another isometric view of the base plate impaction device with the distal engagement structure in contact with the base plate.

FIG. 22D is an isometric view of the base plate impaction device 2200 with the distal engagement structure 2102 in contact with the base plate. And, FIG. 22E is another isometric view of the base plate impaction device with the distal engagement structure in contact with the base plate. It can be seen by the relative size of the impaction device 2200 that the impaction plate 2206 is positioned away from the access area of the posterior shoulder so as to permit application of force to the device 2200.

Block 1730 of the method 1700 of FIG. 17C may include the step of engaging the distal engagement structure 2102 of the base plate impaction device 2200 with the base plate 2150, and impacting the impaction plate 2206 of the device 2200 until the base plate 2150 is fully impacted into the resected bone surface 1950 of the humerus 1852. During impaction, the attachment structure (not seen) of the base plate 2150 cuts into the resected bone surface 1950.

Following impaction of the base plate 2150 into the resected bone surface 1950, the impaction device 2200 may be removed from the access area. And, if needed or desired based on the patient's bone morphology or otherwise, anchors or fasteners 2300 may be used to secure the base plate 2150 to the resected bone surface 1950. Thus, as seen in FIG. 17C, block 1732 of the method 1700 may include anchoring the base plate 2150 to the resected bone surface 1950 via one or more fasteners 2300. Fasteners can be compression screws, locking screws, variable angle locking screws or pegs.

Figure 23A:
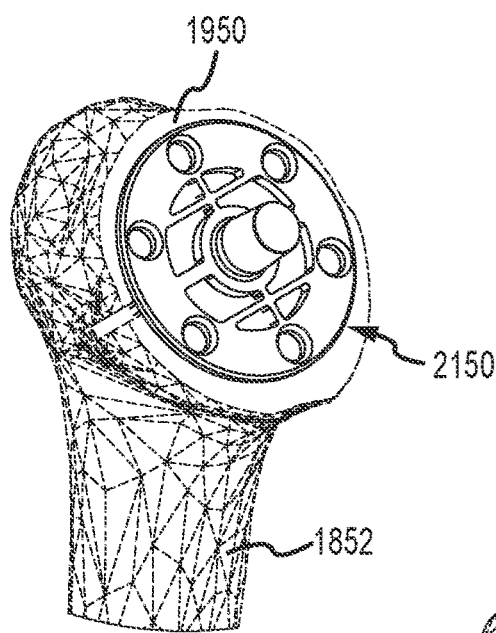
FIG. 23A is a posterior-medial view of the humerus with the base plate positioned thereon following impaction by the impaction device.
Figure 23B:
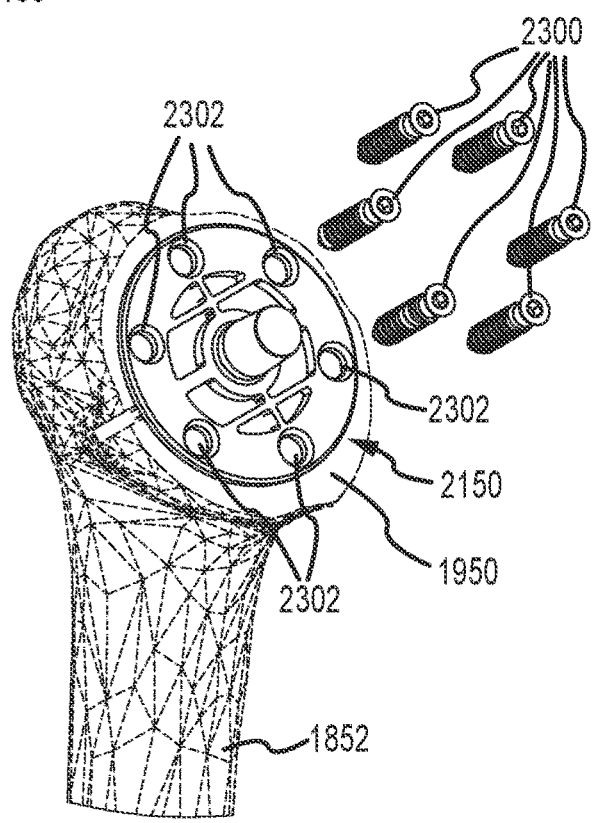
FIG. 23B is a posterior-medial view of the humerus with the base plate positioned thereon following impaction by the impaction device, and showing six bone fasteners about to fasten the base plate to the resected bone surface.
Figure 23C:
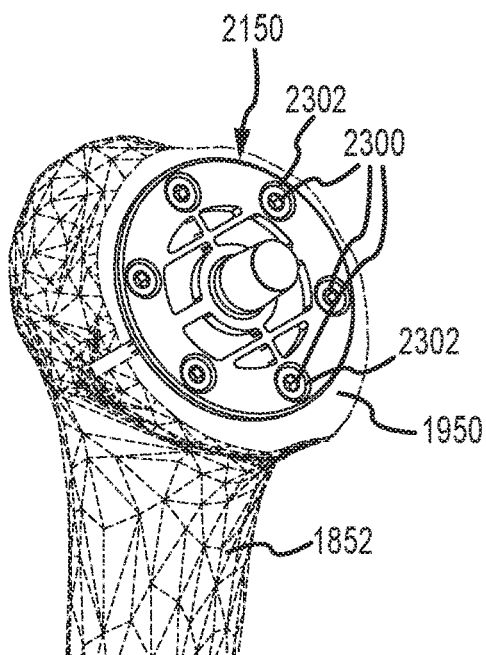
FIG. 23C is a posterior-medial view of the humerus with the base plate positioned thereon following impaction by the impaction device, and showing the six bone fasteners driven into the resected bone surface to secure the base plate to the bone.

To that end, reference is made to FIGS. 23A-23C. FIG. 23A is a posterior-medial view of the humerus 1852 with the base plate 2150 positioned thereon following impaction by the impaction device (not shown). FIG. 23B is a posterior-medial view of the humerus 1852 with the base plate 2150 positioned thereon following impaction, and showing six bone fasteners 2300 about to fasten the base plate 2150 to the resected bone surface 1950. And, FIG. 23C is a posterior-medial view of the humerus 1852 with the base plate 2150 positioned thereon, and showing the six bone fasteners 2300 driven through anchor bores 2302 of the base plate 2150 and into the resected bone surface 1950 to secure the base plate 2150 to the bone. It is noted that various base plate 2150 designs are possible and contemplated herein. For instance, a base plate 2150 may have more or less anchor bores 2302, and may be anchored to the bone in different ways than illustrated herein.

Following the fastening of the base plate 2150 to the humerus, the method may include, at block 1734 of the method 1700 of FIG. 17, attaching the humeral head implant to the base plate 2150.

The following includes descriptions of various base plate designs that may be utilized with the systems, devices, and methods described herein. It is noted that these disclosed embodiments are exemplary and intended to be construed broadly so as to encompass variations and substitutions from the various embodiments disclosed herein.

To begin, reference is made to FIGS. 24A-24E, which are, respectively, top isometric, bottom isometric, top, side, and bottom views of a base plate 2400 having a single, angled fin 2402. As seen in the figures, the base plate 2400 includes a base structure 2404 having a circular perimeter 2406, anchor bores 2408 extending through the base structure 2404, and a male taper or trunnion 2410 extending upward from the top surface of the base structure 2404. The fin 2402 is on the opposite side of the base structure 2404 from the trunnion 2410.

As seen in the figures, the fin 2402 is angled with the deepest part of the fin towards a forward or anterior end 2412 of the base plate 2400, and with the smallest part of the fin towards a back or posterior end 2414 of the base plate 2400. And the anchor bores 2408, in this instance four of them, are situated on the posterior end 2414 of the base plate 2400. Performing a de cote surgery from the posterior side of the patient provides the largest access to the humerus on the posterior side of the bone. Thus, the anchor bores 2408 are situated on the posterior side of the bone for ease of access when fastening anchors through the bores 2408.

The method of performing the surgery with a base plate 2400 having an angled fin 2402 may be modified as follows. The size and fin guide, described with reference to FIGS. 20A-20H, may be used to guide the channel cut into the bone. But, in preparation for a base plate 2400 having an angled fin 2402, the surgeon may cut a deeper channel cut into the anterior portion of the cut, and a shallower cut into the posterior portion of the channel cut in order to match the angled nature of the fin 2402, which is deeper at the anterior end 2412 and shallower at the posterior end 2414. When prepared in this way or otherwise, the base plate 2400 may be delivered and impacted into the resected bone surface in a single step. The longitudinal edge 2416 of the fin 2402 may be set into the channel cut, and the base plate 2400 may be impacted with a diagonal impaction where the base plate 2400 impacts about the posterior end 2414 with the deep end of the fin 2402 impacting into the deepest part of the channel cut at the anterior end of the cut. Thus, in this method of attaching the base plate 2400 to the resected bone surface, there is no need for parallel sliding of the base plate 2400 into the central portion of the resected bone surface. Instead, the base plate 2400 need only be initially placed in the central position, and impacted at an angle so the base plate 2400 impacts into the bone surface. And once impacted into the bone, anchors or fasteners may be delivered through the bores and into the bone.

Figure 24A:
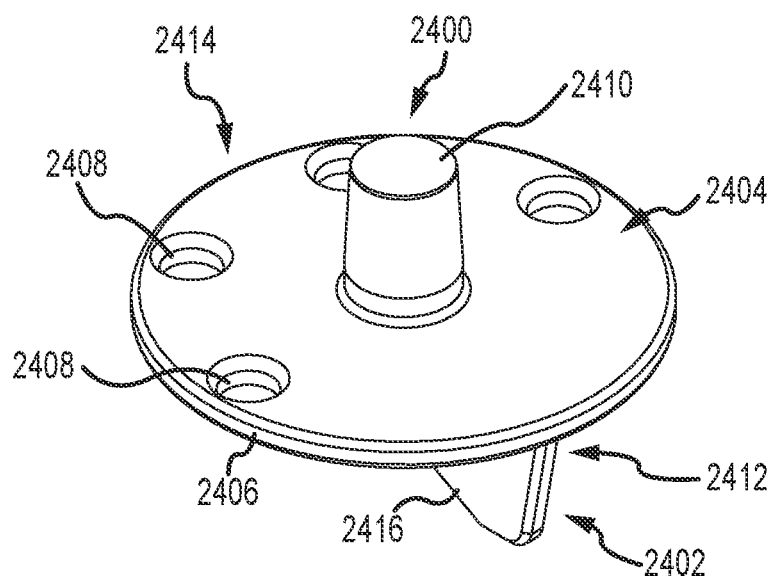
Figure 24B:
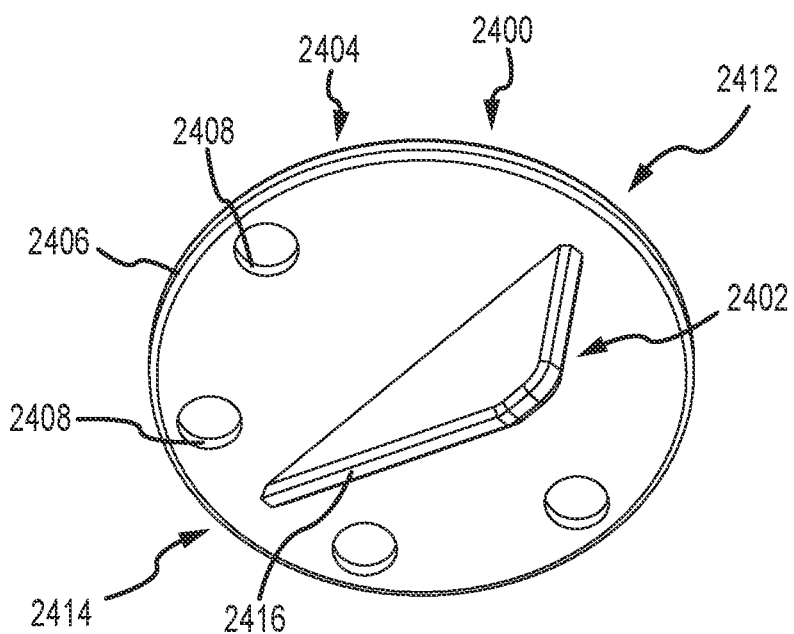
Figure 24F:
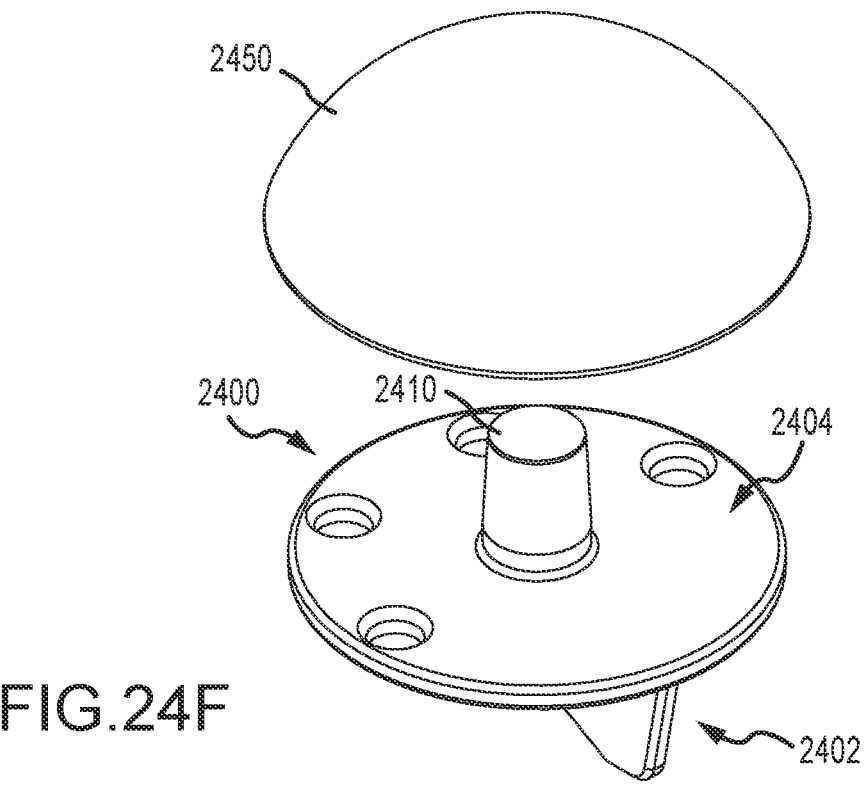
FIG. 24F is a top isometric view of the base plate with a humeral head implant positioned above.
Figure 24G:
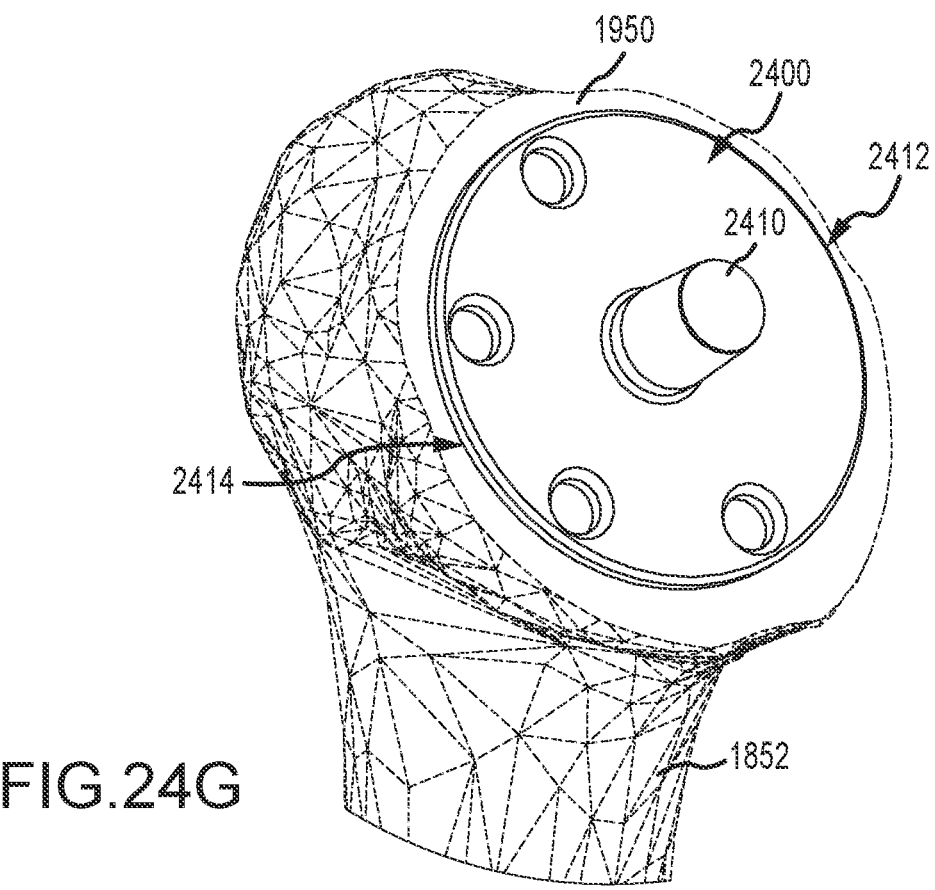
FIG. 24G is a posterior-medial view of the humerus with the base plate positioned thereon.
Figure 24H:
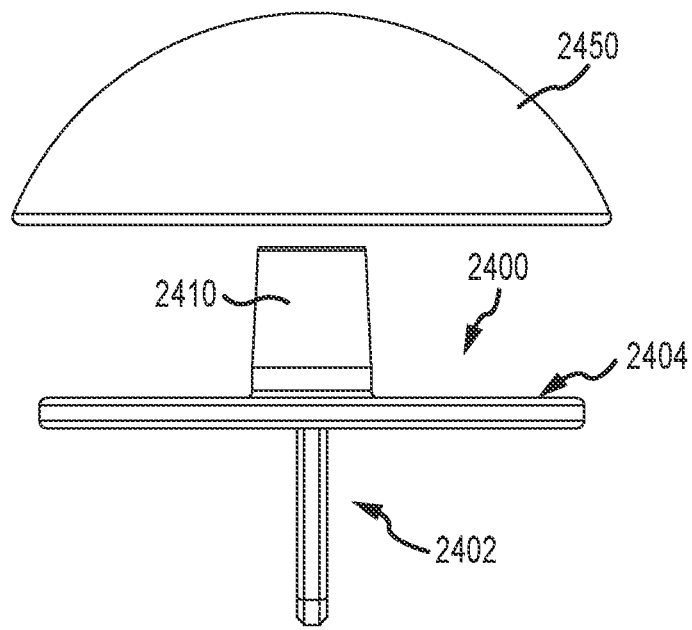
FIGS. 24H-24I are, respectively, side views of the base plate with the humeral head implant positioned above, and the base plate coupled with the humeral head implant.
Figure 24I:
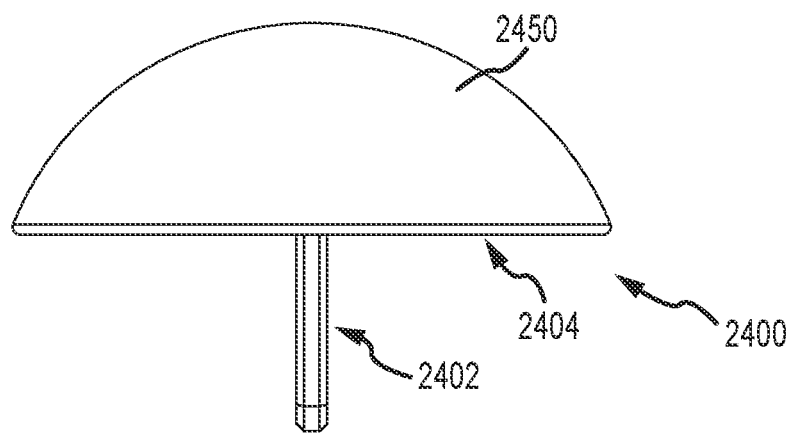

FIG. 24F is a top isometric view of the base plate 2400 with a humeral head implant 2450 positioned above. FIG. 24G is a posterior-medial view of the humerus 1852 with the base plate 2400 positioned thereon. And, FIGS. 24H-24I are, respectively, side views of the base plate 2400 with the humeral head implant 2450 positioned above, and the base plate 2400 coupled with the humeral head implant 2450.

FIGS. 25A-25E are, respectively, top isometric, bottom isometric, top, side, and bottom views of a base plate 2500 having a single, angled fin with a bulb tip 2502. As seen in the figures, the base plate 2500 includes a base structure 2504 having a circular perimeter 2506, anchor bores 2508 extending through the base structure 2504, and a male taper or trunnion 2510 extending upward from the top surface of the base structure 2504. The fin 2502 is on the opposite side of the base structure 2504 from the trunnion 2510.

As seen in the figures, the fin 2502 is angled with the deepest part of the fin towards a forward or anterior end 2512 of the base plate 2500, and with the smallest part of the fin towards a back or posterior end 2514 of the base plate 2500. And the anchor bores 2508, in this instance four of them, are situated on the posterior end 2514 of the base plate 2500. Performing a de cote surgery from the posterior side of the patient provides the largest access to the humerus on the posterior side of the bone. Thus, the anchor bores 2508 are situated on the posterior side of the bone for ease of access when fastening anchors through the bores 2508.

The method of performing the surgery with a base plate 2500 having an angled fin 2502 may be modified as described with reference to FIGS. 24A-24G. As seen in the figures, the bulb tip is generally cylindrical with a pointed tip at the anterior end 2512 to facilitate driving-in of the bulb tip into the bone. The bulb tip recess can be drilled out of the proximal humerus and the bulb tip can fit into the prepared bone like a lock in a key.

Figure 25A:
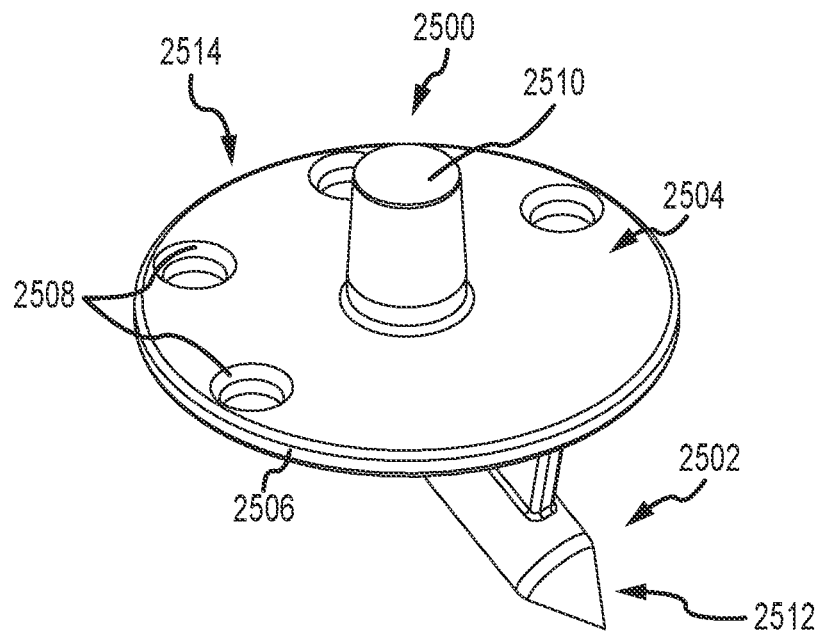
Figure 25B:
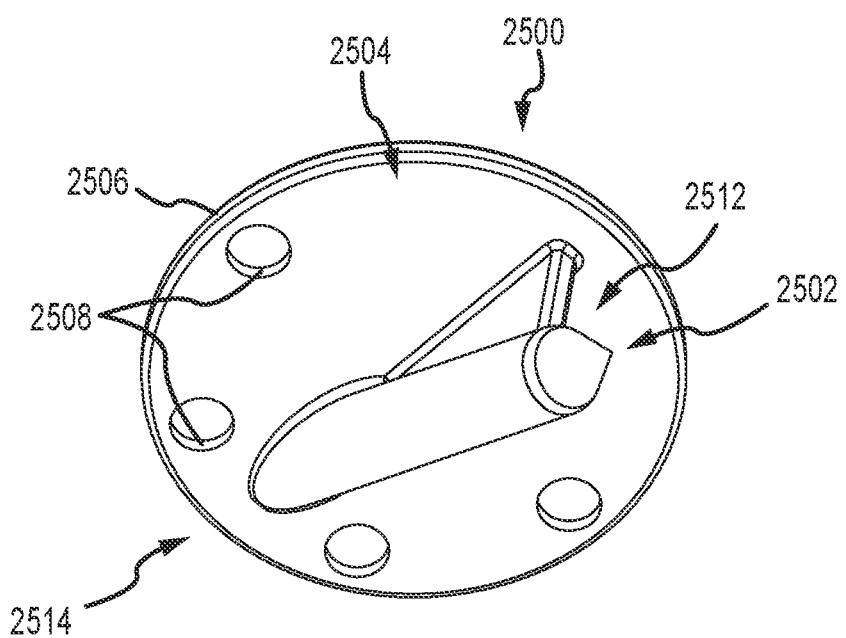
Figure 25F:
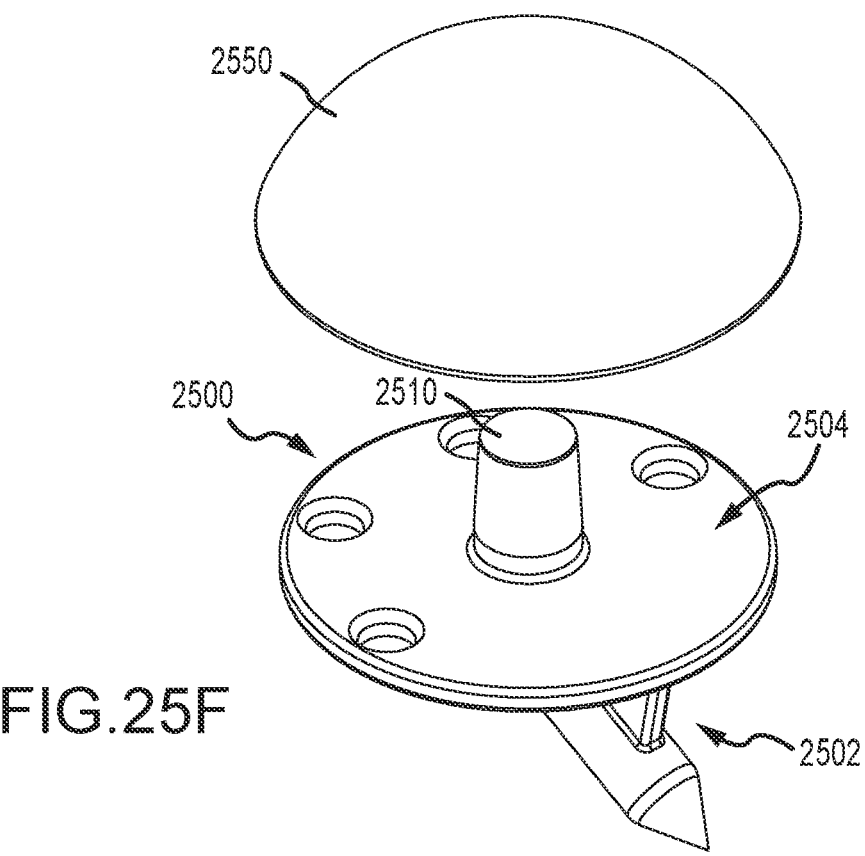
FIG. 25F is a top isometric view of the base plate with a humeral head implant positioned above.
Figure 25G:
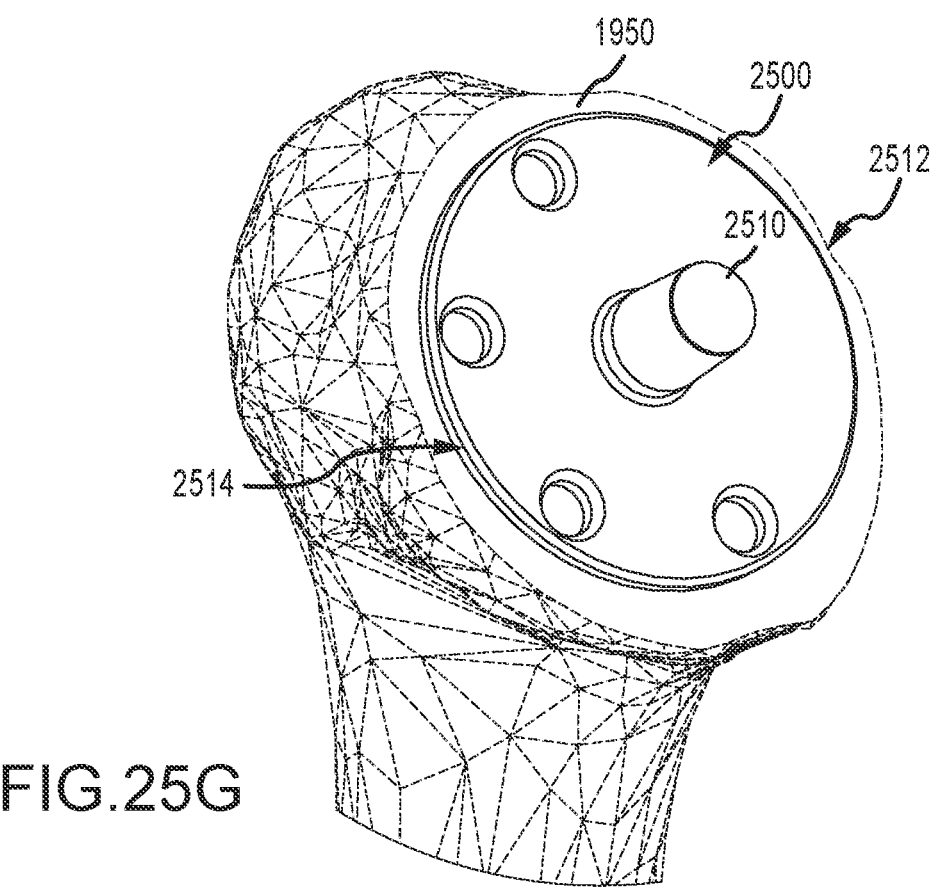
FIG. 25G is a posterior-medial view of the humerus with the base plate positioned thereon.
Figure 25H:
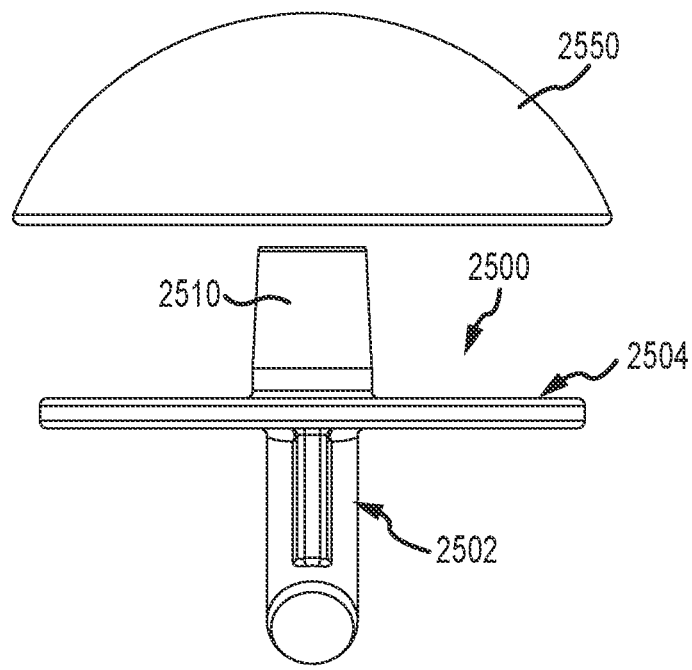
FIGS. 25H-25I are, respectively, side views of the base plate with the humeral head implant positioned above, and the base plate coupled with the humeral head implant.
Figure 25I:
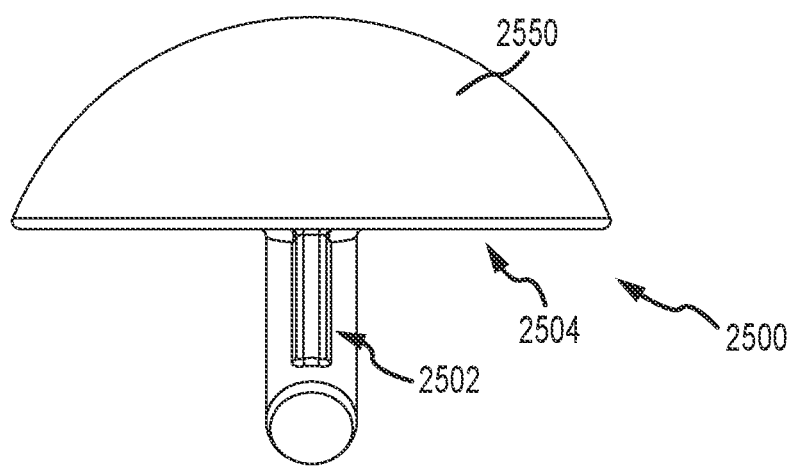

FIG. 25F is a top isometric view of the base plate 2500 with a humeral head implant 2550 positioned above. FIG. 25G is a posterior-medial view of the humerus 1852 with the base plate 2500 positioned thereon. And, FIGS. 25H-25I are, respectively, side views of the base plate 2500 with the humeral head implant 2550 positioned above, and the base plate 2500 coupled with the humeral head implant 2550.

FIGS. 26A-26E are, respectively, top isometric, bottom isometric, top, side, and bottom views of a base plate 2600 having a central, angled fin 2602 (major fin) and a pair of minor fins 2616. As seen in the figures, the base plate 2600 includes a base structure 2604 having a circular perimeter 2606, anchor bores 2608 extending through the base structure 2604, and a male taper or trunnion 2610 extending upward from the top surface of the base structure 2604. The fin 2602 is on the opposite side of the base structure 2604 from the trunnion 2610.

As seen in the figures, the fin 2602 is angled with the deepest part of the fin towards a forward or anterior end 2612 of the base plate 2600, and with the smallest part of the fin towards a back or posterior end 2614 of the base plate 2600. And the anchor bores 2608, in this instance four of them, are situated on the posterior end 2614 of the base plate 2600. Performing a de cote surgery from the posterior side of the patient provides the largest access to the humerus on the posterior side of the bone. Thus, the anchor bores 2608 are situated on the posterior side of the bone for ease of access when fastening anchors through the bores 2608. There is a minor fin 2616 positioned on each side of the major fin 2602. The minor fins 2616 are the same general shape as the central fin 2602. The difference is that the minor fins 2616 are scaled smaller than the central fin 2602.

The method of performing the surgery with a base plate 2600 having an angled fin 2602 and two minor fins 2616 may be modified as described with reference to FIGS. 24A-24G. Minor fin cut slots may be cut into the resected bone surface prior to impacting the base plate 2600 into the bone, or not. As seen in the figures, the central fin 2602 protrudes farther from the base structure 2604 than the minor fins 2616.

Figure 26A:
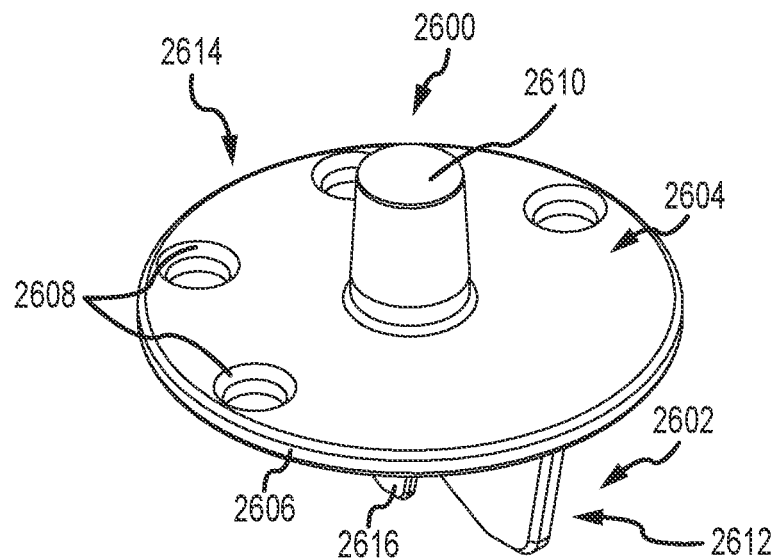
FIGS. 26A-26E are, respectively, top isometric, bottom isometric, top, side, and bottom views of a base plate having a three angled fins.
Figure 26B:
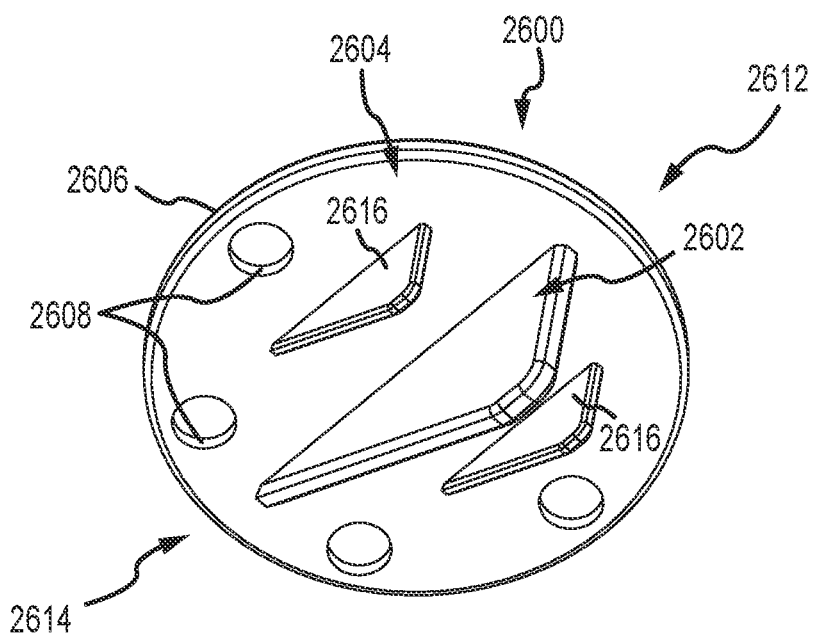
Figure 26C:
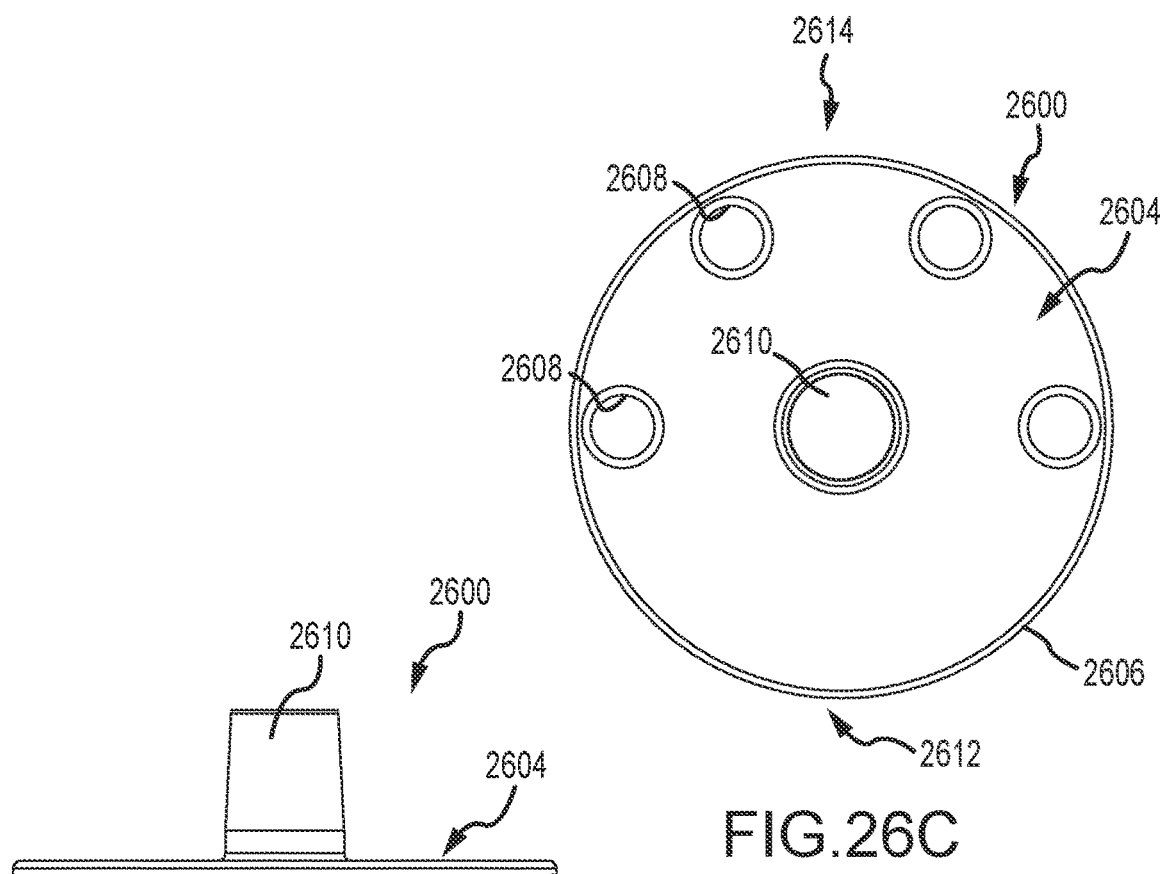
Figure 26D:
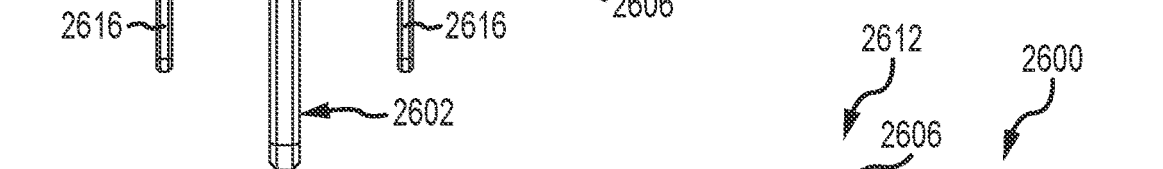
Figure 26E:
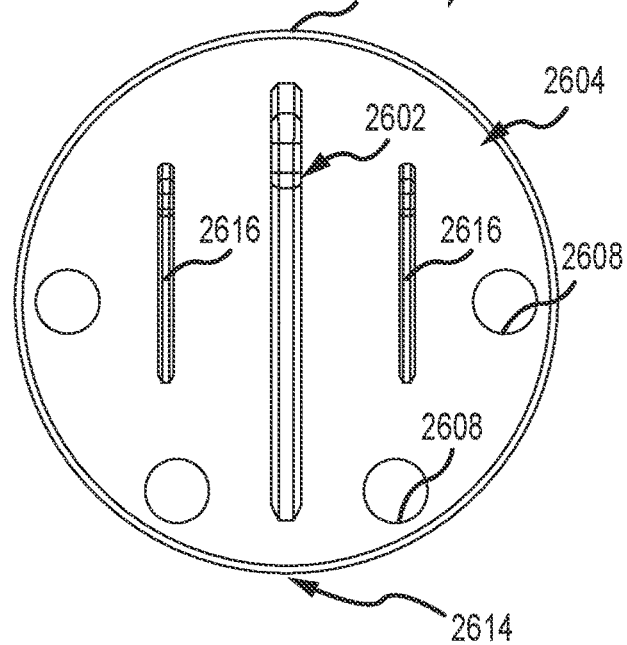
Figure 26F:
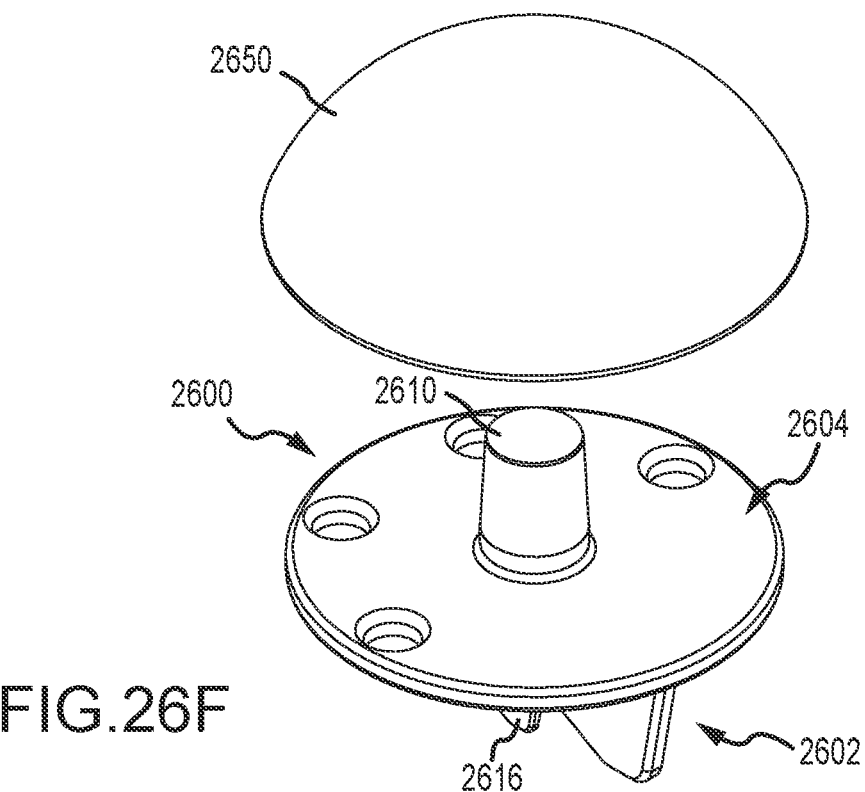
FIG. 26F is a top isometric view of the base plate with a humeral head implant positioned above.
Figure 26G:
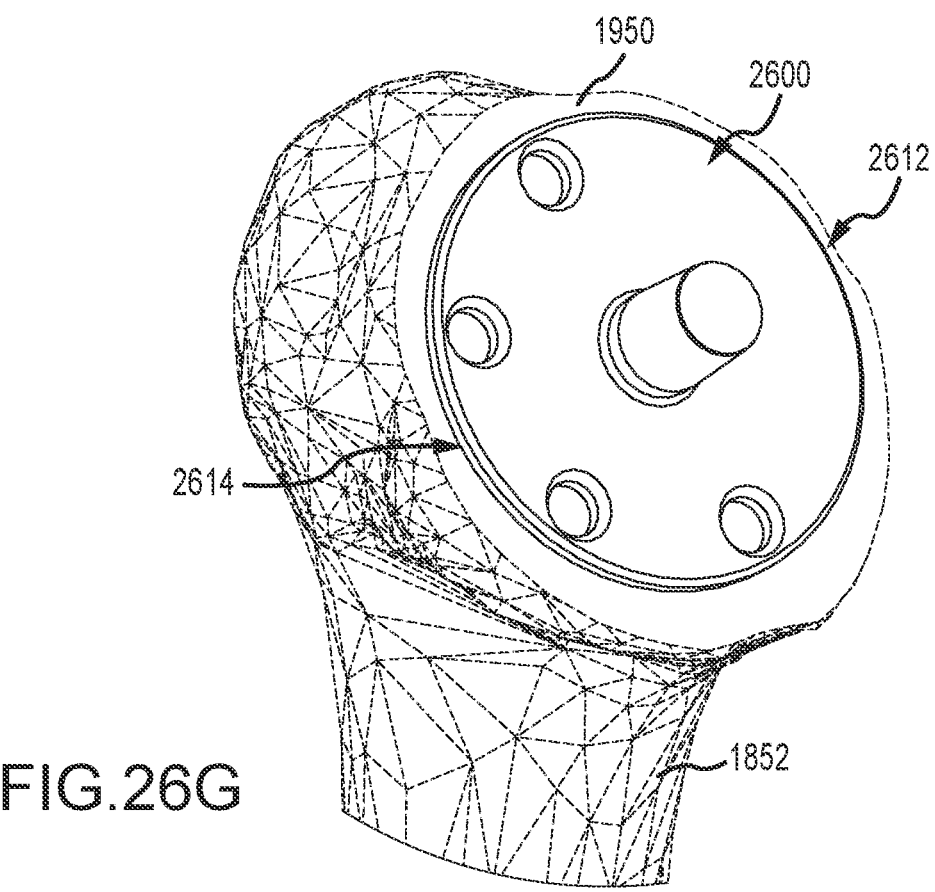
FIG. 26G is a posterior-medial view of the humerus with the base plate positioned thereon.
Figure 26H:
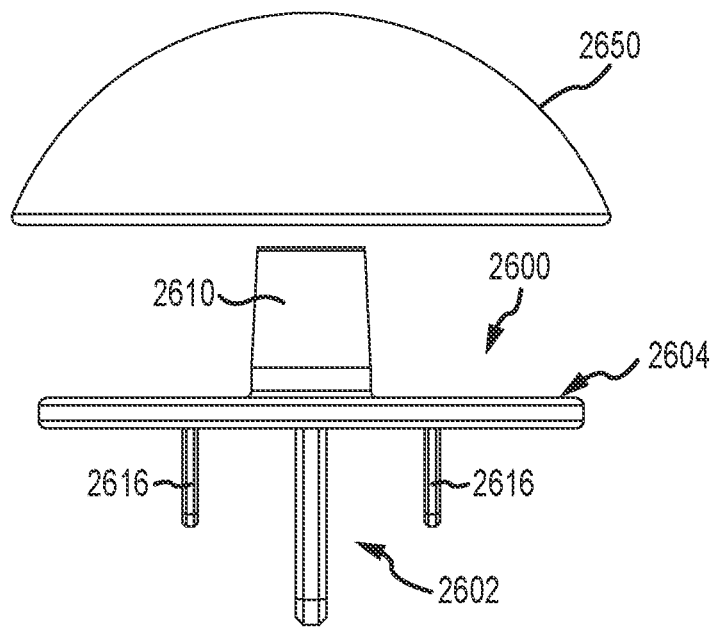
FIGS. 26H-26I are, respectively, side views of the base plate with the humeral head implant positioned above, and the base plate coupled with the humeral head implant.
Figure 26I:
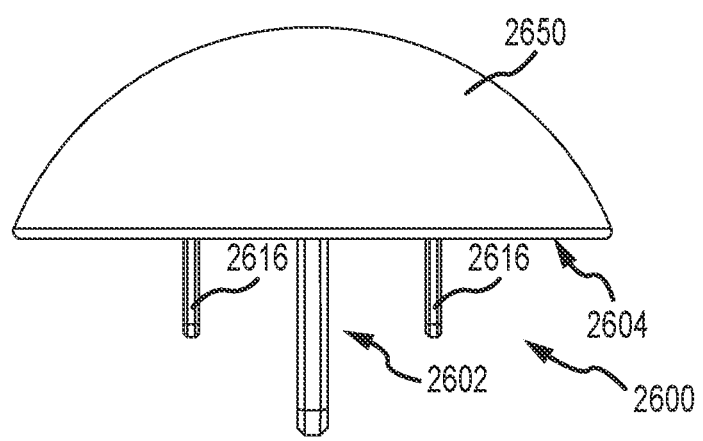

FIG. 26F is a top isometric view of the base plate 2600 with a humeral head implant 2650 positioned above. FIG. 26G is a posterior-medial view of the humerus 1852 with the base plate 2600 positioned thereon. And, FIGS. 26H-26I are, respectively, side views of the base plate 2600 with the humeral head implant 2650 positioned above, and the base plate 2600 coupled with the humeral head implant 2650.

FIGS. 27A-27E are, respectively, top isometric, bottom isometric, top, side, and bottom views of a base plate 2700 having a central fin 2702 (major fin). As seen in the figures, the base plate 2700 includes a base structure 2704 having a circular perimeter 2706, anchor bores 2708 extending through the base structure 2704, and a male taper or trunnion 2710 extending upward from the top surface of the base structure 2704. The fin 2702 is on the opposite side of the base structure 2704 from the trunnion 2710. The base plate 2700 further includes an attachment structure 2716 in the form of a pair of minor fins 2718, one on either side of the central fin 2702, and a transverse minor fin 2720 extending across the minor fins 2718 and the central fin 2702 at a central portion thereof. The base plate 2700 also includes a plurality of windows 2722 extending through the base structure 2704. The windows 2722 are positioned outward of the trunnion 2710 and inwards of the anchor bores 2708. The windows 2722 are defined between the fins 2702, 2720, 2718. The windows 2722 permit boney ingrowth to facilitate attachment of the bone to the base plate 2700. As seen in the figures, the fin 2702 is not angled; rather, it is flat with its bottom with angled anterior and posterior ends, longitudinal edge generally parallel with the base structure 2704.

Figure 27A:
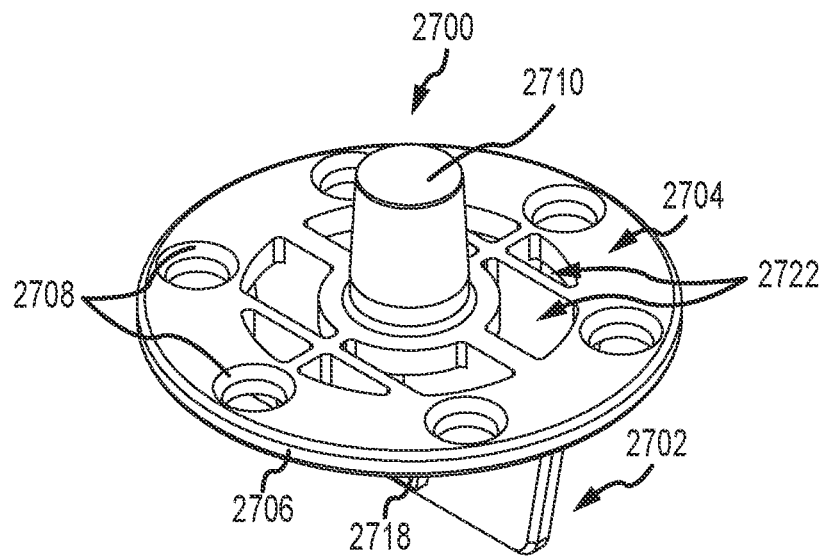
FIGS. 27A-27E are, respectively, top isometric, bottom isometric, top, side, and bottom views of a base plate having a central fin and a grid attachment structure.
Figure 27B:
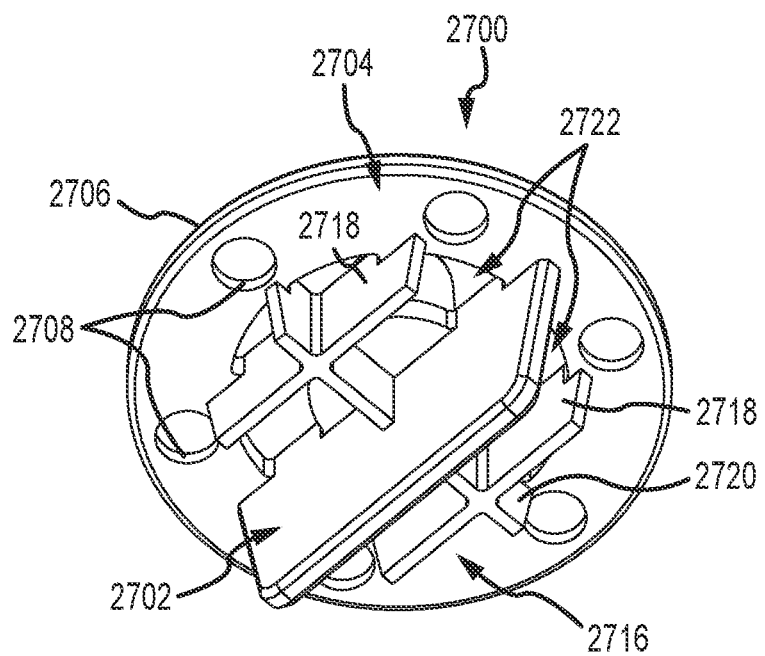
Figure 27C:
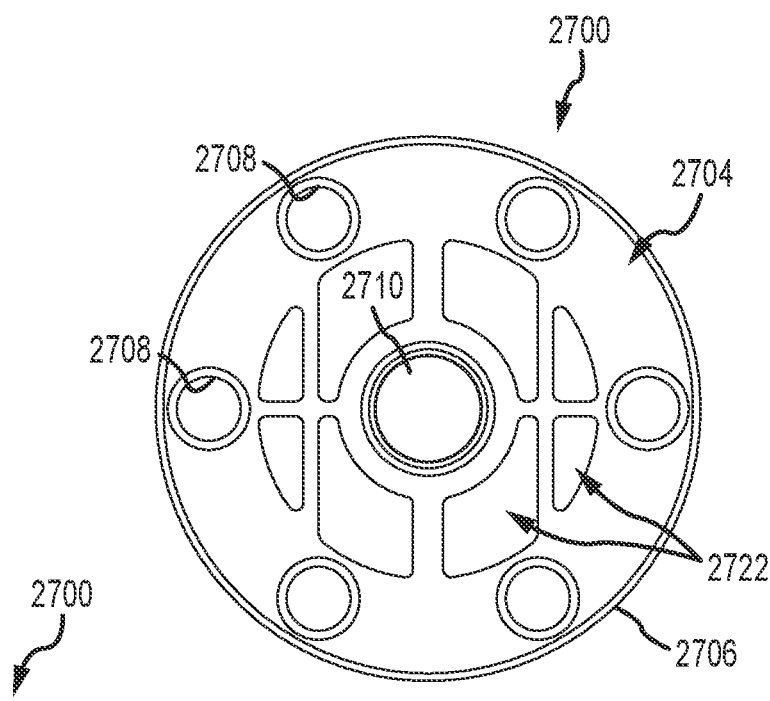
Figure 27D:
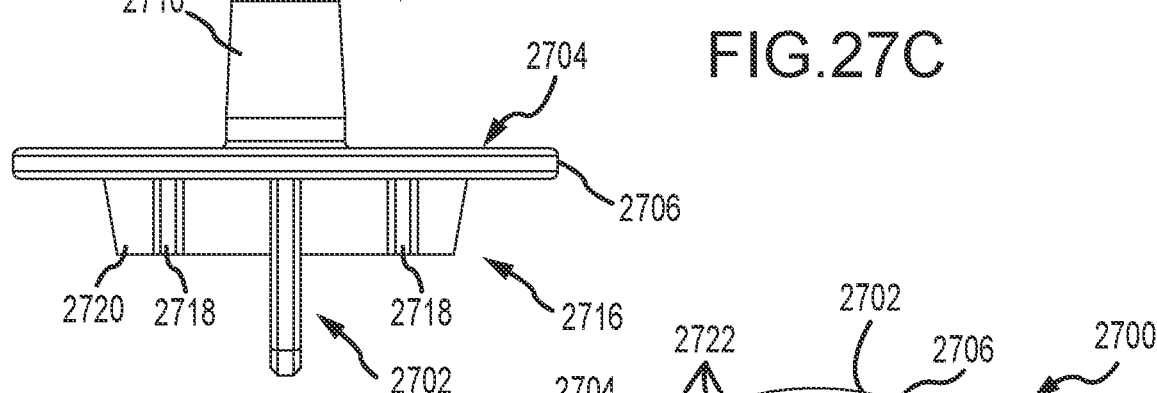
Figure 27E:
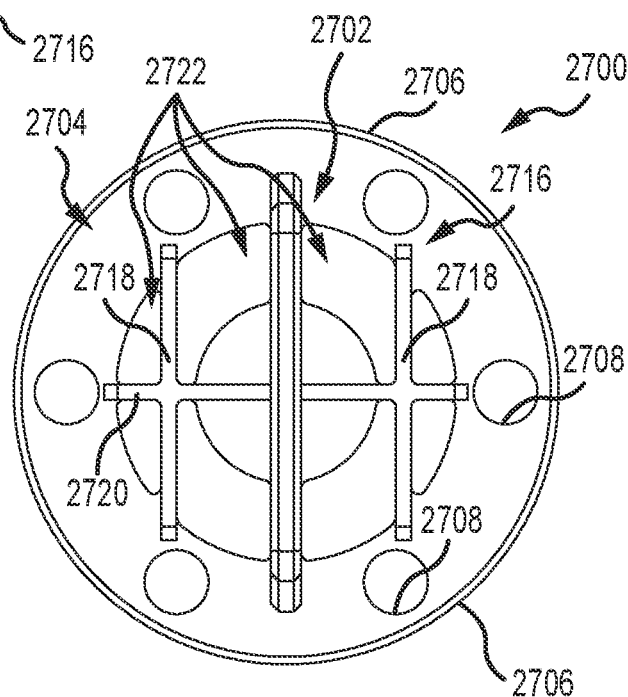
Figure 27F:
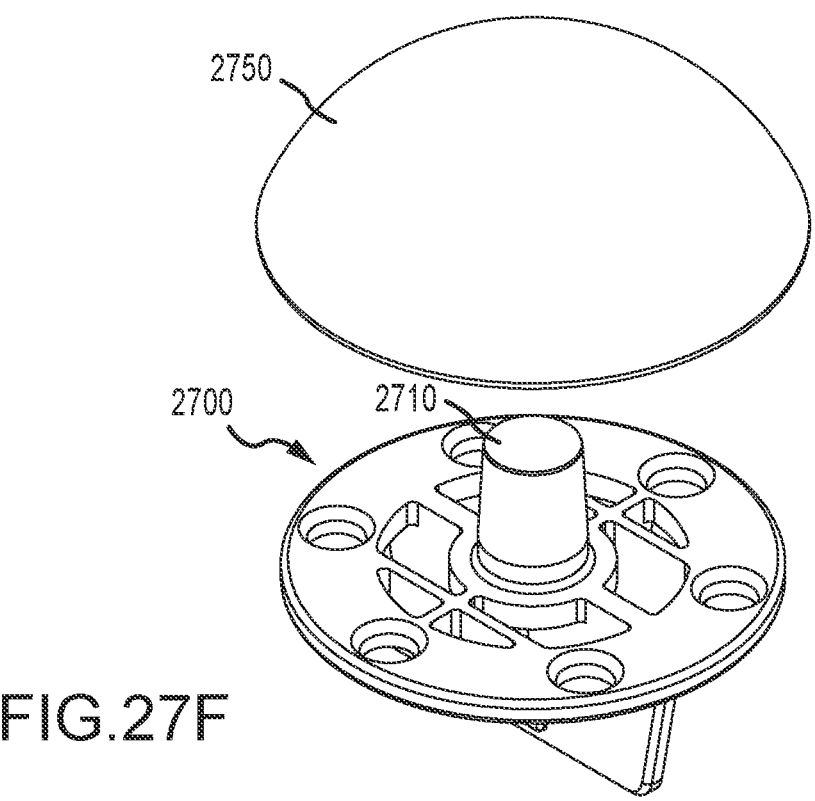
FIG. 27F is a top isometric view of the base plate with a humeral head implant positioned above.
Figure 27G:
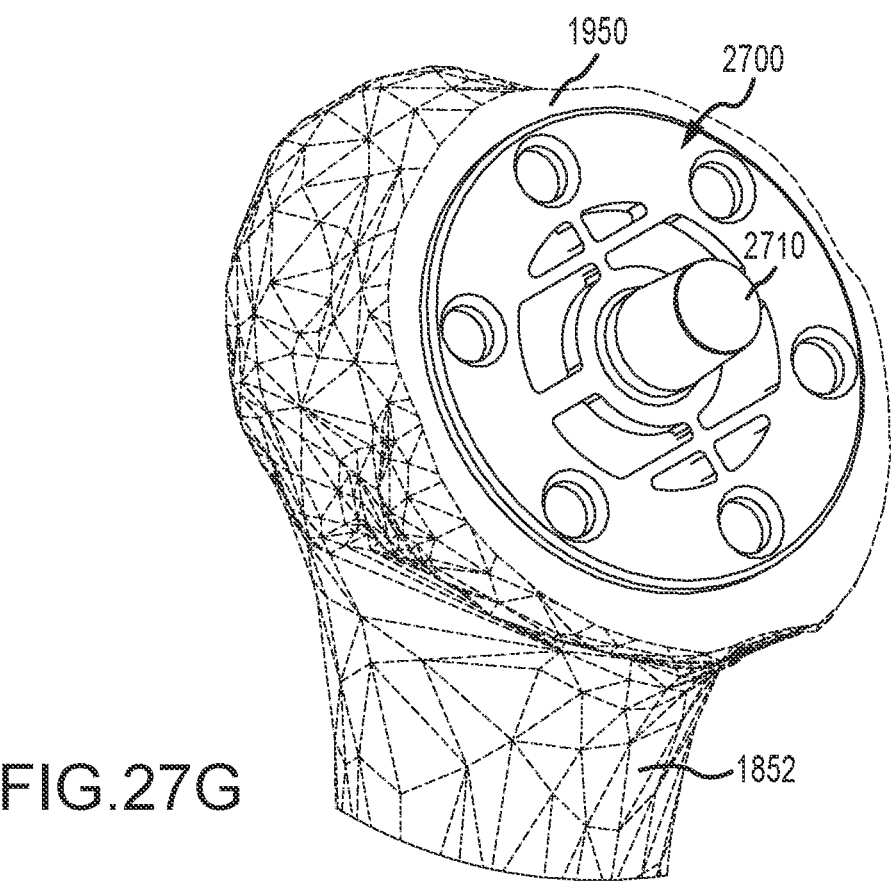
FIG. 27G is a posterior-medial view of the humerus with the base plate positioned thereon.
Figure 27H:
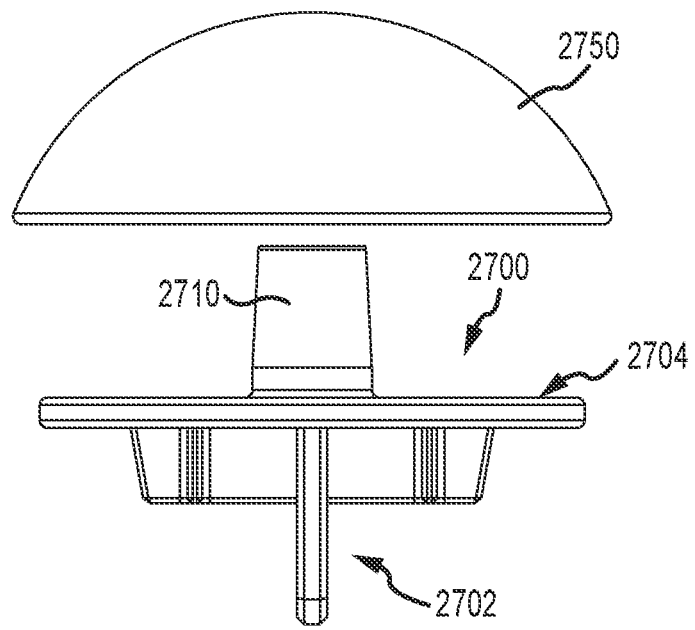
FIGS. 27H-27I are, respectively, side views of the base plate with the humeral head implant positioned above, and the base plate coupled with the humeral head implant.
Figure 27I:
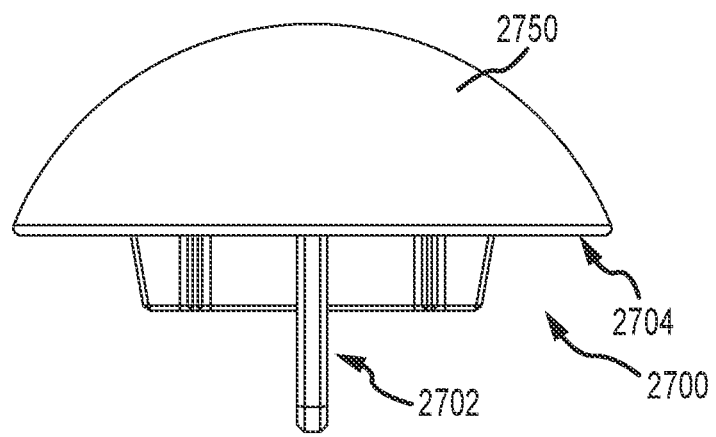

FIG. 27F is a top isometric view of the base plate 2700 with a humeral head implant 2750 positioned above. FIG. 27G is a posterior-medial view of the humerus 1852 with the base plate 2700 positioned thereon. And, FIGS. 27H-27I are, respectively, side views of the base plate 2700 with the humeral head implant 2750 positioned above, and the base plate 2700 coupled with the humeral head implant 2750.

FIGS. 28A-28E are, respectively, top isometric, bottom isometric, top, side, and bottom views of a base plate 2800 having central fin 2802 and an attachment structure 2816. As seen in the figures, the base plate 2800 includes a base structure 2804 having a circular perimeter 2806, anchor bores 2808 extending through the base structure 2804, and a male taper or trunnion 2810 extending upward from the top surface of the base structure 2804. The fin 2802 is on the opposite side of the base structure 2804 from the trunnion 2810.

The base plate 2700 further includes an attachment structure 2816 in the form of a pair of minor fins 2818, one on either side of the central fin 2802, and a trio of transverse minor fins 2820 extending across the minor fins 2818 and the central fin 2802 at a central portion thereof. The base plate 2800 also includes a plurality of windows 2822 extending through the base structure 2804. The windows 2822 are positioned outward of the trunnion 2810 and inwards of the anchor bores 2808. The windows 2822 permit boney ingrowth to facilitate attachment of the bone to the base plate 2800. As seen in the figures, the fin 2802 is not angled; rather, it is flat on its bottom edge with angled anterior and posterior ends. The bottom, longitudinal edge is generally parallel with the base structure 2804.

Figure 28A:
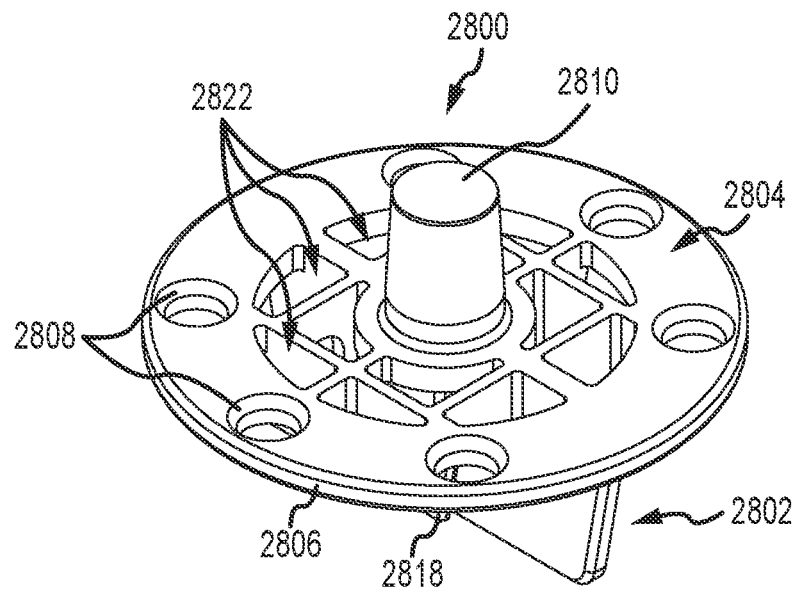
FIGS. 28A-28E are, respectively, top isometric, bottom isometric, top, side, and bottom views of a base plate having a central fin and a grid attachment structure with anchor bores for receiving anchors from the posterior side.
Figure 28B:
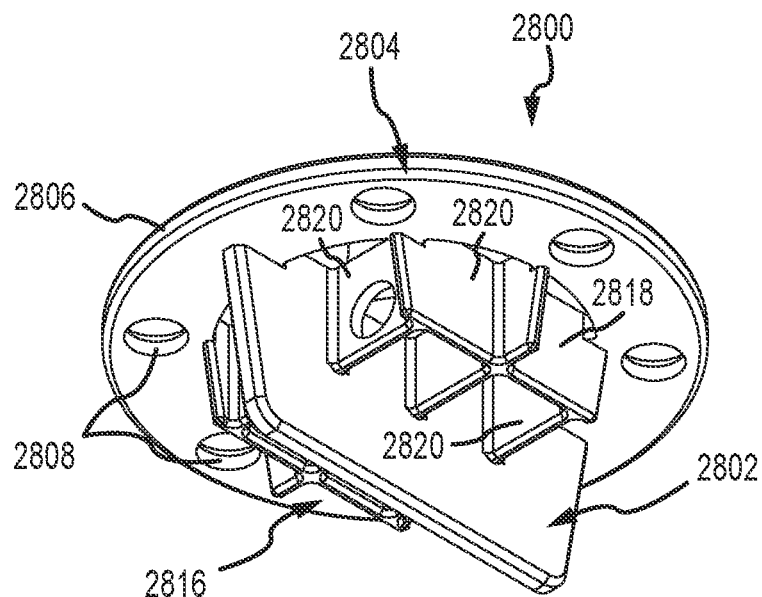
Figure 28C:
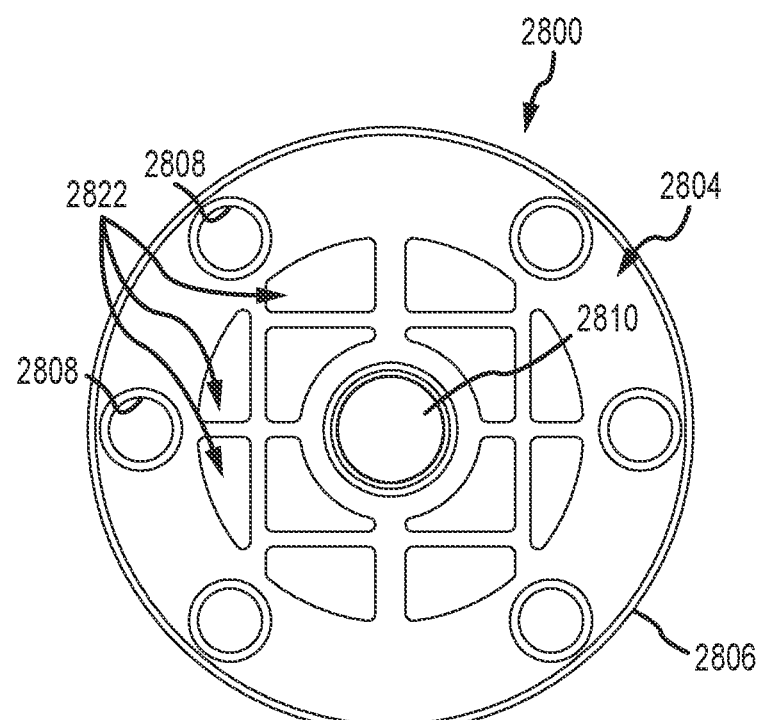
Figure 28D:
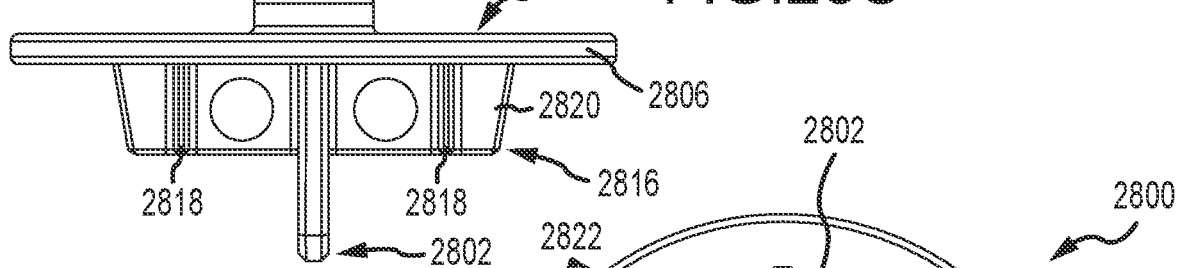
Figure 28E:
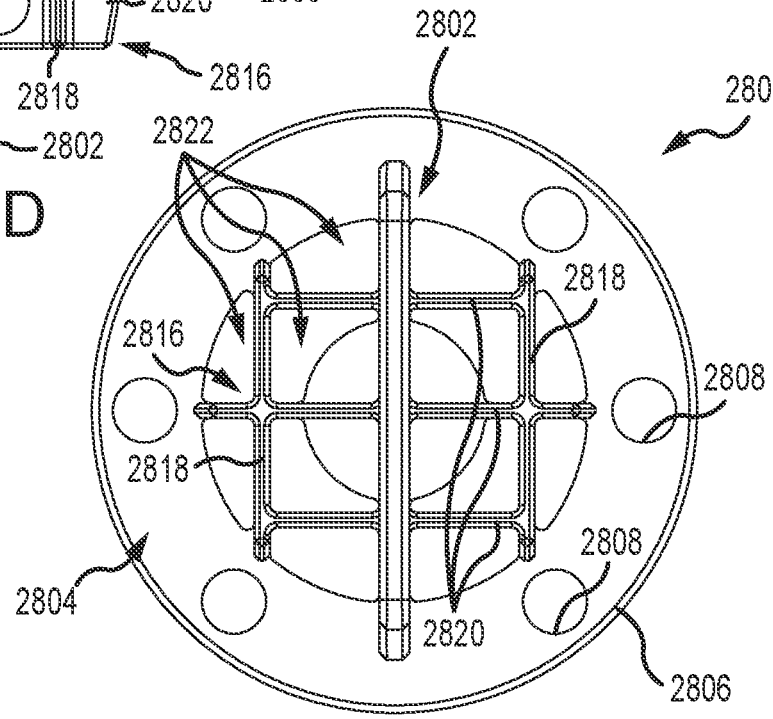
Figure 28F:
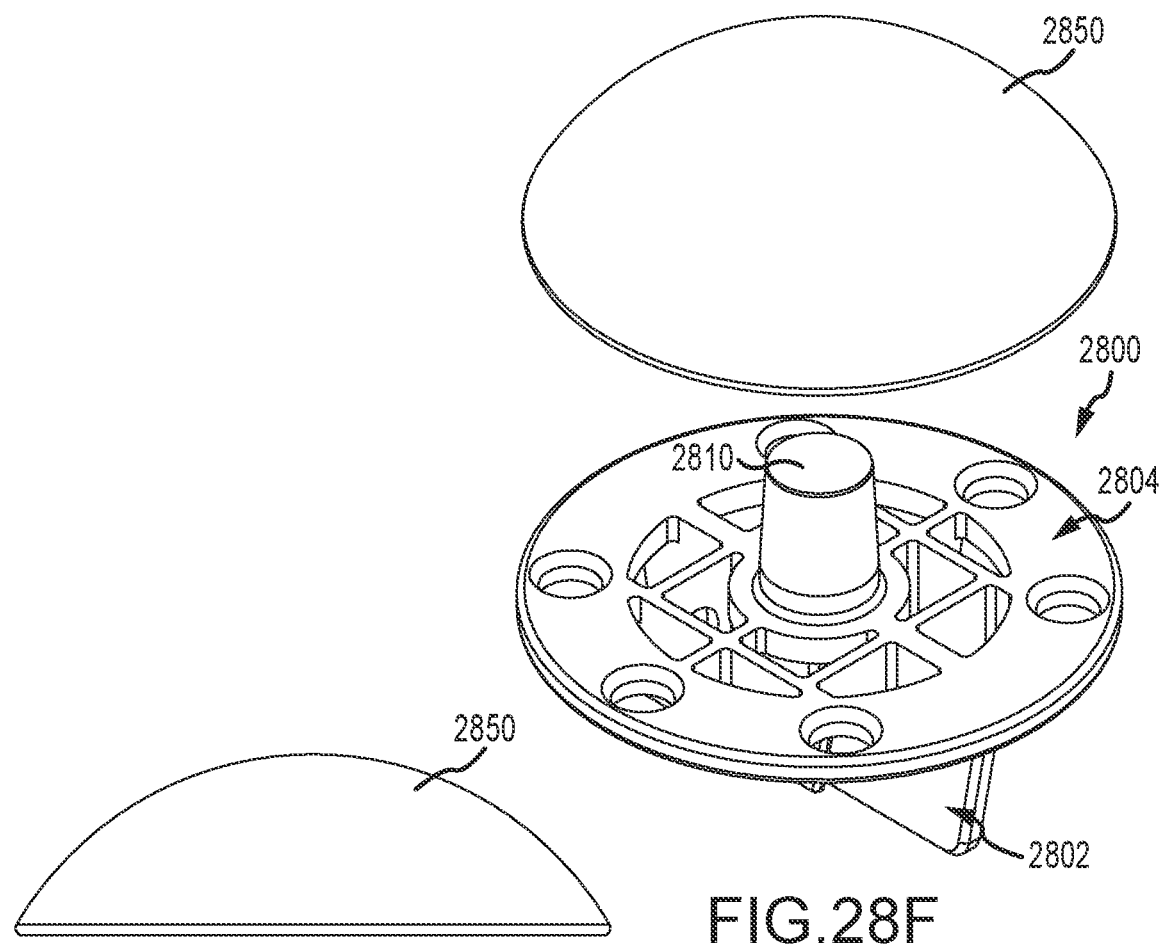
FIGS. 28F-28G are, respectively, top isometric and side views of the base plate with a humeral head implant positioned above.
Figure 28G:
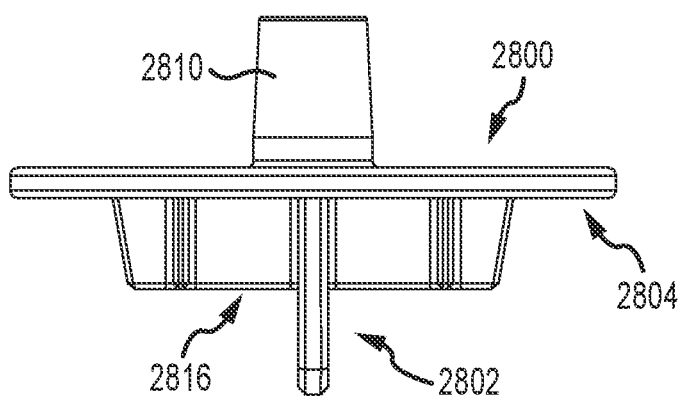
Figure 28H:
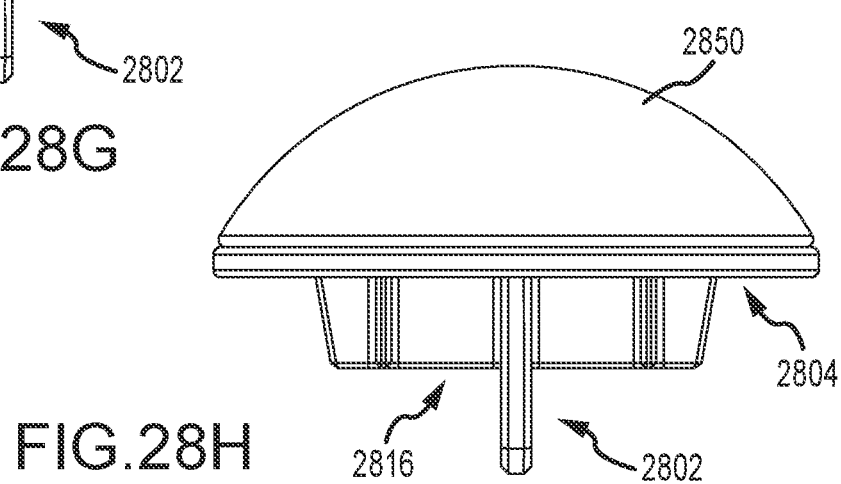
FIG. 28H is a side view of the humeral head implant coupled to the base plate.
Figure 28I:
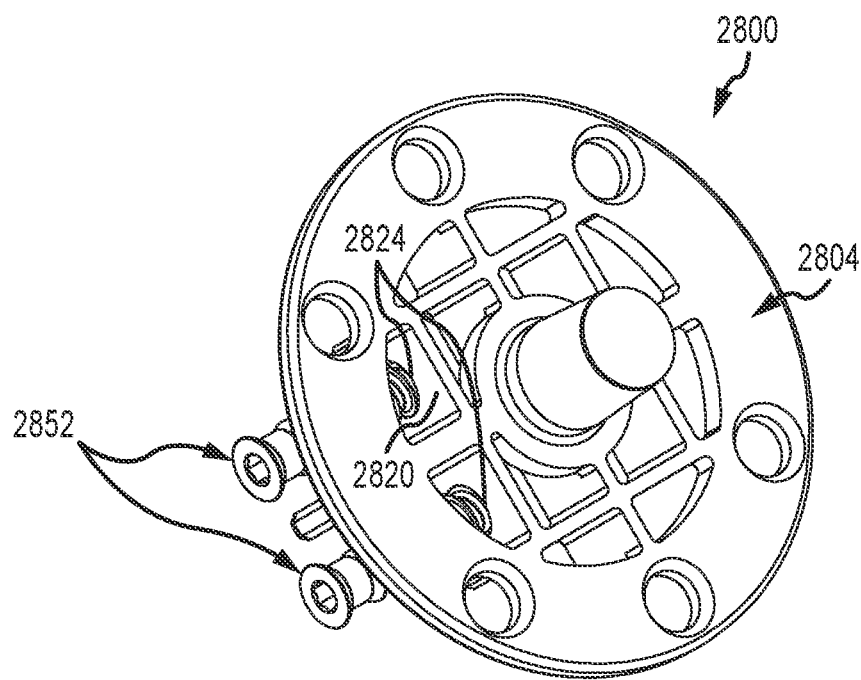
FIGS. 28I-28J are, respectively, top isometric and side views of the base plate with a pair of anchors positioned within the anchor bores.
Figure 28J:
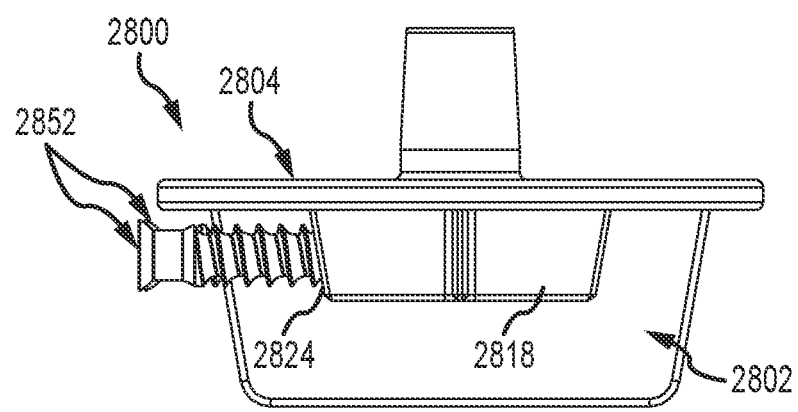
Figure 28K:
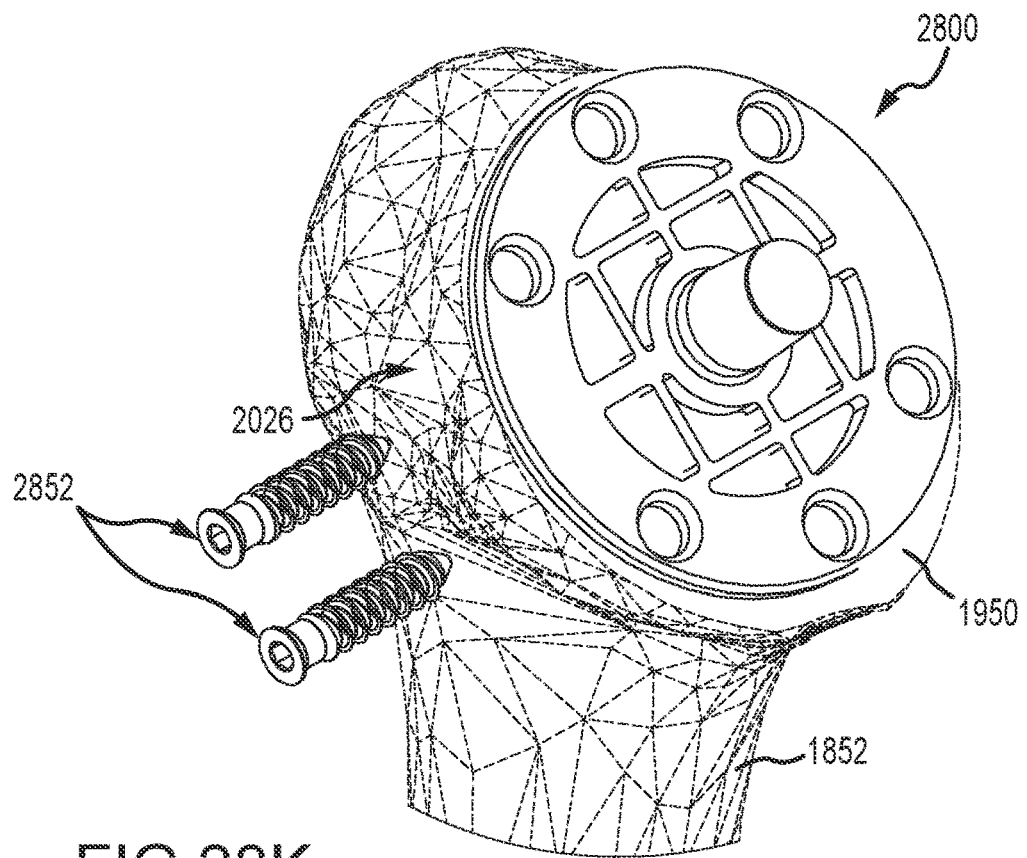
FIG. 28K is a posterior-medial view of the humerus with the base plate positioned thereon, and with two anchors positioned for delivery into the bone and through the anchor bores of the base plate.
Figure 28L:
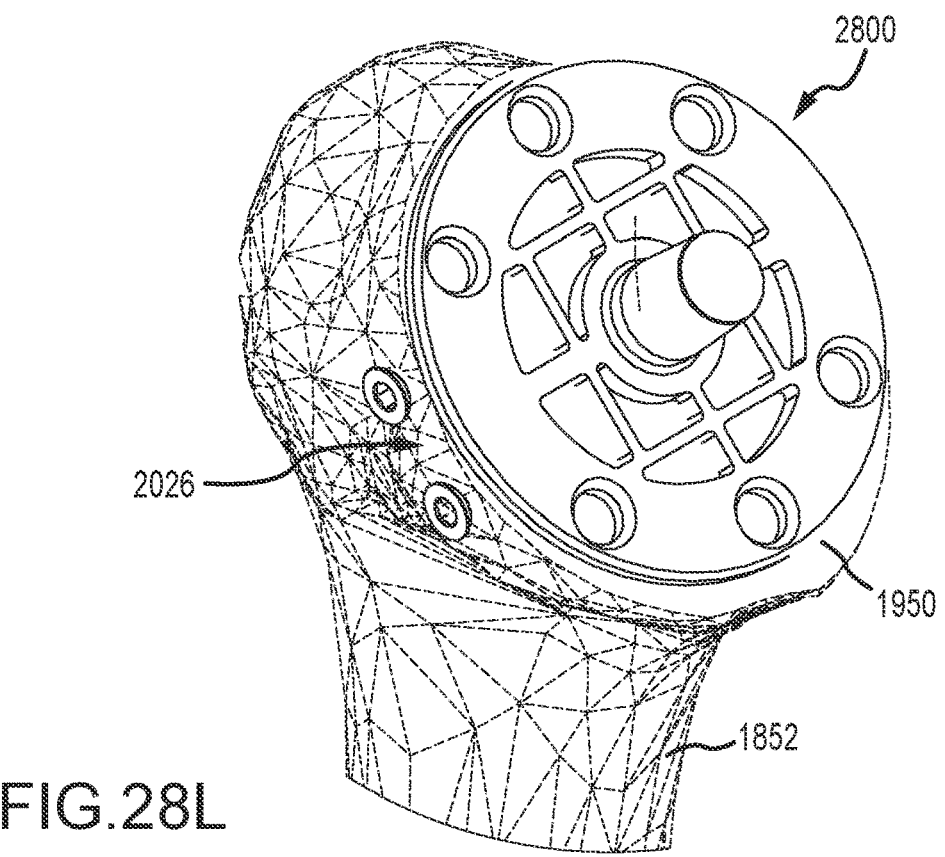
FIG. 28L is a posterior-medial view of the humerus with the base plate positioned thereon, and with two anchors delivered into the bone and through the anchor bores of the base plate.

The base plate 2800 in FIGS. 28A-28J is similar to the base plate 2700 in FIGS. 27A-27I, except the base plate 2800 in FIGS. 28A-28X includes an additional pair of transverse minor fins 2820 that are parallel to the central transverse minor fin 2820. And one of the transverse minor fins 2820 that would be positioned at the posterior end of the humerus includes a pair of anchor bores 2824 positioned therein. This is for receiving anchors through the posterior humeral cortex, as seen in FIG. 28K-28L. FIGS. 28F-28G are, respectively, top isometric and side views of the base plate 2800 with a humeral head implant 2850 positioned above. FIG. 28H is a side view of the humeral head implant 2850 coupled to the base plate 2800. FIGS. 28I-28J are, respectively, top isometric and side views of the base plate 2800 with a pair of anchors 2852 positioned within the anchor bores 2824.

FIG. 28K is a posterior-medial view of the humerus 1852 with the base plate 2800 positioned thereon, and with two anchors 2852 positioned for delivery into the posterior cortical bone 2026 and through the anchor bores (not seen) of the base plate 2800. And, FIG. 28L is a posterior-medial view of the humerus 1852 with the base plate 1852 positioned thereon, and with two anchors 2852 delivered into the posterior cortical bone 2026 and through the anchor bores (not seen) of the base plate 2800.

FIGS. 29A-29E are, respectively, top isometric, bottom isometric, top, side, and bottom views of a base plate 2900 having a central fin 2902 (major fin). As seen in the figures, the base plate 2900 includes a base structure 2904 having a circular perimeter 2906, anchor bores 2908 extending through the base structure 2904, and a male taper or trunnion 2910 extending upward from the top surface of the base structure 2904. The fin 2902 is on the opposite side of the base structure 2904 from the trunnion 2910. The base plate 2900 further includes an attachment structure 2916 in the form of a pair of minor fins 2918, one on either side of the central fin 2902, a transverse minor fin 2920 extending across the minor fins 2918 and the central fin 2902 at a central portion thereof, and a tubular wall 2924 encircling the minor fins 2918 and transverse minor fin 2920. The tubular wall 2924 also intersects the central fin 2902.

The base plate 2900 also includes a plurality of windows 2922 extending through the base structure 2904. The windows 2922 are positioned outward of the trunnion 2910 and inwards of the anchor bores 2908. The windows 2922 are defined between the fins 2902, 2920, 2918. The windows 2922 permit boney ingrowth to facilitate attachment of the bone to the base plate 2900. As seen in the figures, the fin 2902 is not angled; rather, it is flat with angled anterior and posterior ends. The flat longitudinal edge is generally parallel with the base structure 2904.

Figure 29A:
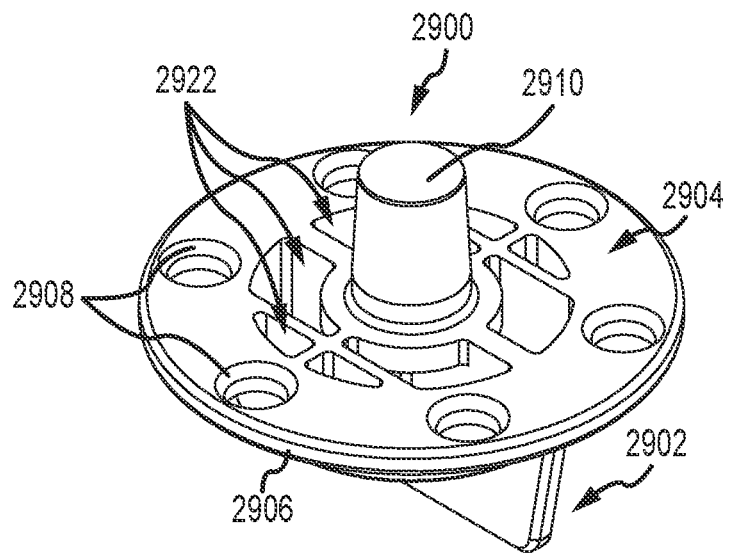
FIGS. 29A-29E are, respectively, top isometric, bottom isometric, top, side, and bottom views of a base plate having a central fin and a grid attachment structure with a tubular wall encircling the grid attachment structure.
Figure 29B:
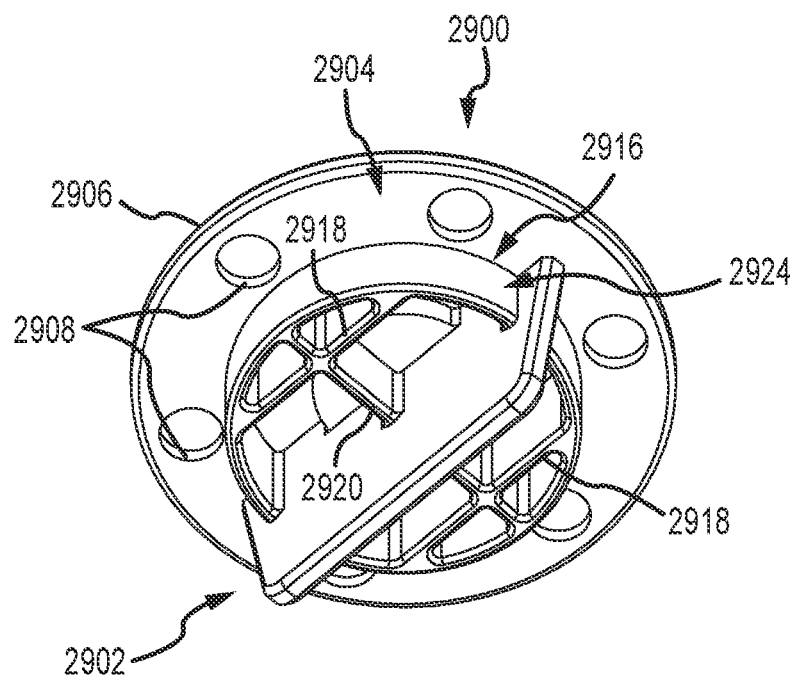
Figure 29C:
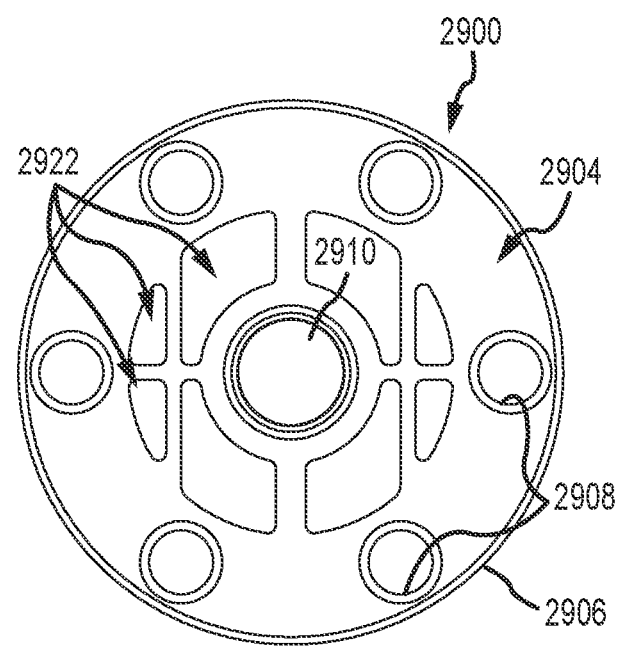
Figure 29D:
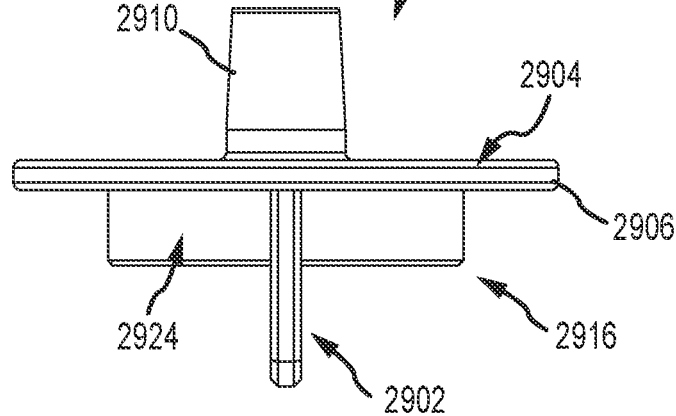
Figure 29E:
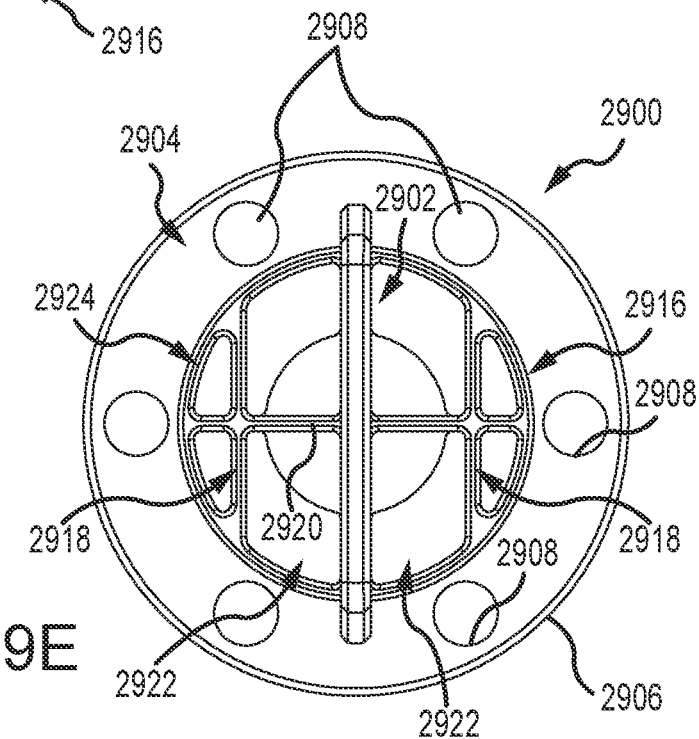
Figure 29F:
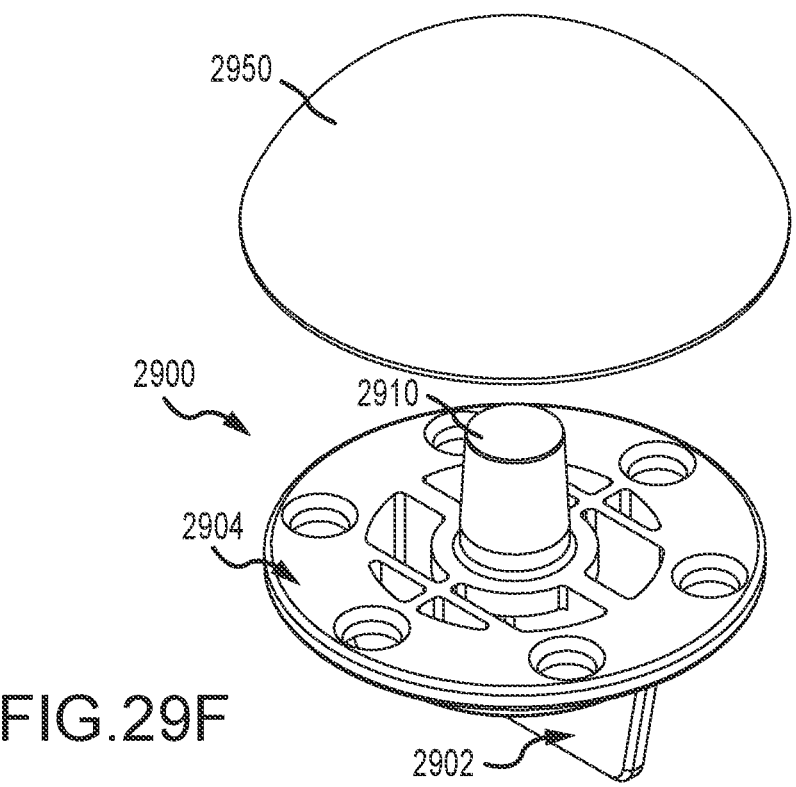
FIG. 29F is a top isometric view of the base plate with a humeral head implant positioned above.
Figure 29G:
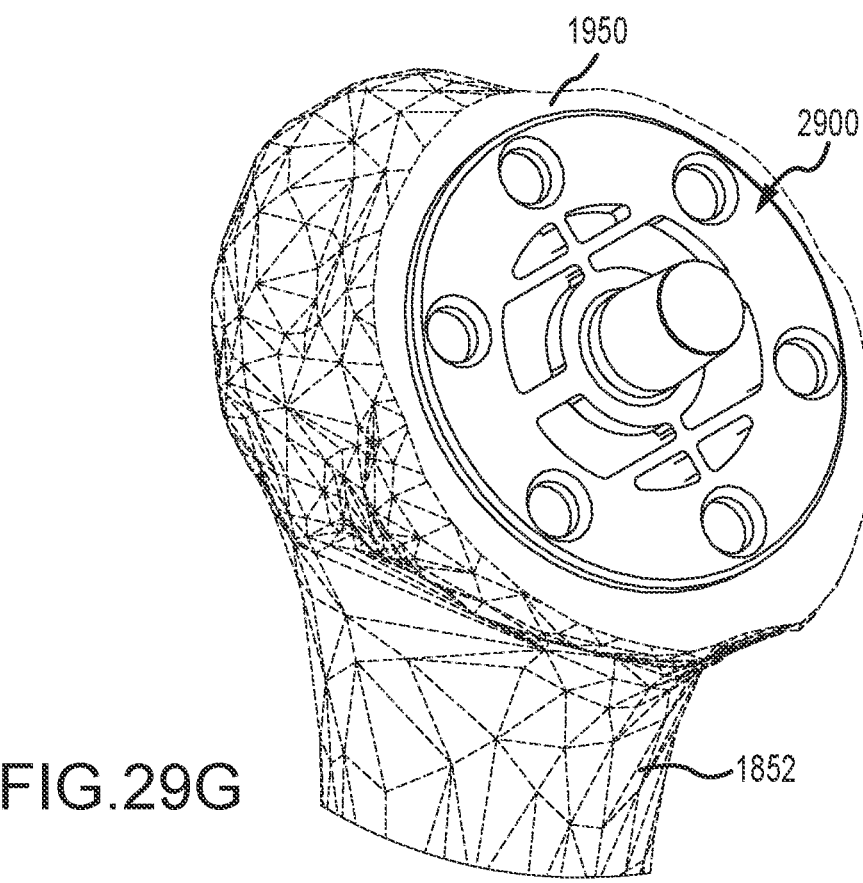
FIG. 29G is a posterior-medial view of the humerus with the base plate positioned thereon.
Figure 29H:
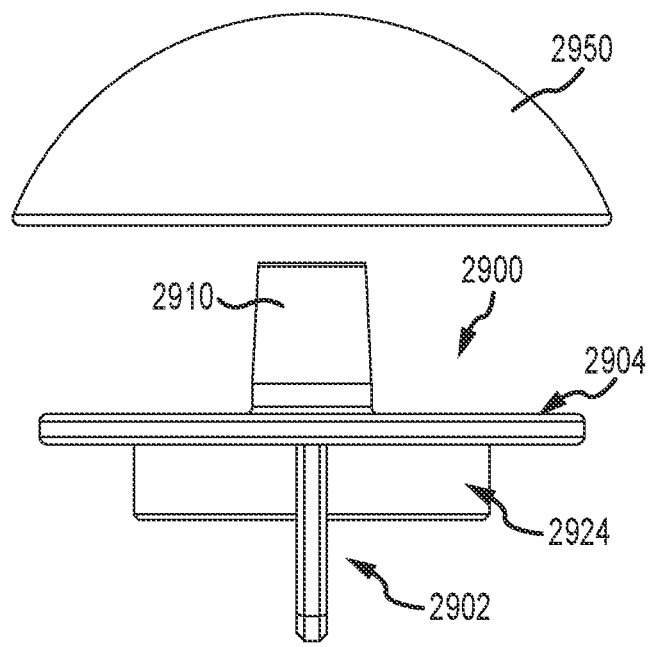
FIGS. 29H-29I are, respectively, side views of the base plate with the humeral head implant positioned above, and the base plate coupled with the humeral head implant.
Figure 29I:
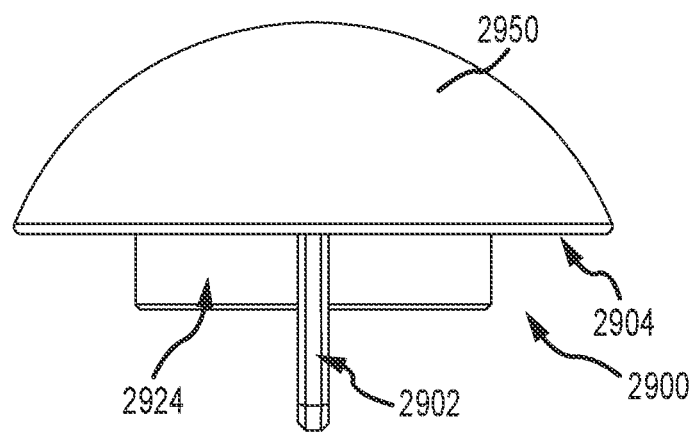

FIG. 29F is a top isometric view of the base plate 2900 with a humeral head implant 2950 positioned above. FIG. 29G is a posterior-medial view of the humerus 1852 with the base plate 2900 positioned thereon. And, FIGS. 29H-29I are, respectively, side views of the base plate 2900 with the humeral head implant 2950 positioned above, and the base plate 2900 coupled with the humeral head implant 2950.

Figure 30A:
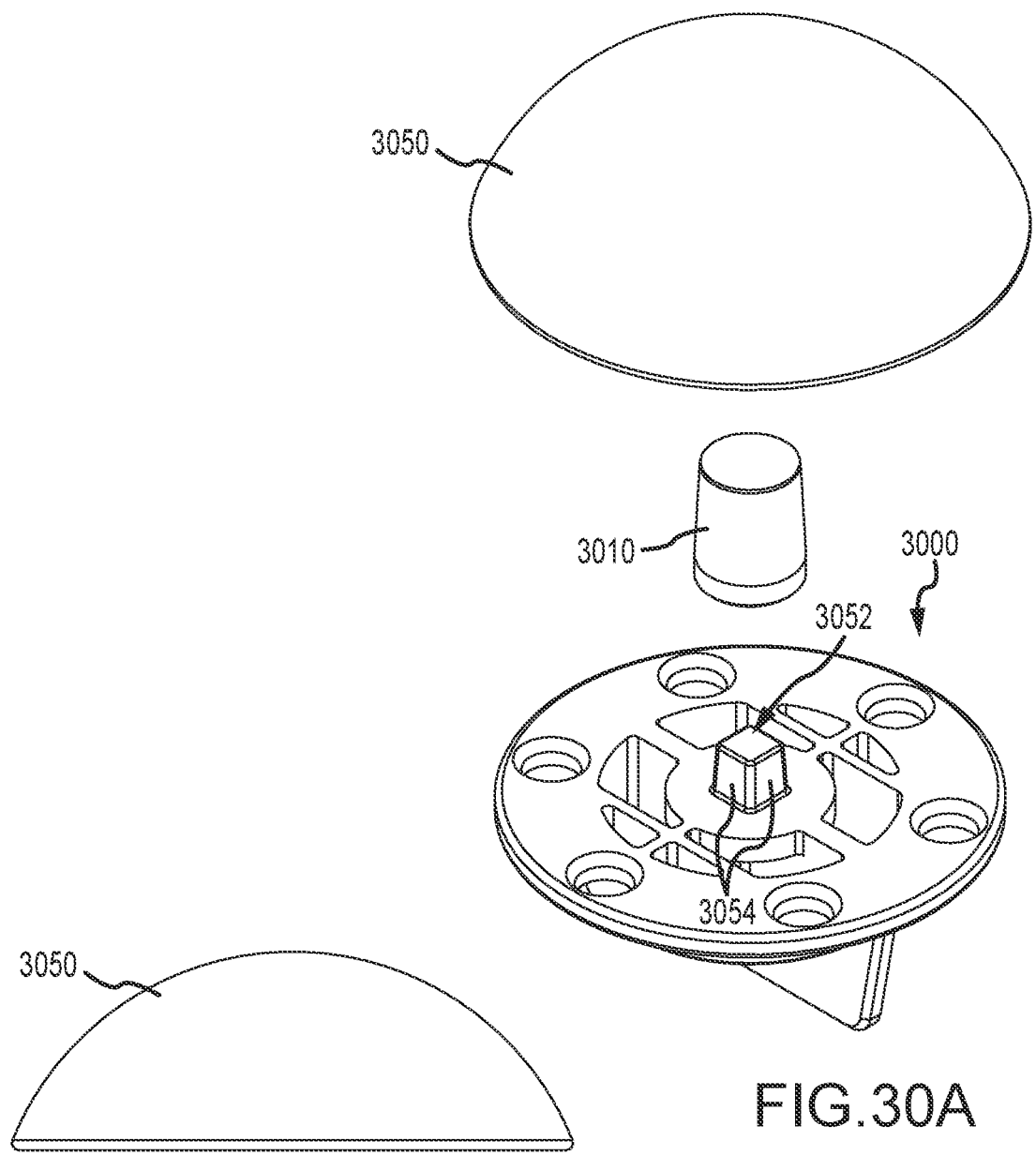
FIGS. 30A-30B are, respectively, top isometric and side views of the base plate with a humeral head implant positioned above, and the trunnion uncoupled with the base plate.
Figure 30B:
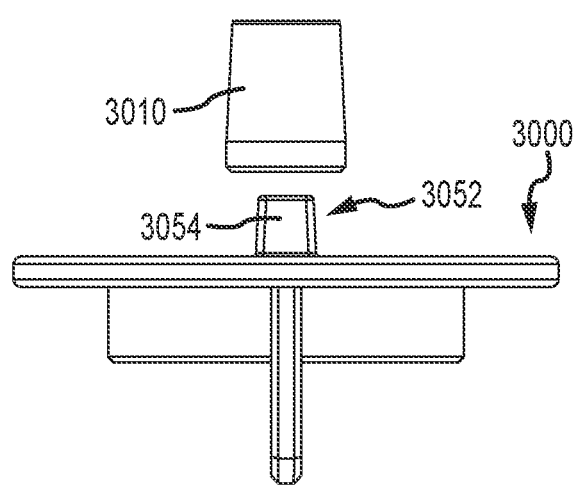

FIGS. 30A-30B are, respectively, top isometric and side views of the base plate 3000 with a humeral head implant 3050 positioned above, and the trunnion 3010 uncoupled with the base plate 3000. The base plate 3000 in FIGS. 30A-30B is the same as the base plate 2900 in FIGS. 29A-29I, except the trunnion 3010 is releasable from the base plate 3000 in FIGS. 30A-30B. Therefore the description of the base plate 2900 in FIGS. 29A-29I is applicable to the base plate 3000 in FIGS. 30A-30B. The base plate 3000 in FIGS. 30A-30B includes a peg 3052 having four planar side surfaces 3054 tapered slightly inward as it extends from the base plate 3000. The trunnion 3010 is releasably coupled to the peg 3052 and includes a socket (not seen) that is generally a negative shape of the peg 3052 (i.e., a box-like socket). Thus, when the trunnion 3010 is positioned on top of the peg 3052, the trunnion 3010 is restricted from rotating. Other than the trunnion 3010 and peg 3052, the base plate 3000 functions the same as previously described.

FIGS. 31A-31E are, respectively, top isometric, bottom isometric, top, side, and bottom views of a base plate 3100 having a central fin 3102 (major fin). As seen in the figures, the base plate 3100 includes a base structure 3104 having a circular perimeter 3106, anchor bores 3108 extending through the base structure 3104, and a male taper or trunnion 3110 extending upward from the top surface of the base structure 3104. The fin 3102 is on the opposite side of the base structure 3104 from the trunnion 3110. The base plate 3100 further includes an attachment structure 3116 in the form of a pair of minor fins 3118, one on either side of the central fin 3102, a transverse minor fin 3120 extending across the minor fins 3118 and the central fin 3102 at a central portion thereof, and a tubular wall 3124 encircling the minor fins 3118 and transverse minor fin 3120. The tubular wall 3124 also intersects the central fin 3102.

The base plate 3100 also includes an angle element 3126 (also described as a flange, a perimeter flange, or lip) extending off of a posterior end of the base plate 3100. The angle element 3100 extends parallel with the base structure 3104 and then angles at a perpendicular angle and extends downward. There are a pair of anchor bores 3128 formed within the angle element 3126 in a direction generally orthogonal to the anchor bores 3108 on the base structure 3104. As seen in FIG. 31D, the bores 3108 are positioned on opposite sides of the central fin 3102 when viewed down a plane defined by the central fin 3012. This permits anchors to be delivered through the anchor bores 3128 without interference by the central fin 3102. The anchor bores 3128 are also positioned deeper than the attachment structure 3116 so the anchors do not interfere with the attachment structure either. The angle element 3126 is sized and shaped to extend off of the posterior end of the resected bone surface 1950, as seen in FIG. 31G.

The base plate 3100 also includes a plurality of windows 3122 extending through the base structure 3104. The windows 3122 are positioned outward of the trunnion 3110 and inwards of the anchor bores 3108. The windows 3122 are defined between the fins 3102, 3120, 3118. The windows 3122 permit boney ingrowth to facilitate attachment of the bone to the base plate 3100. As seen in the figures, the fin 3102 is not angled; rather, it is flat with angled anterior and posterior ends. The flat longitudinal edge is generally parallel with the base structure 3104.

Figure 31A:
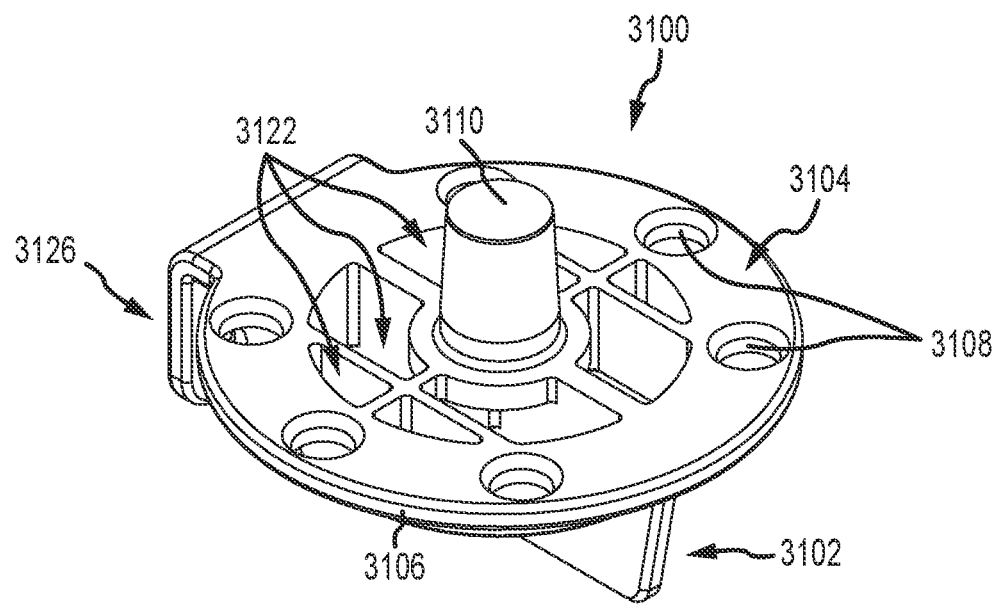
Figure 31B:
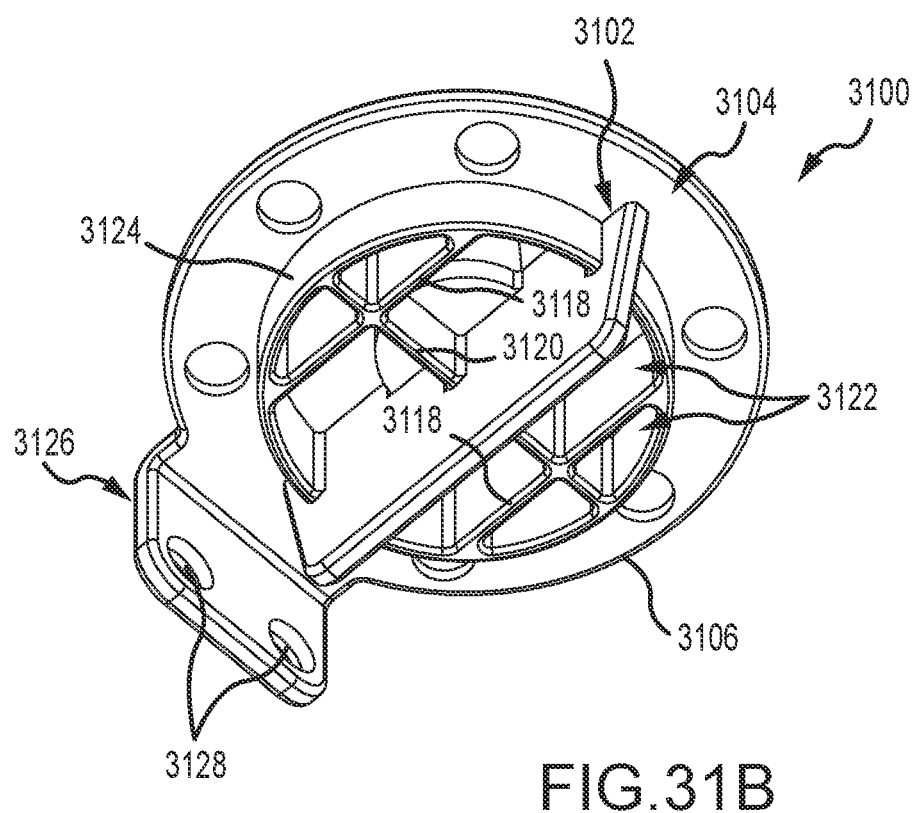
Figure 31F:
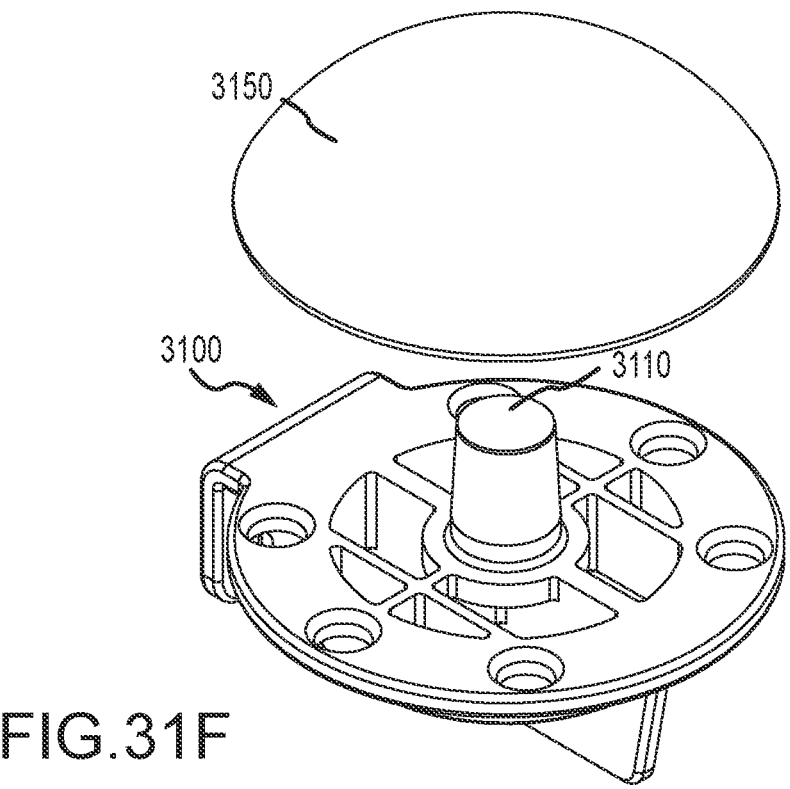
FIG. 31F is a top isometric view of the base plate with a humeral head implant positioned above.
Figure 31G:
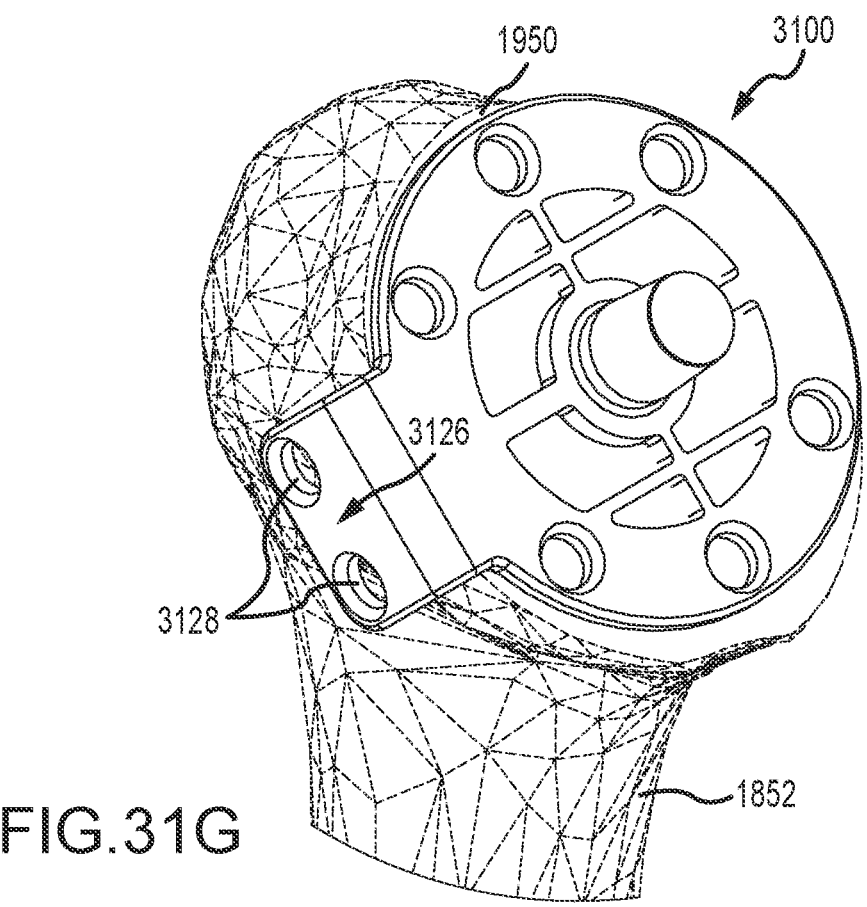
FIG. 31G is a posterior-medial view of the humerus with the base plate positioned thereon.
Figure 31H:
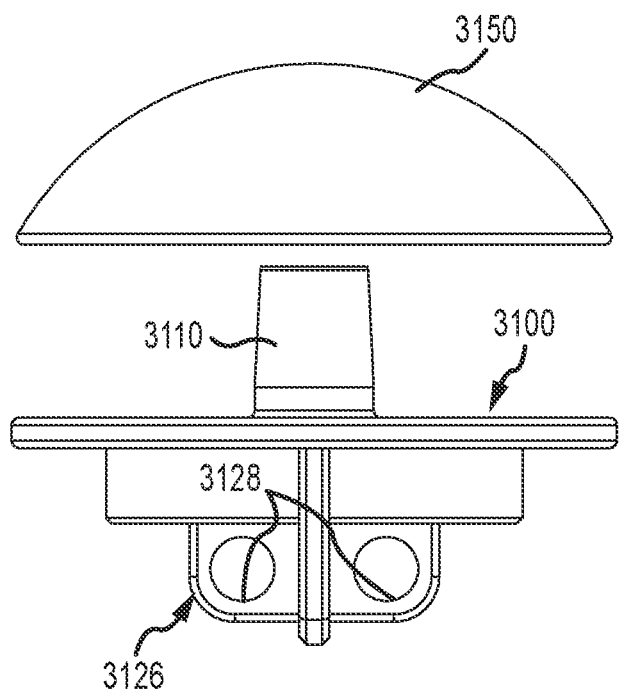
FIGS. 31H-31I are, respectively, side views of the base plate with the humeral head implant positioned above, and the base plate coupled with the humeral head implant.
Figure 31I:
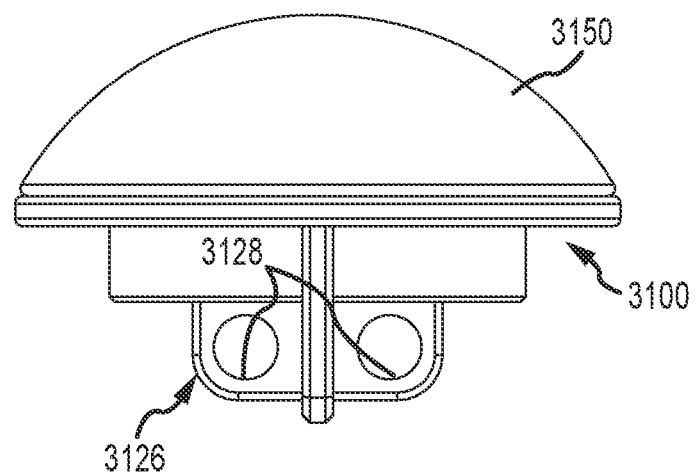

FIG. 31F is a top isometric view of the base plate 3100 with a humeral head implant 3150 positioned above. FIG. 31G is a posterior-medial view of the humerus 1852 with the base plate 3100 positioned thereon. And, FIGS. 31H-31I are, respectively, side views of the base plate 3100 with the humeral head implant 3150 positioned above, and the base plate 3100 coupled with the humeral head implant 3150.

FIGS. 32A-32E are, respectively, top isometric, bottom isometric, top, side, and bottom views of a base plate 3200 having a central fin 3202 (major fin), an attachment structure 3216, and a perimeter of a base structure 3204 with serrations 3230. As seen in the figures, the base plate 3200 includes a base structure 3204 having a circular perimeter 3206 with serrations 3230 extending downward therefrom, anchor bores 3208 extending through the base structure 3204, and a male taper or trunnion 3210 extending upward from the top surface of the base structure 3204. The fin 3202 is on the opposite side of the base structure 3204 from the trunnion 3210. The base plate 3200 further includes an attachment structure 3216 in the form of a pair of minor fins 3218, one on either side of the central fin 3202, and a transverse minor fin 3220 extending across the minor fins 3218 and the central fin 3202 at a central portion thereof. The serrations 3230 define a dentil edge around the perimeter 3206 and include cylindrical inner and outer surfaces, a linear bottom edge, and tapered side edges. The serrations 3230 are designed to cut into the harder cortical bone near the perimeter of the resected bone surface 1950, as seen in FIG. 32G. In certain instances, additional fixation at the periphery aids in overall fixation of the base plate to the bone.

The base plate 3200 also includes a plurality of windows 3222 extending through the base structure 3204. The windows 3222 are positioned outward of the trunnion 3210 and inwards of the anchor bores 3208. The windows 3222 are defined between the fins 3202, 3220, 3218. The windows 3222 permit boney ingrowth to facilitate attachment of the bone to the base plate 3200. As seen in the figures, the fin 3202 is not angled; rather, it is flat with angled anterior and posterior ends. The flat longitudinal edge is generally parallel with the base structure 3204.

Figure 32A:
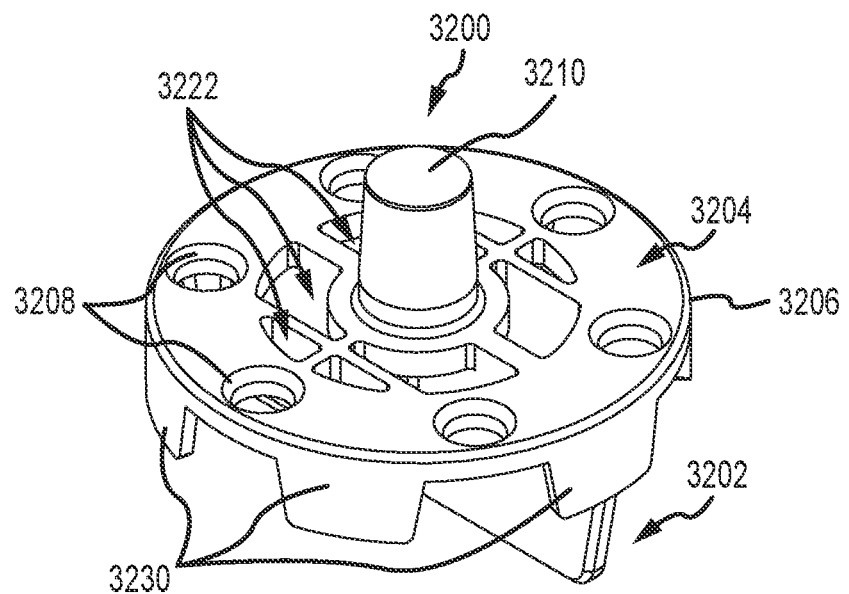
FIGS. 32A-32E are, respectively, top isometric, bottom isometric, top, side, and bottom views of a base plate a central fin, a grid attachment structure, and a downwardly protruding dentil edge at the perimeter thereof.
Figure 32B:
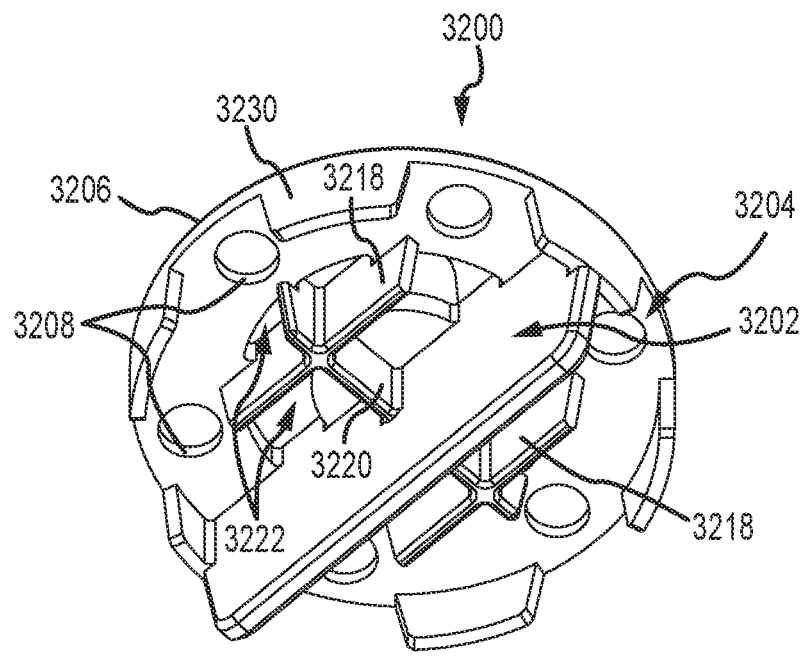
Figure 32C:
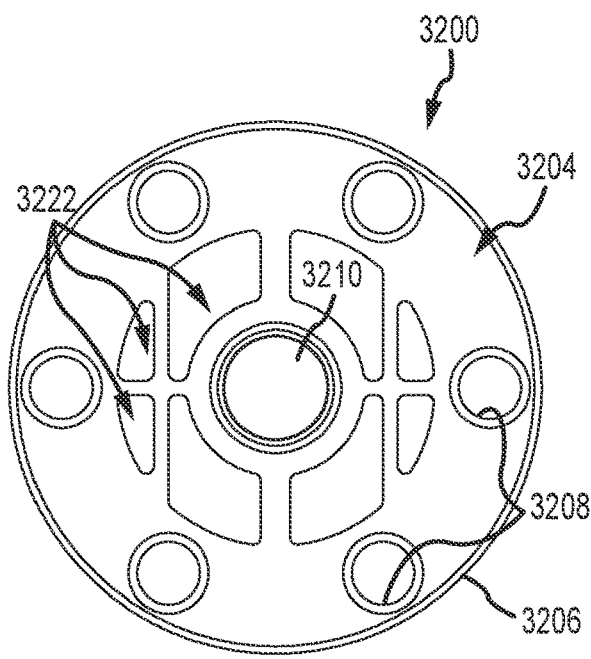
Figure 32D:
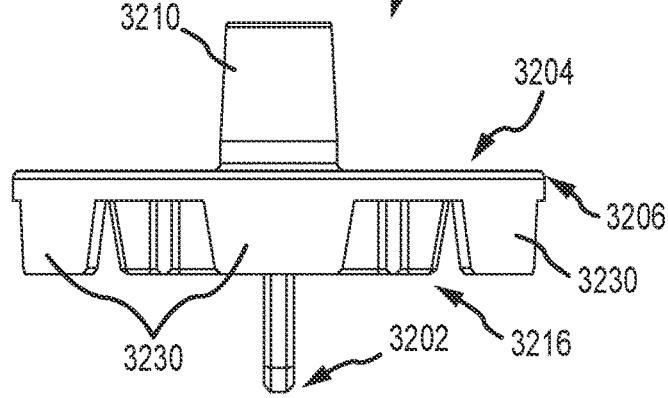
Figure 32E:
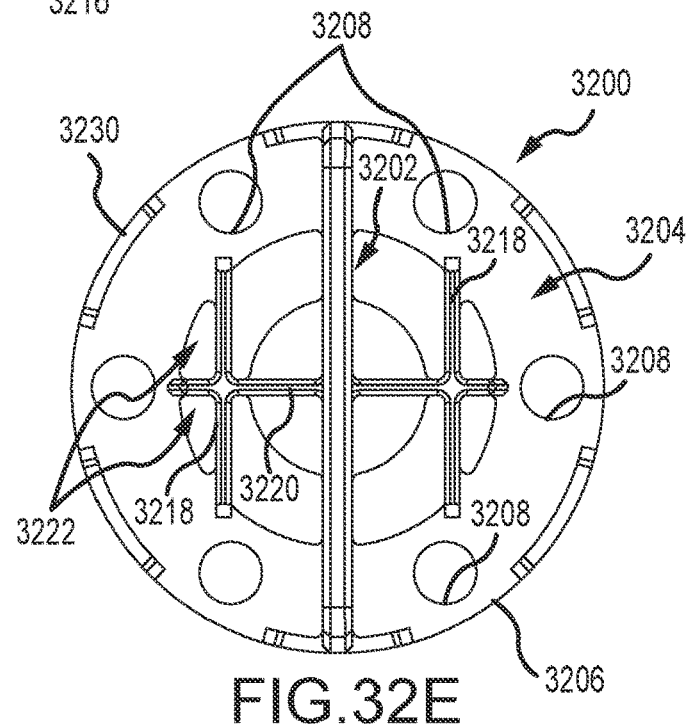
Figure 32F:
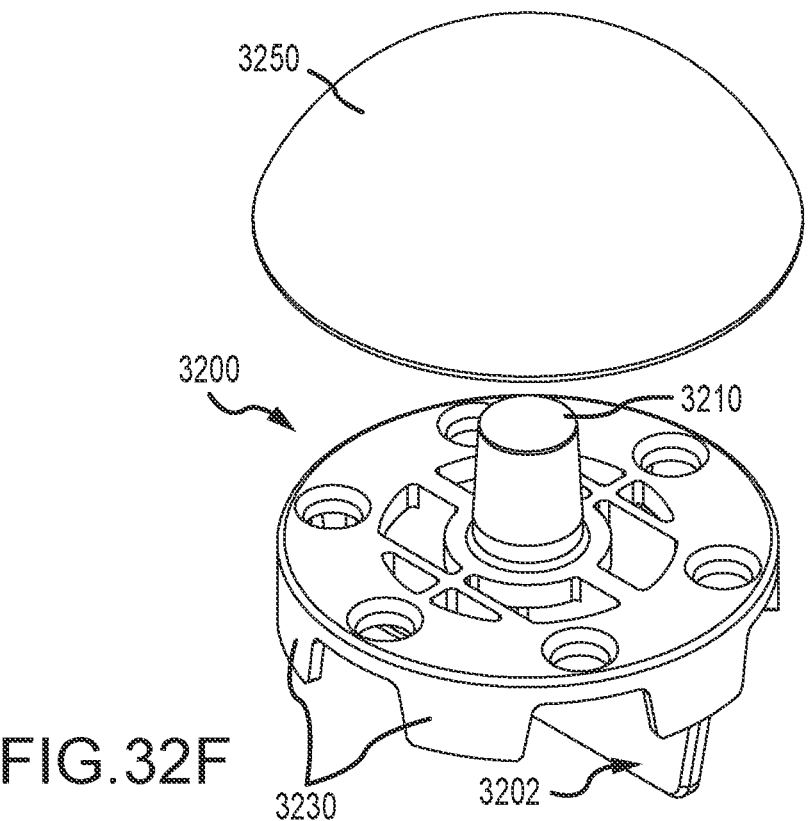
FIG. 32F is a top isometric view of the base plate with a humeral head implant positioned above.
Figure 32G:
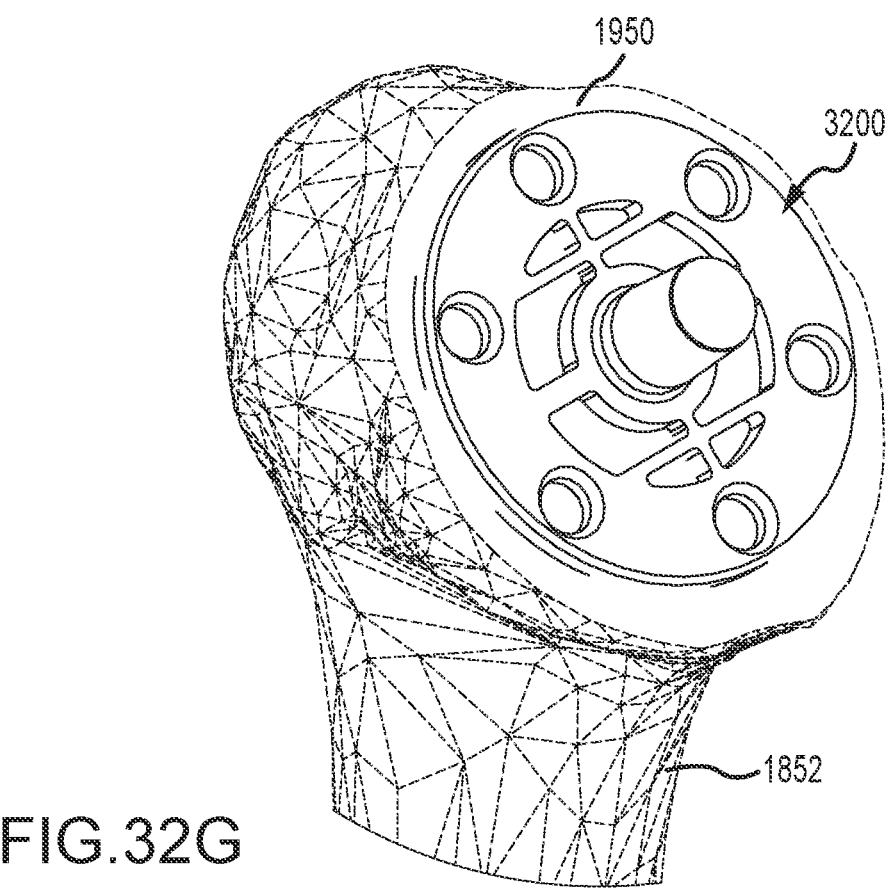
FIG. 32G is a posterior-medial view of the humerus with the base plate positioned thereon.
Figure 32H:
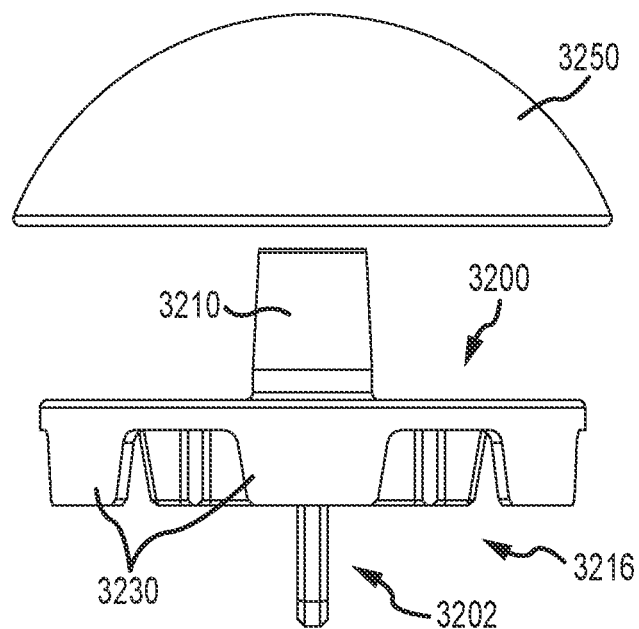
FIGS. 32H-32I are, respectively, side views of the base plate with the humeral head implant positioned above, and the base plate coupled with the humeral head implant.
Figure 32I:
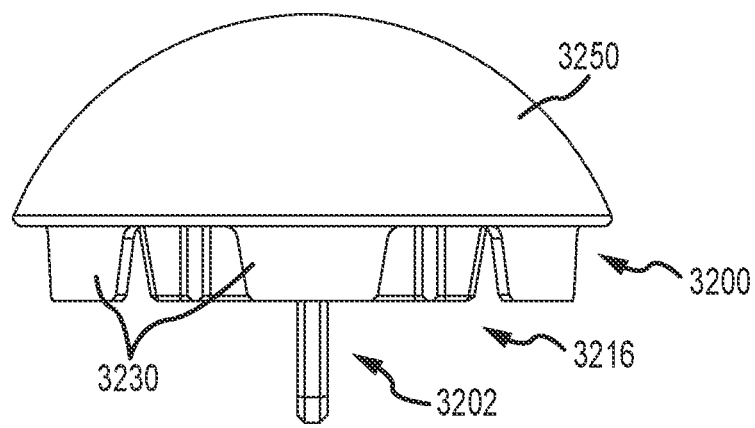

FIG. 32F is a top isometric view of the base plate 3200 with a humeral head implant 3250 positioned above. FIG. 32G is a posterior-medial view of the humerus 1852 with the base plate 3200 positioned thereon. And, FIGS. 32H-32I are, respectively, side views of the base plate 3200 with the humeral head implant 3250 positioned above, and the base plate 3200 coupled with the humeral head implant 3250.

FIGS. 33A-33E are, respectively, top isometric, bottom isometric, top, side, and bottom views of a base plate 3300 having a central fin 3302 (major fin), an attachment structure 3316, and pair of tubular wall portions 3324 positioned near a perimeter 3206 of the base structure 3304. As seen in the figures, the base plate 3300 includes the base structure 3304 having a circular perimeter 3306, a pair anchor bores 3308 extending through the base structure 3304 and positioned on superior and inferior ends of the plate 3300, and a male taper or trunnion 3310 extending upward from the top surface of the base structure 3304. The fin 3302 is on the opposite side of the base structure 3304 from the trunnion 3310. The base plate 3300 further includes an attachment structure 3316 in the form of a pair of minor fins 3318, one on either side of the central fin 3302, and a transverse minor fin 3320 extending across the minor fins 3318 and the central fin 3302 at a central portion thereof. The tubular wall portions 3324 intersects the central fin 3302 and the two minor fins 3318, but does not intersect the transverse minor fin 3320. The tubular wall portions 3324 extend up to the anchor bores 3308, but do not intersect them. As seen in the figures, the tubular wall portions 3324 are positioned radially outward from a center point of the base plate 3300 the same radial distance as the anchor bores 3308. This enables the tubular wall portions 3324 to engage dense cortical bone on the outskirts of the resected bone surface 1950, as seen in FIG. 33G. There are only two anchor bores 3308 on the base plate 3300, and the bores 3308 are positioned at the superior and inferior portions of the resected bone surface 1950, as seen in FIG. 33G, so as to anchor the plate 3300 to dense bone.

The base plate 3300 also includes a plurality of windows 3322 extending through the base structure 3304. The windows 3322 are positioned outward of the trunnion 3310 and inwards of the anchor bores 3308. The windows 3322 are defined between the fins 3302, 3320, 3318. The windows 3322 permit boney ingrowth to facilitate attachment of the bone to the base plate 3300. As seen in the figures, the fin 3302 is not angled; rather, it is flat with angled anterior and posterior ends. The flat longitudinal edge is generally parallel with the base structure 3304.

Figure 33A:
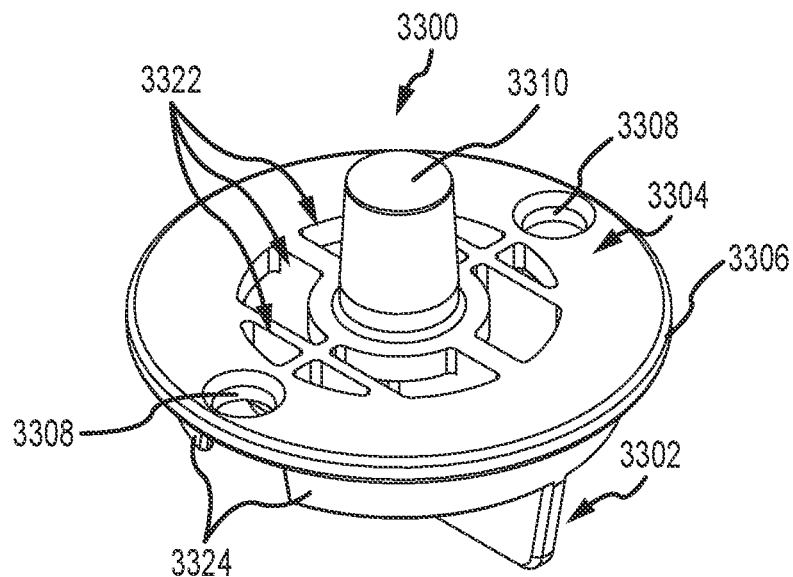
Figure 33B:
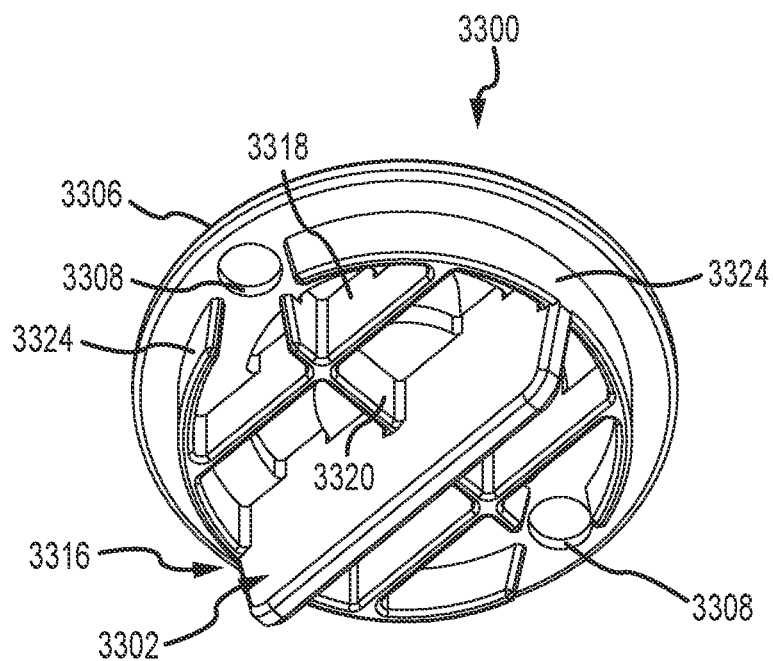
Figure 33F:
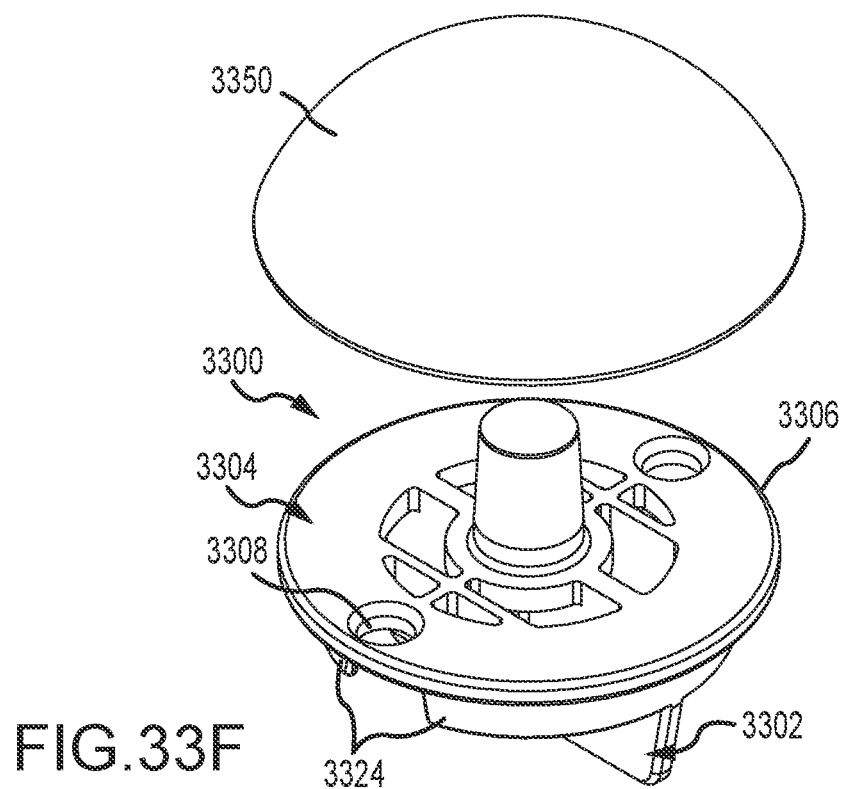
FIG. 33F is a top isometric view of the base plate with a humeral head implant positioned above.
Figure 33G:
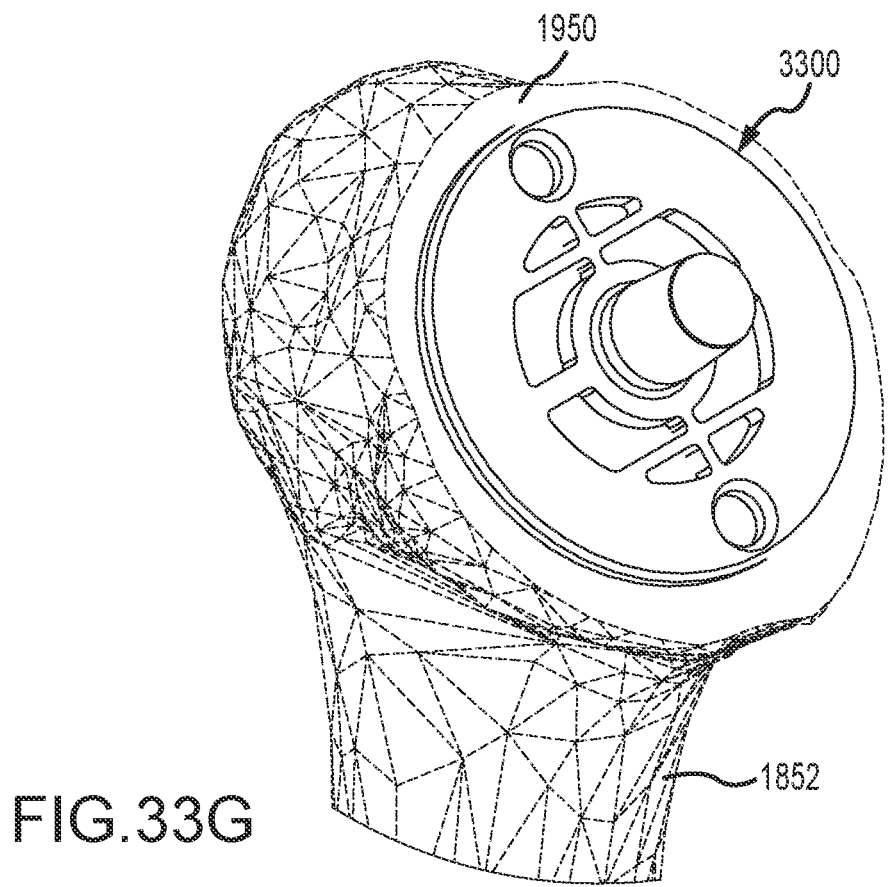
FIG. 33G is a posterior-medial view of the humerus with the base plate positioned thereon.
Figure 33H:
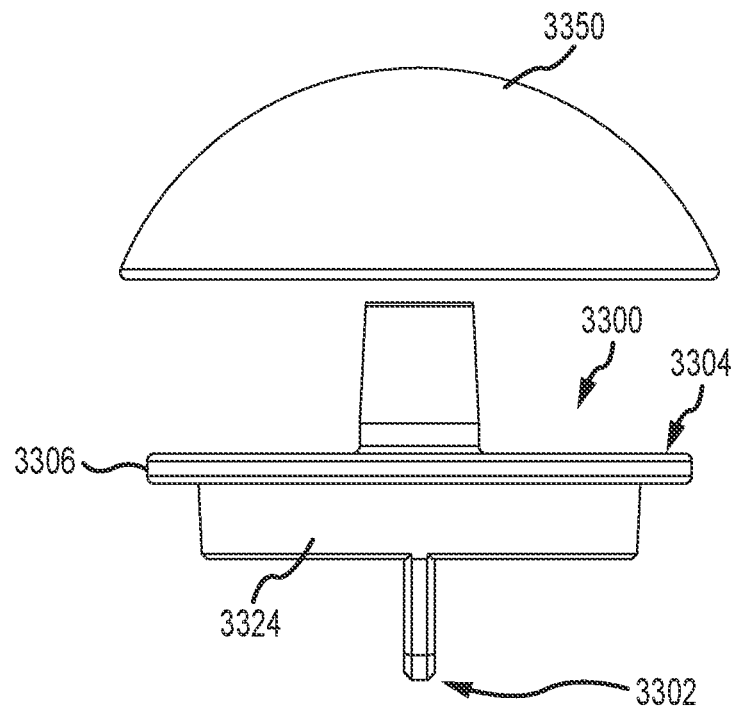
FIGS. 33H-33I are, respectively, side views of the base plate with the humeral head implant positioned above, and the base plate coupled with the humeral head implant.
Figure 33I:
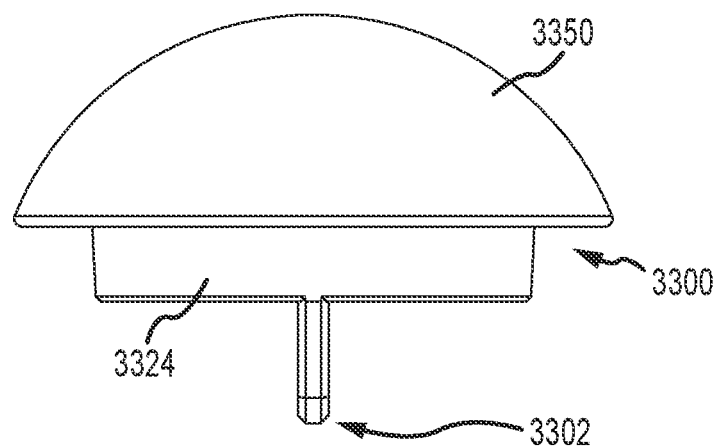

FIG. 33F is a top isometric view of the base plate 3300 with a humeral head implant 3350 positioned above. FIG. 33G is a posterior-medial view of the humerus 1852 with the base plate 3300 positioned thereon. And, FIGS. 33H-33I are, respectively, side views of the base plate 3300 with the humeral head implant 3350 positioned above, and the base plate 3300 coupled with the humeral head implant 3350.

FIGS. 34A-34E are, respectively, top isometric, bottom isometric, top, side, and bottom views of a base plate 3400 having a central fin 3402 (major fin), an attachment structure 3416, and a partial tubular wall 3424 encircling half of the bottom side of the base plate 3400. As seen in the figures, the base plate 3400 includes a base structure 3404 having a circular perimeter 3406, anchor bores 3408 extending through the base structure 3404, and a male taper or trunnion 3410 extending upward from the top surface of the base structure 3404. The fin 3402 is on the opposite side of the base structure 3404 from the trunnion 3410. The base plate 3400 further includes an attachment structure 3416 in the form of a pair of minor fins 3418, one on either side of the central fin 3402, a transverse minor fin 3420 extending across the minor fins 3418 and the central fin 3402 at a central portion thereof, and a partial tubular wall 3424 encircling one half of the minor fins 3418 and transverse minor fin 3420. The tubular wall 3424 also intersects the central fin 3402. The partial tubular wall 3424 is designed to be positioned at either an anterior end or posterior end of the resected bone surface. In the case of positioning the partial tubular wall 3424 at the anterior end of the resected bone surface, this enables more fixation to the bone at the side of the bone with less access by the surgeon. In such a case, anchors may be used to fixate the posterior part of the base plate 3400, while the extra fixation on the base plate 3400 is used to anchor the plate 3400 on the anterior side.

The base plate 3400 also includes a plurality of windows 3422 extending through the base structure 3404. The windows 3422 are positioned outward of the trunnion 3410 and inwards of the anchor bores 3408. The windows 3422 are defined between the fins 3402, 3420, 3418. The windows 3422 permit boney ingrowth to facilitate attachment of the bone to the base plate 3400. As seen in the figures, the fin 3402 is not angled; rather, it is flat with angled anterior and posterior ends. The flat longitudinal edge is generally parallel with the base structure 3404.

Figure 34A:
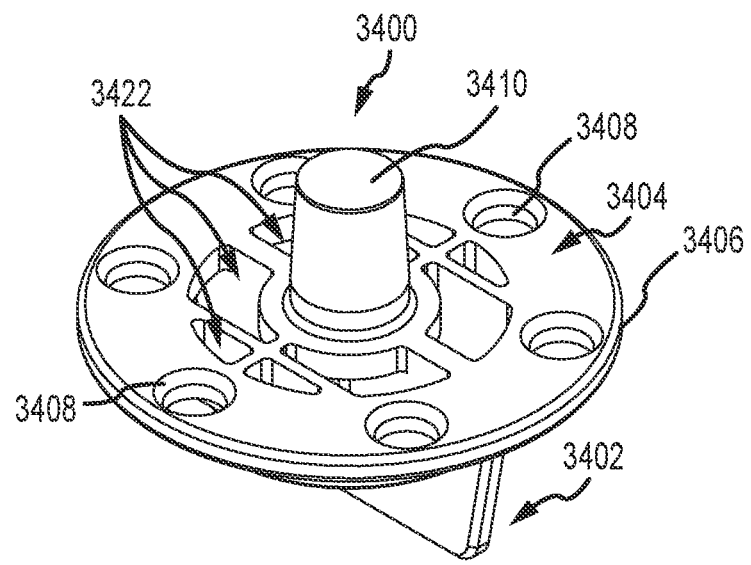
FIGS. 34A-34E are, respectively, top isometric, bottom isometric, top, side, and bottom views of a base plate having a central fin, and a grid attachment structure that is partially encircled by a tubular wall at the anterior end of the base plate.
Figure 34B:
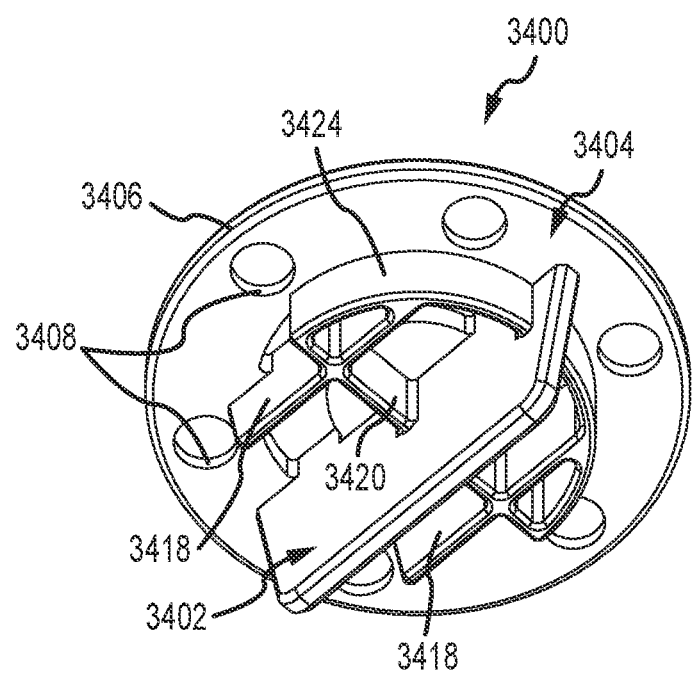
Figure 34C:
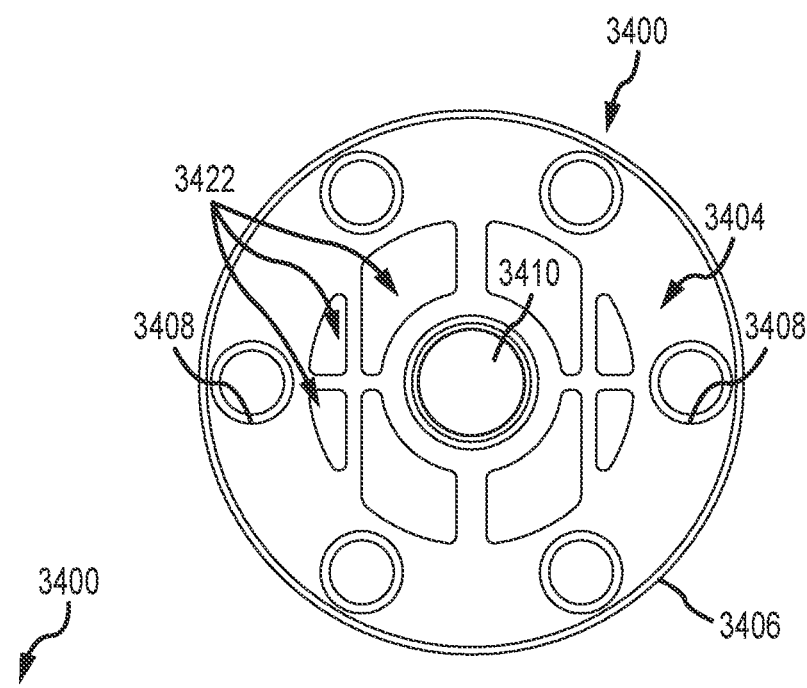
Figure 34D:
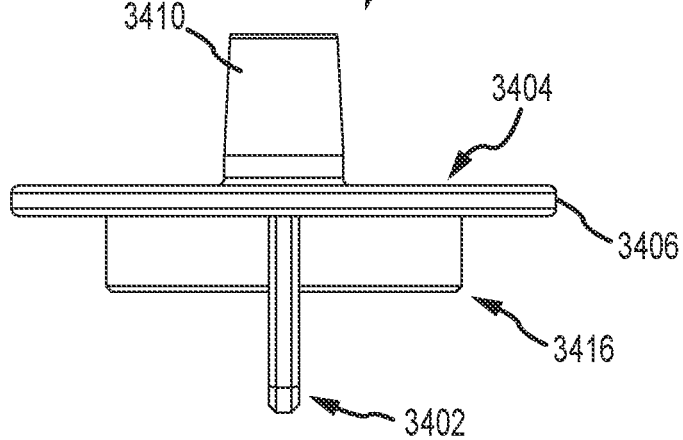
Figure 34E:
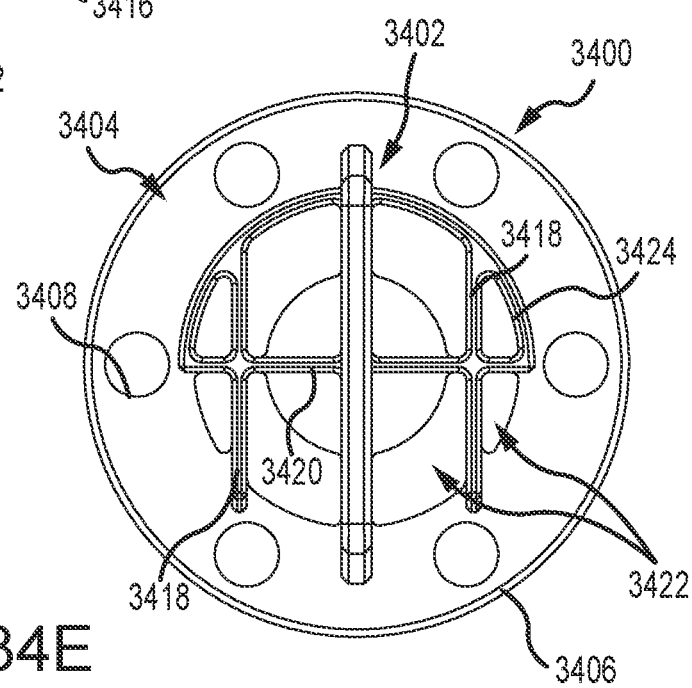
Figure 34F:
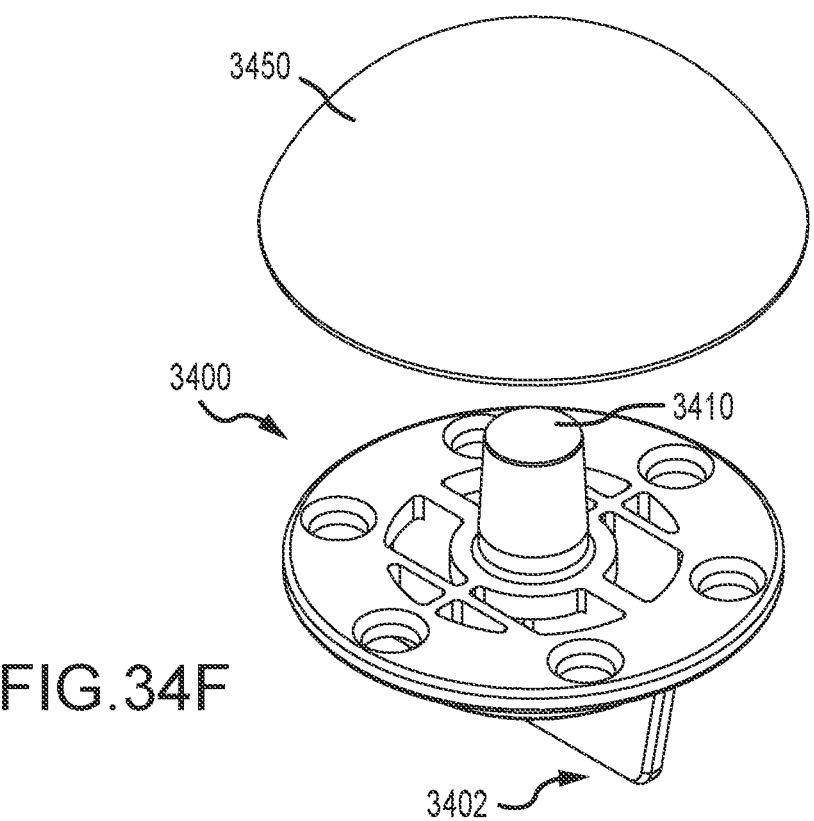
FIG. 34F is a top isometric view of the base plate with a humeral head implant positioned above.
Figure 34G:
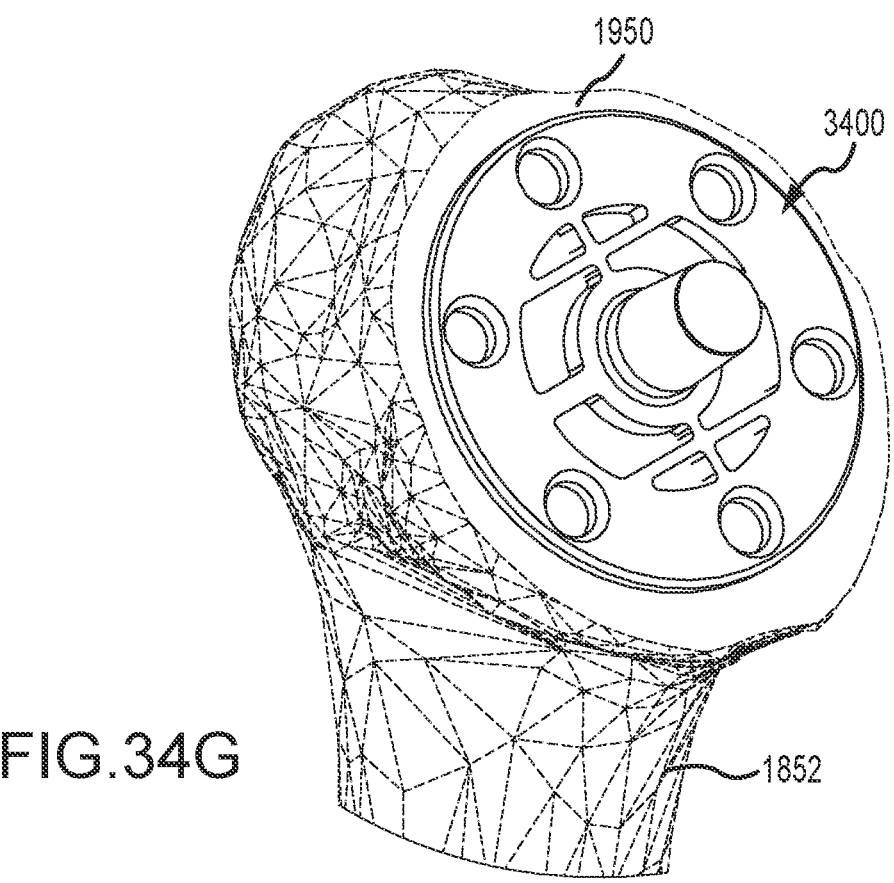
FIG. 34G is a posterior-medial view of the humerus with the base plate positioned thereon.
Figure 34H:
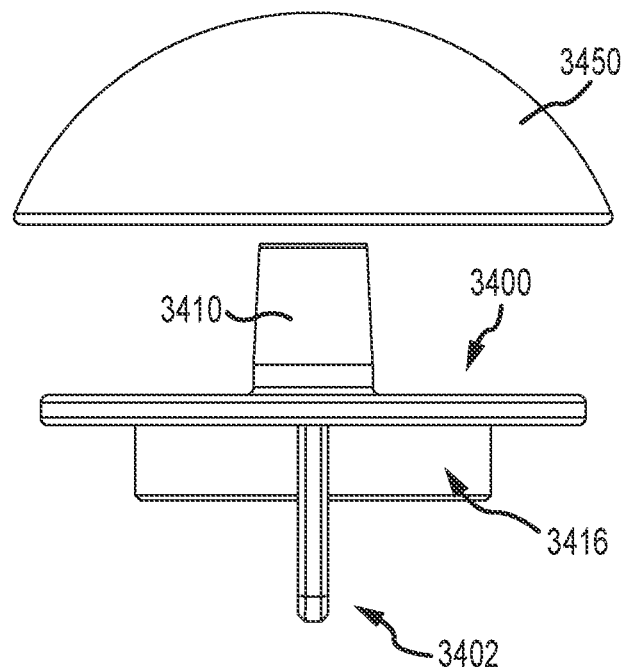
FIGS. 34H-34I are, respectively, side views of the base plate with the humeral head implant positioned above, and the base plate coupled with the humeral head implant.
Figure 34I:
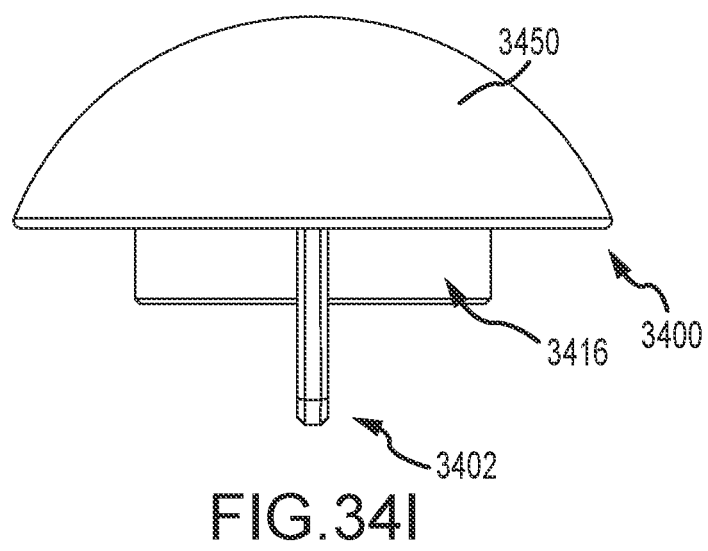

FIG. 34F is a top isometric view of the base plate 3400 with a humeral head implant 3450 positioned above. FIG. 34G is a posterior-medial view of the humerus 1852 with the base plate 3400 positioned thereon. And, FIGS. 34H-34I are, respectively, side views of the base plate 3400 with the humeral head implant 3450 positioned above, and the base plate 3400 coupled with the humeral head implant 3450.

FIGS. 35A-35E are, respectively, top isometric, bottom isometric, top, side, and bottom views of a base plate 3500 having a central fin 3502 (major fin), an attachment structure 3516, and a partial tubular wall 3524 encircling half of the bottom side of the base plate 3500. As seen in the figures, the base plate 3500 includes a base structure 3504 having a circular perimeter 3506, anchor bores 3508 extending through the base structure 3504, and a male taper or trunnion 3510 extending upward from the top surface of the base structure 3504. The fin 3502 is on the opposite side of the base structure 3504 from the trunnion 3510. The base plate 3500 further includes an attachment structure 3516 in the form of a pair of minor fins 3518, one on either side of the central fin 3502, a transverse minor fin 3520 extending across the minor fins 3518 and the central fin 3502 at a central portion thereof, and a partial tubular wall 3524 encircling one of the minor fins 3518 and half of the transverse minor fin 3520. The tubular wall 3524 also abuts the central fin 3502 at opposite ends of the central fin 3502. The partial tubular wall 3524 is designed to be positioned at either a superior end or an inferior end of the resected bone surface. In the case of positioning the partial tubular wall 3524 at the inferior end of the resected bone surface, this enables more fixation to the bone at the side of the bone with strong fixation qualities. That is, the calcar or inferior metaphyseal bone is strong bone for anchoring. In such a case, anchors may be used to fixate the posterior part of the base plate 3500, while the extra fixation on the base plate 3500 is used to anchor the plate 3500 on the inferior side. In certain instances the base plate 3500 may be rotated one hundred eighty degrees such that the partial tubular wall 3524 is positioned at the superior end of the resected bone surface.

The base plate 3500 also includes a plurality of windows 3522 extending through the base structure 3504. The windows 3522 are positioned outward of the trunnion 3510 and inwards of the anchor bores 3508. The windows 3522 are defined between the fins 3502, 3520, 3518. The windows 3522 permit boney ingrowth to facilitate attachment of the bone to the base plate 3500. As seen in the figures, the fin 3502 is not angled; rather, it is flat with angled anterior and posterior ends. The flat longitudinal edge is generally parallel with the base structure 3504.

Figure 35A:
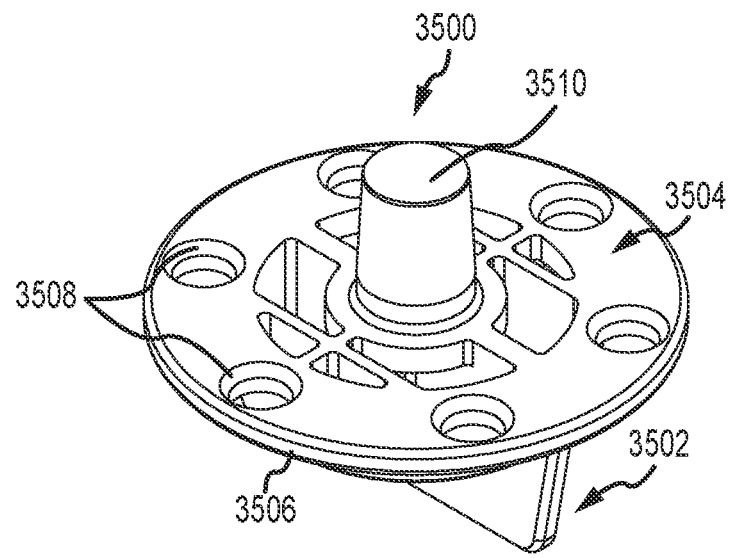
Figure 35B:
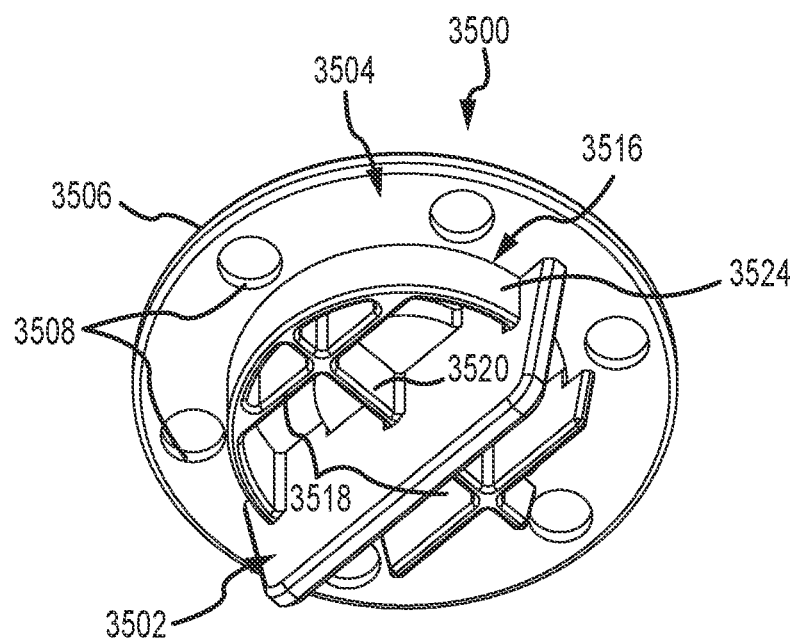
Figure 35F:
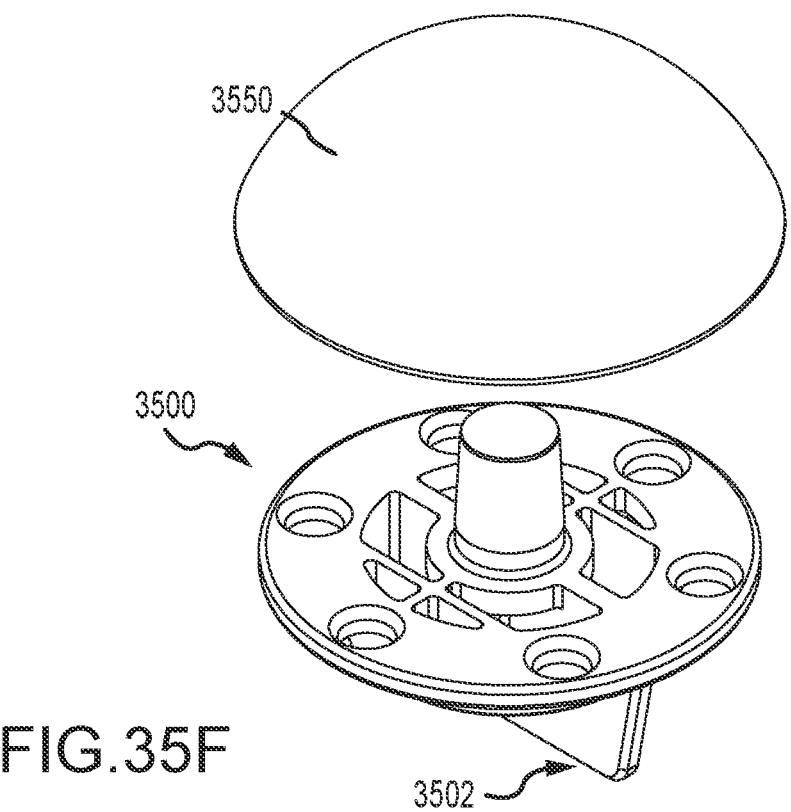
FIG. 35F is a top isometric view of the base plate with a humeral head implant positioned above.
Figure 35G:
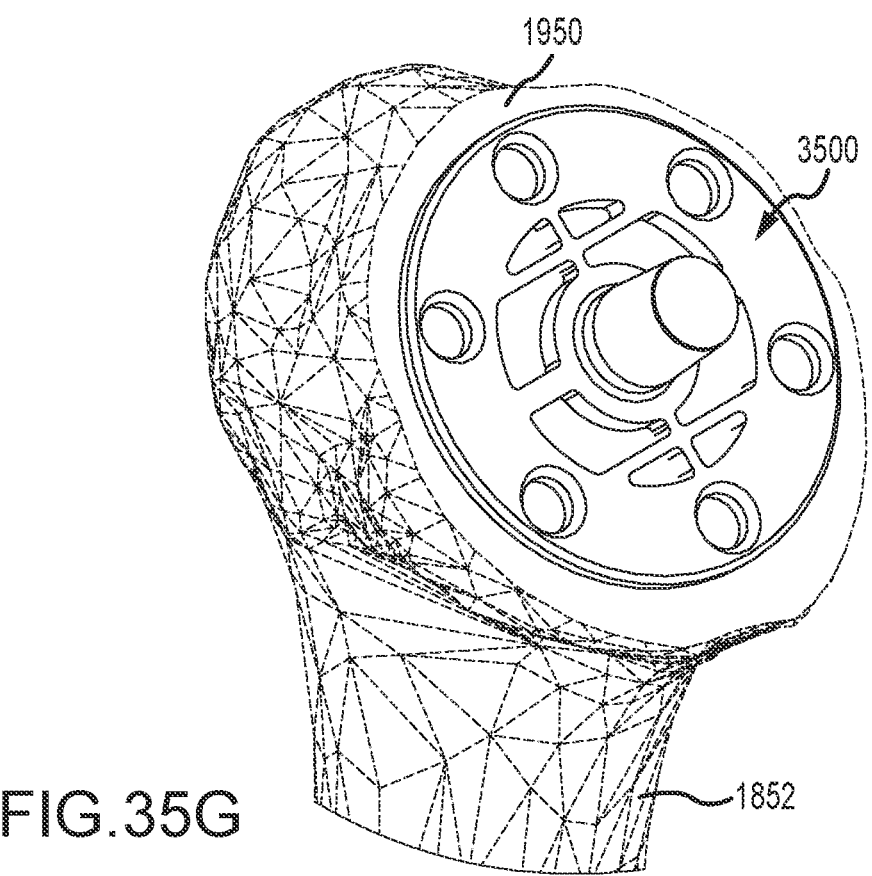
FIG. 35G is a posterior-medial view of the humerus with the base plate positioned thereon.
Figure 35H:
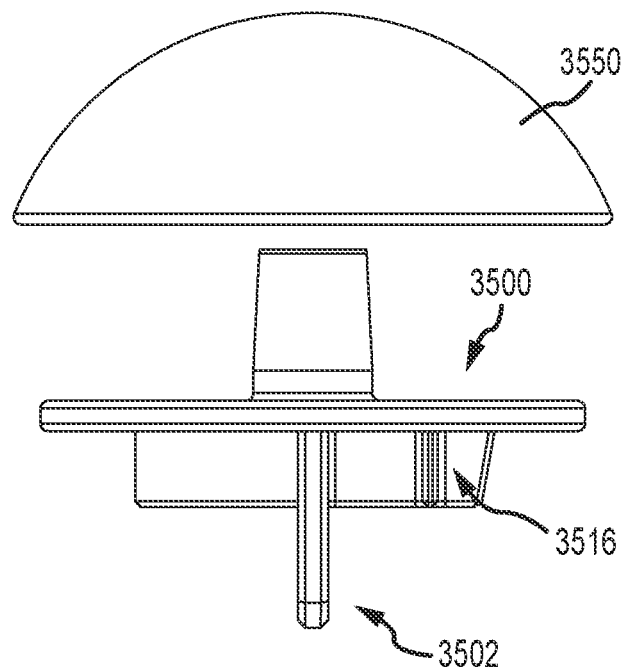
FIGS. 35H-35I are, respectively, side views of the base plate with the humeral head implant positioned above, and the base plate coupled with the humeral head implant.
Figure 35I:
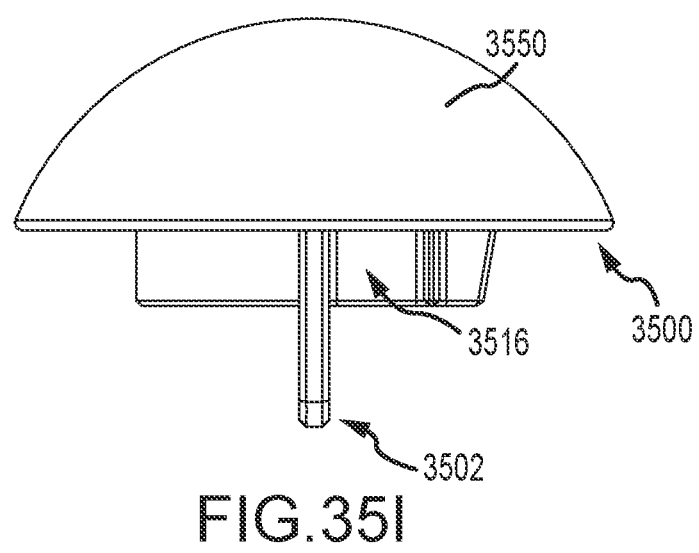

FIG. 35F is a top isometric view of the base plate 3500 with a humeral head implant 3550 positioned above. FIG. 35G is a posterior-medial view of the humerus 1852 with the base plate 3500 positioned thereon. And, FIGS. 35H-35I are, respectively, side views of the base plate 3500 with the humeral head implant 3550 positioned above, and the base plate 3500 coupled with the humeral head implant 3550.

FIGS. 36A-36E are, respectively, top isometric, bottom isometric, top, side, and bottom views of a base plate 3600 having a central fin 3602 (major fin). As seen in the figures, the base plate 3600 includes a base structure 3604 having a scalloped perimeter 3606 for ease of visibility during implantation, anchor bores 3608 extending through the base structure 3604, and a male taper or trunnion 3610 extending upward from the top surface of the base structure 3604. The fin 3602 is on the opposite side of the base structure 3604 from the trunnion 3610. The base plate 3600 further includes an attachment structure 3616 in the form of a pair of minor fins 3618, one on either side of the central fin 3602, a transverse minor fin 3620 extending across the minor fins 3618 and the central fin 3602 at a central portion thereof, and a tubular wall 3624 encircling the minor fins 3618 and transverse minor fin 3620. The tubular wall 3624 also intersects the central fin 3602.

The base plate 3600 also includes a plurality of windows 3622 extending through the base structure 3604. The windows 3622 are positioned outward of the trunnion 3610 and inwards of the anchor bores 3608. The windows 3622 are defined between the fins 3602, 3620, 3618. The windows 3622 permit boney ingrowth to facilitate attachment of the bone to the base plate 3600. As seen in the figures, the fin 3602 is not angled; rather, it is flat with angled anterior and posterior ends. The flat longitudinal edge is generally parallel with the base structure 3604.

Figure 36A:
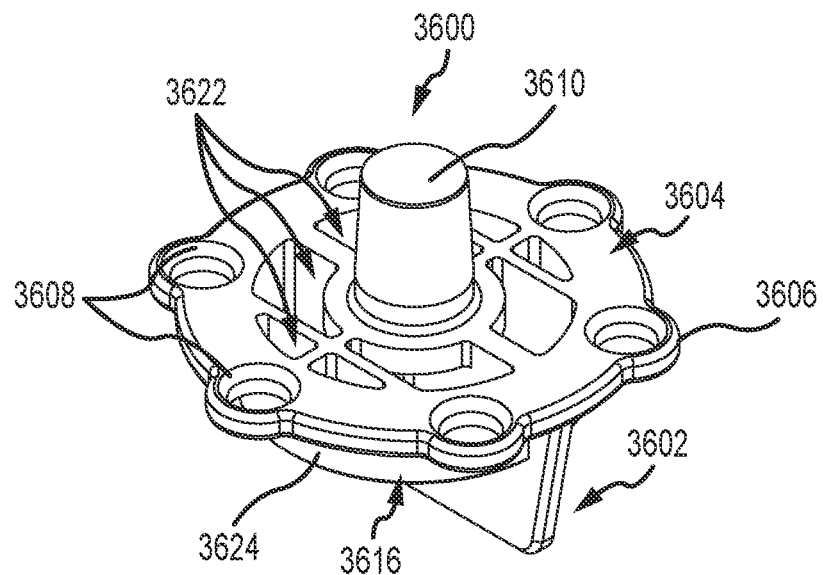
FIGS. 36A-36E are, respectively, top isometric, bottom isometric, top, side, and bottom views of a base plate having a central fin, an grid attachment structure encircled by a tubular wall, and a scalloped perimeter edge of the base of the base plate.
Figure 36B:
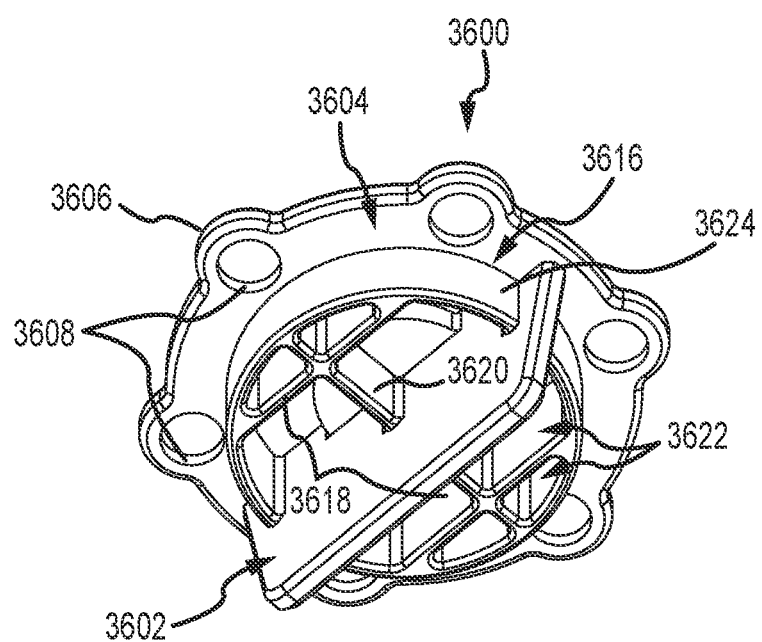
Figure 36C:
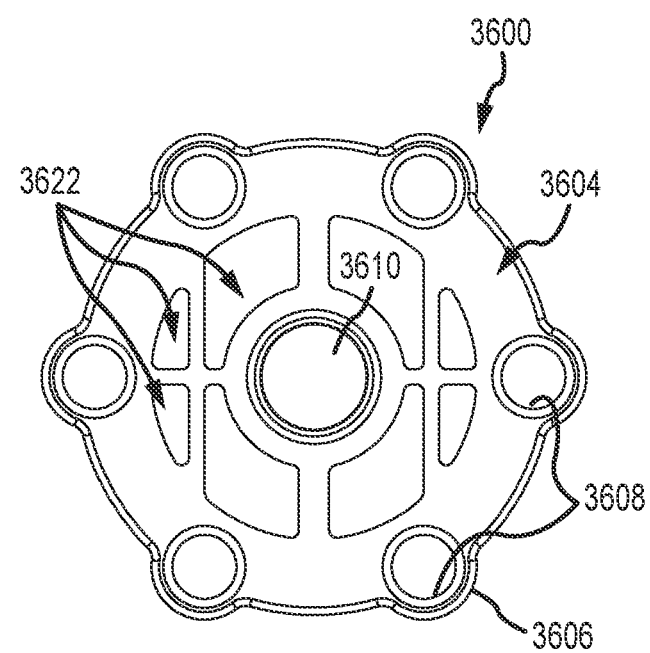
Figure 36D:
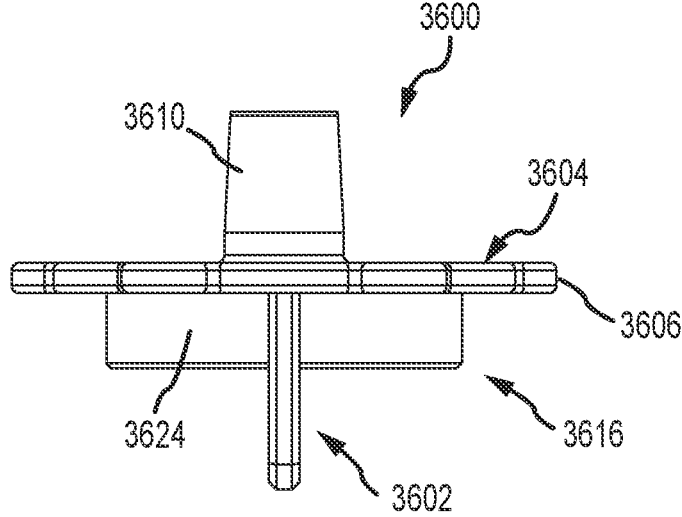
Figure 36E:
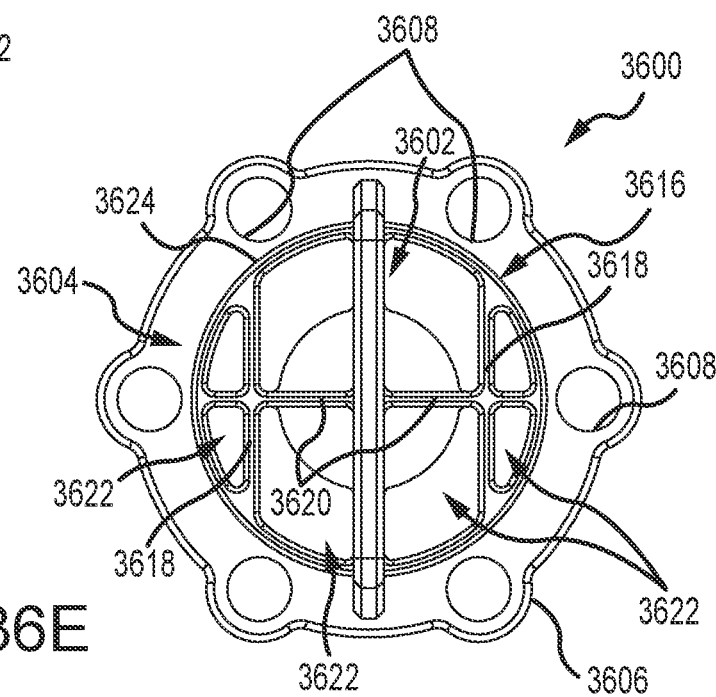
Figure 36F:
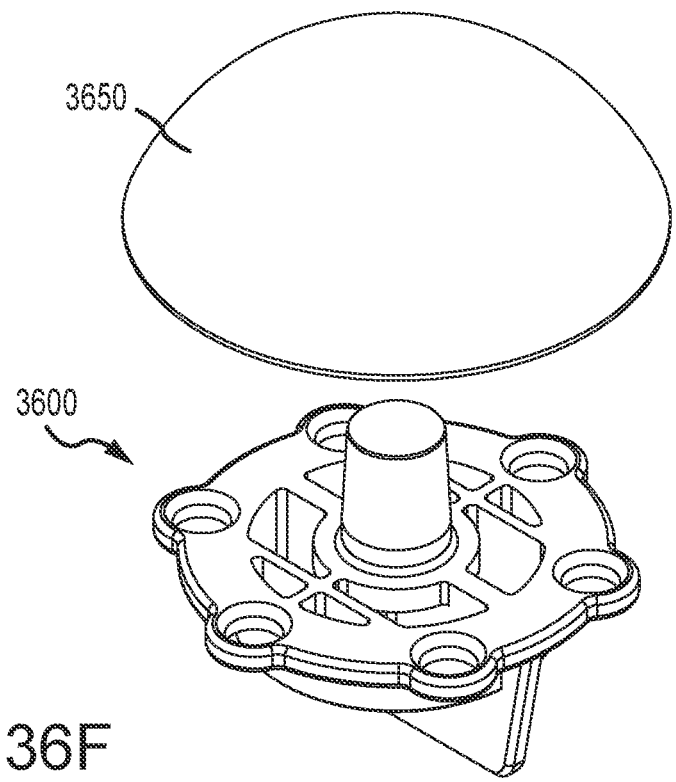
FIG. 36F is a top isometric view of the base plate with a humeral head implant positioned above.
Figure 36G:
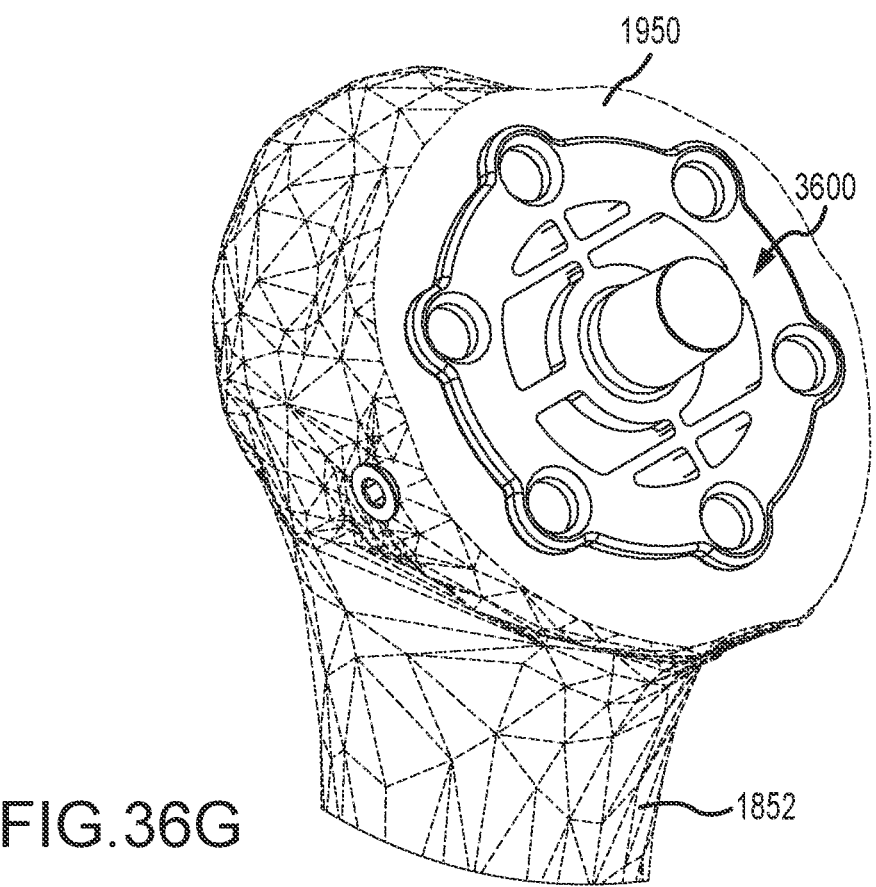
FIG. 36G is a posterior-medial view of the humerus with the base plate positioned thereon.
Figure 36H:
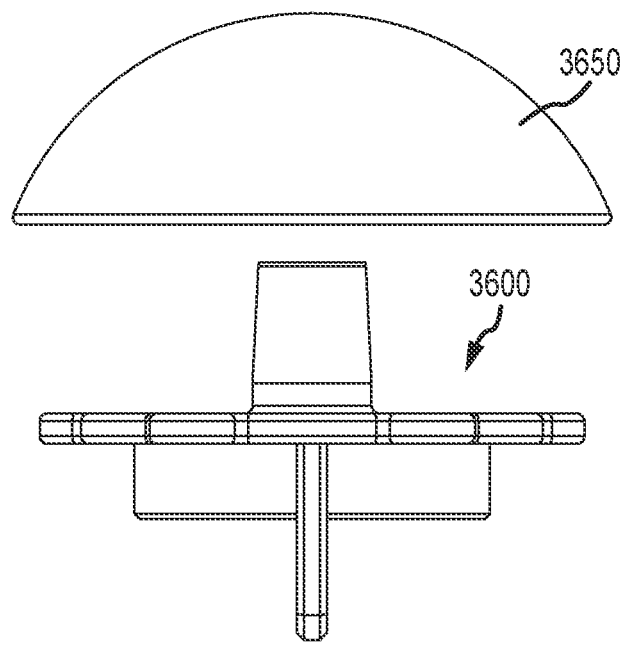
FIGS. 36H-36I are, respectively, side views of the base plate with the humeral head implant positioned above, and the base plate coupled with the humeral head implant.
Figure 36I:
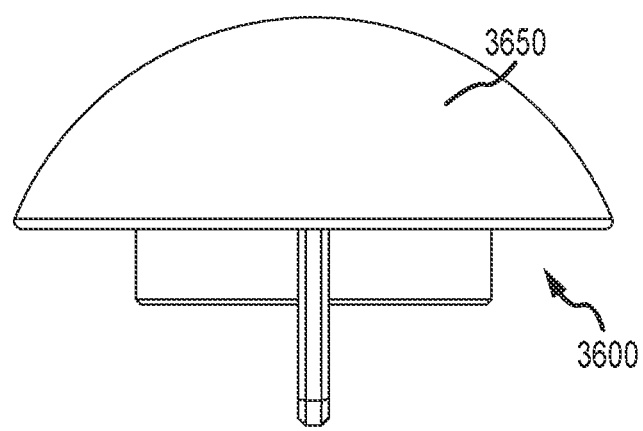

FIG. 36F is a top isometric view of the base plate 3600 with a humeral head implant 3650 positioned above. FIG. 36G is a posterior-medial view of the humerus 1852 with the base plate 3600 positioned thereon. And, FIGS. 36H-36I are, respectively, side views of the base plate 3600 with the humeral head implant 3650 positioned above, and the base plate 3600 coupled with the humeral head implant 3650.

FIGS. 37A-37E are, respectively, top isometric, bottom isometric, top, side, and bottom views of a base plate 3700 having a central fin 3702 (major fin) and a combination male-female taper or trunnion 3710. As seen in the figures, the base plate 3700 includes a base structure 3704 having a circular perimeter 3706, anchor bores 3708 extending through the base structure 3704 around a perimeter thereof, and a combination male-female taper or trunnion 3710 extending upward from the top surface of the base structure 3704. The fin 3702 is on the opposite side of the base structure 3704 from the trunnion 3710. The base plate 3700 further includes an attachment structure 3716 in the form of a pair of minor fins 3718, one on either side of the central fin 3702, a transverse minor fin 3720 extending across the minor fins 3718 and the central fin 3702 at a central portion thereof, and a tubular wall 3724 encircling the minor fins 3718 and transverse minor fin 3720. The tubular wall 3724 also intersects the central fin 3702.

The combination male-female taper 3710 includes an outer surface 3726 protruding upward (male) from the base structure 3704, and an inward socket (female) 3728 formed within the outer protruding surface 3726. The combination male-female taper 3710 may permit use in a tighter shoulder with less clearance for a relatively larger taper. In certain instances, the dimensions of the combination taper 3710 may be an 8 mm male taper and a 2 mm female socket. In certain instances, the dimensions of the combination taper 3710 may be an 6 mm male taper and a 4 mm female socket. In certain instances, the dimensions of the combination taper 3710 may be other dimensions as necessary for a given procedure and the particular anatomy of the patient.

The base plate 3700 also includes a plurality of windows 3722 extending through the base structure 3704. The windows 3722 are positioned outward of the trunnion 3710 and inwards of the anchor bores 3708. The windows 3722 are defined between the fins 3702, 3720, 3718. The windows 3722 permit boney ingrowth to facilitate attachment of the bone to the base plate 3700. As seen in the figures, the fin 3702 is not angled; rather, it is flat with angled anterior and posterior ends. The flat longitudinal edge is generally parallel with the base structure 3704.

Figure 37A:
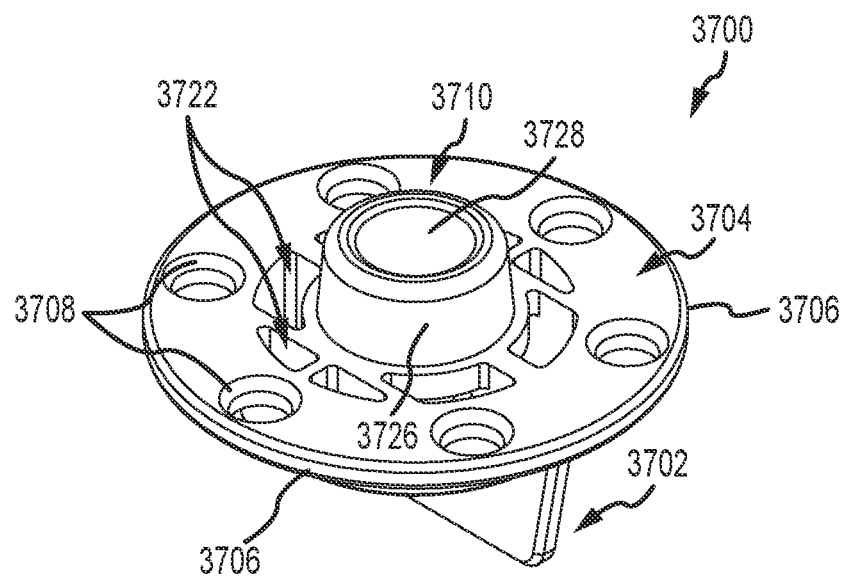
FIGS. 37A-37E are, respectively, top isometric, bottom isometric, top, side, and bottom views of a base plate having a central fin, a grid attachment structure encircled by a tubular wall, and a combination male-female taper.
Figure 37B:
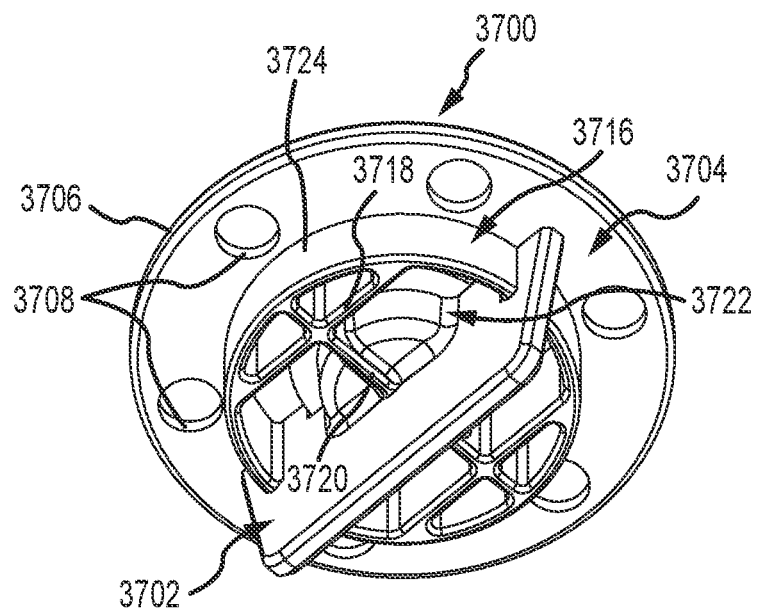
Figure 37C:
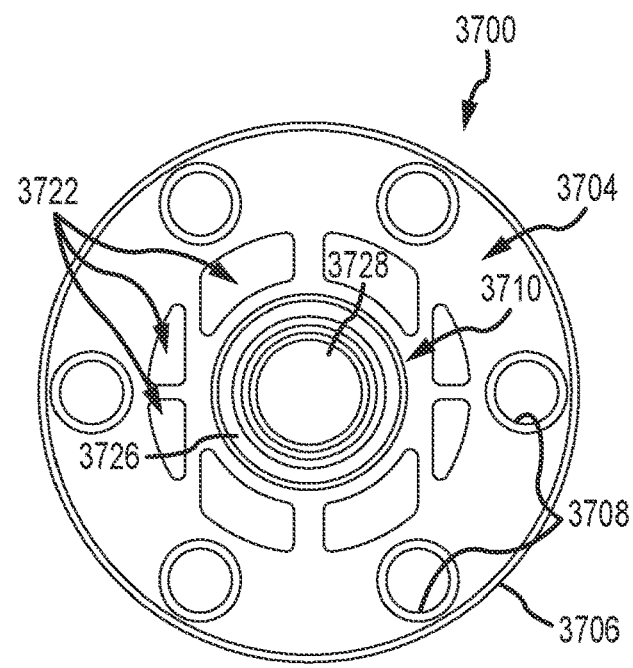
Figure 37D:
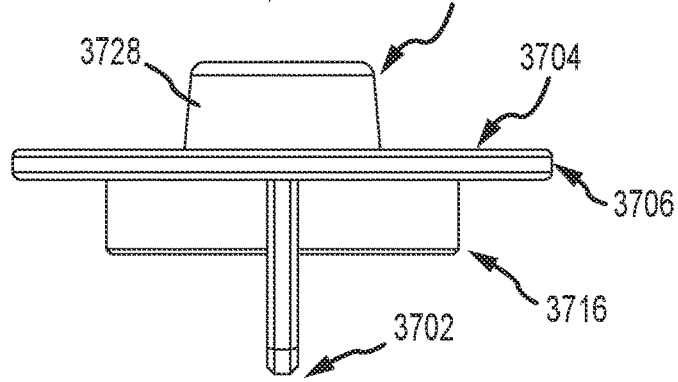
Figure 37E:
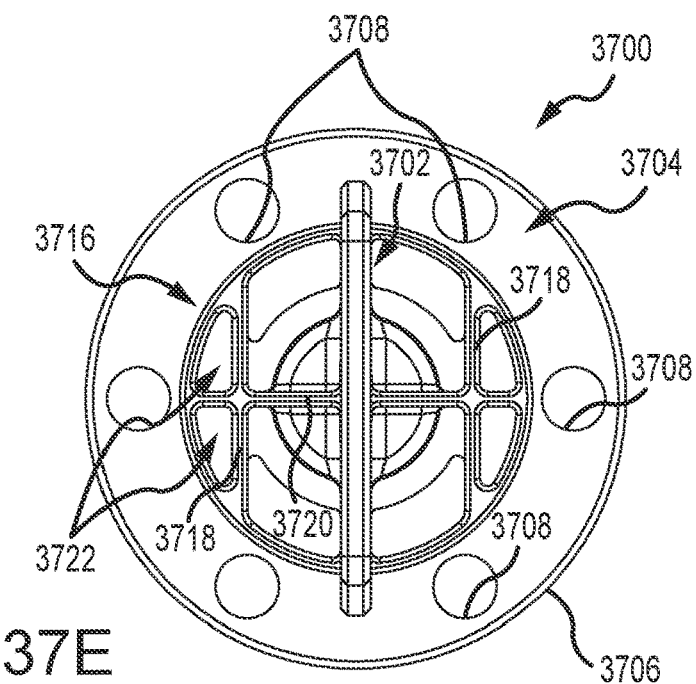
Figure 37F:
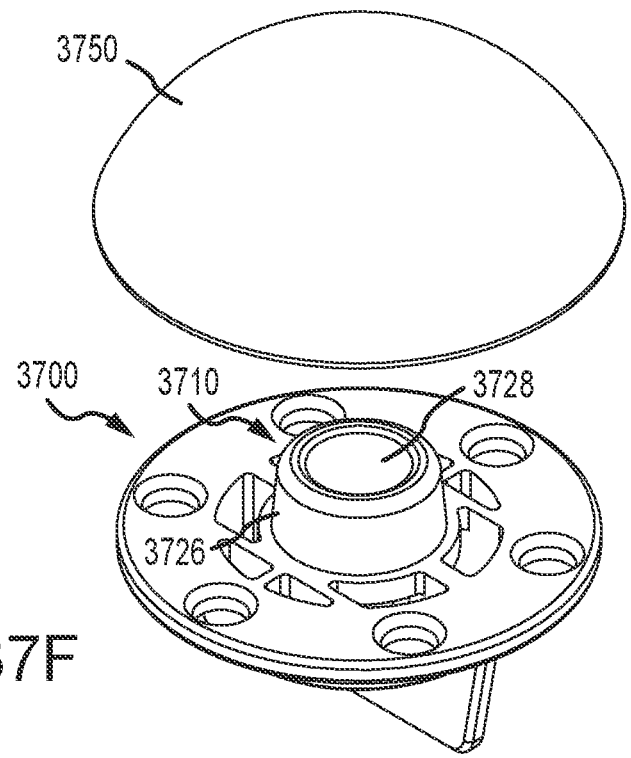
FIG. 37F is a top isometric view of the base plate with a humeral head implant positioned above.
Figure 37G:
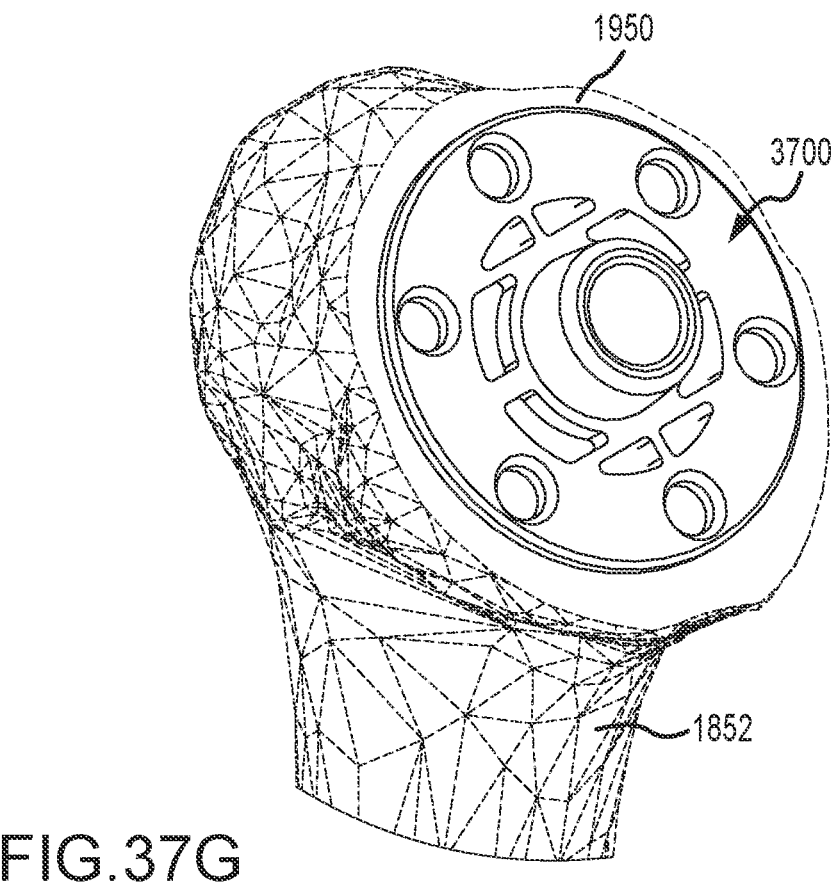
FIG. 37G is a posterior-medial view of the humerus with the base plate positioned thereon.
Figure 37H:
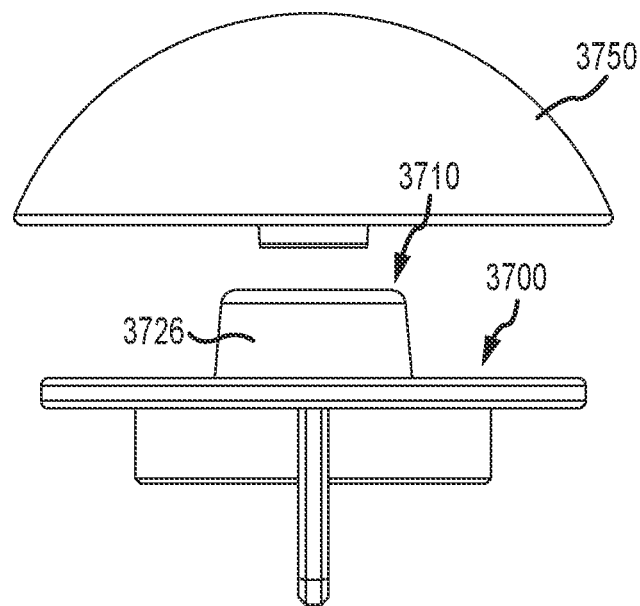
FIGS. 37H-37I are, respectively, side views of the base plate with the humeral head implant positioned above, and the base plate coupled with the humeral head implant.
Figure 37I:
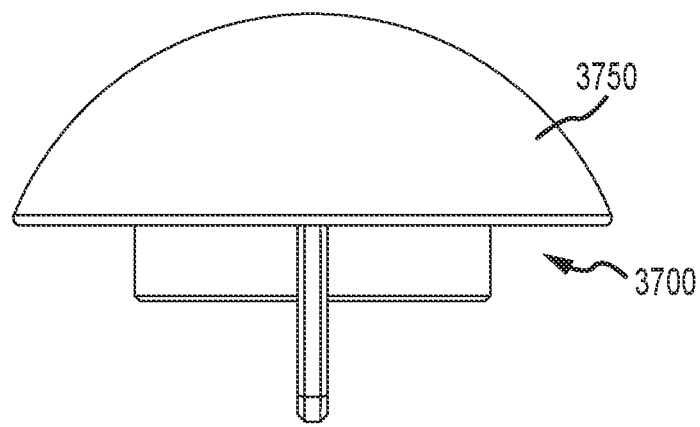

FIG. 37F is a top isometric view of the base plate 3700 with a humeral head implant 3750 positioned above. FIG. 37G is a posterior-medial view of the humerus 1852 with the base plate 3700 positioned thereon. And, FIGS. 37H-37I are, respectively, side views of the base plate 3700 with the humeral head implant 3750 positioned above, and the base plate 3700 coupled with the humeral head implant 3750.

FIGS. 38A-38E are, respectively, top isometric, bottom isometric, top, side, and bottom views of a base plate 3800 having a pair of fins 3802 (major fins) and a female taper or trunnion 3810. As seen in the figures, the base plate 3800 includes a base structure 3804 having a circular perimeter 3806, anchor bores 3808 extending through the base structure 3804 around a perimeter thereof, and a female taper or socket 3810 extending downward from the base structure 3804. The fin 3802 is on the opposite side of the base structure 3804 from the trunnion 3810. The base plate 3800 further includes an attachment structure 3816 in the form of a single minor fin 3818, positioned between the pair of major fins 3802, a transverse minor fin 3820 extending across the minor fin 3818 and the pair of major fins 3802, and a tubular wall 3824 encircling the minor fin 3818 and transverse minor fin 3820. The tubular wall 3824 also intersects the pair of major fins 3802.

The female taper 3810 includes an outer surface 3826 protruding downward from the base structure 3804 between the pair of fins 3802, and an inward socket (female) 3828 formed within the outer protruding surface 3826. The female taper 3810 permits an anatomical humeral head replacement or a reverse arthroplasty procedure involving a cup 3828 and liner 3830, as seen in FIGS. 38J-38L. As seen in FIG. 38K, which is an exploded side views of the base plate 3800, the metal cup 3828 includes a downwardly extending male taper 3832 that is to be received within the female taper 3810 of the base structure 3804. The polymer liner 3830 fits within the metal cup 3828 and is designed as a glenoid replacement, with the spherical implant being affixed to the glenoid in a reverse shoulder arthroplasty.

The base plate 3800 also includes a plurality of windows 3822 extending through the base structure 3804. The windows 3822 are positioned outward of the trunnion 3810 and inwards of the anchor bores 3808. The windows 3822 are defined between the fins 3802, 3820, 3818. The windows 3822 permit boney ingrowth to facilitate attachment of the bone to the base plate 3800. As seen in the figures, the fins 3802 are not angled; rather, they are flat with angled anterior and posterior ends. The flat longitudinal edges are generally parallel with the base structure 3804.

Figure 38A:
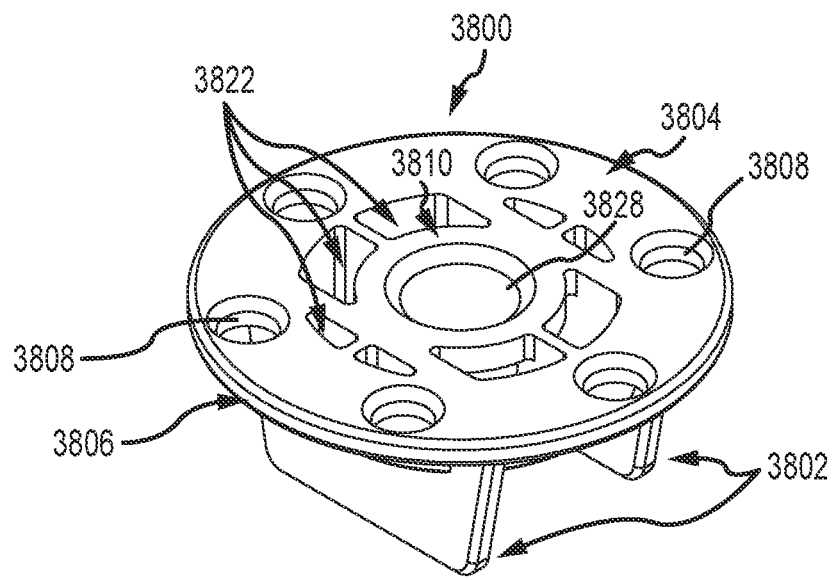
FIGS. 38A-38E are, respectively, top isometric, bottom isometric, top, side, and bottom views of a base plate having a pair of fins, a female socket positioned between the pair of fins, and a tubular wall attachment structure.
Figure 38B:
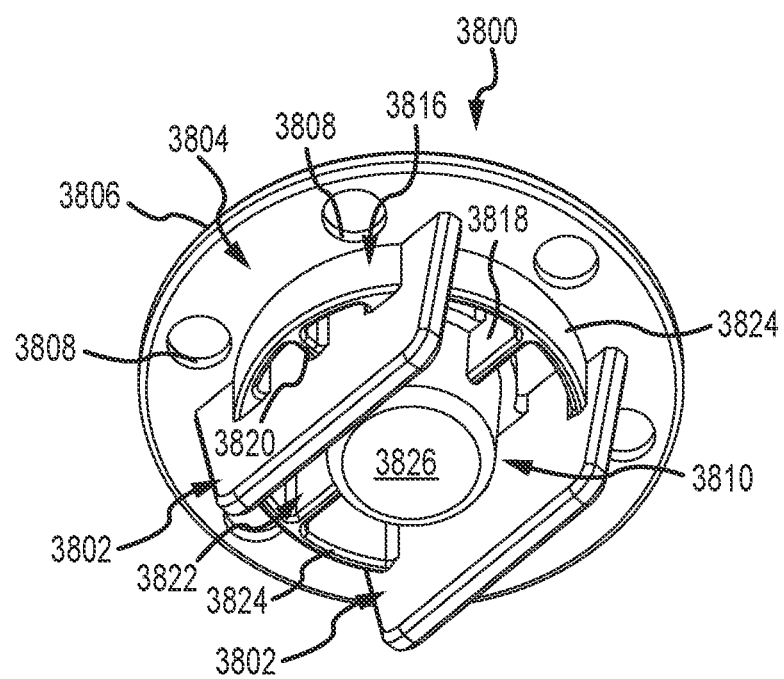
Figure 38C:
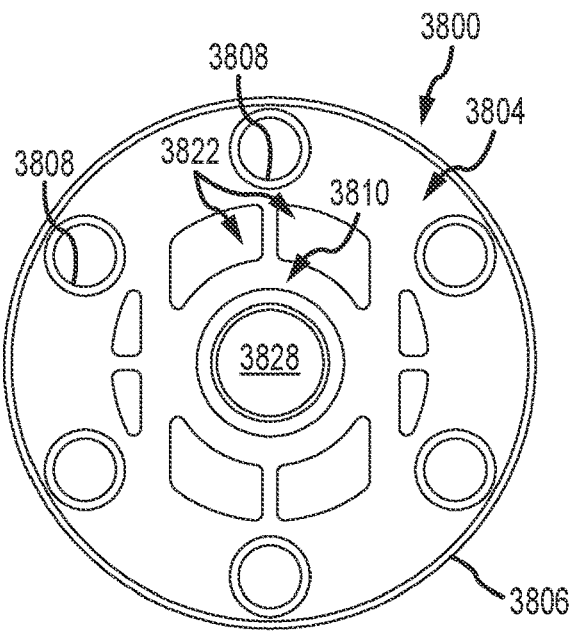
Figure 38D:
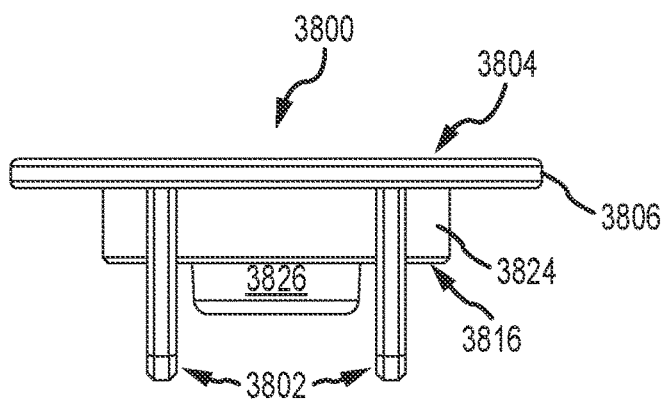
Figure 38E:
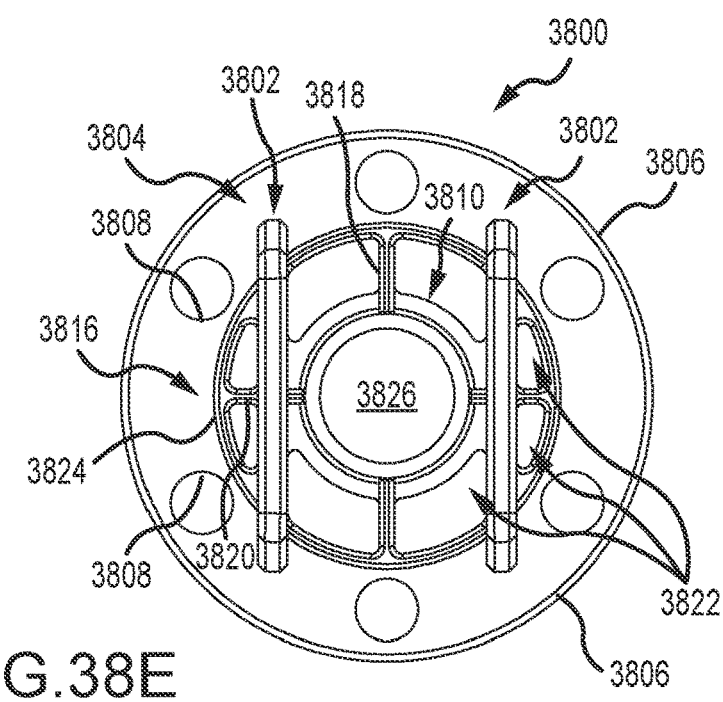
Figure 38F:
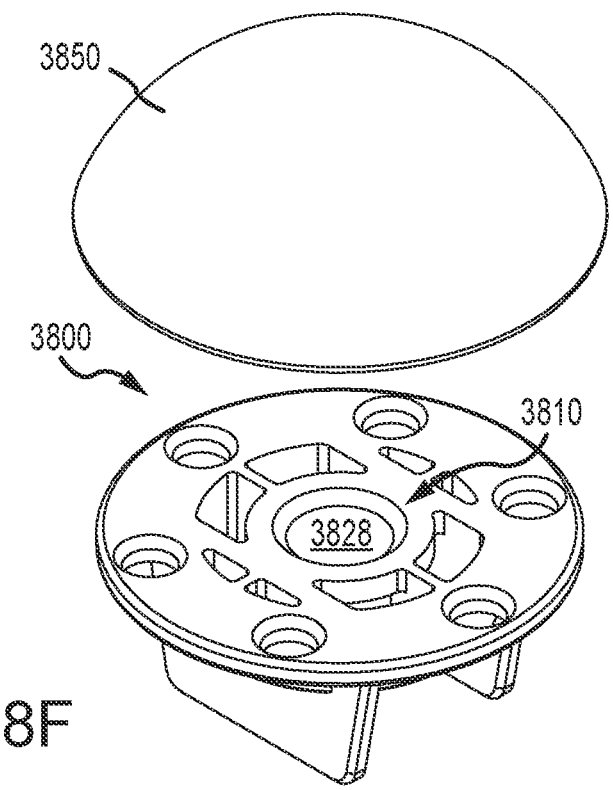
FIG. 38F is a top isometric view of the base plate with a humeral head implant positioned above.
Figure 38G:
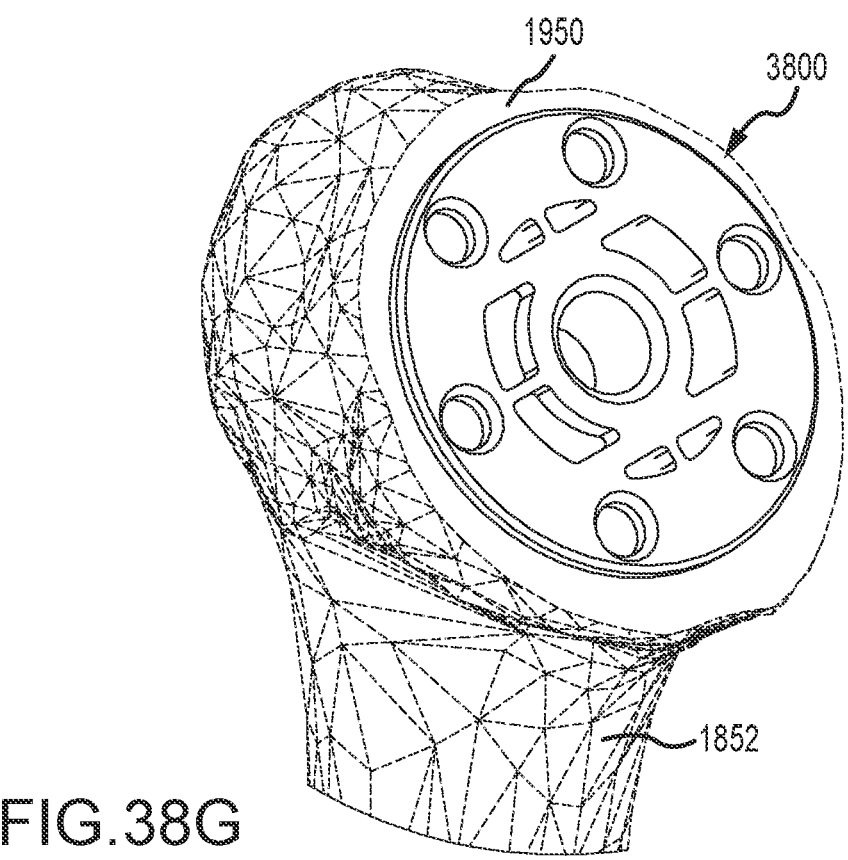
FIG. 38G is a posterior-medial view of the humerus with the base plate positioned thereon.
Figure 38H:
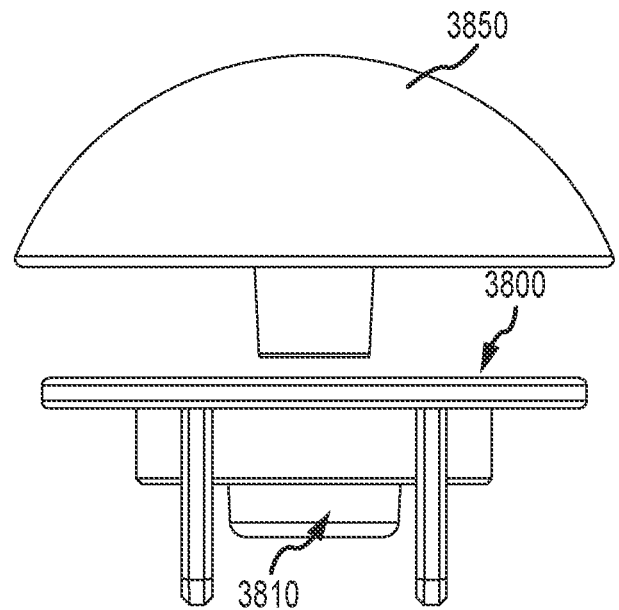
FIGS. 38H-38I are, respectively, side views of the base plate with the humeral head implant positioned above, and the base plate coupled with the humeral head implant.
Figure 38I:
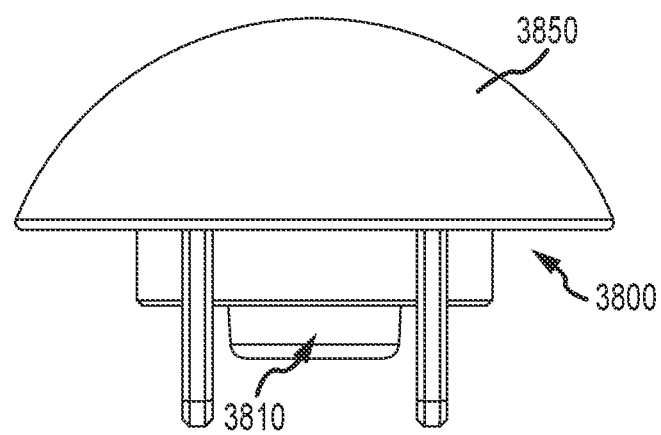
Figure 38J:
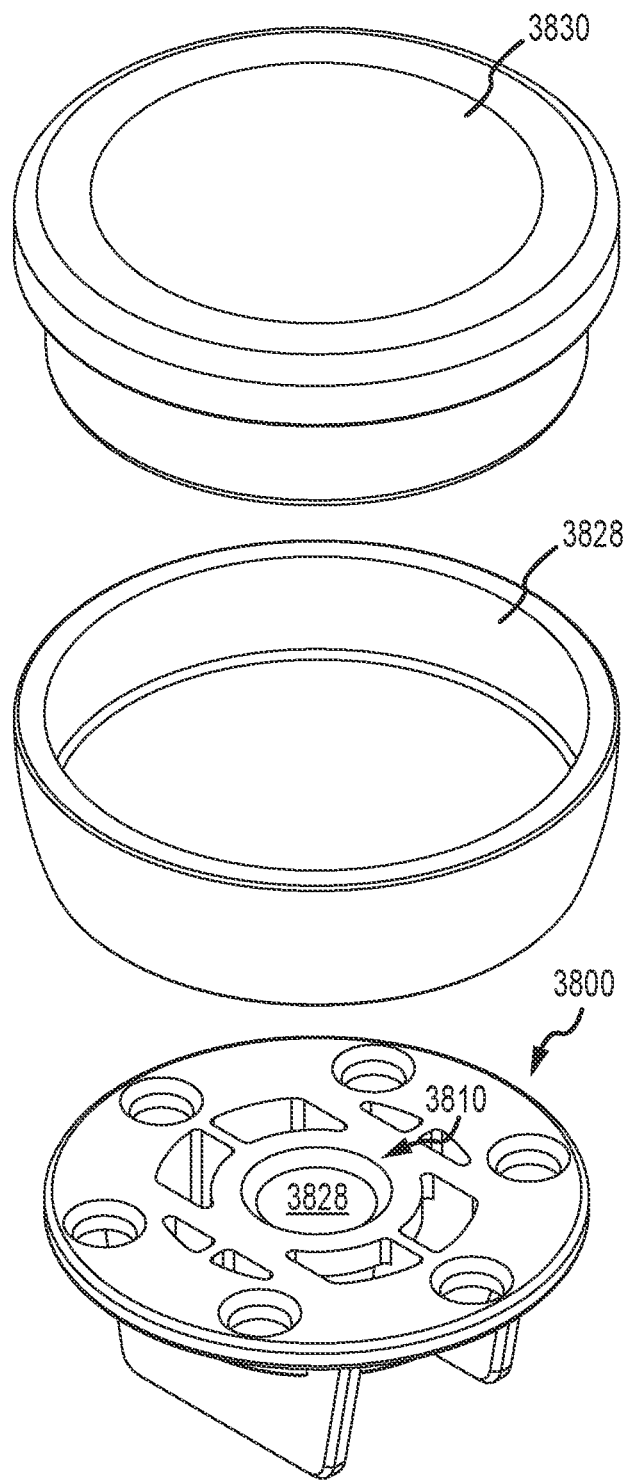
FIGS. 38J-38K are, respectively, isometric exploded top and exploded side views of the base plate, the metal cup, and the polymer liner for use in a reverse shoulder arthroplasty.
Figure 38K:
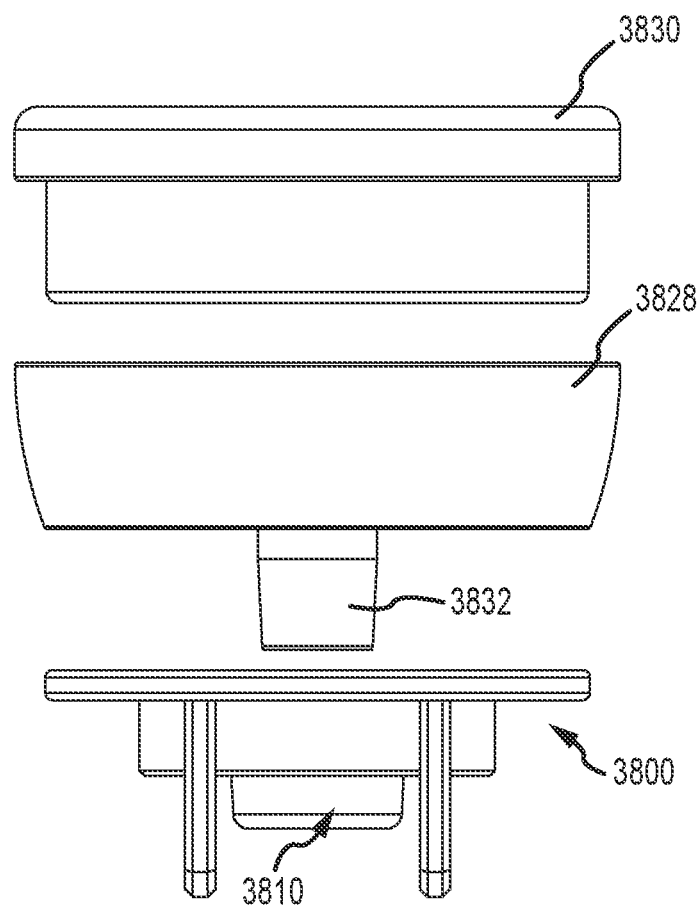
Figure 38L:
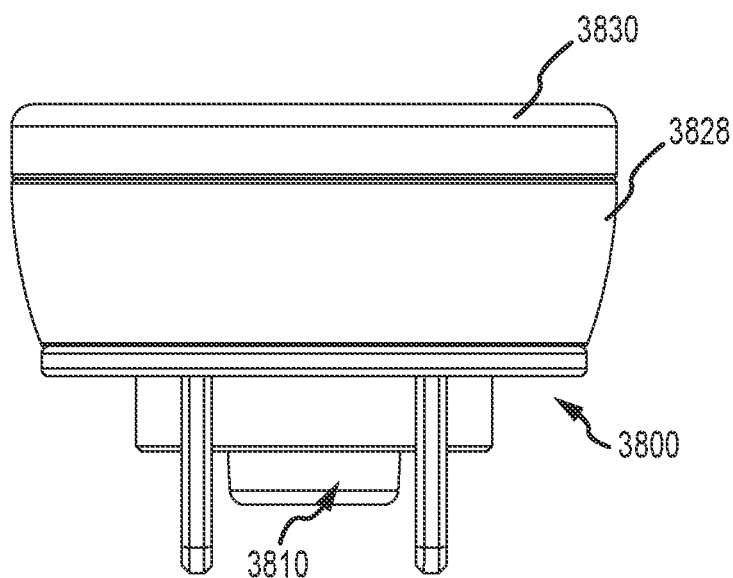
FIG. 38L is a side view of the base plate coupled with the humeral cup and liner coupled thereto.

FIG. 38F is a top isometric view of the base plate 3800 with a humeral head implant 3850 positioned above. FIG. 38G is a posterior-medial view of the humerus 1852 with the base plate 3800 positioned thereon. And, FIGS. 38H-38I are, respectively, side views of the base plate 3800 with the humeral head implant 3850 positioned above, and the base plate 3800 coupled with the humeral head implant 3850.

FIGS. 38J-38K are, respectively, isometric exploded top and exploded side views of the base plate 3800, the metal cup 3828, and the polymer liner 3830 for use in a reverse shoulder arthroplasty. FIG. 38L is a side view of the base plate 3800 coupled with the humeral cup 3828 and liner 3830 coupled thereto.

FIGS. 39A-39E are, respectively, top isometric, bottom isometric, top, side, and bottom views of a base plate 3900 having a single fin 3902, which is part of a modular implant assembly 3990. As seen in the figures, the base plate 3900 includes a base structure 3904 having a circular perimeter 3906, anchor bores 3908 extending through the base structure 3904 (two positioned on each side of the single fin 3902), a trunnion peg 3924 extending upward from the top surface of the base structure 3904, and a pair of key hole slots 3926 extending through the base structure 3904. The fin 3902 is on the opposite side of the base structure 3904 from the trunnion 3910.

As seen in the figures, there is one key hole slot 3926 positioned on each side of the fin 3902. Thus, there are two anchor bores 3908 and a key hole slot 3926 on each side of the fin 3902. Each of the key hole slots 3926 includes a rectangular slot 3928 and a central through bore 3930. In certain instances the central through bore 3930 is threaded in order to receive a threaded set screw. Inner surfaces 3932 of the rectangular slot are tapered inward, as best seen in FIG. 39C, in order to restrict passage of a fin through the key hole slot 3926. A plane extending through the key hole slots 3926 also extends through the trunnion peg 3924.

The base plate 3900 also includes a pair of bores 3934 extending through the base plate structure 3904. The pair of bores 3934 are positioned in a plane that also intersects the fin 3902 and the trunnion peg 3924. The pair of bore 3934 may be threaded in order to threadably receive screws. The trunnion peg 3924 is a protrusion that is sized and shaped to be received within a socket of a removable trunnion cap.

Figure 39A:
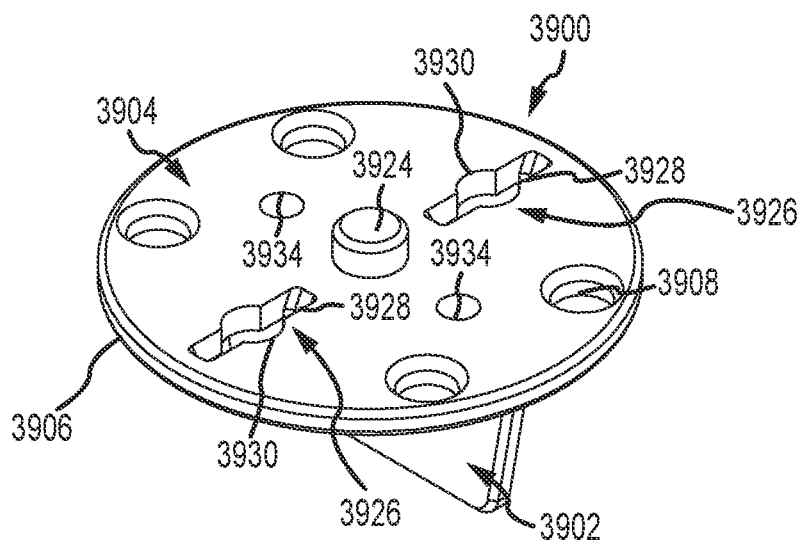
Figure 39B:
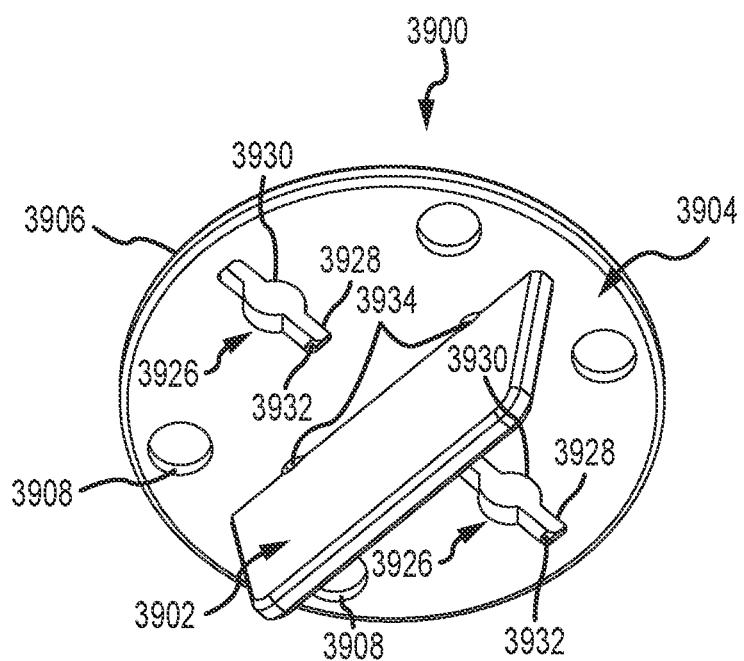
Figure 39C:
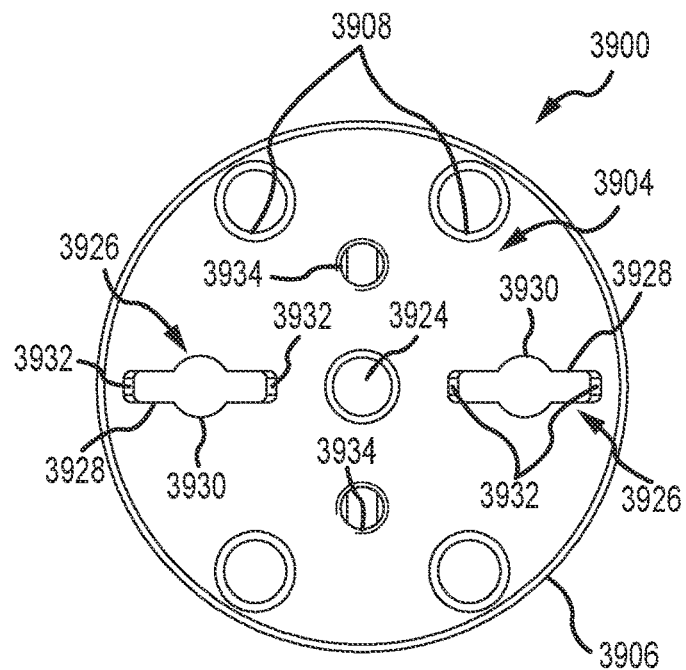
Figure 39D:
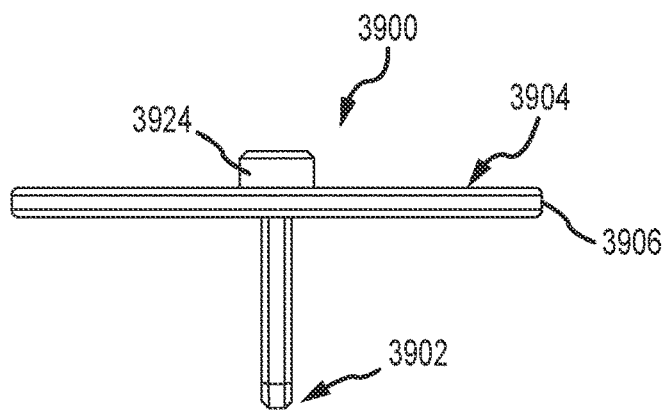
Figure 39E:
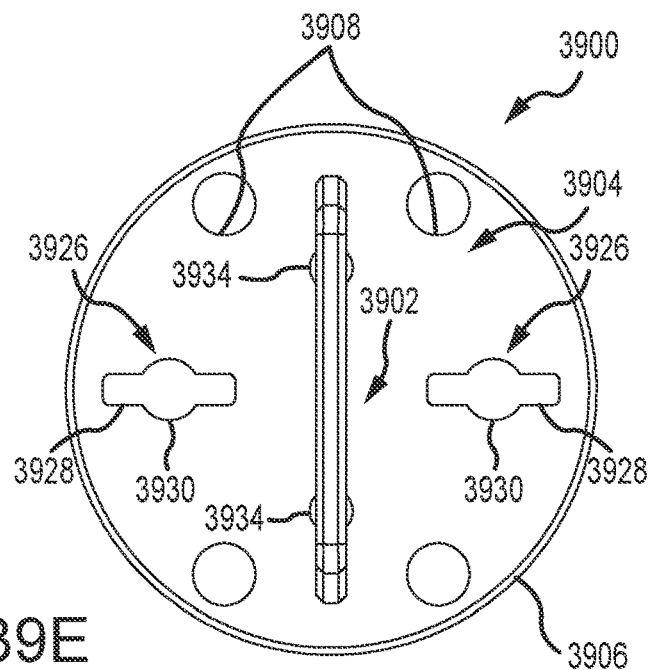

As seen in FIGS. 39B and 39E, the fin 3902 includes angled posterior and anterior ends and a linear section that is generally parallel with the base structure 3904. In use, the base plate 3900 may be slid into a channel cut within the resected bone surface of the humerus into a central position on the humerus. Because there is only a single fin 3900 projecting from the bottom side of the base plate 3900 (i.e., there are no additional fixation elements projecting downward), the base plate structure 3904 may be positioned immediately adjacent (i.e., abutting) the resected bone surface such that there may be little need for tamping down of the base plate 3900.

Figure 39F:
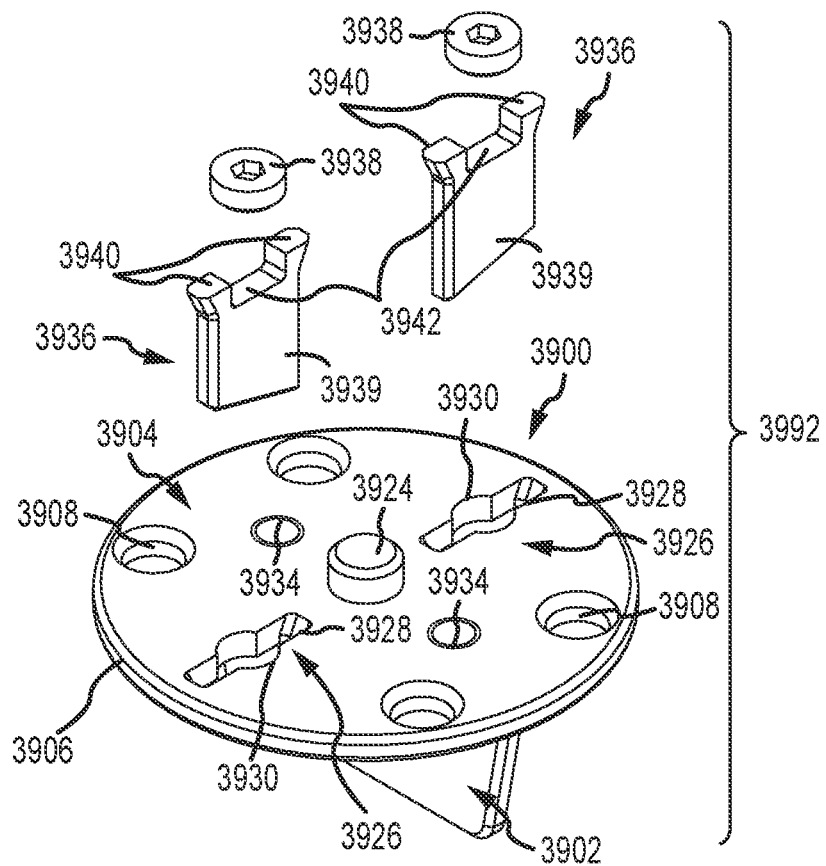

FIG. 39F is an isometric top view of a modular base plate assembly 3992 including the base plate 3900, a pair of modular fins 3936, and a pair of set screws 3938 positioned above. The base plate 3900 is as described previously. The modular fins 3936 include a cutting element 3938 having an angle distal edge, a pair of outwardly projecting shoulders 3940, and recessed neckline 3942 positioned inward of the shoulders 3940. In certain instances, such as shown in the figures, each of the fins 3936 may be identical to each other. In certain instances, the fins may be slightly different from each other. The fins 3936 are sized and shaped to fit within the key hole slots 3926 such that the shoulders 3940 contact and are prevented from passing the inner surfaces 3932 of the rectangular slots 3928. When the fins 3926 are fully positioned within the key hole slots 3926, the recessed neckline 3942 is positioned within the central through bore 3930 to allow passage of the set screw 3938 therein. The set screw 3938 may be engaged with the threaded bore 3934 so as to block retraction or removal of the modular fins 3936.

Figure 39G:
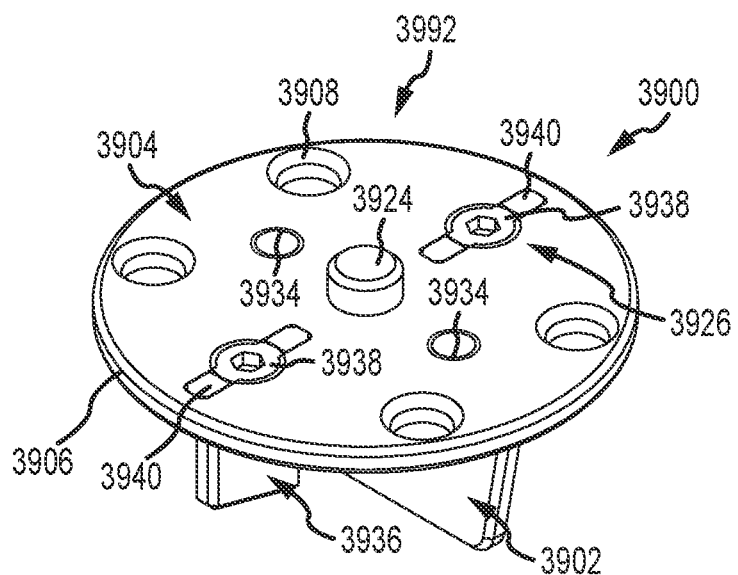

In use, the modular fins 3936 may be inserted into the key hole slots 3926 and into the resected bone surface after the base plate 3900 is engaged with and centered on the resected bone surface of the humerus. The modular fins 3936 may be tamped into the bone with a tool such as a hammer. FIG. 39G depicts an isometric top view of the modular base plate assembly 3992 with the pair of modular fins 3936 inserted into the key hole slots 3926 of the base plate 3900 and secured in place via the set screws 3938. At this point, anchors (e.g., screws) may be driven into the bone through the anchor bores 3908 to further secure the base plate 3900 to the resected bone surface.

Figure 39H:
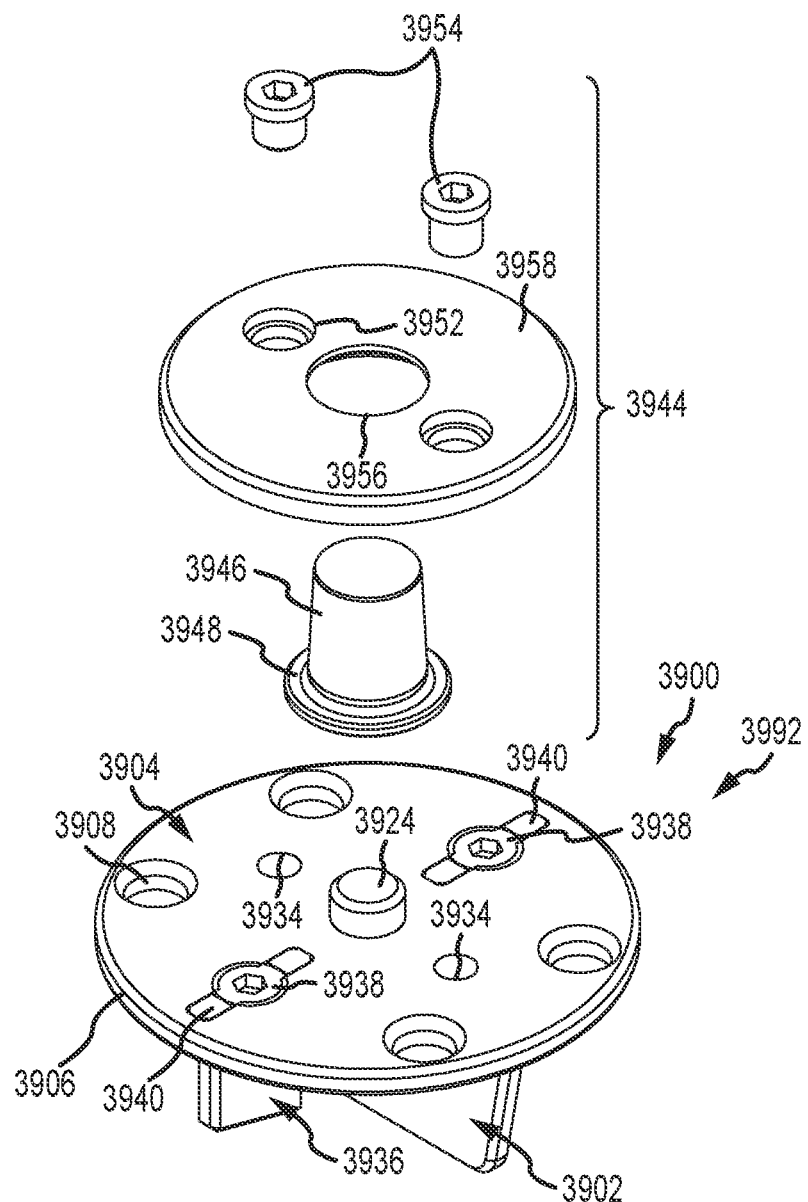
Figure 39I:
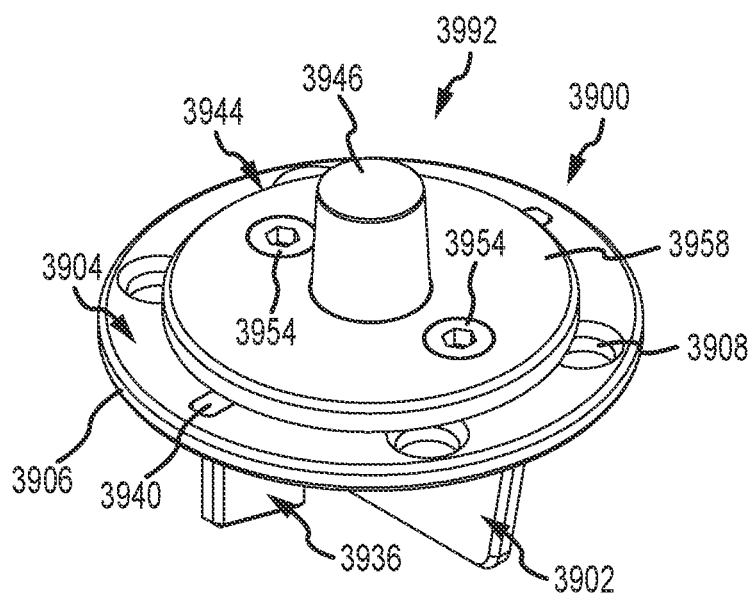

Once the modular base plate assembly 3992 is assembled by securing the fins 3936 to the key hole slots 3926 via the set screws 3938, the assembly 3992 may be coupled with a modular male taper assembly 3944, which is shown in FIG. 39H, which is an isometric top view of a modular male taper assembly 3944 of the modular base plate assembly 3992 positioned above the base plate 3900 with attached fins 3936 and set screws 3938. The modular male taper assembly 3944 includes a male taper or trunnion cap 3946 having a radial flange 3948 positioned near the base thereof. The assembly 3944 also includes a trunnion plate 3958 having a pair of bores 3952 extending there through, a central opening 3956 for receiving the trunnion cap 3946 there through, and a pair of set screws 3954. The set screws 3954 (threaded) may be used to secure the trunnion plate 3958 to the pair of threaded bores 3934 extending through the base structure 3904, as seen in FIG. 39I, which is an isometric top view of the fully assembled modular base plate assembly 3992. The trunnion plate 3958 is sized so that it contacts and holds down the radial flange 3948 of the trunnion cap 3946. The trunnion plate 3958 may also contact the fins 3936 and/or the set screws 3938 in order to prevent any movement thereof.

Figure 39J:
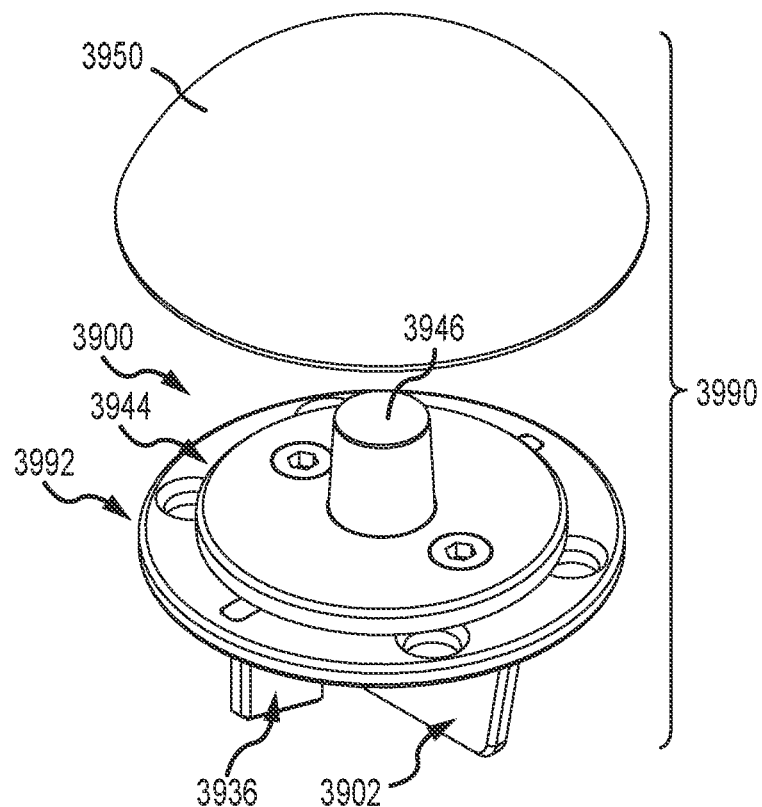
Figure 39K:
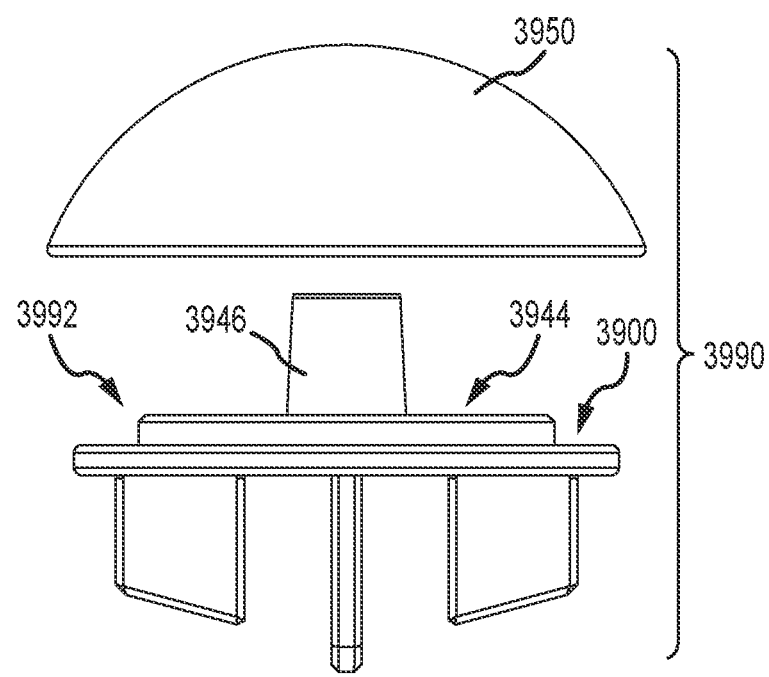
Figure 39L:
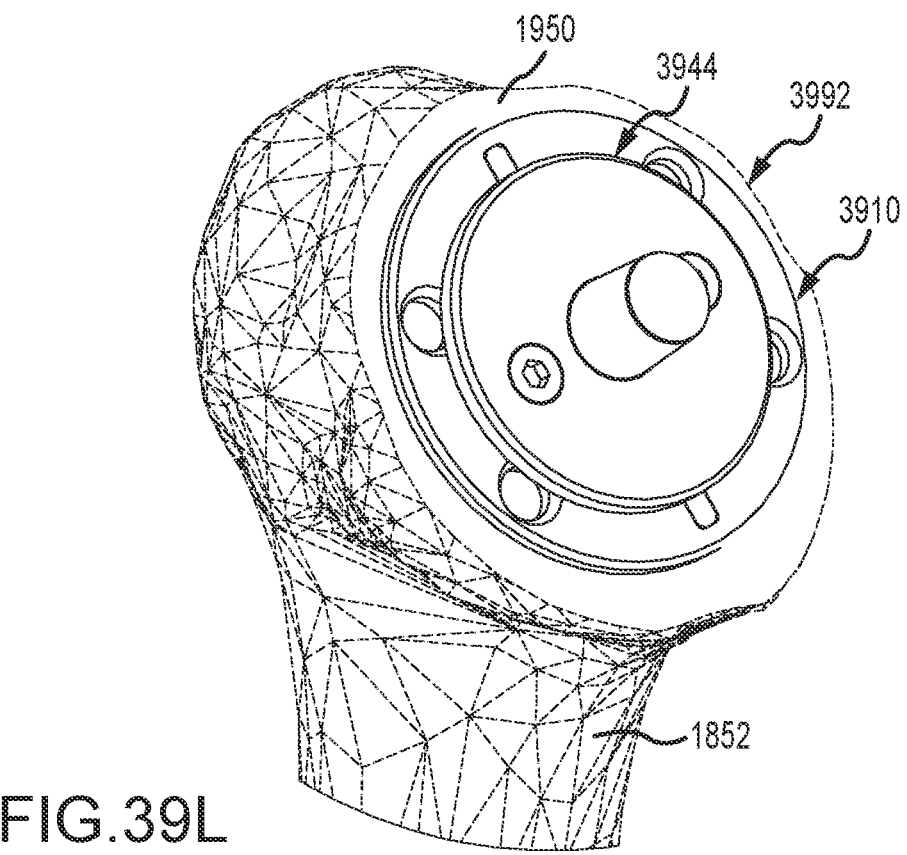

FIGS. 39J-39K are, respectively, isometric top and side views of the fully assembled modular base plate assembly 3992 with a humeral head implant 3950 positioned above. The modular base plate assembly 3992 and a humeral head implant 3950 together form the modular implant assembly 3990. The humeral head implant 3950 is sized and shaped to mate with the trunnion cap 3946 when positioned thereon. FIG. 39L is posterior-medial view of the humerus 1852 with the fully assembled modular base plate assembly 3992 positioned thereon.

The fins and/or attachment structures of the base plates may be made of porous metal, plasma sprayed, coated with bone ingrowth or ongrowth elements, among other treatments. In one instance, the fins and/or attachments structures may be hydroxyapatite coated.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention. Features from any of the embodiments may be substituted, added, or removed from any of the embodiments without limitation.

What is claimed is:

1. A stemless humeral head replacement system comprising:
- a base plate comprising a bone facing side, an implant side opposite the bone facing side, a curvate perimeter, an implant engagement structure protruding from the implant side, and a first fin protruding from the bone facing side a first distance and extending linearly a length between side edges of the curvate perimeter, wherein the curvate perimeter of the base plate defines a central axis, and the first fin extends through the central axis, wherein the first fin includes a pair of planar surfaces that are parallel to each other; and
- a humeral head implant comprising a curvate implant surface and a base plate engagement structure opposite the curvate implant surface, the base plate engagement structure configured to couple to the implant engagement structure of the base plate; and
- a reference guide and a guide pin, the reference guide comprising a targeting arm having a curvate arm configured to be positioned around a spherical bone and terminating at a blunt tip, and a sleeve having a guide hole that is configured to guide the guide pin through the spherical bone to the blunt tip.

2. The system of claim 1, wherein the reference guide further comprises a handle, the sleeve configured to removably couple with the handle, wherein upon delivery of the guide pin via guidance by the guide hole of the sleeve, the sleeve may be decoupled from the handle so as to permit the curvate arm of the targeting arm to be removed from being positioned around the spherical bone.

3. The system of claim 1, further comprising a cutting guide including a first pin guide and a first planar surface configured to guide a planar resection of the spherical bone, the first pin guide configured to receive the guide pin there through so as to orient a bone facing side of the cutting guide towards the spherical bone.

4. The system of claim 3, further comprising a channel guide including a planar referencing surface, a flange having a second pin guide extending from a perimeter of the planar referencing surface, and a slot formed within the planar referencing surface, the second pin guide configured to receive the guide pin there through so as to orient the planar referencing surface atop a resected bone surface, the slot extending atop the resected bone surface in a posterior-anterior direction.

5. The system of claim 1, wherein the base plate further includes a second fin protruding from the bone facing side and extending linearly between side edges of the curvate perimeter, the second fin being generally parallel to the first fin.

6. The system of claim 5, wherein the base plate further includes a third fin protruding from the bone facing side and extending linearly between side edges of the curvate perimeter, the third fin being generally parallel to the first fin.

7. The system of claim 1, wherein the implant engagement structure is a trunnion.

8. A stemless humeral head replacement system comprising:
- a base plate comprising a bone facing side, an implant side opposite the bone facing side, a curvate perimeter, an implant engagement structure protruding from the implant side, and a first fin protruding from the bone facing side a first distance and extending linearly a length between side edges of the curvate perimeter wherein the base plate further includes a second fin protruding from the bone facing side extending linearly between side edges of the curvate perimeter, the second fin being generally parallel to the first fin; and
- a humeral head implant comprising a curvate implant surface and a base plate engagement structure opposite the curvate implant surface, the base plate engagement structure configured to couple to the implant engagement structure of the base plate; and
- a base plate delivery tool comprising a first engagement structure comprising a first pair of tips at a distal end and a first handle at a proximal end, each of the first pair of tips including a first protrusion configured to engage a portion of the base plate, the first engagement structure including a curvate flange configured to abut the curvate perimeter of the base plate when coupled thereto, the first engagement structure further including a bone engagement flange protruding beyond the curvate flange and configured to engage a bone portion when sliding the base plate onto a resected bone surface.

9. The system of claim 8, further comprising a base plate impaction tool comprising a second engagement structure comprising a second pair of tips at a distal end, a second handle at a proximal end, and a C-arm interconnecting the second engagement structure and the second handle, the C-arm including an impaction surface in line with the second engagement structure.

10. The system of claim 8, wherein the base plate further includes a third fin protruding from the bone facing side and extending linearly between side edges of the curvate perimeter, the third fin being generally parallel to the first fin.

11. The system of claim 8, wherein the implant engagement structure is a trunnion.

12. The system of claim 8, wherein the curvate perimeter of the base plate defines a central axis, and the first fin extends through the central axis.

13. The system of claim 12, wherein the first fin includes a pair of planar surfaces that are parallel to each other.

14. A stemless humeral head replacement system comprising:
- a base plate comprising a bone facing side, an implant side opposite the bone facing side, a curvate perimeter defining a central axis, an implant engagement structure on the implant side, and a first fin protruding from the bone facing side a first distance and extending linearly a length between side edges of the curvate perimeter, the first fin extending through the central axis; and
- a humeral head implant comprising a curvate implant surface and a base plate engagement structure opposite the curvate implant surface, the base plate engagement structure configured to couple to the implant engagement structure of the base plate; and
- a reference guide and a guide pin, the reference guide comprising a targeting arm having a curvate arm configured to be positioned around a spherical bone and terminating at a blunt tip, and a sleeve having a guide hole that is configured to guide the guide pin through the spherical bone to the blunt tip, wherein the reference guide further comprises a handle, the sleeve configured to removably couple with the handle, wherein upon delivery of the guide pin via guidance by the guide hole of the sleeve, the sleeve may be decoupled from the handle so as to permit the curvate arm of the targeting arm to be removed from being positioned around the spherical bone.

15. The system of claim 14, further comprising a cutting guide including a first pin guide and a first planar surface configured to guide a planar resection of the spherical bone, the first pin guide configured to receive the guide pin there through so as to orient a bone facing side of the cutting guide towards the spherical bone.

16. The system of claim 15, further comprising a channel guide including a planar referencing surface, a flange having a second pin guide extending from a perimeter of the planar referencing surface, and a slot formed within the planar referencing surface, the second pin guide configured to receive the guide pin there through so as to orient the planar referencing surface atop a resected bone surface, the slot extending atop the resected bone surface in a posterior-anterior direction.

17. A stemless humeral head replacement system comprising:

a base plate comprising a bone facing side, an implant side opposite the bone facing side, a curvate perimeter, an implant engagement structure protruding from the implant side, and a first fin protruding from the bone facing side a first distance and extending linearly a length between side edges of the curvate perimeter; and a humeral head implant comprising a curvate implant surface and a base plate engagement structure opposite the curvate implant surface, the base plate engagement structure configured to couple to the implant engagement structure of the base plate; and a reference guide and a guide pin, the reference guide comprising a targeting arm having a curvate arm configured to be positioned around a spherical bone and terminating at a blunt tip, and a sleeve having a guide hole that is configured to guide the guide pin through the spherical bone to the blunt tip, wherein the reference guide further comprises a handle, the sleeve configured to removably couple with the handle, wherein upon delivery of the guide pin via guidance by the guide hole of the sleeve, the sleeve may be decoupled from the handle so as to permit the curvate arm of the targeting arm to be removed from being positioned around the spherical bone.

\* \* \* \* \*